(12) United States Patent
Jung et al.

(10) Patent No.: US 7,402,585 B2
(45) Date of Patent: Jul. 22, 2008

(54) SUBSTITUTED QUINAZOLINE DERIVATIVES AS INHIBITORS OF AURORA KINASES

(75) Inventors: Frederic Henri Jung, Reims (FR); Georges Rene Pasquet, Reims (FR)

(73) Assignee: AstraZeneca AB, Södertälje (SE)

( * ) Notice: Subject to any disclaimer, the term of this patent is extended or adjusted under 35 U.S.C. 154(b) by 68 days.

(21) Appl. No.: 10/499,684

(22) PCT Filed: Dec. 20, 2002

(86) PCT No.: PCT/GB02/05845

§ 371 (c)(1),
(2), (4) Date: Nov. 17, 2004

(87) PCT Pub. No.: WO03/055491

PCT Pub. Date: Jul. 10, 2003

(65) Prior Publication Data

US 2005/0070561 A1    Mar. 31, 2005

(30) Foreign Application Priority Data

Dec. 24, 2001    (EP) .................................. 01403357

(51) Int. Cl.
*A61K 31/517* (2006.01)
*C07D 239/72* (2006.01)
*C07D 403/12* (2006.01)

(52) U.S. Cl. .................................. 514/266.23; 544/284
(58) Field of Classification Search ............ 514/266.23; 544/284
See application file for complete search history.

(56) References Cited

U.S. PATENT DOCUMENTS

| 5,480,883 A | 1/1996 | Spada et al. ................. 514/249 |
| 5,710,158 A | 1/1998 | Myers et al. ............. 514/266.2 |
| 6,610,677 B2 * | 8/2003 | Davies et al. ............... 514/183 |

FOREIGN PATENT DOCUMENTS

| EP | 0326330 B1 | 7/2002 |
| WO | WO-92/20642 | 11/1992 |
| WO | WO-95/15758 | 6/1995 |
| WO | 96/09294 A1 | 3/1996 |
| WO | 96/15118 A1 | 5/1996 |
| WO | 96/39145 A | 12/1996 |
| WO | WO-96/39145 | 12/1996 |
| WO | WO-97/03069 | 1/1997 |
| WO | 99/06378 A1 | 2/1999 |
| WO | 00/21955 A | 4/2000 |
| WO | 00/21955 A1 | 4/2000 |
| WO | WO-00/21955 | 4/2000 |
| WO | 01/21596 A | 3/2001 |
| WO | 01/21596 A1 | 3/2001 |
| WO | 01/21597 A | 3/2001 |
| WO | WO-01/21597 A1 | 3/2001 |
| WO | 02/00649 A | 1/2002 |
| WO | WO-02/00649 A1 | 1/2002 |

OTHER PUBLICATIONS

Wilkinson et al., "AZD1152, a Selective Inhibitor of Aurora B Kinase, Inhibits Human Tumor Xenograft Growth by Including Apoptosis", Clinical CAncer REsearch (2007), 3682-3688, 13(12).
Mortlock et al., "Discovery, Synthesis, and in Vivo Activity of a New Class of Pyrazolylaminoquinazolines as Selective Inhibitors of Aurora B Kinase". Journal of Medicinal Chemistry (2007), 2213-2224, 50(9).
Heron et al., "SAR and inhibitor complex structure determination of a novel class of potent and specific Aurora kinase inhibitors". Bioorganic & Medicinal Chemistry Letters (2006), 1320-1323, 16(5).
Jung et al., "Discovery of Novel and Potent Thiazoloquinazolines as Selective Aurora A and B Kinase Inhibitors". Journal of Medicinal Chemistry (2006), 955-970, 49(3).
Mortlock et al., "Progress in the Development of Selective Inhibitors of Aurora Kinases". Current Topics in Medicinal Chemistry (2005), 807-821, 5(8).

* cited by examiner

*Primary Examiner*—James O. Wilson
*Assistant Examiner*—Tamthom N Truong

(57) ABSTRACT

The invention provides quinazoline derivatives of formula (I): in the preparation of a medicament for use in the inhibition of Aurora kinase and also novel quinazoline derivatives, processes for their preparation, pharamceutical compositions containing them and their use in therapy

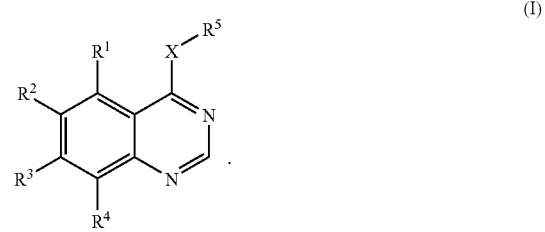

33 Claims, No Drawings

SUBSTITUTED QUINAZOLINE DERIVATIVES AS INHIBITORS OF AURORA KINASES

CROSS-REFERENCE TO RELATED APPLICATIONS

This application is a US National Stage under 35 U.S.C § 371 of International Application No. PCT/GB02/05845 (filed 20 Dec. 2002) which claims priority under 35 U.S.C. § 119 (a)-(d) to Application No. EP01403357.5 filed on 24 Dec. 2001.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, an ordered cascade of protein phosphorylation is thought to control the cell cycle. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle. For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672-1677; Pines, 1995, Seminars in Cancer Biology 6: 63-72). Other studies (Loda et al., 1997, Nature Medicine 3(2): 231-234; Gemma et al., 1996, International Journal of Cancer 68(5): 605-11; Elledge et al. 1996, Trends in Cell Biology 6; 388-392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ip11 proteins. The three human homologues of these genes Aurora-A, Aurora-B and Aurora-C (also known as aurora2, aurora1 and aurora3 respectively) encode cell cycle regulated serine-threonine protein kinases (summarised in Adams et al., 2001, Trends in Cell Biology. 11(2): 49-54). These show a peak of expression and kinase activity through G2 and mitosis. Several observations implicate the involvement of human aurora proteins in cancer. This evidence is particularly strong for Aurora-A. The Aurora-A gene maps to chromosome 20q13, a region that is frequently amplified in human tumours including both breast and colon tumours. Aurora-A may be the major target gene of this amplicon, since Aurora-A DNA is amplified and mRNA overexpressed in greater than 50% of primary human colorectal cancers. In these tumours Aurora-A protein levels appear greatly elevated compared to adjacent normal tissue. In addition, transfection of rodent fibroblasts with human Aurora-A leads to transformation, conferring the ability to grow in soft agar and form tumours in nude mice (Bischoff et al., 1998, The EMBO Journal. 17(11): 3052-3065). Other work (Zhou et al., 1998, Nature Genetics. 20(2): 189-93) has shown that artificial overexpression of Aurora-A leads to an increase in centrosome number and an increase in aneuploidy, a known event in the development of cancer. Other work has shown an increase in expression of Aurora-B (Adams et al., 2001, Chromsoma. 110(2):65-74) and Aurora-C (Kimura et al., 1999, Journal of Biological Chemistry, 274(11): 7334-40) in tumour cells when compared to normal cells.

Importantly, it has also been demonstrated that abrogation of Aurora-A expression and function by antisense oligonucleotide treatment of human tumour cell lines (WO 97/22702 and WO 99/37788) leads to cell cycle arrest and exerts an antiproliferative effect in these tumour cell lines. Additionally, small molecule inhibitors of Aurora-A and Aurora-B have been demonstrated to have an antiproliferative effect in human tumour cells (Keen et al. 2001, Poster #2455, American Association of Cancer research annual meeting). This indicates that inhibition of the function of Aurora-A (and possibly Aurora-B) will have an antiproliferative effect that may be useful in the treatment of human tumours and other hyperproliferative diseases. Further, inhibition of Aurora kinases as a therapeutic approach to these diseases may have significant advantages over targeting signalling pathways upstream of the cell cycle (e.g. those activated by growth factor receptor tyrosine kinases such as epidermal growth factor receptor (EGFR) or other receptors). Since the cell cycle is ultimately downstream of all of these diverse signalling events, cell cycle directed therapies such as inhibition of Aurora kinases would be predicted to be active across all proliferating tumour cells, whilst approaches directed at specific signalling molecules (e.g. EGFR) would be predicted to be active only in the subset of tumour cells which express those receptors. It is also believed that significant "cross talk" exists between these signalling pathways meaning that inhibition of one component may be compensated for by another.

A number of quinazoline derivatives have been proposed hitherto for use in the inhibition of various kinases. For example, WO 96/09294, WO 96/15118 and WO 99/06378 to describe the use of certain quinazoline compounds as receptor tyrosine kinase inhibitors, which may be useful in the treatment of proliferative disease and WO 00/21955 discloses certain quinazoline derivatives as inhibitors of the effects of VEGF.

Quinazoline derivatives have also been disclosed for use in the inhibition of Aurora-A kinase. WO 02/00649 discloses quinazoline derivative beaming a 5-membered heteroaromatic ring where the ring is, in particular, substituted thiazole or substituted thiophene. However despite the compounds of WO 02/00649 there still exists the need for further compounds having Aurora kinase inhibitory properties.

The applicants have been successful in finding a novel series of compounds which inhibit the effects of the Aurora kinases and in particular Aurora-A kinase and which are thus of use in the treatment of proliferative disease such as cancer, in particular in such diseases such as colorectal or breast cancer where Aurora kinases are known to be active.

According to one aspect of the present invention there is provided the use of a compound of formula (I)

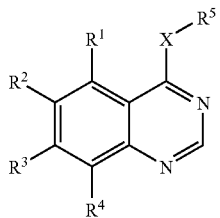

(I)

or a salt, ester or amide thereof;

where:

X is O or S, S(O) or S(O)$_2$, or NR$^6$ where R$^6$ is hydrogen or C$_{1-6}$alkyl;

R$^5$ is a group of formula (a) or (b):

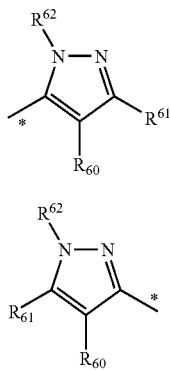

where * indicates the point of attachment to the group X in formula (I);

R$^1$, R$^2$, R$^3$, R$^4$ are independently selected from hydrogen, halo, cyano, nitro, trifluoromethyl, C$_{1-3}$alkyl, —NR$^7$R$^8$ or —X$^1$R$^9$;

R$^7$ and R$^8$ are independently hydrogen or C$_{1-3}$alkyl;

X$^1$ is a direct bond, —O—, —CH$_2$—, —OCO—, carbonyl, —S—, —SO—, —SO$_2$—, —NR$^{10}$CO—, —CONR$^{11}$—, —SO$_2$NR$^{12}$—, —NR$^{13}$SO$_2$— or —NR$^{14}$—;

R$^{10}$, R$^{11}$, R$^{12}$, R$^{13}$ and R$^{14}$ are independently hydrogen, C$_{1-3}$alkyl or C$_{1-3}$alkoxyC$_{2-3}$alkyl;

R$^9$ is selected from one of the following groups:

1) hydrogen or C$_{1-5}$alkyl which may be unsubstituted or which may be substituted with one or more groups selected from hydroxy, fluoro or amino;

2) C$_{1-5}$alkylX$^2$COR$^{15}$ (wherein X$^2$ represents —O— or —NR$^{16}$— (in which R$^{15}$ represents hydrogen, C$_{1-3}$alkyl or C$_{1-3}$alkoxyC$_{2-3}$alkyl) and R$^{16}$ represents C$_{1-3}$alkyl, —NR$^{17}$R$^{18}$ or —OR$^{19}$ (wherein R$^{17}$, R$^{18}$ and R$^{19}$ which may be the same or different each represents hydrogen, C$_{1-3}$alkyl or C$_{1-3}$alkoxyC$_{2-3}$alkyl));

3) C$_{1-5}$alkylX$^3$R$^{20}$ (wherein X$^3$ represents —O—, —S—, —SO—, —SO$_2$—, —OCO—, —NR$^{21}$CO—, —CONR$^{22}$—, —SO$_2$NR$^{23}$—, —NR$^{24}$SO$_2$— or —NR$^{25}$— (wherein R$^{21}$, R$^{22}$, R$^{23}$, R$^{24}$ and R$^{25}$ each independently represents hydrogen, C$_{1-3}$alkyl or C$_{1-3}$alkoxyC$_{2-3}$alkyl) and R$^{20}$ represents hydrogen, C$_{1-3}$alkyl, cyclopentyl, cyclohexyl or a 5- or 6-membered saturated heterocyclic group with 1 or 2 heteroatoms, selected independently from O, S and N, which C$_{1-3}$alkyl group may bear 1 or 2 substituents selected from oxo, hydroxy, halo and C$_{1-4}$alkoxy and which cyclic group may bear 1 or 2 substituents selected from oxo, hydroxy, halo, C$_{1-4}$alkyl, C$_{1-4}$hydroxyalkyl and C$_{1-4}$alkoxy);

4) C$_{1-5}$alkylX$^4$C$_{1-5}$alkylX$^5$R$^{26}$ (wherein X$^4$ and X$^5$ which may be the same or different are each —O—, —S—, —SO—, —SO$_2$—, —NR$^{27}$CO—, —CONR$^{28}$—, —SO$_2$NR$^{29}$—, —NR$^{30}$SO$_2$— or —NR$^{31}$— (wherein R$^{27}$, R$^{28}$, R$^{29}$, R$^{30}$ and R$^{31}$ each independently represents hydrogen, C$_{1-3}$alkyl or C$_{1-3}$alkoxyC$_{2-3}$alkyl) and R$^{26}$ represents hydrogen or C$_{1-3}$alkyl);

5) R$^{32}$ (wherein R$^{32}$ is a 5- or 6-membered saturated heterocyclic group (linked via carbon or nitrogen) with 1 or 2 heteroatoms, selected independently from O, S and N, which heterocyclic group may bear 1 or 2 substituents selected from oxo, hydroxy, halo, C$_{1-4}$alkyl, C$_{1-4}$hydroxyalkyl, C$_{1-4}$alkoxy, C$_{1-4}$alkoxyC$_{1-4}$alkyl and C$_{1-4}$alkylsulphonylC$_{1-4}$alkyl);

6) C$_{1-5}$alkylR$^{32}$ (wherein R$^{32}$ is as defined hereinbefore);

7) C$_{2-5}$alkenylR$^{32}$ (wherein R$^{32}$ is as defined hereinbefore);

8) C$_{2-5}$alkynylR$^{32}$ (wherein R$^{32}$ is as defined hereinbefore);

9) R$^{33}$ (wherein R$^{33}$ represents a pyridone group, a phenyl group or a 5- or 6-membered aromatic heterocyclic group (linked via carbon or nitrogen) with 1, 2 or 3 heteroatoms selected from O, N and S, which pyridone, phenyl or aromatic heterocyclic group may carry up to 5 substituents on available carbon atoms selected from hydroxy, halo, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —CONR$^{34}$R$^{35}$ and —NR$^{36}$COR$^{37}$ (wherein R$^{34}$, R$^{35}$, R$^{36}$ and R$^{37}$, which may be the same or different, each represents hydrogen, C$_{1-4}$alkyl or C$_{1-3}$alkoxyC$_{2-3}$alkyl));

10) C$_{1-5}$alkylR$^{33}$ (wherein R$^{33}$ is as defined hereinbefore);

11) C$_{2-5}$alkenylR$^{33}$ (wherein R$^{33}$ is as defined hereinbefore);

12) C$_{2-5}$alkynylR$^{33}$ (wherein R$^{33}$ is as defined hereinbefore);

13) C$_{1-5}$alkylX$^6$R$^{33}$ (wherein X$^6$ represents —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— (wherein R$^{38}$, R$^{39}$, R$^{40}$, R$^{41}$ and R$^{42}$ each independently represents hydrogen, C$_{1-3}$alkyl or C$_{1-3}$alkoxyC$_{2-3}$alkyl) and R$^{33}$ is as defined hereinbefore);

14) C$_{2-5}$alkenylX$^7$R$^{33}$ (wherein X$^7$ represents —O—, —S—, —SO—, —SO$_2$—, —NR$^{43}$CO—, —CONR$^{44}$—, —SO$_2$NR$^{45}$—, —NR$^{46}$SO$_2$— or —NR$^{47}$— (wherein R$^{43}$, R$^{44}$, R$^{45}$, R$^{46}$ and R$^{47}$ each independently represents hydrogen, C$_{1-3}$alkyl or C$_{1-3}$alkoxyC$_{2-3}$alkyl) and R$^{33}$ is as defined hereinbefore);

15) C$_{2-5}$alkynylX$^8$R$^{33}$ (wherein X$^8$ represents —O—, —S—, —SO—, —SO$_2$—, —NR$^{48}$CO—, —CONR$^{49}$—, —SO$_2$NR$^{50}$—, —NR$^{51}$SO$_2$— or —NR$^{52}$— (wherein R$^{48}$, R$^{49}$, R$^{50}$, R$^{51}$ and R$^{52}$ each independently represents hydrogen, C$_{1-3}$alkyl or C$_{1-3}$alkoxyC$_{2-3}$alkyl) and R$^{33}$ is as defined hereinbefore);

16) C$_{1-3}$alkylX$^9$C$_{1-3}$alkylR$^{33}$ (wherein X$^9$ represents —O—, —S—, —SO—, —SO$_2$—, —NR$^{53}$CO—, —CONR$^{54}$—, —SO$_2$NR$^{55}$—, —NR$^{56}$SO$_2$— or —NR$^{57}$— (wherein R$^{53}$, R$^{54}$, R$^{55}$, R$^{56}$ and R$^{57}$ each independently represents hydrogen, C$_{1-3}$alkyl or C$_{1-3}$alkoxyC$_{2-3}$alkyl) and R$^{33}$ is as defined hereinbefore);

17) C$_{1-3}$alkylX$^9$C$_{1-3}$alkylR$^{32}$ (wherein X$^9$ and R$^{28}$ are as defined hereinbefore);

18) $C_{1-5}$alkyl optionally substituted by 1, 2 or 3 halo;
19) $C_{1-5}$alkylX$^{10}C_{1-5}$alkylX$^{11}$R$^{90}$ (wherein X$^{10}$ and X$^{11}$, which may be the same or different, are each —O—, —S—, —SO—, —SO$_2$—, —NR$^{91}$CO—, —CONR$^{92}$—, —SO$_2$NR$^{93}$—, —NR$^{94}$SO$_2$— or —NR$^{95}$— (wherein R$^{91}$, R$^{92}$, R$^{93}$, R$^{94}$ and R$^{95}$ each independently represents $C_{1-5}$alkyl, $C_{1-3}$alkyl (substituted by 1, 2 or 3 halo, $C_{1-4}$alkyl or $C_{1-4}$alkoxy groups (and where there are 2 $C_{1-4}$alkoxy groups the $C_{1-4}$alkyl groups of alkoxy may together form a 5- or 6-membered saturated heterocyclic group having 2 oxygen atoms)), $C_{2-5}$alkenyl, $C_{2-5}$alkynyl, $C_{3-6}$cycloalkyl (optionally substituted by halo, hydroxy, $C_{1-3}$alkyl or $C_{1-4}$hydroxyalkyl), $C_{3-6}$cycloalkylC$_{1-3}$alkyl (optionally substituted by halo, hydroxy, $C_{1-3}$alkyl or $C_{1-4}$hydroxyalkyl) or $C_{1-3}$alkoxyC$_{2-3}$alkyl) and R$^{90}$ represents hydrogen or $C_{1-3}$alkyl);
20) $C_{3-6}$cycloalkyl;
21) R$^{96}$ (wherein R$^{96}$ is a 5- or 6-membered heterocyclic group which may be saturated or unsaturated (linked via carbon or nitrogen) with 1 or 2 heteroatoms, selected independently from O, S and N which heterocyclic group may bear 1 or 2 substitutents selected from $C_{1-4}$hydroxyalkyl, $C_{1-4}$alkyl, hydroxy and $C_{1-4}$alkoxyC$_{1-4}$alkyl;
22) $C_{1-5}$alkylR$^{96}$ (wherein R$^{96}$ is defined hereinbefore);

and where:
R$^{60}$, R$^{61}$ and R$^{62}$ are independently hydrogen, nitro, cyano, halo, oxo, amino, trifluoromethyl, $C_{1-4}$alkoxymethyl, di($C_{1-4}$alkoxy)methyl or $C_{1-6}$alkanoyl or a group selected from $C_{1-10}$alkyl, $C_{2-10}$alkenyl, $C_{2-10}$alkynyl, heterocyclyl, heterocyclylC$_{1-10}$alkyl, $C_{1-10}$alkoxy, arylC$_{1-10}$alkyl, aryl, $C_{3-10}$cycloalkyl, $C_{3-10}$cycloalkenyl and $C_{3-10}$cycloalkynyl (which group is optionally substituted by 1, 2 or 3 substituents independently selected from halo, $C_{1-4}$alkyl (optionally substituted by 1, 2 or 3 halo), mercapto, hydroxy, carboxy, $C_{1-10}$alkoxy, nitro, cyano, aryl, heteroaryl, heteroaryloxy, $C_{2-10}$alkenyloxy, $C_{2-10}$alkynyloxy, $C_{1-4}$alkoxyC$_{1-4}$alkoxy, aryloxy (where the aryl group may be substituted by halo, nitro, or hydroxy), amino, cyano, nitro, mono- or di($C_{1-6}$alkyl)amino, oximino or S(O)$_y$, where y is 0, 1, 2 or 3), or a group selected from =CR$^{78}$R$^{79}$, C(O)$_x$R$^{77}$, OR$^{77}$, S(O)$_y$R$^{77}$, NR$^{78}$R$^{79}$, C(O)NR$^{78}$R$^{79}$, OC(O)NR$^{78}$R$^{79}$, =NOR$^{77}$, —NR C(O)$_x$R$^{78}$, —NR$^{77}$CONR$^{78}$R$^{79}$, —N=CR$^{78}$R$^{79}$, S(O)$_y$NR$^{78}$R$^{79}$ or —NR$^{77}$S(O)$_y$R$^{78}$ or a group selected from phenyl, benzyl or a 5- to 6-membered heterocyclic group with 1, 2 or 3 heteroatoms, selected independently from O, S and N, which heterocyclic group may be aromatic or non-aromatic and may be saturated (linked via a ring carbon or nitrogen atom) or unsaturated (linked via a ring carbon atom), which phenyl, benzyl or heterocyclic group may bear on one or more carbon ring atoms up to 5 substituents selected from hydroxy, halo, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-C$_{1-4}$alkylcarbamoyl, N,N-di($C_{1-4}$alkyl)carbamoyl, aminosulphonyl, N-C$_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperdinyl, imidazolidinyl and pyrazolidinyl, which saturated heterocyclic group may bear 1 or 2 substituents selected from oxo, hydroxy, halo, $C_{1-3}$alkyl, $C_{1-3}$alkoxy, $C_{1-3}$alkanoyloxy, trifluoromethyl, cyano, amino, nitro and $C_{1-4}$alkoxycarbonyl, or a group of sub-formula (k):

or a group of sub-formula (II):

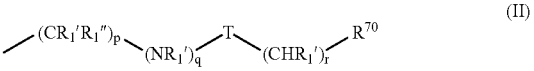

or a group of sub-formula (VI):

where:
p and q are independently 0 or 1;
r is 0, 1, 2, 3 or 4;
R$_1'$ and R$_1''$ are independently hydrogen, hydroxy, halo, cyano, $C_{1-10}$alkyl, $C_{3-10}$cycloalkyl, $C_{2-10}$alkenyl or $C_{2-10}$alkynyl (wherein $C_{1-10}$alkyl, $C_{3-10}$cycloalkyl, $C_{2-10}$alkenyl and $C_{2-10}$alkynyl are optionally substituted by halo, nitro, cyano, hydroxy, trifluoromethyl, amino, carboxy, carbamoyl, mercapto, sulphamoyl, $C_{1-4}$alkyl, $C_{2-4}$alkenyl, $C_{2-4}$alkynyl, $C_{3-6}$cycloalkyl, $C_{3-6}$cycloalkenyl, $C_{1-4}$alkoxy, $C_{1-4}$alkanoyl, $C_{1-4}$alkanoyloxy, $C_{1-4}$alkanoylamino, N,N-di($C_{1-4}$alkanoyl)amino, N-($C_{1-4}$alkyl)carbamoyl, N,N-di($C_{1-4}$alkyl)carbamoyl, $C_{1-4}$alkylS, $C_{1-4}$alkylS(O), $C_{1-4}$alkylS(O)$_2$, $C_{1-4}$alkoxycarbonyl, N-($C_{1-4}$alkyl)sulphamoyl, N,N-di($C_{1-4}$alkyl)sulphamoyl, $C_{1-4}$alkylsulphonylamino or heterocyclyl);

or R$_1'$ and R$_1''$ can together form a 3- to 6-membered ring which may be saturated or unsaturated;

T is C=O, SO$_n$ (where n is 0, 1 or 2), C(=NOR)CO, C(O) C(O), C=NCN or CV=NO;

V is independently R$^{63}$ or N(R$^{63}$)R$^{64}$;

R$^{63}$ and R$^{64}$ are independently selected from hydrogen, —(CH$^2$)$_q$R$^{70}$ (q' is 0 or 1), aryl (optionally substituted by 1, 2 or 3 $C_{1-6}$alkyl (optionally substituted by 1, 2 or 3 hydroxy groups)), $C_{1-10}$alkyl (optionally substituted by 1, 2 or 3 groups independently selected from aryl or heterocyclic group where aryl and heterocyclic group are optionally substituted by 1, 2, or 3 groups independently selected from $C_{1-6}$alkyl, nitro, cyano, halo, oxo, =CR$^{78}$R$^{79}$, C(O)$_x$R$^{77}$, OR$^{77}$, S(O)$_y$R$^{77}$, NR$^{78}$R$^{79}$, C(O)NR$^{78}$R$^{79}$, OC(O)NR$^{78}$R$^{79}$, =NOR$^{77}$, —NR$^{77}$C(O)$_x$R$^{78}$, —NR$^{77}$CONR$^{78}$R$^{79}$, —N=CR$^{78}$R$^{79}$, S(O)$_y$NR$^{78}$R$^{79}$, —NR$^{77}$S(O)$_y$R$^{78}$) or a group selected from $C_{1-10}$alkyl, $C_{2-10}$alkenyl, $C_{2-10}$alkynyl, heterocyclyl, $C_{1-10}$alkoxy, $C_{1-10}$alkyl, aryl, $C_{3-10}$cycloalkyl, $C_{3-10}$cycloalkenyl and $C_{3-10}$cycloalkynyl (which group is optionally substituted by 1, 2 or 3 groups independently selected from $C_{1-6}$alkyl, $C_{1-4}$alkoxy, trifluoromethyl, trifluoromethoxy, difluoromethyl, difluoromethoxy, nitro, cyano, halo, oxo, $=CR^{78}R^{79}$, $C(O)_xR^{77}$, $OR^{77}$, $S(O)_yR^{77}$, $NC(O)NR^{78}R^{79}$, $OC(O)NR^{78}R^{79}$, $=NOR^{77}$, $-NR^{77}C(O)_xR^{78}$, $-NR^{77}CONR^{78}R^{79}$, $-N=CR^{78}R^{79}$, $S(O)_yNR^{78}R^{79}$, $-NR^{77}S(O)_yR^{78}$);

or $R^{63}$ and $R^{64}$ together with the nitrogen atom to which they are attached form a heterocyclic ring which ring is aromatic or non-aromatic and which is optionally substituted by hydroxy, $C_{1-6}$alkoxy or $C_{1-6}$alkyl (optionally substituted by hydroxy);

$R^{70}$ is hydrogen, hydroxy (other than when q is 0), $C_{1-6}$alkyl, $C_{1-6}$alkoxy, amino, N-$C_{1-6}$alkylamino, N,N-di($C_{1-6}$alkyl)amino, $C_{2-6}$hydroxyalkoxy, $C_{1-6}$alkoxy$C_{2-6}$alkoxy, amino$C_{2-6}$alkoxy, N-$C_{1-6}$alkylamino$C_{2-6}$alkoxy, N,N-di($C_{1-6}$alkyl)amino$C_{2-6}$alkoxy, $C_{3-7}$cycloalkyl (optionally substituted by 1 or 2 oxo or thioxo substitutents) or of formula (III):

K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O), —SO$_2$NH—, —NHSO$_2$—, —NHC(O)$C_{1-6}$alkylene-, —OCO— or $C_{2-4}$alkenylene;

J is aryl, heteroaryl or heterocyclyl (where hetrocyclyl is optionally substituents by 1 or 2 oxo or thioxo substituents);

and wherein any aryl, heteroaryl or heterocyclyl group in a $R^{70}$ group is optionally substituted by 1, 2, 3 or 4 groups selected from hydroxy, halo, trifluoromethyl, cyano, mercapto, nitro, amino, carboxy, carbamoyl, formyl, aminosulphonyl, $C_{1-6}$alkyl, $C_{2-6}$alkenyl, $C_{2-6}$alkynyl, $C_{1-6}$alkoxy, —O—($C_{1-3}$alkyl)—O—, $C_{1-6}$alkylS(O)$_n$— (where n is 0, 1 or 2), N-$C_{1-6}$alkylamino, N,N-di($C_{1-6}$alkyl)amino, $C_{1-6}$alkoxycarbonyl, N-$C_{1-6}$alkylcarbamoyl, N,N-di($C_{1-6}$alkyl)carbamoyl, $C_{2-6}$alkanoyl, $C_{1-6}$alkanoyloxy, $C_{1-6}$alkanoylamino, N-$C_{1-6}$alkylaminosulphonyl, N,N-di($C_{1-6}$alkyl)aminosulphonyl, $C_{1-6}$alkylsulphonylamino and $C_{1-6}$alkylsulphonyl-N-($C_{1-6}$alkyl)amino or by 1, 2, 3 or 4 groups selected from:

a group of formula (IV)

(wherein $A^1$ is halo, hydroxy, $C_{1-6}$alkoxy, cyano, amino, $C_{1-6}$alkylamino, di($C_{1-6}$alkyl)amino, carboxy, $C_{1-6}$alkoxycarbonyl, carbamoyl, N-$C_{1-6}$alkylcarbamoyl or N,N-di($C_{1-6}$alkyl)carbamoyl; p' is 1, 2, 3, 4, 5 or 6; and $B^1$ is a bond, oxy, imino, N-($C_{1-6}$alkyl)imino or —NHC(O)—; with the proviso that p is 2 or more unless $B^1$ is a bond or —NHC(O)—); and a group of formula (V)

(wherein $D^1$ is aryl, heteroaryl or heterocyclyl (where heterocyclyl is optionally substituted by 1 or 2 oxo or thioxo substituents) and $E^1$ is a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl)imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$alkyl)-imino$C_{1-6}$alkylene, —NHC(O)—, —NHSO$_2$—, —SO$_2$NH— or —NHC(O)—$C_{1-6}$alkylene-, and any aryl, heteroaryl or heterocyclyl group in a substituent on $D^1$ is optionally substituted with 1, 2, 3 or 4 groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N,N-di($C_{1-6}$alkyl)carbamoyl, $C_{2-6}$alkanoyl, amino, $C_{1-6}$alkylamino and di($C_{1-6}$alkyl)amino);

and any of the $R^{70}$ groups defined hereinbefore which comprises a CH$_2$ group which is attached to 2 carbon atoms or a CH$_3$ group which is attached to a carbon atom optionally bears on each said CH$_2$ or CH$_3$ group a substituent selected from hydroxy, amino, $C_{1-6}$alkoxy, $C_{1-6}$alkylamino, di($C_{1-6}$alkyl)amino and heterocyclyl;

$R^{71}$ and $R^{72}$ are independently selected from hydrogen or $C_{1-4}$alkyl or $R^{71}$ and $R^{72}$ together form a bond;

$R^{73}$ is $OR^{74}$ or $NR^{75}R^{76}$;

$R^{74}$, $R^{75}$ and $R^{76}$ are independently $C_{1-10}$alkyl, $C_{2-10}$alkenyl, $C_{2-10}$alkynyl, aryl, heterocyclyl, $C_{1-10}$alkoxy, aryl$C_{1-10}$alkyl, $C_{3-10}$cycloalkyl, $C_{3-10}$cycloalkenyl, $C_{3-10}$cycloalkynyl, each of which is optionally substituted by 1, 2, 3 or 4 groups selected from nitro, cyano, halo, oxo, $=CR^{78}R^{79}$, $C(O)_xR^{77}$, $OR^{77}$, $S(O)_yR^{77}$, $NR^{78}R^{79}$, $C(O)NR^{78}R^{79}$, $OC(O)NR^{78}R^{79}$, $=NOR^{77}$, $-NR^{77}C(O)_xR^{78}$, $-NR^{77}CONR^{78}R^{79}$, $-N=CR^{78}R^{79}$, $S(O)_yNR^{78}R^{79}$ or $-NR^{77}S(O)_yR^{78}$ where y is 0, 1, 2 or 3; or $R^{74}$, $R^{75}$ and $R^{76}$ are independently heterocyclyl optionally substituted by $C_{1-4}$alkyl, $C_{2-4}$alkenyl, $C_{2-4}$alkynyl and $C_{3-6}$cycloalkyl;

or $R^{75}$ and $R^{76}$ together with the nitrogen to which they are attached form an aromatic or non-aromatic ring which optionally contains 1, 2 or 3 further heteroatoms independently selected from N, O and S;

$R^{77}$, $R^{78}$ and $R^{79}$ are independently selected from hydrogen or a group selected from $C_{1-10}$alkyl, $C_{2-10}$alkenyl, $C_{2-10}$alkynyl, aryl, heterocyclyl, $C_{1-10}$alkoxy, aryl$C_{1-10}$alkyl, $C_{3-10}$cycloalkyl, $C_{3-10}$cycloalkenyl, $C_{3-10}$cycloalkynyl where the group is optionally substituted by halo, $C_{1-4}$perhaloalkyl such as trifluoromethyl, mercapto, hydroxy, carboxy, $C_{1-10}$alkoxy, aryl, heteroaryl, heteroaryloxy, $C_{2-10}$alkenyloxy, $C_{2-10}$alkynyloxy, $C_{1-6}$alkoxy$C_{1-6}$alkoxy, aryloxy (where the aryl group may be substituted by halo, nitro, or hydroxy), cyano, nitro, amino, mono- or di($C_{1-6}$alkyl)amino, oximino or S(O)$_y$ where y is 0, 1, 2 or 3;

or $R^{78}$ and $R^{79}$ together form a ring which optionally contains further heteroatoms such as S(O)$_y$ oxygen and nitrogen, x is an integer of 1 or 2, y is 0, 1, 2 or 3 which ring is optionally substituted by 1, 2 or 3 groups independently selected from halo, $C_{1-4}$perhaloalkyl such as trifluoromethyl, mercapto, hydroxy, carboxy, $C_{1-10}$alkoxy, aryl, heteroaryl, heteroaryloxy, $C_{2-10}$alkenyloxy, $C_{2-10}$alkynyloxy, $C_{1-6}$alkoxy$C_{1-6}$alkoxy, aryloxy (where the aryl group may be substituted by halo, nitro, or hydroxy), cyano, nitro, amino, mono- or di($C_{1-6}$alkyl)amino, oximino or S(O)$_y$ where y is 0, 1, 2 or 3;

in the preparation of a medicament for use in the inhibition of Aurora kinase.

Also provided is the use of a compound of formula (I) in the preparation of a medicament for use in the inhibition of Aurora-A kinase.

Also provided is the use of a compound of formula (I) in the preparation of a medicament for use in the inhibition of Aurora-B kinase.

In particular, medicaments containing compounds of the present invention are useful in the treatment of proliferative disease such as cancer, and in particular cancers where Aurora-A is upregulated such as colon or breast cancers.

In a further aspect the present invention provides the use of a compound of formula (I)

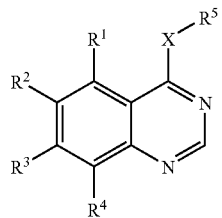

(I)

or a salt, ester or amide thereof;

where X is O, or S, S(O) or S(O)$_2$, or NR$^6$ where R$^6$ is hydrogen or C$_{1-6}$alkyl;

R$^5$ is a group of formula (a) or (b):

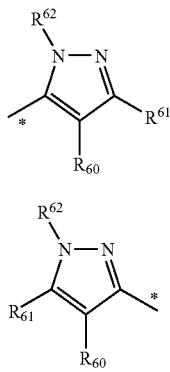

R$^{60}$, R$^{61}$ and R$^{62}$ are independently selected from hydrogen or a substituent group and * indicates the point of attachment to the group X in formula (I);

R$^1$, R$^2$, R$^3$, R$^4$ are independently selected from, halo, cyano, nitro, trifluoromethyl, C$_{1-3}$alkyl, —NR$^7$R$^8$ (wherein R$^7$ and R$^8$, which may be the same or different, each represents hydrogen or C$_{1-3}$alkyl), or —X$^1$R$^9$ (wherein X$^1$ represents a direct bond, —O—, —CH$_2$—, —OCO—, carbonyl, —S—, —SO—, —SO$_2$—, —NR$^{10}$CO—, —CONR$^{11}$—, —SO$_2$NR$^{12}$—, —NR$^{13}$SO$_2$— or —NR$^{14}$— (wherein R$^{10}$, R$^{11}$, R$^{12}$, R$^{13}$ and R$^{14}$ each independently represents hydrogen, C$_{1-3}$alkyl or C$_{1-3}$alkoxyC$_{2-3}$alkyl), and R$^9$ is selected from one of the following groups:

1) hydrogen or C$_{1-5}$alkyl which may be unsubstituted or which may be substituted with one or more groups selected from hydroxy, fluoro or amino,
2) C$_{1-5}$alkylX$^2$COR$^{15}$ (wherein X$^2$ represents —O— or —NR$^{16}$— (in which R$^{15}$ represents hydrogen, C$_{1-3}$alkyl or C$_{1-3}$alkoxyC$_{2-3}$alkyl) and R$^{16}$ represents C$_{1-3}$alkyl, —NR$^{17}$R$^{18}$ or —OR$^{19}$ (wherein R$^{17}$, R$^{18}$ and R$^{19}$ which may be the same or different each represents hydrogen, C$_{1-3}$alkyl or C$_{1-3}$alkoxyC$_{2-3}$alkyl));
3) C$_{1-5}$alkylX$^3$R$^{20}$ (wherein X$^3$ represents —O—, —S—, —SO—, —SO$_2$—, —OCO—, —NR$^{21}$CO—, —CONR$^{22}$—, —SO$_2$NR$^{23}$—, —NR$^{24}$SO$_2$— or —NR$^{25}$— (wherein R$^{21}$, R$^{22}$, R$^{23}$, R$^{24}$ and R$^{25}$ each independently represents hydrogen, C$_{1-3}$alkyl or C$_{1-3}$alkoxyC$_{2-3}$alkyl) and R$^{20}$ represents hydrogen, C$_{1-3}$alkyl, cyclopentyl, cyclohexyl or a 5-6-membered saturated heterocyclic group with 1-2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, C$_{1-4}$alkyl, C$_{1-4}$hydroxyalkyl and C$_{1-4}$alkoxy);
4) C$_{1-5}$alkylX$^4$C$_{1-5}$alkylX$^5$R$^{26}$ (wherein X$^4$ and X$^5$ which may be the same or different are each —O—, —S—, —SO—, —SO$_2$—, —NR$^{27}$CO—, —CONR$^{28}$—, —SO$_2$NR$^{29}$—, —NR$^{30}$SO$_2$— or —NR$^{31}$— (wherein R$^{27}$, R$^{28}$, R$^{29}$, R$^{30}$ and R$^{31}$ each independently represents hydrogen, C$_{1-3}$alkyl or C$_{1-3}$alkoxyC$_{2-3}$alkyl) and R$^{26}$ represents hydrogen or C$_{1-3}$alkyl);
5) R$^{32}$ (wherein R$^{32}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$alkoxyC$_{1-4}$alkyl and C$_{1-4}$alkylsulphonylC$_{1-4}$alkyl);
6) C$_{1-5}$alkylR$^{32}$ (wherein R$^{32}$ is as defined hereinbefore);
7) C$_{2-5}$alkenylR$^{32}$ (wherein R$^{32}$ is as defined hereinbefore);
8) C$_{2-5}$alkynylR$^{32}$ (wherein R$^{32}$ is as defined hereinbefore);
9) R$^{33}$ (wherein R$^{33}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents on an available carbon atom selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —CONR$^{34}$R$^{35}$ and —NR$^{36}$COR$^{37}$ (wherein R$^{34}$, R$^{35}$, R$^{36}$ and R$^{37}$, which may be the same or different, each represents hydrogen, C$_{1-4}$alkyl or C$_{1-3}$alkoxyC$_{2-3}$alkyl));
10) C$_{1-5}$alkylR$^{33}$ (wherein R$^{33}$ is as defined hereinbefore);
11) C$_{2-5}$alkenylR$^{33}$ (wherein R$^{33}$ is as defined hereinbefore);
12) C$_{2-5}$alkynylR$^{33}$ (wherein R$^{33}$ is as defined hereinbefore);
13) C$_{1-5}$alkylX$^6$R$^{33}$ (wherein X$^6$ represents —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— (wherein R$^{38}$, R$^{39}$, R$^{40}$, R$^{41}$ and R$^{42}$ each independently represents hydrogen, C$_{1-3}$alkyl or C$_{1-3}$alkoxyC$_{2-3}$alkyl) and R$^{33}$ is as defined hereinbefore);
14) C$_{2-5}$alkenylX$^7$R$^{33}$ (wherein X$^7$ represents —O—, —S—, —SO—, —SO$_2$—, —NR$^{43}$CO—, —CONR$^{44}$—, —SO$_2$NR$^{45}$—, —NR$^{46}$SO$_2$— or —NR$^{47}$— (wherein R$^{43}$, R$^{44}$, R$^{45}$, R$^{46}$ and R$^{47}$ each independently represents hydrogen, C$_{1-3}$alkyl or C$_{1-3}$alkoxyC$_{2-3}$alkyl) and R$^{33}$ is as defined hereinbefore);
15) C$_{2-5}$alkynylX$^8$R$^{33}$ (wherein X$^8$ represents —O—, —S—, —SO—, —SO$_2$—, —NR$^{48}$CO—, —CONR$^{49}$—, —SO$_2$NR$^{50}$—, —NR$^{51}$SO$_2$— or —NR$^{52}$— (wherein R$^{48}$, R$^{49}$, R$^{50}$, R$^{51}$ and R$^{52}$ each independently represents hydrogen, C$_{1-3}$alkyl or C$_{1-3}$alkoxyC$_{2-3}$alkyl) and R$^{33}$ is as defined hereinbefore);
16) C$_{1-3}$alkylX$^9$C$_{1-3}$alkylR$^{33}$ (wherein X$^9$ represents —O—, —S—, —SO—, —SO$_2$—, —NR$^{53}$CO—, —CONR$^{54}$—, —SO$_2$NR$^{55}$—, —NR$^{56}$SO$_2$— or —NR$^{57}$— (wherein R$^{53}$, R$^{54}$, R$^{55}$, R$^{56}$ and R$^{57}$ each independently represents hydrogen, C$_{1-3}$alkyl or C$_{1-3}$alkoxyC$_{2-3}$alkyl) and R$^{33}$ is as defined hereinbefore); and
17) C$_{1-3}$alkylX$^9$C$_{1-3}$alkylR$^{32}$ (wherein X$^9$ and R$^{28}$ are as defined hereinbefore):

in the preparation of a medicament for use in the inhibition of aurora 2 kinase.

In this specification the term alkyl when used either alone or as a suffix or prefix includes straight-chain and branched-chain saturated structures comprising carbon and hydrogen atoms. Unless otherwise stated, these groups may contain up to 10 carbon atoms ($C_{1-10}$alkyl), preferably up to 6 carbon atoms ($C_{1-6}$alkyl) and more preferably up to 4 carbon atoms ($C_{1-4}$alkyl). References to individual alkyl groups are specific for the straight-chain version only and references to individual branched-chain alkyl groups such as t-butyl are specific for the branched chain version only. For example $C_{1-4}$alkyl includes the examples of methyl, ethyl, propyl, butyl and tert-butyl where the ethyl, propyl and butyl groups may be bonded at the 1 or 2 position (e.g. prop-1-yl and prop-2-yl). A similar analysis of alkyl groups having different ranges of carbon atoms can be performed.

Similarly the terms alkenyl and alkynyl refer to unsaturated straight-chain or branched-chain structures containing for example from 2 to 10 carbon atoms ($C_{2-10}$alkenyl and $C_{2-10}$alkynyl) and preferably from 2 to 6 carbon atoms ($C_{2-6}$alkenyl and $C_{2-6}$alkynyl) and more preferably 2 to 4 carbon atoms ($C_{2-4}$alkenyl and $C_{2-4}$alkynyl). Again references to individual groups are specific for the straight-chain version only and references to individual branched-chain groups are specific for the branched chain version only. The above comment concerning the bonding position of alkyl is applicable to alkenyl and alkynyl groups.

Cyclic moieties such as cycloalkyl, cycloalkenyl and cycloalkynyl are similar in nature but have at least 3 carbon atoms, the following terms thus being used in the specification to indicate the minimum and maximum number of carbon atoms in the rings: $C_{3-10}$cycloalkyl, $C_{3-10}$cycloalkenyl and $C_{3-10}$cycloalkynyl and preferably $C_{3-6}$cycloalkyl, $C_{3-6}$cycloalkenyl and $C_{3-6}$cycloalkynyl and most preferably $C_{3-4}$cycloalkyl.

Terms such as alkoxy comprise alkyl groups as is understood in the art and thus contain up to 10 carbon atoms ($C_{1-10}$alkoxy), preferably up to 6 carbon atoms ($C_{1-6}$alkoxy) and more preferably up to 4 carbon atoms ($C_{1-4}$alkoxy).

The term halo includes fluoro, chloro, bromo and iodo.

References to aryl groups include aromatic carbocyclic groups such as phenyl and naphthyl.

The terms heterocyclyl and heterocyclic group include (unless specifically stated) aromatic or non-aromatic rings and may comprise more than one ring (e.g. they are monocyclic, bicyclic or tricyclic and preferably they are monocyclic and bicyclic), for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

Heteroaryl refers to those heterocyclyl groups described above which have an aromatic character.

The term aralkyl refers to aryl substituted alkyl groups such as benzyl.

Other expressions used in the specification include hydrocarbyl which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The tern functional group refers to reactive substituents such as nitro, cyano, halo, oxo, $=CR^{78}R^{79}$, $C(O)_xR^{77}$, $OR^{77}$, $S(O)_yR^{77}$, $NR^{78}R^{79}$, $C(O)NR^{78}R^{79}$, $OC(O)NR^{78}R^{79}$, $=NOR^{77}$, $-NR^{77}C(O)_xR^{78}$, $-NR^{77}CONR^{78}R^{79}$, $-N=CR^{78}R^{79}$, $S(O)_yNR^{78}R^{79}$ or $-NR^{77}S(O)_yR^{78}$ where $R^{77}$, $R^{78}$ and $R^{79}$ are independently selected from hydrogen or optionally substituted hydrocarbyl, or $R^{78}$ and $R^{79}$ together form an optionally substituted ring which optionally contains further heteroatoms such as $S(O)_y$, oxygen and nitrogen, x is an integer of 1 or 2, y is 0, 1, 2 or 3.

Suitable optional substituents for hydrocarbyl groups $R^{77}$, $R^{78}$ and $R^{79}$ include halo, perhaloalkyl such as trifluoromethyl, mercapto, hydroxy, carboxy, alkoxy, aryl, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_y$ where y is as defined above.

Suitable optional substituents for any hydrocarbyl group, heterocyclyl group or $C_{1-10}$alkoxy group (unless specifically stated) include halo, perhaloalkyl such as trifluoromethyl, mercapto, hydroxy, carboxy, alkoxy, aryl, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_y$ where y is as defined above.

Where optional substituents are chosen from one of more groups or substituents it is to be understood that this definition includes all substituents being chosen from one of the specified groups i.e. all substituents being the same, or the substituents being chosen from two or more of the specified groups i.e. the substituents not being the same. Preferably one or more means 1, 2, 3 or 4 but one or more may also means 1, 2 or 3 or 1 or 2.

Where a compound of formula (I), formula (IA) or formula (IB) contains more than one specific R group it is to be understood that each selection made for such a group is independent from any other selection made for that same group, for example when a compound of formula (I) contains more than one $R^{77}$ group, each $R^{77}$ group can the same as the other $R^{77}$ groups or different.

Within this specification composite terms are used to describe group comprising more than one functionality such as $C_{1-3}$alkoxy$C_{2-3}$alkyl. Such terms are to be interpreted as is understood in the art.

Unless specifically stated the bonding atom of a group may be any atom of that group so for example propyl includes prop-1-yl and prop-2-yl.

Suitable values for any of the R groups ($R^1$ to $R^{96}$) or any part or substitutents for such groups include:— for $C_{1-3}$alkyl: methyl, ethyl and propyl
for $C_{1-4}$alkyl: $C_{1-3}$alkyl, butyl and tert-butyl
for $C_{1-5}$alkyl: $C_{1-4}$alkyl, pentyl and 2,2-dimethylpropyl
for $C_{1-6}$alkyl: $C_{1-5}$alkyl, hexyl and 2,3-dimethylbutyl
for $C_{1-10}$alkyl: $C_{1-6}$alkyl, octanyl and decanyl
for $C_{2-4}$alkenyl: vinyl, allyl and but-2-enyl
for $C_{2-4}$alkenylene $CH=CH-$, $-CH_2-CH=CH-$, $-CH=CH-CH_2-$ and $-CH_2-CH=CH-CH_2-$
for $C_{2-5}$alkenyl: $C_{2-4}$alkenyl and 3-methylbut-2-enyl
for $C_{2-6}$alkenyl: $C_{2-5}$alkenyl and 3-methylpent-2-enyl
for $C_{2-10}$alkenyl: $C_{2-6}$alkenyl and octenyl
for $C_{2-4}$alkynyl: ethynyl, propargyl and prop-1-ynyl
for $C_{2-5}$alkynyl: $C_{2-4}$alkynyl and pent-4-ynyl
for $C_{2-6}$alkynyl: $C_{2-5}$alkynyl and 2-methylpent-4-ynyl
for $C_{2-10}$alkynyl: $C_{2-6}$alkynyl and oct-4-ynyl
for $C_{3-6}$cycloalkyl: cyclopropyl, cyclobutyl, cyclopentyl and cyclohexyl
for $C_{3-7}$cycloalkyl: $C_{3-6}$cycloalkyl and cyclopentyl
for $C_{3-10}$cycloalkyl: $C_{3-7}$cycloalkyl and cyclononyl for $C_{3-6}$cycloalkenyl: cyclobutenyl, cyclopentenyl, cyclohexenyl and cyclohex-1,4-dienyl
for $C_{3-10}$cycloalkenyl: $C_{3-6}$cycloalkenyl, cycloheptenyl and cyclooctenyl
for $C_{3-10}$cycloalkynyl: cyclodecynyl
for $C_{3-6}$cycloalkyl$C_{1-3}$alkyl: cyclopropylmethyl, cyclobutylmethyl, cyclopentylmethyl, cyclopropylethyl and cyclobutylethyl
for $C_{1-3}$alkoxy: methoxy, ethoxy and propoxy
for $C_{1-4}$alkoxy: $C_{1-3}$alkoxy, butoxy and tert-butoxy
for $C_{1-6}$alkoxy: $C_{1-4}$alkoxy, 3,3-dimethylpentoxy and hexyloxy
for $C_{1-10}$alkoxy: $C_{1-6}$alkoxy, 2,2,4,4-tetramethylpentoxy
for $C_{2-10}$alkenyloxy: allyloxy, but-2-enyloxy, 3-methylbut-2-enyloxy, 3-methylpent-2-enyloxy and octenyloxy
for $C_{2-10}$alkynyloxy: propargyloxy, pent-4-ynyloxy and oct-4-ynyloxy
for aryl: phenyl and naphthyl
for aryl$C_{1-10}$alkyl: benzyl, phenethyl, naphylmethyl and naphthylethyl
for aryl$C_{1-6}$alkyl: benzyl, phenethyl, naphylmethyl and naphthylethyl
for aryloxy: phenoxy and naphthyloxy
for heteroaryl: furyl, thienyl, pyrrolyl, pyrazolyl, pyridyl, pyrazinyl, pyridazinyl, pyrimidinyl and quinolinyl
for heteroaryloxy: pyridyloxy and quinolinyloxy
for heterocyclyl: furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl
for heterocyclyl$C_{1-6}$alkyl: furylmethyl, thienylethyl, pyrrolylethyl, pyridlymethyl and pyrimidinylethyl
for $C_{1-4}$hydroxyalkyl: hydroxymethyl, 1-hydroxyethyl, 2-hydroxyethyl, 3-hydroxypropyl, 1-hydroxyprop-2-yl and 1-hydroxy-2-methylprop-2-yl
for $C_{1-3}$alkoxy$C_{2-3}$alkyl: methoxyethyl, ethoxyethyl and methoxypropyl
for $C_{1-4}$alkoxy$C_{1-4}$alkyl: methoxymethyl, ethoxymethyl, methoxyethyl, ethoxyethyl, methoxypropyl and ethoxybutyl
for $C_{1-4}$alkoxymethyl: methoxymethyl, ethoxymethyl, propoxymethyl and prop-2-oxymethyl
for di($C_{1-4}$alkoxy)methyl: dimethoxymethyl and diethoxymethyl
for $C_{1-4}$hydroxyalkoxy: 2-hydroxyethoxy, 3-hydroxypropoxy and 2-hydroxypropoxy
for $C_{2-6}$hydroxyalkoxy: 2-hydroxyethoxy, 3-hydroxypropoxy and 4-hydroxybutoxy
for $C_{1-4}$alkoxy$C_{1-4}$alkoxy: methoxymethoxy, methoxyethoxy, ethoxyethoxy, propoxymethoxy and propoxyethoxy
for $C_{1-6}$alkoxy$C_{2-6}$alkoxy: methoxyethoxy and ethoxybutoxy
for $C_{1-4}$aminoalkyl: aminomethyl, aminoethyl, 3-aminopropyl and 2-aminopropyl
for $C_{1-4}$alkyl amino: methylamino, ethylamino and propylamino
for $C_{1-6}$alkylamino: $C_{1-4}$alkylamino and 2-methylbutyl amino
for di($C_{1-4}$alkyl)amino: dimethylamino, N-methyl-N-ethylamino and diethylamino
for di($C_{1-6}$alkyl)amino: N-methyl-N-pentylamino
for amino$C_{2-6}$alkoxy: aminoethoxy and 3-aminopropoxy
for N-$C_{1-4}$alkylamino$C_{2-6}$alkoxy: N-ethylaminoethoxy
for N,N-di($C_{1-6}$alkyl)amino$C_{2-6}$alkoxy: N,N-dimethylaminoethoxy
for $C_{2-4}$alkanoyl: acetyl and propionyl
for $C_{1-4}$alkanoyl: acetyl and propionyl
for $C_{2-6}$alkanoyl: $C_{2-4}$alkanoyl and pentanoyl
for $C_{1-6}$alkanoyl: $C_{1-4}$alkanoyl and hexanoyl
for $C_{1-3}$alkanoyloxy: acetyloxy and propionyloxy
for $C_{1-4}$alkanoyloxy: $C_{1-3}$alkanoyloxy and butanoyloxy
for $C_{1-6}$alkanoyloxy: $C_{1-4}$alkanoyloxy and hexanoyloxy
for $C_{1-4}$alkanoylamino: acetylamino and propionylamino
for $C_{1-6}$alkanoylamino: $C_{1-4}$alkanoylamino and pentanoylamino
for N,N-di($C_{1-4}$alkanoyl)amino: N,N-diacetylamino
for $C_{1-4}$alkoxycarbonyl: methoxycarbonyl, ethoxycarbonyl and tert-butoxycarbonyl
for $C_{1-6}$alkoxycarbonyl: $C_{1-4}$alkoxycarbonyl and pentoxycarbonyl
for N-$C_{1-6}$alkylcarbamoyl: N-methylcarbamoyl and N-ethylcarbamoyl
for N,N-di($C_{1-6}$alkyl)carbamoyl: N,N-dimethylcarbamoyl and N,N-diethylcarbamoyl
for $C_{1-4}$alkylsulphonyl$C_{1-4}$alkyl: methylsulphonylmethyl and methylsulphonylethyl
for $C_{1-4}$alkylsulphanyl: methylsulphanyl and ethylsulphanyl
for $C_{1-4}$alkylsulphinyl: methylsulphinyl and ethylsulphinyl
for $C_{1-4}$alkylsulphonyl: methylsulphonyl and ethylsulphonyl
for N-$C_{1-4}$alkylcarbamoyl: N-methylcarbamoyl and N-ethylcarbambyl
for N,N-di($C_{1-4}$alkyl)carbamoyl: N,N-dimethylcarbamoyl and N-ethyl-N-methylcarbamoyl
for N-($C_{1-4}$alkyl)aminosulphonyl: N-methylaminosulphonyl and N-ethylaminosulphonyl
for N-($C_{1-6}$alkyl)aminosulphonyl: N-($C_{1-4}$alkyl)aminosulphonyl and N-hexylaminosulphonyl
for N,N-di($C_{1-4}$alkyl)aminosulphonyl: N,N-dimethylaminosulphonyl
for N,N-di($C_{1-6}$alkyl)aminosulphonyl: N,N-di($C_{1-4}$alkyl)aminosulphonyl and N-hexyl-N-methylaminosulphonyl
for $C_{1-4}$alkylsulphonylamino: methylsulphonylamino and ethylsulphonylamino
for $C_{1-6}$alkylsulphonylamino: $C_{1-4}$alkylsulphonylamino and hexylsulphonylamino
for $C_{1-6}$alkylsulphonyl-N-($C_{1-6}$alkyl)amino: methylsulphonyl-N-ethylamino
for N-($C_{1-6}$alkyl)imino: N-methylimino and N-ethylimino
for imino$C_{1-6}$alkylene: iminomethylene and iminoethylene
for $C_{1-6}$alkylene-imino$C_{1-6}$alkylene: methyleneiminomethylene
for N-($C_{1-6}$alkyl)imino$C_{1-6}$alkylene: N-ethyliminomethylene
for $C_{1-6}$alkylene-N-($C_{1-6}$alkyl)imino$C_{1-6}$alkylene: ethylene-N-methyliminomethylene
for $C_{1-6}$alkylene: methylene, ethylene and propylene
for oxy$C_{1-6}$alkylene: oxymethylene, oxyethylene and oxypropylene
for $C_{1-6}$alkylene oxy$C_{1-6}$alkylene: methyleneoxyethylene.

Within the present invention it is to be understood that a compound of the formula (I), formula (IA) or formula (IB) or a salt, ester or amide thereof may exhibit the phenomenon of tautomerism and that the formulae drawings within this specification can represent only one of the possible tautomeric forms. It is to be understood that the invention encompasses any tautomeric form which has Aurora kinase inhibition activity and in particular Aurora-A kinase or Aurora-B kinase inhibition activity and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein. The possibility of tautomeric forms is particular pertinent for $R^5$ when $R^{62}$ is hydrogen.

It is also to be understood that, insofar as certain compounds of the invention may exist in optically active or racemic forms by virtue of one of more racemic carbon or sulphur atom, the invention includes in its definition any such optically active or racemic form which possesses Aurora kinase inhibitory activity and in particular Aurora-A kinase inhibitory activity. The synthesis of optically active forms may be carrier out by standard techniques of organic chemistry well known in the art, for example by synthesis from optically active starting materials or by resolution of a racemic form.

It is also to be understood that certain compounds of the formula (I), formula (IA) or formula (IB) and salts thereof can exist in solvated as well as unsolvated forms such as, for example, hydrated forms. It is to be understood that the invention encompasses all such solvated forms which have Aurora kinase inhibition activity and in particular Aurora-A kinase inhibition activity.

Compounds of the present invention have been named using computer software (ACD/Name version 6.6 or ACD/Name batch version 6.0).

Preferred values of X, $R^1$, $R^2$, $R^3$, $R^4$ and $R^5$ are as follows. Such values may be used where appropriate with any of the definitions, claims or embodiments defined hereinbefore or hereinafter.

In one aspect of the invention X is $NR^6$ or O. In another aspect X is NH.

In one aspect of the invention $R^6$ is hydrogen or $C_{1-3}$alkyl. In another aspect $R^6$ is hydrogen.

In one aspect of the invention $R^1$ is hydrogen or —$X^1R^9$. In another aspect $R^1$ is hydrogen or —$X^1R^9$ where $X^1$ is a direct bond, —O—, —NH— or —NMe— and $R^9$ is selected from a group 1), 3), 5), 9) or 20) as defined above. In a yet another aspect $R^1$ is hydrogen or —$X^1R^9$ where $X^1$ is a direct bond, —O— or —NH— and $R^9$ is hydrogen, $C_{1-5}$alkyl, $C_{3-6}$cycloalkyl, $C_{1-5}$alkyl-O—$C_{1-3}$alkyl or a 5- to 6-membered saturated heterocyclic group (linked via carbon or nitrogen) with 1 or 2 heteroatoms selected independently from O, S or N which heterocyclic groups is optionally substituted by $C_{1-4}$alkyl or a 5- or 6-membered aromatic heterocyclic group (linked via carbon or nitrogen with 1, 2 or 3 heteroatoms. In a further aspect $R^1$ is hydrogen, methoxy, N-($C_{1-5}$alkyl)piperidin-4-yloxy, prop-2-yloxy or methoxyethoxy. In an even further aspect $R^1$ is hydrogen.

In one aspect of the invention $R^2$ is hydrogen, halo or —$X^1R^9$. In a further aspect of the invention $R^2$ is hydrogen, halo or —$X^1R^9$ where $X^1$ is a direct bond or —O— and $R^9$ is a group 1) as defined above. In yet another aspect $R^2$ is hydrogen, halo, hydroxy, methoxy or —$OC_{1-3}$alkyl (optionally substituted by 1 or 2 hydroxy or halo). In a further aspect $R^2$ is hydrogen or methoxy.

In one aspect $R^3$ is —$X^1R^9$. In another aspect $R^3$ is —$X^1R^9$ where $X^1$ is —O— and $R^9$ is selected from a group 3), 4), 6), 18), 19) or 22) as defined above. In yet another aspect $R^3$ is —$X^1R^9$ where $X^1$ is —O— and $R^9$ is $C_{1-5}$alkyl$R^{32}$, $C_{1-5}$alkyl$R^{96}$, $C_{1-5}$alkyl (optionally substituted by halo), —$C_{1-5}$alkyl-$OR^{20}$, —$C_{1-5}$alkyl-$NHR^{20}$, —$C_{1-5}$alkyl-$N(C_{1-3}$alkyl)-$R^{20}$, —$C_{1-5}$alkyl-NH—$C_{1-5}$alkyl-OH, —$C_{1-5}$alkyl-N($C_{1-3}$alkyl)-$C_{1-5}$alkyl-OH and —$C_{1-5}$alkyl-$NR^{95}$—$C_{1-5}$alkyl-OH. In yet another aspect $R^3$ is —$X^1R^9$ where $X^1$ is —O— and $R^9$ is —$C_{1-5}$alkyl$R^{32}$ (where $R^{32}$ is pyrrolidinyl, piperidinyl or piperazinyl each being optionally substituted by hydroxy, hydroxymethyl, 2-hydroxyethyl, methyl or 2-(ten-butoxy)ethyl), —$C_{1-5}$alkyl-$NHR^{20}$, —$C_{1-5}$alkyl-NH—$C_{1-5}$alkyl-OH, —$C_{1-5}$alkyl-N($C_{1-3}$alkyl)—$C_{1-5}$alkyl-OH and —$C_{1-5}$alkyl-$NR^{95}$—$C_{1-5}$alkyl-OH. In a further aspect $R^3$ is 3-morpholinopropoxy, 3-chloropropoxy, 3-[N-ethyl-N-(2-hydroxyethyl)amino]propoxy, 3-(2-hydroxymethylpyrrolidin-1-yl)propoxy, 3-(piperidin-1-yl)propoxy, 3-(pyrrolidin-1-yl)propoxy, 3-(N-(2-hydroxyethyl)amino]propoxy, 3-[N-(2-hydroxy-1,1-dimethylethyl)amino}propoxy, 3-[N-methyl-N-(2-hydroxyethyl)amino)propoxy, 3-[N-(1-hydroxymethyl-2-methylpropyl)amino]propoxy, 3-(4-methylpiperazin-1-yl)propoxy, 3-[N-(2-hydroxy-1-methylethyl)amino]propoxy, 3-[N-(4-hydroxybutyl)amino]propoxy, 3-(4-hydroxypiperidin-1-yl)propoxy, 3-[2-(2-hydroxyethyl)piperidin-1-yl]propoxy, 3-[4-(2-hydroxyethyl)piperazin-1-yl]propoxy, 3-[4-(2-hydroxyethyl)piperidin-1-yl]propoxy, 3-(3-hydroxypiperidin-1-yl)propoxy, 3-[N-2-(hydroxybutyl)amino]propoxy, 3-(4-hydroxymethylpiperidin-1-yl)propoxy, 3-[N-(3-hydroxy-2,2-methylpropyl)amino]propoxy, 3-[N-(1-hydroxymethylcyclopent-1-yl)amino]propoxy, 3-[N-(2-hydroxypropyl)amino]propoxy, 3-(3-hydroxypyrrolidin-1-yl)propoxy, 3-[N-(2-fluoroethyl)-N-(2-hydroxyethyl)amino]propoxy, 2-[1-(2-hydroxyethyl)piperidin-4-yl]ethoxy, 3-[N-(2-hydroxyethyl)-N-propylamino]propoxy, 3-[N-(2-hydroxyethyl)-N-(prop-2-yl)amino]propoxy, 3-[N-(2-hydroxyethyl)-N-isobutylamino]propoxy, 3-[N-(2-hydroxyethyl)-N-neopentylamino]propoxy, 3-[N-allyl-N-(2-hydroxyethyl)amino]propoxy, 3-[N-(2-hydroxyethyl)-N-(prop-2-yn-1-yl)amino]propoxy, 3-[N-cyclopropyl-N-(2-hydroxyethyl)amino]propoxy, 3-[N-cyclopropylmethyl-N-(2-hydroxyethyl)amino]propoxy, 3-[N-cyclobutyl-N-(2-hydroxyethyl)amino]propoxy, 3-[N-cyclopentyl-N-(2-hydroxyethyl)amino]propoxy, 3-[N-(2,2-dimethoxyethyl)-N-(2-hydroxyethyl)amino]propoxy, 3-[N-(2,2-difluoroethyl)-N-(2-hydroxyethyl)amino]propoxy, 3-[N-(2-hydroxyethyl)-N-(3,3,3-trifluoropropyl)amino]propoxy, 3-[N-cyclobutylmethyl-N-(2-hydroxyethyl)amino]propoxy, 3-[N-(2-hydroxyethyl)-N-(2-methoxyethyl)amino]propoxy, 3-[N-(1,3-dioxolan-2-ylmethyl)-N-(2-hydroxyethyl)amino]propoxy, 4-chlorobutoxy, 4-[(2-hydroxymethyl)pyrrolidin-1-yl]butoxy, 4[N-(2-hydroxyethyl)-N-isobutylamino]butoxy, 1-(2-tert-butoxyethyl)pyrrolidin-2-ylmethoxy, 1-(2-hydroxyethyl)pyrrolidin-2-ylmethoxy, 3-[N-2-(hydroxyethyl)-N-(iso-butyl)amino]propoxy, 3-[N-2-(hydroxyethyl)-N-(neopentyl)amino]propoxy, 3-CN-2-(hydroxyethyl)-N-(tert-butyl)amino]propoxy, methoxy and methoxyethoxy.

In one aspect of the invention $R^{32}$ is a 5- or 6-membered saturated heterocyclic group (linked via carbon or nitrogen) with 1 or 2 heteroatoms selected independently from O, S, and N which group is optionally substituted by 1 or 2 substituents selected from $C_{1-4}$hydroxyalkyl, $C_{1-4}$alkyl, hydroxy and $C_{1-4}$alkoxy$C_{1-4}$alkyl. In another aspect $R^{32}$ is morpholino, pyrrolidinyl, piperidinyl or piperazinyl each being optionally substituted by hydroxy, hydroxymethyl, 2-hydroxyethyl, methyl or 2-(tert-butoxy)ethyl. In a further aspect $R^{32}$ is 2-hydroxymethylpyrrolidin-1-yl, piperidin-1-yl, pyrrolidin-1-yl, 4-methylpiperazin-1-yl, 4-hydroxypiperidin-1-yl, 2-(2-hydroxyethyl)piperidin-1-yl, 4-(2-hydroxyethyl)piperazin-1-yl, 4-(2-hydroxyethyl)piperidin-1-yl, 4-hydroxymethylpiperidin-1-yl, 3-hydroxypyrrolidin-1-yl, 1-(2-hydroxyethyl)piperidin-4-yl, 1-(2-tert-butoxyethyl)pyrrolidin-2-yl and 1-(2-hydroxyethyl)pyrrolidin-2-yl.

In one aspect of the invention $R^{20}$ is $C_{1-3}$alkyl (optionally substituted by hydroxy) or cyclopentyl (optionally substituted by $C_{1-4}$hydroxyalkyl). In a further aspect $R^{20}$ is 2-hydroxyethyl, 1-hydroxyprop-2-yl, 2-hydroxyprop-1-yl and 1-hydroxymethylcyclopentyl In one aspect of the invention $R^{95}$ is methyl, ethyl, 2-fluoroethyl, prop-1-yl, prop-2-yl, isobutyl, neopentyl, allyl, propargyl, cyclopropyl, cyclopropylmethyl, cyclobutyl, cyclopentyl, 2,2-difluoroethyl, 2,2,2-trifluoroethyl, cyclobutylmethyl, methoxyethyl, 1,3-dioxolan-2-ylmethyl and 2,2-dimethoxyethyl.

In one aspect of the invention $R^{96}$ is 4,5-dihydro-1H-imidazoyl optionally substituted by hydroxy or $C_{1-4}$hydroxyalkyl.

In one aspect of the invention $R^4$ is hydrogen.

In one aspect of the invention $X^1$ is a direct bond, —O— or —N($C_{1-3}$alkyl)—. In another aspect $X^1$ is —O—.

In one aspect of the invention $R^9$ is a group selected from group 1), 3), 4), 5), 6), 9), 18), 19), 20) and 22). In another aspect $R^9$ is hydrogen, $C_{3-6}$cycloalkyl, —$C_{1-5}$alkyl-O—$C_{1-3}$ alkyl or a 5- to 6-membered saturated heterocyclic group (linked via carbon or nitrogen) with 1 or 2 heteroatoms selected independently from O, S or N which heterocyclic group is optionally substituted by $C_{1-4}$alkyl or $R^9$ is a 5- or 6-membered aromatic heterocyclic group (linked via carbon or nitrogen) with 1, 2 or 3 heteroatoms or $R^9$ is —$C_{1-5}$alkyl$R^{32}$, —$C_{1-5}$alkyl$R^{96}$, $C_{1-5}$alkyl (optionally substituted by halo), —$C_{1-5}$alkyl-O$R^{20}$, —$C_{1-5}$alkyl-NH$R^{20}$, —$C_{1-5}$alkyl-N($C_{1-3}$alkyl)—$R^{20}$, —$C_{1-5}$alkyl-NH—$C_{1-5}$alkyl-OH, —$C_{1-5}$alkyl-N($C_{1-3}$alkyl)-$C_{1-5}$alkyl-OH and —$C_{1-5}$alkyl-N$R^{95}$—$C_{1-5}$alkyl-OH.

In one aspect of the invention $R^{60}$ is hydrogen, nitro, halo, cyano, oxo or $C_{1-3}$alkyl. In another aspect $R^{60}$ is a group of sub-formula (k) as defined above. In a further aspect $R^{60}$ is hydrogen.

In one aspect of the invention $R^{61}$ is a group selected from hydrogen, cyano, nitro halo, $C_{1-6}$alkyl, aryl, aryl$C_{1-6}$alkyl, heterocyclyl, heterocyclyl$C_{1-6}$alkyl (where aryl and heterocyclyl of the latter four groups are optionally substituted by 1, 2 or 3 substitutents independently selected from halo, hydroxy, mercapto, carboxy, $C_{1-4}$alkyl (optionally substituted by 1, 2 or 3 halo), aryl, heteroaryl, amino, cyano, nitro, $C_{1-4}$alkylamino, di($C_{1-4}$alkyl)amino and S(O)$_y$ where y is 0, 1 or 2), a group of sub-formula (k) as defined above, a group of sub-formula (II) as defined above and a group of formula (VI) as defined above. In another aspect $R^{61}$ is a group of sub-formula (k) as defined above. In yet a further aspect of the invention $R^{61}$ is J, —(CH$_2$)—J, —(CH$_2$)$_2$—J, —O—J, —(CH$_2$)—O—J, —O—(CH$_2$)—J, —(CH$_2$)—O—(CH$_2$)—J, —CO—J, —(CH$_2$)—CO—J, —CO—(CH$_2$)—J, —(CH$_2$)—CO—(CH$_2$)—J, —S—J, —(CH$_2$)—S—J, —S—(CH$_2$)—J, —(CH$_2$)—S—(CH$_2$)—J, —SO—J, —(CH$_2$)—SO—J, —SO—(CH$_2$)—J, —(CH$_2$)—SO—(CH$_2$)—J, —SO$_2$—J, —(CH$_2$)—SO$_2$—J, —SO$_2$—(CH$_2$)—J, —(CH$_2$)—SO$_2$—(CH$_2$)—J, —(NR$_1$')CO—J, —(CH$_2$)(NR$_1$')CO—J, —(NR$_1$')CO—(CH$_2$)—J, —(CH$_2$)—(NR$_1$')CO—(CH$_2$)—J, —(NR$_1$')SO$_2$—J, —(CH$_2$)—(NR$_1$')SO$_2$—J, —(NR$_1$')SO$_2$—(CH$_2$)—J, —(CH$_2$)—(NR$_1$')SO$_2$—(CH$_2$)—J, —NR$^{64}$—J, —(CH$_2$)—NR$^{64}$—J, —NR$^{64}$—(CH$_2$)—J, —(CH$_2$)—NR$^{64}$—(CH$_2$)—J, —CONR$^{64}$—J, —(CH$_2$)-CONR$^{64}$—J, —CONR$^{64}$—(CH$_2$)—J, —(CH$_2$)-CONR$^{64}$—(CH$_2$)—J, —SO$_2$NR$^{64}$—J, —(CH$_2$)—SO$_2$NR$^{64}$—J, —SO$_2$NR$^{64}$—(CH$_2$)—J, —(CH$_2$)—SO$_2$NR$^{64}$—(CH$_2$)—J, —NR$_1$'CO—NH—J, —(CH$_2$)—NR$_1$'CO—NH—J, —NR$_1$'CO—NH—(CH$_2$)—J, —(CH$_2$)—NR$_1$'CO—NH—(CH$_2$)—J, —NR$_1$'CO—N(C$_{1-4}$alkyl)—J, —(CH$_2$)—NR$_1$'CO—N(C$_{1-4}$alkyl)—J, —NR$_1$'CO—N(C$_{1-4}$alkyl)-(CH$_2$)—J, —(CH$_2$)—NR$_1$'CO—N(C$_{1-4}$alkyl)-(CH$_2$)—J, —NR$_1$'CO—J, —(CH$_2$)—NR$_1$'CO—J, —NR$_1$'CO—(CH$_2$)—J, —(CH$_2$)—NR$_1$'CO—O—J, —NR$_1$'C—O—(CH$_2$)—J, OCO—J, —CH$_2$—OCO—J, —CH=CH—J, —CH$_2$—CH=CH—J, —CH=CH—CH$_2$—J and —CH$_2$—CH=CH—CH$_2$—J. In yet a further aspect $R^{61}$ is —CONR$^{64}$—J or —(CH$_2$)CONR$^{64}$—J. In another aspect $R^{61}$ is —(CH$_2$)CONR$^{64}$—J.

In one aspect of the invention $R^{62}$ is a group selected from hydrogen, cyano, nitro halo, $C_{1-6}$alkyl, aryl, aryl$C_{1-6}$alkyl, heterocyclyl, heterocyclyl$C_{1-6}$alkyl (where aryl and heterocyclyl of the latter four groups are optionally substituted by 1, 2 or 3 substitutents independently selected from halo, hydroxy, mercapto, carboxy, $C_{1-4}$alkyl (optionally substituted by 1, 2 or 3 halo), aryl, heteroaryl, amino, cyano, nitro, $C_{1-4}$alkylamino, di($C_{1-4}$alkyl)amino and S(O)$_y$ where y is 0, 1 or 2), a group of sub-formula (K) as defined above, a group of sub-formula (II) as defined above and a group of formula (VI) as defined above. In another aspect $R^{62}$ is a group of sub-formula (k) as defined above. In yet another aspect of the invention $R^{62}$ is hydrogen, halo or $C_{1-3}$alkyl. In a further aspect $R^{62}$ is hydrogen.

Preferred values of $R_1$', $R_1$", p, T, V, r and $R^{70}$ are as follows. Such values may be used where appropriate with any of the definitions, claims or embodiments defined hereinbefore or hereinafter.

In one aspect of the invention $R_1$' is hydrogen or $C_{1-3}$alkyl.

In one aspect of the invention $R_1$" is hydrogen or $C_{1-3}$alkyl.

In one aspect of the invention p is 1.

In one aspect of the invention T is C=O, SO$_n$ (where n is 0, 1 or 2), C(=NOR)CO, C(O)C(O) or C=NCN. In another aspect T is C=O.

In one aspect of the invention q is 1.

In one aspect of the invention V is N($R^{63}$)$R^{64}$.

In one aspect of the invention $R^{63}$ is —(CH$_2$)$_q$.$R^{70}$ or aryl or heteroaryl where the latter two groups are optionally substituted by 1 or 2 substituents independently selected from halo, $C_{1-4}$alkyl, $C_{1-4}$alkoxy, trifluoromethyl, trifluoromethoxy, hydroxy, nitro, difluoromethyl, difluoromethoxy and cyano. In another aspect $R^{63}$ is aryl optionally substituted by 1 or 2 substituents independently selected from halo, $C_{1-4}$alkyl, $C_{1-4}$alkoxy, trifluoromethyl, trifluoromethoxy, hydroxy, nitro, difluoromethyl, difluoromethoxy and cyano.

In one aspect of the invention $R^{64}$ is hydrogen or $C_{1-3}$alkyl. In another aspect $R^{64}$ is hydrogen.

In one aspect of the invention $R^{70}$ is a group of formula (III) —K—J.

In one aspect of the invention K is a bond, oxy, imino, N-($C_{1-4}$alkyl)imino, oxy$C_{1-4}$alkylene, imino$C_{1-4}$alkylene and N-($C_{1-4}$alkyl)imino$C_{1-4}$alkylene. In another aspect K is a bond.

In one aspect of the invention J is aryl or heteroaryl which are both optionally substituted by 1, 2 or 3 substituents selected from halo, $C_{1-3}$alkyl, $C_{3-4}$cycloalkyl, $C_{3-4}$cycloalkyl$C_{1-3}$alkyl, cyano and $C_{1-3}$alkoxy. In another aspect J is a group select from phenyl, pyridyl, pyrimidinyl, furyl, thienyl and pyrrolyl which group is optionally substituent by 1 or 2 substituents selected from halo, methyl, ethyl, methoxy, cyano, cyclopropyl and cyclopropylmethyl. In yet another aspect J is phenyl optionally substituted by 1 or 2 halo. In a further aspect of the invention J is 3-fluorophenyl, 2,3-difluorophenyl, 3,5-difluorophenyl, 3-chlorophenyl, 3-methoxyphenyl, phenyl, 4-fluorophenyl, 3,5-dichlorophenyl, 5-chloro-2-methoxyphenyl, 3-trifluoromethylphenyl, 3-hydroxyphenyl, 3-nitrophenyl, 4-bromo-2-fluorophenyl, 3,5-dimethoxyphenyl, 3-chloro-2-fluorophenyl, 2-fluoro-3-trifluormethylphenyl, 3,4-difluorophenyl, 2,4-difluorophenyl, 3-chloro-4-fluorophenyl, 2-difluoromethoxyphenyl, 3-cyanophenyl, 3-bromophenyl, 5-indanzolyl and 5-methylpyridin-2-yl.

Preferably $R^4$ is hydrogen.

Suitably $R^1$ is hydrogen or a group set out for $R^2$ or $R^3$ below. Frequently, $R^1$ is hydrogen.

In a preferred embodiment, at least one group $R^1$, $R^2$ or $R^3$, preferably $R^3$, comprises a chain of at least 3 and preferably at least 4 optionally substituted carbon atoms or heteroatoms such as oxygen, nitrogen or sulphur. Most preferably the chain is substituted by a polar group which assists in solubility.

Suitably $R^3$ is a group $X^1R^9$. Preferably in this case, $X^1$ is oxygen and $R^9$ is selected from a group of formula (1) or (10) above. Particular groups $R^9$ are those in group (1) above, especially alkyl such as methyl or halo substituted alkyl, or those in group (10) above. In one preferred embodiment, at least one of $R^2$ or $R^3$ is a group —$OC_{1-5}$alkyl$R^{33}$ and $R^{33}$ is a heterocyclic ring such as an N-linked morpholine ring such as 3-morpholinopropoxy.

Suitably $R^2$ is selected from, halo, cyano, nitro, trifluoromethyl, $C_{1-3}$alkyl, —$NR^9R^{10}$ (wherein $R^9$ and $R^{10}$, which may be the same or different, each represents hydrogen or $C_{1-3}$alkyl), or a group —$X^1R^{11}$. Preferred examples of —$X^1R^{11}$ for $R^2$ include those listed above in relation to $R^3$.

Other examples for $R^2$ and $R^3$ include methoxy or 3,3,3-trifluoroethoxy.

Preferably X is NH or O and is most preferably NH.

In one aspect of the invention, one of $R^{60}$, $R^{61}$ or $R^{62}$ is a substituent group and the others are either hydrogen or a small substituent such as $C_{1-3}$ alkyl, for instance methyl.

Suitably $R^{62}$ is hydrogen. Preferably $R^{61}$ is other than hydrogen.

Suitable substituents for groups $R^5$ include optionally substituted hydrocarbyl, optionally substituted heterocylyl or a functional group as defined above.

In particular, $R^{60}$, $R^{61}$ or $R^{62}$ is a group of sub-formula (k)

where p and q are independently 0 or 1 and wherein $R_1'$ and $R_1''$ are independently hydrogen, hydroxy, optionally substituted alkyl, optionally substituted cycloalkyl, halogen, cyano, optionally substituted alkyl, optionally substituted alkyenyl. The optionally substituted alkyl or alkynyl may be substituted with halo, nitro, cyano, hydroxy, trifluoromethyl, amino, carboxy, carbamoyl, mercapto, sulphamoyl, $C_{1-4}$ alkyl, $C_{2-4}$alkenyl, $C_{2-4}$ alkynyl, $C_{3-6}$ cycloalkyl, $C_{3-4}$ cycloalkenyl, $C_{1-4}$ alkoxy, $C_{1-4}$ alkanoyl, $C_{1-4}$ alkanoyloxy, N-($C_{1-4}$ alkyl), N($C_{1-4}$ alkyl)$_2$, $C_{1-4}$ alkanoylamino, ($C_{1-4}$ alkanoyl)$_2$amino, N-($C_{1-4}$alkyl)carbamoyl, N,N-($C_{1-4}$)$_2$carbamoyl, $C_{1-4}$)S, $C_{1-4}$S(O), ($C_{1-4}$alkyl)S(O)$_2$, ($C_{1-4}$)alkoxycarbonyl, N-($C_{1-4}$ alkyl)sulphamoyl, N,N-$C_{1-4}$ alkyl)sulphamoyl, $C_{1-4}$ alkylsulphonylamino, or heterocyclyl. R is preferably $C_{1-4}$ alkyl, $C_{2-4}$alkenyl, or $C_{2-4}$ alkynyl, and $R_1'$ can form with $R_1''$ a 3 to 6 membered ring.

T is C=O, SO$_n$, C(=NOR)CO, C(O)C(O), C=NCN, CV=NO or wherein n=0, 1 or 2 and V is independently $R^{63}$ or N($R^{63}$)$R^{64}$ wherein $R^{63}$ and $R^{64}$ are independently selected from hydrogen, optionally substituted hydrocarbyl or optionally substituted heterocyclyl, or $R^{63}$ and $R^{64}$ together with the nitrogen atom to which they are attached form an optionally substituted heterocyclic ring.

Examples of groups for $R^{63}$ and $R^{64}$ include the group —(CH$^2$)$_q R^{70}$ where q and $R^{70}$ are as defined below in relation to formula (II).

Suitably one of $R^{63}$ or $R^{64}$ is hydrogen, or methyl, ethyl or propyl optionally substituted with hydroxy and preferably one of $R^{63}$ or $R^{64}$ is hydrogen. In this case, the other is suitably a larger substituent for example of at least 4 carbon or heteroatoms, and is optionally substituted hydrocarbyl or optionally substituted heterocyclyl. Particular optionally substituted hydrocarbyl groups for $R^{63}$ or $R^{64}$ include alkyl, cycloalkyl, alkenyl, or aryl any of which is optionally substituted with a functional group as defined above, or in the case of aryl groups, with an alkyl group and in the case of alkyl group, with an aryl or heterocyclic group either of which may themselves be optionally substituted with alkyl or a functional group. Examples of optionally substituted aryl groups $R^{63}$ or $R^{64}$ include phenyl optionally substituted with one or more groups selected from $C_{1-6}$ alkyl group such as methyl or ethyl (either of which may be optionally substituted with a functional group such as hydroxy), or a functional group as defined above (such as halo like fluoro, chloro or bromo, hydroxy, alkoxy such as methoxy, trifluoromethyl, nitro, cyano, trifluoromethoxy, CONH$_2$, C(O)CH$_3$, amino, or dimethylamino).

When $R^{63}$ or $R^{64}$ is an optionally substituted alkyl group, it is suitably a $C_{1-6}$alkyl group, optionally substituted with one or more functional groups (such as cyano, hydroxy, alkoxy, in particular methoxy, COOalkyl such as COOCH$_3$), or aryl optionally substituted with a functional group as defined above (in particular in relation to $R^{63}$ or $R^{64}$ themselves, or an optionally substituted heterocyclic group such as N-methyl pyrrole.

When $R^{63}$ and $R^{64}$ is optionally substituted cycloalkyl, it is suitable cyclohexyl optionally substituted with a functional group such as hydroxy.

When $R^{63}$ and $R^{64}$ is optionally substituted alkenyl, it is suitably prop-2-enyl.

When $R^{63}$ or $R^{64}$ is optionally substituted heterocyclyl, or $R^{63}$ and $R^{64}$ together form a heterocyclic group, then this may be aromatic or non-aromatic and includes in particular, piperidine, piperazine, morpholino, pyrrolidine or pyridine any of which may be optionally substituted with a functional group such as hydroxy, alkoxy such as methoxy, or alkyl such as methyl which may itself be substituted with for instance a hydroxy group.

Alternatively at least one of $R^{60}$, $R^{61}$ or $R^{62}$ is a functional group, and in particular, one of $R^{60}$, $R^{61}$ or $R^{62}$ is a functional group a group of formula (CR$_2$)$_p$C(O)$_x R^{77}$ where R, p, x and $R^{77}$ are as defined above, and in particular x is 2 and $R^{77}$ is hydrogen or alkyl such as methyl.

Alternatively, $R^5$ is substituted by one or more groups selected from nitro, halo, $C_{1-6}$alkyl, optionally substituted $C_{1-6}$ alkoxy, $C_{1-4}$alkoxymethyl, di($C_{1-4}$alkoxy)methyl, $C_{1-6}$alkanoyl, trifluoromethyl, cyano, amino, $C_{2-6}$alkenyl, $C_{2-6}$alkynyl, a phenyl group, a benzyl group or a 5-6-membered heterocyclic group with 1-3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl.

Suitably $R^5$ is substituted with at least one group which has at least 4 atoms which may be carbon or heteroatoms forming a chain. A particular example of such a substituent is optionally substituted alkoxy or alkoxy methyl. Suitable substituents for the alkoxy group include those listed above in relation to $R^{77}$, $R^{78}$ and $R^{79}$.

A further particular substituent group for $R^5$ is a group of sub-formula (II)

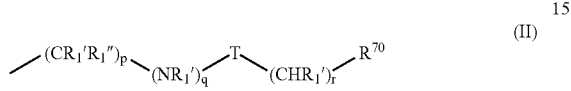

(II)

where p and q are independently 0 or 1, and r is 0, 1, 2, 3 or 4 and, R1', R1" and T are as previously defined above;

$R^{70}$ is hydrogen, hydroxy (other than where q is 0), $C_{1-6}$alkyl, $C_{1-6}$alkoxy, amino, N-$C_{1-6}$alkylamino, N,N-($C_{1-6}$alkyl)$_2$ amino, hydroxy$C_{2-6}$alkoxy, $C_{1-6}$alkoxy$C_{2-6}$alkoxy, amino$C_{2-6}$alkoxy, N-$C_{1-6}$alkylamino$C_{2-6}$alkoxy, N,N-($C_{1-6}$alkyl)$_2$amino$C_{2-6}$alkoxy or $C_{3-7}$cycloalkyl, or $R^{70}$ is of the Formula (III):

(III)

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —SO$_2$NH—, —NHSO$_2$— or —NHC(O)-$C_{1-6}$alkylene-, and any aryl, heteroaryl or heterocyclyl group in a $R^{70}$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)-O—, $C_{1-6}$alkylS(O)$_n$— (wherein n is 0-2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N-($C_{1-6}$alkyl)amino, or any aryl, heteroaryl or heterocyclyl group in a $R^{70}$ group may be optionally substituted with one or more groups of the Formula (IV):

(IV)

wherein $A^1$ is halo, hydroxy, $C_{1-6}$alkoxy, cyano, amino, N-$C_{1-6}$ alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1-6, and $B^1$ is a bond, oxy, imino, N-($C_{1-6}$alkyl)imino or —NHC(O)—, with the proviso that p is 2 or more unless $B^1$ is a bond or —NHC(O)—;

or any aryl, heteroaryl or heterocyclyl group in a $R^{70}$ group may be optionally substituted with one or more groups of the Formula (V):

(V)

wherein $D^1$ is aryl, heteroaryl or heterocyclyl and $E^1$ is a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl)-imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$alkyl)-imino$C_{1-6}$alkylene, —NHC(O)—, —NHSO$_2$—, —SO$_2$NH— or —NHC(O)-$C_{1-6}$alkylene-, and any aryl, heteroaryl or heterocyclyl group in a substituent on $D^1$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N-($C_{1-6}$alkyl)$_2$carbamoyl, $C_{2-6}$alkanoyl, amino, N-$C_{1-6}$alkylamino and N,N-($C_{1-6}$alkyl)$_2$ amino, and any $C_{3-7}$cycloalkyl or heterocyclyl group in a $R^{70}$ group may be optionally substituted with one or two oxo or thioxo substituents, and any of the $R^{70}$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, $C_{1-6}$alkoxy, N-$C_{1-6}$alkylamino, N,N-($C_{1-6}$alkyl)$_2$amino and heterocyclyl.

A preferred example of a substituent of formula (II) is a group where q is 0.

A particular example of a group $R^{70}$ in formula (II) is phenyl.

Another preferred substituent group for $R^5$ is a group of formula (VI)

(VI)

where $R^{71}$ and $R^{72}$ are independently selected from hydrogen or $C_{1-4}$alkyl, or $R^{71}$ and $R^{72}$ together form a bond, and $R^{73}$ is a group $OR^{74}$, $NR^{75}R^{76}$ where $R^{74}$, $R^{75}$ and $R^{76}$ are independently selected from optionally substituted hydrocarbyl or optionally substituted heterocyclic groups, and $R^{75}$ and $R^{76}$ may additionally form together with the nitrogen atom to which they are attached, an aromatic or non-aromatic heterocyclic ring which may contain further heteroatoms.

Suitable optional substituents for hydrocarbyl or heterocyclic groups $R^{74}$, $R^{75}$ and $R^{76}$ include functional groups as defined above. Heterocyclic groups $R^{74}$, $R^{75}$ and $R^{76}$ may further be substituted by hydrocarbyl groups.

In particular, $R^{71}$ and $R^{72}$ in sub-formula (VI) are hydrogen.

Particular examples of $R^{73}$ are groups $OR^{74}$ where $R^{74}$ is $C_{1-4}$alkyl.

Further examples of $R^{73}$ are groups of formula $NR^{75}R^{76}$ where one of $R^{75}$ or $R^{76}$ is hydrogen and the other is optionally substituted $C_{1-6}$alkyl, optionally substituted aryl or optionally substituted heterocyclyl.

In particular, one of $R^{75}$ or $R^{76}$ is hydrogen and the other is $C_{1-6}$alkyl optionally substituted with trifluoromethyl, $C_{1-3}$alkoxy such as methoxy, cyano, thio$C_{1-4}$alkyl such as methylthio, or heterocyclyl optionally substituted with hydrocarbyl, such as indane, furan optionally substituted with $C_{1-4}$alkyl such as methyl.

In another embodiment, one of $R^{75}$ or $R^{76}$ is hydrogen and the other is an optionally substituted heterocyclic group such as pyridine, or a phenyl group optionally substituted with for example one or more groups selected from halo, nitro, alkyl such as methyl, or alkoxy such as methoxy.

A preferred class of compounds is of formula (I) wherein:
X is NH;

$R^1$ is hydrogen, methoxy, N-($C_{1-5}$alkyl)piperidin-4-yloxy, prop-2-yloxy or methoxyethoxy;

$R^2$ is hydrogen or methoxy;

$R^3$ is 3-morpholinopropoxy, 3-chloropropoxy, 3-[N-ethyl-N-(2-hydroxyethyl)amino]propoxy, 3-(2-hydroxymethylpyrrolidin-1-yl)propoxy, 3-(piperidin-1-yl)propoxy, 3-(pyrrolidin-1-yl)propoxy, 3-(N-(2-hydroxyethyl)amino]propoxy, 3-[N-(2-hydroxy-1,1-dimethylethyl)amino]propoxy, 3-[N-methyl-N-(2-hydroxyethyl)amino]propoxy, 3-[N-(1-hydroxymethyl-2-methylpropyl)amino]propoxy, 3-(4-methylpiperazin-1-yl)propoxy, 3-[N-(2-hydroxy-1-methylethyl)amino]propoxy, 3-[N-(4-hydroxybutyl)amino]propoxy, 3-(4-hydroxypiperidin-1-yl)propoxy, 3-[2-(2-hydroxyethyl)piperidin-1-yl]propoxy, 3-[4-(2-hydroxyethyl)piperazin-1-yl]propoxy, 3-[4-(2-hydroxyethyl)piperidin-1-yl]propoxy, 3-(3-hydroxypiperidin-1-yl)propoxy, 3-[N-2-(hydroxybutyl)amino]propoxy, 3-(4-hydroxymethylpiperidin-1-yl)propoxy, 3-[N-(3-hydroxy-2,2-dimethylpropyl)amino]propoxy, 3-[N-(1-hydroxymethylcyclopent-1-yl)amino]propoxy, 3-[N-(2-hydroxypropyl)amino]propoxy, 3-(3-hydroxypyrrolidin-1-yl)propoxy, 3-[N-(2-fluoroethyl)-N-(2-hydroxyethyl)amino]propoxy, 2-[1-(2-hydroxyethyl)piperidin-4-yl]ethoxy, 3-[N-(2-hydroxyethyl)-N-propylamino]propoxy, 3-[N-(2-hydroxyethyl)-N-(prop-2-yl)amino]propoxy, 3-[N-(2-hydroxyethyl)-N-isobutylamino]propoxy, 3-[N-(2-hydroxyethyl)-N-neopentylamino]propoxy, 3-[N-allyl-N-(2-hydroxyethyl)amino]propoxy, 3-[N-(2-hydroxyethyl)-N-(prop-2-yn-1-yl)amino]propoxy, 3-[N-cyclopropyl-N-(2-hydroxyethyl)amino]propoxy, 3-[N-cyclopropylmethyl-N-(2-hydroxyethyl)amino]propoxy, 3-[N-cyclobutyl-N-(2-hydroxyethyl)amino]propoxy, 3-[N-cyclopentyl-N-(2-hydroxyethyl)amino]propoxy, 3-[N-(2,2-dimethoxyethyl)-N-(2-hydroxyethyl)amino]propoxy, 3-[N-(2,2-difluoroethyl)-N-(2-hydroxyethyl)amino]propoxy, 3-[N-(2-hydroxyethyl)-N-(3,3,3-trifluoropropyl)amino]propoxy, 3-[N-cyclobutylmethyl-N-(2-hydroxyethyl)amino]propoxy, 3-[N-(2-hydroxyethyl)-N-(2-methoxyethyl)amino]propoxy, 3-[N-(1,3-dioxolan-2-ylmethyl)-N-(2-hydroxyethyl)amino]propoxy, 4-chlorobutoxy, 4-[(2-hydroxymethyl)pyrrolidin-1-yl]butoxy, 4-[N-(2-hydroxyethyl)-N-isobutylamino]butoxy, 1-(2-tert-butoxyethyl)pyrrolidin-2-ylmethoxy, 1-(2-hydroxyethyl)pyrrolidin-2-ylmethoxy, 3-[N-2-(hydroxyethyl)-N-(iso-butyl)amino]propoxy, 3-[N-2-(hydroxyethyl)-N-(neopentyl)amino]propoxy, 3-[N-2-(hydroxyethyl)-N-(tert-butyl)amino]propoxy, methoxy and methoxyethoxy;

$R^4$ is hydrogen;
$R^{60}$ is hydrogen;
$R^{61}$ is a group of sub-formula (k) as defined above;
$R^{62}$ is hydrogen;
$R_1'$ is hydrogen or $C_{1-3}$alkyl;
$R_1''$ it hydrogen or $C_{1-3}$alkyl;
p is 1;
T is C=O;
q is 1;
V is $N(R^{63})R^{64}$;
$R^{63}$ is —$(CH_2)_q$.$R^{70}$ or aryl or heteroaryl where the latter two groups are optionally substituted by 1 or 2 substituents independently selected from halo, $C_{1-4}$alkyl, $C_{1-4}$alkoxy, trifluoromethyl, trifluoromethoxy, hydroxy, nitro, difluoromethyl, difluoromethoxy and cyano;
$R^{64}$ is hydrogen;
$R^{70}$ is a group of formula (III) —K—J;
K is a bond; and J is 3-fluorophenyl, 2,3-difluorophenyl, 3,5-difluorophenyl, 3-chlorophenyl, 3-methoxyphenyl, phenyl, 4-fluorophenyl, 3,5-dichlorophenyl, 5-chloro-2-methoxyphenyl, 3-trifluoromethylphenyl, 3-hydroxyphenyl, 3-nitrophenyl, 4-bromo-2-fluorophenyl, 3,5-dimethoxyphenyl, 3-chloro-2-fluorophenyl, 2-fluoro-3-trifluormethylphenyl, 3,4-difluorophenyl, 2,4-difluorophenyl, 3-chloro-4-fluorophenyl, 2-difluoromethoxyphenyl, 3-cyanophenyl, 3-bromophenyl, 5-indanzolyl and 5-methylpyridin-2-yl.

A further preferred class of compounds is of formula (I) wherein:

X is $NR^6$ or O;

$R^6$ is hydrogen or $C_{1-3}$alkyl;

$R^1$ is hydrogen or —$X^1R^9$ where $X^1$ is a direct bond, —O— or —NH— and $R^9$ is hydrogen, $C_{1-5}$alkyl, $C_{3-6}$cycloalkyl, —$C_{1-5}$alkyl-O—$C_{1-3}$alkyl or a 5- to 6-membered saturated heterocyclic group (linked via carbon or nitrogen) with 1 or 2 heteroatoms selected independently from O, S or N which heterocyclic groups is optionally substituted by $C_{1-4}$alkyl or a 5- or 6-membered aromatic heterocyclic group (linked via carbon or nitrogen with 1, 2 or 3 heteroatoms;

$R^2$ is hydrogen, hydroxy, halo, methoxy or —$OC_{1-3}$alkyl (optionally substituted by 1 or 2 hydroxy or halo);

$R^3$ is —$X^1R^9$ where $X^1$ is —O— and $R^9$ is —$C_{1-5}$alkyl$R^{32}$, —$C_{1-5}$alkyl$R_{96}$, $C_{1-5}$alkyl (optionally substituted by halo), —$C_{1-5}$alkyl-$OR^{20}$, —$C_{1-5}$alkyl-$NHR^{20}$, —$C_{1-5}$alkyl-N($C_{1-3}$alkyl)-$R^{20}$, —$C_{1-5}$alkyl-NH—$C_{1-5}$alkyl-OH, —$C_{1-5}$alkyl-N($C_{1-3}$alkyl)-$C_{1-5}$alkyl-OH and —$C_{1-5}$alkyl-$NR^{95}$—$C_{1-5}$alkyl-OH;

$R^{32}$ is morpholino, pyrrolidinyl, piperidinyl or piperazinyl optionally substituted by hydroxymethyl, 2-hydroxyethyl, methyl, hydroxy or 2-(tert-butoxy)ethyl;

$R^{20}$ is $C_{1-3}$alkyl optionally substituted by hydroxy) or cyclopentyl (optionally substituted by $C_{1-4}$hydroxyalkyl);

$R^{95}$ is methyl, ethyl, 2-fluoroethyl, prop-1-yl, prop-2-yl, isobutyl, neopentyl, allyl, propargyl, cyclopropyl, cyclopropylmethyl, cyclobutyl, cyclopentyl, 2,2-difluoroethyl, 2,2,2-trifluoroethyl, cyclobutylmethyl, methoxyethyl, 1,3-dioxolan-2-ylmethyl and 2,2-dimethoxyethyl;

$R^{96}$ is 4,5-dihydro-1H-imidazoyl optionally substituted by $C_{1-4}$hydroxyalkyl;

$R^4$ is hydrogen;
$R^{60}$ is hydrogen;
$R^{61}$ is J, —$(CH_2)$—J, —$(CH_2)_2$—J, —O—J, —$(CH_2)$—O—J, —O—$(CH_2)$—J, —$(CH_2)$—O—$(CH_2)$—J, —CO—J, —$(CH_2)$—CO—J, —CO—$(CH_2)$—J, —$(CH_2)$—CO—$(CH_2)$—J, —S—J, —$(CH_2)$—S—J, —S—$(CH_2)$—J, —$(CH_2)$—S—$(CH_2)$—J, —SO—J, —$(CH_2)$—SO—J, —SO—$(CH_2)$—J, —$(CH_2)$—SO—$(CH_2)$—J, —$SO_2$—J, —$(CH_2)$—$SO_2$—J, —$SO_2$—$(CH_2)$—J, —$(CH_2)$—$SO_2$—$(CH_2)$—J, —$(NR_1')$CO—J, —$(CH_2)$—$(NR_1')$CO—J, —$(NR_1')$CO—$(CH_2)$—J, —$(CH_2)$—$(NR_1')$CO—$(CH_2)$—J, —$(NR_1')SO_2$—J, —$(CH_2)$—$(NR_1')SO_2$—J, —$(NR_1')SO_2$—$(CH_2)$—J, —$(CH_2)$—$(NR_1')SO_2$—$(CH_2)$—J, —$NR^{64}$—J, —$(CH_2)$—$NR^{64}$—J, —$NR^{64}$—$(CH_2)$—J, —$(CH_2)$—$NR^{64}$—$(CH_2)$—J, —$CONR^{64}$—J, —$(CH_2)$—$CONR^{64}$—J, —$CONR^{64}$—$(CH_2)$—J, —$(CH_2)$—$CONR^{64}$—$(CH_2)$—J, —$SO_2NR^{64}$—J, —$(CH_2)$—$SO_2NR^{64}$—J, —$SO_2NR^{64}$—$(CH_2)$—J, —$(CH_2)$—$SO_2NR^{64}$—$(CH_2)$—J, —$NR_1'$CO—NH—J, —$(CH_2)$—$NR_1'$CO—NH—J, —$NR_1'$CO—NH—$(CH_2)$—J, —$(CH_2)$—$NR_1'$CO—NH—$(CH_2)$—J, —$NR_1'$CO—N($C_{1-4}$alkyl)—J, —$(CH_2)$—$NR_1'$CO—N($C_{1-4}$alkyl)—J, —$NR_1'$CO—N($C_{1-4}$alkyl)-$(CH_2)$—J, —$(CH_2)$—$NR_1'$CO—N($C_{1-4}$alkyl)-$(CH_2)$—J, —$NR_1'$CO—O—J, —$(CH_2)$—$NR_1'$CO—O—J, —$NR_1'$CO—O—$(CH_2)$—J, —$(CH_2)$—$NR_1'$CO—O—$(CH_2)$—J, —OCO—J, —$CH_2$—

OCO—J, —CH═CH—J, —CH₂CH═CH—J, —CH═CH—CH₂—J and —CH₂CH═CH—CH₂—J;

$R^{62}$ is hydrogen, halo or $C_{1-3}$alkyl;

$R_1'$ is hydrogen or $C_{1-3}$alkyl;

$R^{64}$ is hydrogen or $C_{1-3}$alkyl; and

J is a group select from phenyl, pyridyl, pyrimidinyl, furyl, thienyl and pyrrolyl which group is optionally substituent by 1 or 2 substituents selected from halo, methyl, ethyl, methoxy, cyano, cyclopropyl and cyclopropylmethyl.

In another aspect of the invention, preferred compounds are any one of:

2-(3-{[6-methoxy-7-(3-morpholin-4-ylpropoxy)quinazolin-4-yl]amino}-1H-pyrazol-5-yl)-N-phenylacetamide;

N-(3-fluorophenyl)-2-(3-{[6-methoxy-7-(3-morpholin-4-ylpropoxy)quinazolin-4-yl]amino}-1H-pyrazol-5-yl)acetamide;

2-(3-{[7-(3-chloropropoxy)-6-methoxyquinazolin-4-yl]amino}-1H-pyrazol-5-yl)-N-(3-fluorophenyl)acetamide;

2-(3-{[7-(3-chloropropoxy)-6-methoxyquinazolin-4-yl]amino}-1H-pyrazol-5-yl)-N-(3,5-difluorophenyl)acetamide;

2-(3-{[7-(3-chloropropoxy)-6-methoxyquinazolin-4-yl]amino}-1H-pyrazol-5-yl)-N-(2,3-difluorophenyl)acetamide;

N-(3-chlorophenyl)-2-(3-{[7-(3-chloropropoxy)-6-methoxyquinazolin-4-yl]amino}-1H-pyrazol-5-yl)acetamide;

2-{3-[(7-{3-[ethyl(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(3-fluorophenyl)-2-(3-{[6-methoxy-7-(3-piperidin-1-ylpropoxy)quinazolin-4-yl]amino}-1H-pyrazol-5-yl)acetamide;

N-(3-fluorophenyl)-2-(3-([6-methoxy-7-(3-pyrrolidin-1-ylpropoxy)quinazolin 4-yl]amino}-1H-pyrazol-5-yl)acetamide;

N-(3-fluorophenyl)-2-{3-[(7-{3-[(2-hydroxyethyl)amino]propoxy}-6-methoxyquinazolin-4-yl)amino]-1H-pyrazol-5-yl}acetamide;

N-(3-fluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide;

N-(3-fluorophenyl)-2-{3-[(7-{3-[(2-hydroxyethyl)(methyl)amino]propoxy}-6-methoxyquinazolin-4-yl)amino]-1H-pyrazol-5-yl}acetamide;

N-(3-fluorophenyl)-2-(3-{[7-(3-{[1-(hydroxymethyl)-2-methylpropyl]amino}propoxy)-6-methoxyquinazolin-4-yl]amino}-1H-pyrazol-5-yl)acetamide;

N-(3-fluorophenyl)-2-[3-({6-methoxy-7-[3-(4-methylpiperazin-1-yl)propoxy]quinazolin-4-yl}amino)-1H-pyrazol-5-yl]acetamide;

N-(3-fluorophenyl)-2-{3-[(7-{3-[(2-hydroxy-1-methylethyl)amino]propoxy}-6-methoxyquinazolin-4-yl)amino]-1H-pyrazol-5-yl}acetamide;

N-(3-fluorophenyl)-2-{3-[(7-{3-[(4-hydroxybutyl)amino]propoxy}-6-methoxyquinazolin-4-yl)amino]-1H-pyrazol-5-yl}acetamide;

N-(3-fluorophenyl)-2-[3-({7-{3-(4-hydroxypiperidin-1-yl)propoxy]-6-methoxyquinazolin-4-yl}amino)-1H-pyrazol-5-yl]acetamide;

N-(3-fluorophenyl)-2-{3-[(7-{3-[2-(2-hydroxyethyl)piperidin-1-yl]propoxy}--6-methoxyquinazolin-4-yl)amino]-1H-pyrazol-5-yl}acetamide;

N-(3-fluorophenyl)-2-{3-[(7-{3-[4-(2-hydroxyethyl)piperazin-1-yl]propoxy}--6-methoxyquinazolin-4-yl)amino]-1H-pyrazol-5-yl}acetamide;

N-(3-fluorophenyl)-2-{3-[(7-{3-[4-(2-hydroxyethyl)piperidin-1-yl]propoxy}--6-methoxyquinazolin-4-yl)amino]-1H-pyrazol-5-yl}acetamide;

N-(3-fluorophenyl)-2-[3-({7-[3-(3-hydroxypiperidin-1-yl)propoxy]-6-methoxyquinazolin-4-yl}amino)-1H-pyrazol-5-yl]acetamide;

N-(3-fluorophenyl)-2-{3-[(7-{3-[(2-hydroxybutyl)amino]propoxy}-6-methoxyquinazolin-4-yl)amino]-1H-pyrazol-5-yl}acetamide;

N-(3-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-fluorophenyl)-2-{3-[(7-{3-[(3-hydroxy-2,2-dimethylpropyl)amino]propoxy}-6-methoxyquinazolin-4-yl)amino]-1H-pyrazol-5-yl}acetamide;

N-(3-fluorophenyl)-2-(3-{[7-(3-{[1-(hydroxymethyl)cyclopentyl]amino}propoxy)-6-methoxyquinazolin-4-yl]amino}-1H-pyrazol-5-yl)acetamide;

N-(3-fluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(3-fluorophenyl)-2-(3-{[7-(3-{[(2S)-2-hydroxypropyl]amino}propoxy)-6-methoxyquinazolin-4-yl]amino}-1H-pyrazol-5-yl)acetamide;

N-(3-fluorophenyl)-2-(3-{[7-{3-[(2R)-2-hydroxypropyl]amino}propoxy)-6-methoxyquinazolin-4-yl]amino}-1H-pyrazol-5-yl)acetamide;

N-(3-fluorophenyl)-2-{3-[(7-{3-[(3S)-3-hydroxypyrrolidin-1-yl]propoxy}-6-methoxyquinazolin-4-yl)amino]-1H-pyrazol-5-yl}acetamide;

N-(3-fluorophenyl)-2-{3-[(7-{3-[(3R)-3-hydroxypyrrolidin-1-yl]propoxy}-6-methoxyquinazolin-4-yl)amino]-1H-pyrazol-5-yl}acetamide;

2-{3-[(7-{3-[(2-fluoroethyl)(2-hydroxyethyl)amino]propoxy}-6-methoxyquinazolin--4-yl)amino]-1H-pyrazol-5-yl}-N-(3-fluorophenyl)acetamide;

N-(3-fluorophenyl)-2-{3-[(7-{2-[1-(2-hydroxyethyl)piperidin-4-yl]ethoxy}-6-methoxyquinazolin-4-yl)amino]-1H-pyrazol-5-yl}acetamide;

N-(3-fluorophenyl)-2-{3-[(7-{3-[(2-hydroxyethyl)(propyl)amino]propoxy}-6-methoxyquinazolin-4-yl)amino]-1H-pyrazol-5-yl}acetamide;

N-(3-fluorophenyl)-2-{3-[(7-{3-[(2-hydroxyethyl)(isopropyl)amino]propoxy}-6-methoxyquinazolin-4-yl)amino]-1H-pyrazol-5-yl}acetamide;

N-(3-fluorophenyl)-2-{3-[(7-{3-[(2-hydroxyethyl)(isobutyl)amino]propoxy}-6-methoxyquinazolin-4-yl)amino]-1H-pyrazol-5-yl}acetamide;

2-{3-[(7-{3-[(2,2-dimethylpropyl)(2-hydroxyethyl)amino]propoxy}-6-methoxyquinazolin-4-yl)amino]-1H-pyrazol-5-yl}-N-(3-fluorophenyl)acetamide;

2-{3-[(7-{3-[allyl(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide;

2-{3-[(7-{3-[cyclopropyl(2-hydroxyethyl)amino]propoxy}-6-methoxyquinazolin-4-yl)amino]-1H-pyrazol-5-yl}-N-(3-fluorophenyl)acetamide;

2-{3-[(7-{3-[(cyclopropylmethyl)(2-hydroxyethyl)amino]propoxy}-6-methoxyquinazolin-4-yl)amino]-1H-pyrazol-5-yl}-N-(3-fluorophenyl)acetamide;

2-{3-[(7-{3-[cyclobutyl(2-hydroxyethyl)amino]propoxy}-6-methoxyquinazolin-4-yl)amino]-1H-pyrazol-5-yl}-N-(3-fluorophenyl)acetamide;

2-{3-[(7-{3-[cyclopentyl(2-hydroxyethyl)amino]propoxy}-6-methoxyquinazolin-4-yl)amino]-1H-pyrazol-5-yl}-N-(3-fluorophenyl)acetamide;

2-{3-[(7-{3-[(2,2-dimethoxyethyl)(2-hydroxyethyl)amino]propoxy}-6-methoxyquinazolin-4-yl)amino]-1H-pyrazol-5-yl}-N-(3-fluorophenyl)acetamide;

2-{3-[(7-{3-[(2,2-difluoroethyl)(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{3-[(2-hydroxyethyl)(3,3,3-trifluoropropyl)amino]propoxy}-6-methoxyquinazolin-4-yl)amino]-1H-pyrazol-5-yl}acetamide;

2-{3-[(7-{3-[(cyclobutylmethyl)(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide;

2-{3-[(7-{3-[(1,3-dioxolan-2-ylmethyl)(2-hydroxyethyl)amino]propoxy}-6-methoxyquinazolin-4-yl)amino]-1H-pyrazol-5-yl}-N-(3-fluorophenyl)acetamide;

2-(3-{[7-(4-chlorobutoxy)-6-methoxyquinazolin-4-yl]amino}-1H-pyrazol-5-yl)-N-(3-fluorophenyl)acetamide;

N-(3-fluorophenyl)-2-{3-[(7-{4[(2R)-2-(hydroxymethyl)pyrrolidin-1-yl]butoxy}-6-methoxyquinazolin-4-yl)amino]-1H-pyrazol-5-yl}acetamide;

N-(3-fluorophenyl)-2-{3-[(7-{4-[(2-hydroxyethyl)(isobutyl)amino]butoxy}-6-methoxyquinazolin-4-yl)amino]-1H-pyrazol-5-yl}acetamide;

2-{3-[(7-{[(2R)-1-(2-tert-butoxyethyl)pyrrolidin-2-yl]methoxy}-6-methoxyquinazolin-4-yl)amino]-1H-pyrazol-5-yl}-N-(3-fluorophenyl)acetamide;

N-(3-fluorophenyl)-2-{3-[(7-{[(2R)-1-(2-hydroxyethyl)pyrrolidin-2-yl]methoxy}-6-methoxyquinazolin-4-yl)amino]-1H-pyrazol-5-yl}acetamide;

N-(3,5-difluorophenyl)-2-(3-{[6-methoxy-7-(3-pyrrolidin-1-ylpropoxy)quinazolin-4-yl]amino}-1H-pyrazol-5-yl)acetamide;

N-(3,5-difluorophenyl)-2-{3-[(7-{3-[(2-hydroxyethyl)amino]propoxy}-6-methoxyquinazolin-4-yl)amino]-1H-pyrazol-5-yl}acetamide;

N-(3,5-difluorophenyl)-2-{3-[(7-{3-[(2-hydroxy-1,1-dimethylethyl)amino]propoxy}-6-methoxyquinazolin 4-yl)amino]-1H-pyrazol-5-yl}acetamide;

N-(3,5-difluorophenyl)-2-[3-({6-methoxy-7-{3-(4-methylpiperazin-1-yl)propoxy]quinazolin-4-yl}amino)-1H-pyrazol-5-yl]acetamide;

N-(3,5-difluorophenyl)-2-{3-[(7-{3-[ethyl(2-hydroxyethyl)amino]propoxy}-6-methoxyquinazolin-4-yl)amino]-1H-pyrazol-5-yl}acetamide;

N-(3,5-difluorophenyl)-2-{3-[(7-{3-[2-(2-hydroxyethyl)piperidin-1-yl]propoxy}-6-methoxyquinazolin-4-yl)amino]-1H-pyrazol-5-yl}acetamide;

N-(3,5-difluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide;

N-(3,5-difluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide;

N-(3,5-difluorophenyl)-2-[3-({7-[3-(3-hydroxypiperidin-1-yl)propoxy]-6-methoxyquinazolin-4-yl}amino)-1H-pyrazol-5-yl]acetamide;

N-(3,5-difluorophenyl)-2-{3-[(7-{3-[(2-hydroxybutyl)amino]propoxy}-6-methoxyquinazolin-4-yl)amino]-1H-pyrazol-5-yl}acetamide;

N-(3,5-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3,5-difluorophenyl)-2-{3-[(7-{3-[(3-hydroxy-2,2-dimethylpropyl)amino]propoxy}-6-methoxyquinazolin-4-yl)amino]-1H-pyrazol-5-yl}acetamide;

N-(3,5-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(3,5-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(3,5-difluorophenyl)-2-{3-[7-(3-{[(2S)-2-hydroxypropyl]amino}propoxy)-6-methoxyquinazolin-4-yl]amino}-1H-pyrazol-5-yl)acetamide;

N-(3,5-difluorophenyl)-2-(3-{[7-(3-{[(2R)-7-2-hydroxypropyl]amino}propoxy)-6-methoxyquinazolin-4-yl]amino}-1H-pyrazol-5-yl)acetamide;

N-(3,5-difluorophenyl)-2-{3-[(7-{3-[(3S)-3-hydroxypyrrolidin-1-yl]propoxy}-6-methoxyquinazolin-4-yl)amino]-1H-pyrazol-5-yl}acetamide;

N-(3,5-difluorophenyl)-2-{3-[(7-{3-[(3R)-3-hydroxypyrrolidin-1-yl]propoxy}-6-methoxyquinazolin-4-yl)amino]-1H-pyrazol-5-yl}acetamide;

N-(3,5-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide;

N-(3,5-difluorophenyl)-2-{3-[(7-{3-[(2-hydroxyethyl)(propyl)amino]propoxy}-6-methoxyquinazolin-4-yl)amino]-1H-pyrazol-5-yl}acetamide;

2-{3-[(7-{3-[allyl(2-hydroxyethyl)amino]propoxy}-6-methoxyquinazolin-4-yl)amino]-1H-pyrazol-5-yl}-N-(3,5-difluorophenyl)acetamide;

N-(3,5-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide;

N-(3,5-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide;

N-(3,5-difluorophenyl)-2-{3-[(7-{3-[(2,2-dimethylpropyl)(2-hydroxyethyl)amino]propoxy}-6-methoxyquinazolin-4-yl)amino]-1H-pyrazol-5-yl}acetamide;

2-{3-[(7-{3-[cyclobutyl(2-hydroxyethyl)amino]propoxy}-6-methoxyquinazolin-4-yl)amino]-1H-pyrazol-5-yl}-N-(3,5-difluorophenyl)acetamide;

2-{3-[(7-{3-[(cyclopropylmethyl)(2-hydroxyethyl)amino]propoxy}-6-methoxyquinazolin-4-yl)amino]-1H-pyrazol-5-yl}-N-(3,5-difluorophenyl)acetamide;

N-(2,3-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(2,3-difluorophenyl)-2-{3-[(7-{3-[(2,2-dimethylpropyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(propyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide;

2-{3-[(7-{3-[cyclobutyl(2-hydroxyethyl)amino]propoxy}-6-methoxyquinazolin-4-yl)amino]-1H-pyrazol-5-yl}-N-(2,3-difluorophenyl)acetamide;

2-{3-[(7-{3-[cyclopentyl(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(prop-2-yn-1-yl)amino]propoxy]-6-methoxyquinazolin-4-yl)amino]-1H-pyrazol-5-yl}acetamide;

2-{3-[(7-{3-[(cyclopropylmethyl)(2-hydroxyethyl)amino]propoxy}-6-methoxyquinazolin-4-yl)amino]-1H-pyrazol-5-yl}-N-(2,3-difluorophenyl)acetamide;

2-{3-[(7-{3-[(cyclobutylmethyl)(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(2,2-dimethoxyethyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide;

N-(2,3-difluorophenyl)-2-[3-({7-[3-(4-hydroxypiperidin-1-yl)propoxy]-6-methoxyquinazolin-4-yl}amino)-1H-pyrazol-5-yl]acetamide;

N-(2,3-difluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide;

2-{3-[(7-{3-[allyl(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(1,3-dioxolan-2-ylmethyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[ethyl(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide;

N-(2,3-difluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide;

N-(2,3-difluorophenyl)-2-{3-[(7-{[(2R)-1-(2-hydroxyethyl)pyrrolidin-2-yl]methoxy-6-methoxyquinazolin-4-yl)amino]-1H-pyrazol-5-yl}acetamide;

N-(3-chlorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(3-chlorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(3-chlorophenyl)-2-[3-({7-[3-(3-hydroxypiperidin-1-yl)propoxy]-6-methoxyquinazolin-4-yl}amino)-1H-pyrazol-5-yl]acetamide;

N-(3-chlorophenyl)-2-{3-[(7-{3-[ethyl(2-hydroxyethyl)amino]propoxy}-6-methoxyquinazolin-4-yl)amino]-1H-pyrazol-5-yl}acetamide;

2-{3-[(7-{3-[4-(hydroxymethyl)piperidin-1-yl]propoxy}-6-methoxyquinazolin-4-yl)amino]-1H-pyrazol-5-yl}-N-(3-methoxyphenyl)acetamide;

2-{3-[(7-{3-[4-(hydroxymethyl)piperidin-1-yl]propoxy}-6-methoxyquinazolin-4-yl)-amino]-1H-pyrazol-5-yl}-N-phenylacetamide;

N-(4-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3,5-dichlorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(5-chloro-2-methoxyphenyl)-2-{3-[(7-{3-[4-(hydroxymethyl)piperidin-1-yl]propooxy}-6-methoxyquinazolin-4-yl)amino]-1H-pyrazol-5-yl}acetamide;

2-{3-[(7-{3-[4-(hydroxymethyl)piperidin-1-yl]propoxy}-6-methoxyquinazolin-4-yl)amino]-1H-pyrazol-5-yl}-N-[3-(trifluoromethyl)phenyl]acetamide;

2-{3-[(7-{3-[4-(hydroxymethyl)piperidin-1-yl]propoxy}-6-methoxyquinazolin-4-yl)amino]-1H-pyrazol-5-yl}-N-(3-hydroxyphenyl)acetamide;

2-{3-[(7-{3-[4-(hydroxymethyl)piperidin-1-yl]propoxy}-6-methoxyquinazolin-4-yl)amino]-1H-pyrazol-5-yl}-N-(3-nitrophenyl)acetamide;

2-{3-[(7-{3-[4-(hydroxymethyl)piperidin-1-yl]propoxy}-6-methoxyquinazolin-4-yl)amino]-1H-pyrazol-5-yl}-N-1H-indazol-5-ylacetamide;

N-(4-bromo-2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-chlorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3,5-dimethoxyphenyl)-2-{3-[(7-{3-[4-(hydroxymethyl)piperidin-1-yl]propoxy}-6-methoxyquinazolin-4-yl)amino]-1H-pyrazol-5-yl}acetamide;

2-{3-[(7-{3-[4-(hydroxymethyl)piperidin-1-yl]propoxy}-6-methoxyquinazolin-4-yl)amino]1H-pyrazol-5-yl}-N-(5-methylpyridin-2-yl)acetamide;

N-(2,3-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-chloro-2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2,5-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-[2-fluoro-5-(trifluoromethyl)phenyl]-2-{3-[(7-{3-[4-(hydroxymethyl)piperidin-1-yl]propoxy}-6-methoxyquinazolin-4-yl)amino]-1H-pyrazol-5-yl}acetamide;

N-(3,4-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2,4-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-chloro-4-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-[2-(difluoromethoxy)phenyl]-2-{3-[(7-{3-[4-(hydroxymethyl)piperidin-1-yl]propoxy}-6-methoxyquinazolin-4-yl)amino]-1H-pyrazol-5-yl}acetamide;

N-(3-cyanophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-bromophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2,3-difluorophenyl)-2-{3-[(7-{3-[ethyl(2-hydroxyethyl) amino]propoxy}quinazolin-4-yl)amino]-1H-pyrazol-5-yl}acetamide;

N-(2,3-difluorophenyl)-2-{3-[(7-{3-[(2-hydroxyethyl)(isopropyl)amino]propoxy}quinazolin-4-yl)amino]-1H-pyrazol-5-yl}acetamide;

N-(2,3-difluorophenyl)-2-{3-[(7-{3-[(2R)-2-(hydroxymethyl)pyrrolidin-1-yl]propoxy}quinazolin-4-yl)amino]-1H-pyrazol-5-yl}acetamide;

N-(2,3-difluorophenyl)-2-{3-[(7-{3-[(2-hydroxyethyl)(isopropyl)amino]propoxy}quinazolin-4-yl)amino]-1H-pyrazol-5-yl}acetamide;

N-(2,3-difluorophenyl)-2-{3-[(7-{3-[(2-hydroxyethyl)(prop-2-yn-1-yl)amino]propoxy}quinazolin-4-yl)amino]-1H-pyrazol-5-yl}acetamide;

N-(2,3-difluorophenyl)-2-{3-[(7-{3-[(2-hydroxyethyl)(isobutyl)amino]propoxy}quinazolin-4-yl)amino]-1H-pyrazol-5-yl}acetamide;

N-(2,3-difluorophenyl)-2-{3-[(7-{3-[(2,2-dimethylpropyl)(2-hydroxyethyl)amino]propoxy}quinazolin-4-yl)amino]-1H-pyrazol-5-yl}acetamide;

N-(3-fluorophenyl)-2-[3-({5-{[1-(2-hydroxyethyl)piperidin-4-yl]oxy}-7-[3-(4-methylpiperazin-1-yl)propoxy]quinazolin-4-yl}amino)-1H-pyrazol-5-yl]acetamide;

N-(3-fluorophenyl)-2-[5-({7-methoxy-5-[(1-methylpiperidin-4-yl)oxy]quinazolin-4-yl}amino)-1H-pyrazol-3-yl]acetamide;

N-(2,3-difluorophenyl)-2-{3-[(5,7-dimethoxyquinazolin-4-yl)amino]-1H-pyrazol-5-yl}acetamide;

2-(3-{[5,7-bis(2-methoxyethoxy)quinazolin-4-yl]amino}-1H-pyrazol-5-yl)-N-(2,3-difluorophenyl)acetamide;

N-(2,3-difluorophenyl)-2-(3-{[5-isopropoxy-7-(2-methoxyethoxy)quinazolin-4-yl]amino}-5-yl)acetamide;

N-(3-fluorophenyl)-2-(3-{[5-isopropoxy-7-(2-methoxyethoxy)quinazolin-4-yl]amino}-1H-pyrazol-5-yl)acetamide;

N-(3-fluorophenyl)-2-{3-[(5-{[1-(2-hydroxyethyl)piperidin-4-yl]oxy}-7-methoxyquinazolin-4-yl)amino]-1H-pyrazol-5-yl}acetamide;

2-{3-[(5,7-dimethoxyquinazolin-4-yl)amino]-1H-pyrazol-5-yl}-N-(3-fluorophenyl)acetamide;

2-(3-{[5,7-bis(2-methoxyethoxy)quinazolin-4-yl]amino}-1H-pyrazol-5-yl)-N-(3-fluorophenyl)acetamide;

N-(3-fluorophenyl)-3-[(7-{3-[(2-hydroxyethyl)(isobutyl)amino]propoxy}-6-methoxyquinazolin-4-yl)amino]-1H-pyrazole-5-carboxamide; and N-(2,3-difluorophenyl)-3-[(7-{3-[(2-hydroxyethyl)(isobutyl)amino]propoxy}-6-methoxyquinazolin-4-yl)amino]-1H-pyrazole-5-carboxamide.

In a further aspect of the invention, even more preferred compounds are any one of:

N-(2,3-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(2,3-difluorophenyl)-2-{3-[(7-{3-[(2,2-dimethylpropyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(propyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide;

2-{3-[(7-{3-[cyclobutyl(2-hydroxyethyl)amino]propoxy}-6-methoxyquinazolin-4-yl)amidino]-1H-pyrazol-5-yl}-N-(2,3-difluorophenyl)acetamide;

2-{3-[(7-{3-[cyclopentyl(2-hydroxyethyl)amino]propoxy}-6-methoxyquinazolin-4-yl)ammino]-1H-pyrazol-5-yl}-N-(2,3-difluorophenyl)acetamide;

N-(2,3-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide;

2-{3-[(7-{3-[(cyclopropylmethyl)(2-hydroxyethyl)amino]propoxy}-6-methoxyquinazolin-4-yl)amino]-1H-pyrazol-5-yl}-N-(2,3-difluorophenyl)acetamide;

2-{3-[(7-{3-[(cyclobutylmethyl)(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(2,2-dimethoxyethyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide;

N-(2,3-difluorophenyl)-2-[3-({7-[3-(4-hydroxypiperidin-1-yl)propoxy]-6-methoxyquinazolin-4-yl}amino)-1H-pyrazol-5-yl]acetamide;

N-(2,3-difluorophenyl)-2-{3-[(7-{3-[4-(2-hydroxyethyl)piperazin-1-yl]propoxy}-methoxyquinazolin-4-yl)amino]-1H-pyrazol-5-yl}acetamide;

N-(2,3-difluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide;

2-{3-[(7-{3-[allyl(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(1,3-dioxolan-2-ylmethyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[ethyl(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide;

N-(2,3-difluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide; and N-(2,3-difluorophenyl)-2-{3-[(7-{[(2R)-1-(2-hydroxyethyl)pyrrolidin-2-yl]methoxy}-6-methoxyquinazolin-4-yl)amino]-1H-pyrazol-5-yl}acetamide.

The present invention relates to the compounds of formula (I), formula (IA) or formula (IB) as defined herein as well as to the salts thereof. Salts for use in pharmaceutical compositions will be pharmaceutically acceptable salts, but other salts may be useful in the production of compounds of formula (I), formula (IA) or formula (IB) and their pharmaceutically acceptable salts. Suitable pharmaceutically acceptable salts of compounds of formula (I), formula (IA) or formula (IB) include acid addition salts such as methanesulphonate, fumarate, hydrochloride, hydrobromide, citrate, maleate and salts formed with phosphoric and sulphuric acid. There may be more than one cation or anion depending on the number of charged functions and the valency of the cations or anions. Where the compound of formula (I), formula (IA) or formula (IB) includes an acid functionality, salts may be base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, ethanolamine, diethanolamine or amino acids for example lysine. A preferred pharmaceutically acceptable salt is a sodium salt.

The invention also provides for an in vivo hydrolysable ester of a compound of formula (I), formula (IA) or formula (IB) containing carboxy or hydroxy group. Such an ester is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxy-carbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of formula (I), formula (IA) or formula (IB) containing a hydroxy group includes inorganic esters such as phosphate esters and $\alpha$-acyloxyalkyl ethers and related compounds which as a result of the in vivo hydrolysis of the ester breakdown to give the parent hydroxy group. Examples of $\alpha$-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides are derived from compounds of formula (I), formula (IA) or formula (IB) which have a carboxy group which is derivatised into an amide such as a N-$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

Preferred compounds of formula (I), formula (IA) or formula (IB) are those that are stable in mouse, rat, or human serum, preferably those that are stable in human serum.

Esters which are not in vivo hydrolysable may be useful as intermediates in the production of the compounds of formula (I), formula (IA) or formula (IB).

Compounds of formula (I), formula (IA) or formula (IB) may be prepared by various methods which would be apparent from the literature. For example compounds of formula (I), formula (IA) or formula (IB) where X is NH may be prepared by reacting a compound of formula (VII)

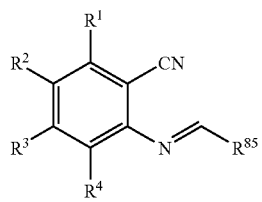

(VII)

where $R^1$, $R^2$, $R^3$, and $R^4$ are $R^1$, $R^2$, $R^3$, and $R^4$ as defined in relation to formula (I) or formula (IB) or $R^{1'}$, $R^{2'}$, $R^{3'}$, and $R^{4'}$ as defined in relation to formula (IA) and $R^{85}$ is a group $NR^{86}R^{87}$ where $R^{86}$ and $R^{87}$ are independently selected from alkyl such as methyl, with a compound of formula (VI)

 (VIII)

where $R^{5'}$ is a group $R^5$ as defined in relation to formula (I) or a group $R^{5a}$ as defined in relation to formula (IA) or a precursor group thereof; and thereafter if desired or necessary, converting a precursor group $R^{5'}$ to a group $R^5$ or $R^{5a}$ and/or modifying substituents on the group $R^5$ or $R^{5a}$. The reaction is suitably effected in an organic solvent such as an acetic acid at elevated temperatures, conveniently at the reflux temperature of the solvent.

Examples of reactions in which a precursor group $R^{5'}$ is converted to a group $R^5$ or $R^{5a}$ and/or substituents on the group $R^5$ or $R^{5a}$ are modified are standard chemical reactions, such as conversion of esters to acids, and thereafter, if required to the preferred amides. Examples of such reactions are provided hereinafter.

Compounds of formula (VII) are suitably prepared by reacting a compound of formula (IX)

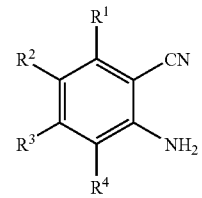

(IX)

with an appropriate acetal such as N,N-dimethylformamide dimethyl acetal. The reaction is suitably effected in an organic solvent such as benzene, at elevated temperature, conveniently at the reflux temperature of the solvent.

Alternatively compounds of formula (I), formula (IA) or formula (IB) may be prepared by reacting a compound of formula (X)

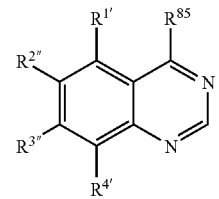

(X)

where $R^{1'}$, $R^{2''}$, $R^{3''}$, and $R^{4'}$ are equivalent to a group $R^1$, $R^2$, $R^3$ and $R^4$ as defined in relation to formula (I) or formula (IB) or $R^{1'}$, $R^{2'}$, $R^{3'}$ and $R^{4'}$ as defined in relation formula (IA) or a precursor thereof, and $R^{85}$ is a leaving group, with a compound of formula (XI)

 (XI)

where X as defined in relation to formula (I) or formula (IA) and $R^5$ is $R^5$ as defined in relation to formula (I) or $R^{5a}$ as defined in relation to formula (IA): and thereafter if desired or necessary converting a group $R^{1'}$, $R^{2''}$, $R^{3''}$ or $R^{4'}$ to a group $R^1$, $R^2$, $R^3$ and $R^4$ respectively or a group $R^{1'}$, $R^{2'}$, $R^{3'}$ and $R^{4'}$ respectively or to a different such group.

Suitable leaving groups for $R^{85}$ include halo such as chloro, mesylate and tosylate. The reaction is suitably effected in an organic solvent such as an alcohol like isopropanol, at elevated temperatures, conveniently at the reflux temperature of the solvent.

The conversion of a group $R^{1'}$, $R^{2''}$, $R^{3''}$ or $R^{4'}$ to a group $R^1$, $R^2$, $R^3$ and $R^4$ respectively or to a group $R^{1'}$, $R^{2'}$, $R^{3'}$ and $R^{4'}$ respectively or to a different such group, may be particularly useful in connection with the preparation of compounds of formula (I), formula (IA) or formula (IB) where these groups are complex in nature and examples of these preparations are provided hereinafter.

In a particular embodiment, $R^{1'}$, $R^{2''}$, $R^{3'''}$ or $R^{4'}$ are groups $R^1$, $R^2$, $R^3$ and $R^4$ respectively.

Compounds of formula (X) and (XI) are either known compounds or they can be derived from known compounds by conventional methods which would be apparent from the literature.

Alternatively, compounds of formula (I), formula (IA) or formula (IB) where X is NH may be prepared by rearranging a compound of formula (XII)

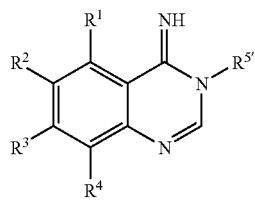

(XII)

where $R^1$, $R^2$, $R^3$ and $R^4$ are $R^1$, $R^2$, $R^3$ and $R^4$ as defined in relation to formula (I) or formula (IB) or $R^{1'}$, $R^{2'}$, $R^{3'}$ and $R^{4'}$ as defined in relation to formula (IA) and $R^{5'}$ is as defined in relation to formula (VIII) above, and thereafter if desired or necessary, converting a precursor group $R^{5'}$ to a group $R^5$ or $R^{5a}$ and/or modifying substituents on the group $R^5$ or $R^{5a}$, for example as described generally above.

The rearrangement reaction is suitably effected in an organic solvent such as an alkyl alcohol, in particular methanol, ethanol or cyclohexanol, acetic acid, or dimethylformamide, using a strong base such as sodium hydride, sodium hydroxide, sodium acetate, sodium methylate, or dimethylamine. Elevated temperatures, for example of from 20'-120° C. and preferably at about 75° C. are employed.

Compounds of formula (XII) are suitably obtained by reacting a compound of formula (XIII)

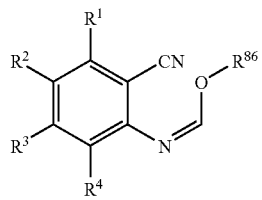

(XIII)

where $R^1$, $R^2$, $R^3$ and $R^4$ are $R^1$, $R^2$, $R^3$ and $R^4$ as defined in relation to formula (I) or formula (IB) or $R^{1'}$, $R^{2'}$, $R^{3'}$ and $R^{4'}$ as defined in relation to formula (IA) and $R^{86}$ is an alkyl group such as methyl; with a compound of formula (XV)

 (XIV)

where $R^{5'}$ is as defined in relation to formula (VIII). The reaction is suitably effected in an organic solvent such as methylene chloride, in the presence of a salt such as pyridinium hydrochloride. Moderate temperatures for example of from 0°-50° C. and conveniently ambient temperature are employed.

Compounds of formula (XIII) are suitably prepared by reacting a compound of formula (IX) as defined above, with a trialkylorthoformate such as trimethylorthoformate. The reaction is suitably effected at elevated temperature, for example of from 50° C. to 120° C., and preferably at about 100° C., in the presence of a catalytic amount of an acid such as p-toluene sulphonic acid.

Compounds of formula (IX) are either known compounds or they can be prepared by conventional methods. In particular, compounds of formula (IX) may be prepared by reduction of the corresponding nitro compound of formula (XV)

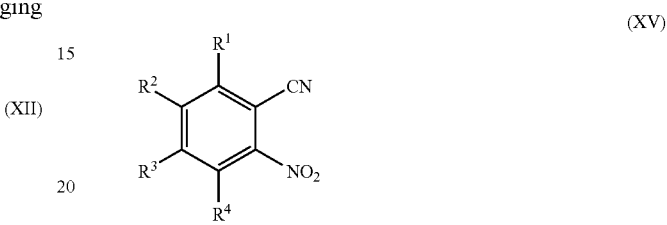

(XV)

where $R^1$, $R^2$, $R^3$ and $R^4$ are $R^1$, $R^2$, $R^3$ and $R^4$ as defined in relation to formula (I) or formula (IB) or $R^{1'}$, $R^{2'}$, $R^{3'}$ and $R^{4'}$ as defined in relation to formula (IA). Suitable reaction conditions are illustrated hereinafter.

Compounds of formula (XV) may be obtained by nitration of a compound of formula (XVI)

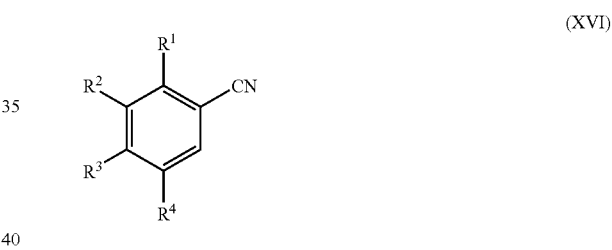

(XVI)

for example, using nitric acid as the nitrating agent. Again, suitable reaction conditions are illustrated hereinafter.

The nitrile of formula (XVI) may be derived by reaction of the corresponding formamide with hydroxylamine as illustrated hereinafter.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl. It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Compounds of formula (I) and formula (IA) are inhibitors of Aurora kinase and in particular Aurora A kinase. As a result, these compounds can be used to treat disease mediated by these agents, in particular proliferative disease.

According to a further aspect of the present invention there is provided a method for inhibiting Aurora kinase in a warm blooded animal, such as man, in need of such treatment, which comprises administering to said animal an effective amount of a compound of formula (I), formula (IA) or formula (IB), or a pharmaceutically acceptable salt, or an in vivo hydrolysable ester thereof. There is further provided a method of inhibiting Aurora-A kinase as described above and a method of inhibiting Aurora-B kinase as described above.

A further aspect of the invention relates to a method of treating a human suffering from a disease in which inhibition of Aurora kinase is beneficial, comprising the steps of administering to a person in need thereof a therapeutically effective amount of a compound of formula (I), formula (IA) or formula (IB). In particular it is envisaged that inhibition of Aurora-A kinase will be beneficial although inhibition of Aurora-B kinase may also be beneficial.

Certain compounds of formula (I) are novel and these form a further aspect of the invention. Thus the invention further comprises a compound of formula (IA)

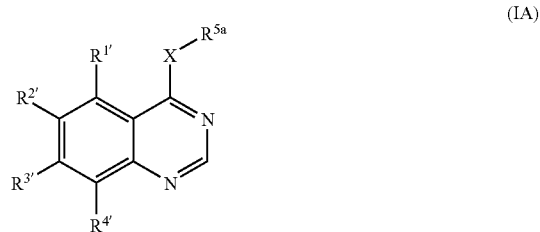

(IA)

or a salt, ester or amide thereof;
where X is as defined in relation to formula (I);
$R^{1'}$, $R^{2'}$, $R^{3'}$, $R^{4'}$ are equivalent to $R^1$, $R^2$, $R^3$, $R^4$ as defined in relation to formula (I) and $R^{5a}$ is equivalent to $R^5$ defined in relation to formula (I).

Also provided is a compound of formula (IA) or a salt, ester or amide thereof;
where X is as defined in relation to formula (I);
$R^{1'}$, $R^{2'}$, $R^{3'}$, $R^{4'}$ are equivalent to $R^1$, $R^2$, $R^3$, $R^4$ as defined in relation to formula (I); and
$R^{5a}$ is equivalent to $R^5$ as defined in relation to formula (I);
provided that one of $R^{60}$, $R^{61}$ and $R^{62}$ of $R^{5a}$ is other than hydrogen and that if $R^{61}$ is other than hydrogen, it is not a group selected from:
phenyl$C_{1-3}$alkyl, heteroaryl or optionally substituted phenyl; and
$C_{3-5}$cycloalkyl, $C_{3-5}$cycloalkyl$C_{1-3}$alkyl, $C_{2-5}$alkenyl or optionally substituted $C_{1-4}$alkyl; where optional substitutents for phenyl and $C_{1-4}$alkyl are $C_{1-4}$alkyl, halo, methoxy, nitro or trifluoromethyl.

In a particular aspect of the invention $R^{61}$ of a compound of formula (IA) is —O-J, —(CH$_2$)—O-J, —O—(CH$_2$)-J, —(CH$_2$)—O—(CH$_2$)-J, —CO-J, —(CH$_2$)—O-J, —CO—(CH$_2$)-J, —(CH$_2$)—CO—(CH$_2$)-J, —S-J, —(CH$_2$)S-J, —S—(CH$_2$)-J, —(CH$_2$)S—(CH$_2$)-J, —SO-J, —(CH$_2$)—SO-J, —SO—(CH$_2$)-J, —(CH$_2$)—SO—(CH$_2$)-J, —S—(CH$_2$)—SO$_2$-J, —SO$_2$—(CH$_2$)-J, —(CH$_2$)—SO$_2$—(CH$_2$)-J, —(NR$_1$')CO-J, —(CH$_2$)—(NR$_1$')CO-J, —(NR$_1$')CO—(CH$_2$)—(CH$_2$)—(NR$_1$')CO—(CH$_2$)-J, —(NR$_1$')SO$_2$-J, —(CH$_2$)—(NR$_1$')SO$_2$-J, —(NR$_1$')SO$_2$—(CH$_2$)-J, —(CH$_2$)(NR$_1$')SO$_2$—(CH$_2$)-J, —NR$^{64}$-J, —(CH$_2$)—NR$^{64}$-J, —NR$^{64}$—(CH$_2$)-J, —(CH$_2$)—NR$^{64}$—(CH$_2$)-J, —CONR$^{64}$-J, —(CH$_2$)—CONR$^{64}$-J, —CONR$^{64}$—(CH$_2$)-J, —(CH$_2$)—CONR$^{64}$—(CH$_2$)-J, —SO$_2$NR$^{64}$-J, —(CH$_2$)—SO$_2$NR$^{64}$-J, —SO$_2$NR$^{64}$—(CH$_2$)-J, —(CH$_2$)—SO$_2$NR$^{64}$—(CH$_2$)-J, —NR$_1$'CONH-J, —(CH$_2$)—NR$_1$'CO—NH-J, —NR$_1$'CO—NH—(CH$_2$)-J, —(CH$_2$)—NR$_1$'CO—NH—(CH$_2$)-J, —NR$_1$'CO—N(C$_{1-4}$alkyl)-J, —(CH$_2$)—NR$_1$'CO—N(C$_{1-4}$alkyl)-J, —NR$_1$'CO—N(C$_{1-4}$alkyl)-(CH$_2$)-J, —(CH$_2$)—NR$_1$'CO—N(C$_{1-4}$alkyl)-(CH$_2$)-J, —NR$_1$'CO-J, —(CH$_2$)—NR$_1$'CO-J, —NR$_1$'CO—O—(CH$_2$)-J, —(CH$_2$)—NR$_1$'CO—O—(CH$_2$)-J, —OCO-J, —CH$_2$—OC—O-J, —CH═CH-J, —CH$_2$—CH═CH-J, —CH═CH—CH$_2$-J and —CH$_2$—CH═CH—CH$_2$-J. Other aspects of the invention relating to a compound of formula (IA) are the preferred values of X, R$^1$, R$^2$, R$^3$, R$^4$ and R$^5$ as described above.

Where R$^{5a}$ is a pyrazole group, it carries a substituent of formula (k), (II) of (VI) above, (ii) that where x is NH and R$^{5a}$ is a substituted pyrazolone or tetrazolyl group, at least one of R$^{1'}$, R$^{2'}$, R$^{3'}$ and R$^{4'}$ is other than hydrogen; or (iii) that where X is O and R$^{5a}$ is 1-methyl-4-nitro-1H-imidazol-5-yl, at least one of R$^{1'}$, R$^{2'}$, R$^{3'}$ and R$^{4'}$ is other than hydrogen.]

Preferably at least one of R$^{1'}$, R$^{2'}$, R$^{3'}$ and R$^{4'}$ is other than hydrogen.

In particular, R$^{5a}$ is substituted by at least one group of formula (k), (II) of (VI) above.

Other preferred or particular groups and substitutents in formula (IA) are as set out for the equivalent groups in formula (I) above.

Additionally a compound of formula (IB) is provided:

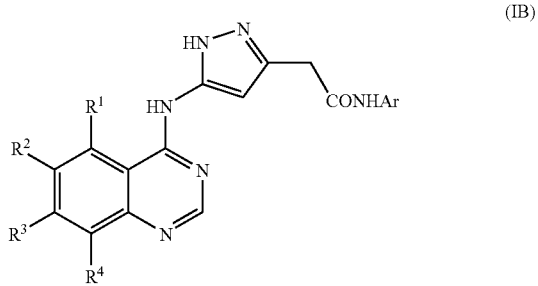

wherein R$^1$, R$^2$, R$^3$ and R$^4$ are as defined in relation to formula (I); and Ar is indazole or pyridine (optionally substituted by methyl) or aryl (optionally substituted by 1 or 2 substituents independently selected from halo, methoxy, trifluoromethyl, hydroxy, nitro, cyano and difluoromethoxy).

Preferred values of R$^1$, R$^2$, R$^3$ and R$^4$ are as described above.

Also provided is a compound of Formula (XVa):

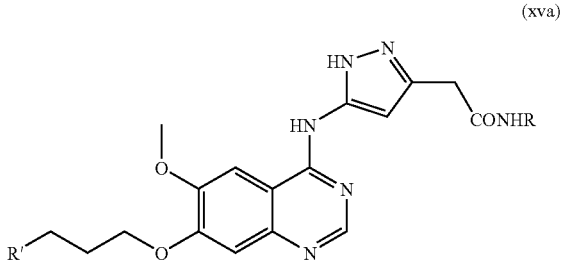

wherein R is phenyl, 3 fluorophenyl, 3,5-difluorophenyl, or 3-chlorophenyl; and R' is morpholin-4-yl, ethyl(2-hydroxyethyl)amino, (2S)-2(hydroxymethyl)pyrrolidin-1-yl, piperidin-1-yl, pyrrolidin-1-yl, (2-hydroxyethyl)amino, (2-hydroxy-1,1-dimethylethyl)amino, methyl(2-hydroxyethyl)amino, (1-(hydroxymethyl)-2-methylpropyl)amino, 4-methylpiperazin-1-yl, (2-hydroxy-1-methylethyl)amino, (4-hydroxybutyl)amino, 4-hydroxypiperidin-1-yl 2-(2-hydroxyethyl)piperidin-1-yl, 4-(2-hydroxyethyl)piperazin-1-yl, 4-(2-hydroxyethyl)piperidin-1-yl, 3-hydroxypiperidin-1-yl, (2-hydroxybutyl)amino 4-(hydroxymethyl)piperidin-1-yl, (3-hydroxy-2,2-dimethylpropyl)amino (1-(hydroxymethyl)cyclopentyl)amino, (2R)-2-(hydroxymethyl)pyrrolidin-1-yl ((2R)-2-hydroxypropyl)amino, ((2S)-2-hydroxypropyl)amino, (3R)-3-hydroxypyrrolidin-1-yl (3S)-3-hydroxypyrrolidin-1-yl, pyrrolidin-1-yl, (2-hydroxyethyl)amino, (2-hydroxy-1,1-dimethylethyl)amino, 4-methylpiperazin-1-yl, ethyl(2-hydroxyethyl)amino, 4-(2-hydroxyethyl)piperidin-1-yl, 4-(2-hydroxyethyl)piperazin-1-yl, 4-(2-hydroxyethyl)piperidin-1-yl, 3-hydroxypiperidin-1-y, (2-hydroxybutyl)amino, 4-(hydroxymethyl)piperidin-1-yl, (3-hydroxy-2,2-dimethylpropyl)amino, (2R)-2-(hydroxymethyl)pyrrolidin-1-yl, (2S)-2-(hydroxymethyl)pyrrolidin-1-yl, ((2R)-2-hydroxypropyl)amino, ((2S)-2-hydroxypropyl)amino (3R)-3-hydroxypyrrolidin-1-yl, (3S)-3-hydroxypyrrolidin-1-yl, (2S)-2-(hydroxymethyl)pyrrolidin-1-yl, 3-hydroxypiperidin-1-yl, (2R)-2-(hydroxymethyl)pyrrolidin-1-yl, or ethyl(2-hydroxyethyl)amino; or a pharmaceutically acceptable salt, ester or amide thereof.

Further provided is a compound of formula (IA) as defined herein for use as a medicament.

According to yet a further aspect of the invention there is provided a compound of the formula (IA) as defined herein, or a pharmaceutically acceptable salt or an in vivo hydrolysable ester thereof, for use in a method of treatment of the human or animal body by therapy. In particular, the compounds are used in methods of treatment of proliferative disease such as cancer and in particular cancers such as colorectal or breast cancer where Aurora-A is upregulated. The compounds are also useful in the treatment of disease where Aurora-B kinase inhibition is beneficial.

A compound of formula (IA) also has use in the preparation of a medicament for use in the inhibition of Aurora kinase and in particular a medicament for the treatment of disease where Aurora kinase inhibition is beneficial. Preferably Aurora-A kinase is inhibited but the invention also provides for such use where Aurora-B kinase is inhibited.

The invention also provides a pharmaceutical composition comprising a compound of formula (IA) as defined herein, or a pharmaceutically acceptable salt, or an in vivo hydrolysable ester thereof, in combination with a pharmaceutically acceptable carrier. Preferred or particular compounds of formula (IA) for use in the compositions of the invention are as described above in relation to preferred compounds of formula (I).

A compound of formula (IB) also has use as a medicament, use in a method of treatment of proliferative diseases and use in the preparation of a medicament for use in the inhibition of Aurora kinase whereby each use is distinct and is as described above for a compound of formula (IA).

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing or as a dispersed dosage form).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, soya bean oil, coconut oil, or preferably olive oil, or any other acceptable vehicle.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 µm or much less preferably 5 µm or less and more preferably between 5 µm and 1 µm, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insulation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the formula (I), formula (IA) or formula (IB) will naturally vary according to the nature and severity of the conditions, the age and sex of the animal or patient and the route of administration, according to well known principles of medicine. As mentioned above, compounds of the formula (I), formula (IB) or formula (IA) are useful in treating diseases or medical conditions which are due alone or in part to the effects of Aurora-A kinase and also due alone or in part to the effects of Aurora-B kinase.

In using a compound of the formula (I), formula (IA) or formula (IB) for therapeutic or prophylactic purposes it will generally be administered so that a daily dose in the range, for example, 0.5 mg to 75 mg per kg body weight is received and but a range of 0.1 mg to 75 mg may also be required, given if required in divided doses. In general lower doses will be administered when a parenteral route is employed. Thus, for example, for intravenous administration, a dose in the range, for example, 0.5 mg to 30 mg per kg body weight will generally be used but a range of 0.1 mg to 25 mg may be required. Similarly, for administration by inhalation, a dose in the range, for example, 0.5 mg to 25 mg per kg body weight will be used.

A further aspect of the invention comprises a compound of formula (I), formula (IA) or formula (IB) as defined above, or a pharmaceutically acceptable salt or in vivo hydrolysable ester thereof, for use in the preparation of a medicament for the treatment of proliferative disease. Preferred compounds of formula (I), formula (IA) or formula (IB) for this purpose are as described above.

In addition to their use in therapeutic medicine, a compound of formula (I) or formula (IA) and the pharmaceutically acceptable salt is also useful as pharmacological tool in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

The treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), anti androgens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finastertde;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine-threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

As stated hereinbefore the compounds of the invention inhibit the serine-threonine kinase activity of Aurora kinase and in particular of Aurora-A kinase and/or Aurora-B kinase and thus inhibit the cell cycle and cell proliferation. These properties may be assessed, for example, using one or more of the procedures set out below:

(a) In Vitro Aurora-A Kinase Inhibition Test

This assay determines the ability of a test compound to inhibit serine-threonine kinase activity. DNA encoding Aurora-A may be obtained by total gene synthesis or by cloning. This DNA may then be expressed in a suitable expression system to obtain polypeptide with serine-threonine kinase activity. In the case of Aurora-A, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamHI 5' to the Aurora-A coding sequence. This allowed the insertion of the Aurora-A gene in frame with the 6 histidine residues, spacer region and rTEV protease cleavage site encoded by the pFastBac HTc vector. The 3' PCR primer replaced the Aurora-A stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged Aurora-A protein. Details of the methods for the assembly of recombinant DNA molecules can be found in standard texts, for example Sambrook et al. 1989, Molecular Cloning—A Laboratory Manual, 2$^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the Aurora-A gene was transformed into E. coli DH10Bac cells containing the baculovirus genome (bacmid DNA) and via a transposition event in the cells, a region of the pFastBac vector containing gentamycin resistance gene and the Aurora-A gene including the baculovirus polyhedrin promoter was transposed directly into the bacmid DNA. By selection on gentamycin, kanamycin, tetracycline and X-gal, resultant white colonies should contain recombinant bacmid DNA encoding Aurora-A. Bacmid DNA was extracted from a small scale culture of several BH10Bac white colonies and transfected into *Spodoptera frugiperda* Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing 1×10$^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant Aurora-A protein.

For the large scale expression of Aurora-A kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached 1.2×10$^6$ cells ml$^{-1}$ they were infected with plaque-pure Aurora-A recombinant virus at a multiplicity of infection of 1 and harvested 48 hours later. All subsequent purification steps were performed at 4° C. Frozen insect cell pellets containing a total of 2.0×10$^8$ cells were thawed and diluted with lysis buffer (25 mM HEPES (N-[2-hydroxy-ethyl]piperazine-N'-[2-ethanesulphonic acid]) pH7.4 at 4° C. 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 µg/ml aprotinin, 1 µg/ml pepstatin, 1 µg/ml leupeptin), using 1.0 ml per 3×10$^7$ cells. Lysis was achieved using a dounce homogeniser, following which the lysate was centrifuged at 41,000 g for 35 minutes. Aspirated supernatant was pumped onto a 5 mm diameter chromatography column containing 500 µl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound Aurora-A protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active Aurora-A kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of Aurora-A enzyme was titrated in the assay by dilution with enzyme diluent (25 mM Tris-HCl pH7.5, 12.5 mM KCl, 0.6 mM DTT). For a typical batch, stock enzyme is diluted 1 in 666 with enzyme diluent & 20 µl of dilute enzyme is used for each assay well. Test compounds (at 10 mM in dimethylsulphoxide (DMSO) were diluted with water & 10 µl of diluted compound was transferred to wells in the assay plates. "Total" & "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4 mM KCl, 2.5 mM NaF, 0.6 mM dithiothreitol, 6.25 mM MnCl$_2$, 6.25 mM ATP, 7.5 µM peptide substrate [biotin-LRRWSLGLRRWSLGLRRWSLGL-RRWSLG]) containing 0.2 µCi [γ$^{33}$P]ATP (Amersham Pharmacia, specific activity ≧2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity.

In this test, the compounds of the invention give 50% inhibition of enzyme activity at concentrations of 0.0001 µM to 1.5 µM and in particular compound 8 in Table 3 gave 50% inhibition of enzyme activity at a concentration of 0.01 µM and compound 13 in Table 3 gave 50% inhibition of enzyme activity at a concentration of 0.001 μM.

(b) In Vitro Aurora-B Kinase Inhibition Test

This assay determines the ability of a test compound to inhibit serine-threonine kinase activity. DNA encoding Aurora-B may be obtained by total gene synthesis or by cloning. This DNA may then be expressed in a suitable expression system to obtain polypeptide with serine-threonine kinase activity. In the case of Aurora-B, the coding sequence was isolated from cDNA by polymerase chain reaction (PCR) and cloned into the pFastBac system in a manner similar to that described above for Aurora-A (i.e. to direct expression of a 6-histidine tagged Aurora-B protein).

For the large scale expression of Aurora-B kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells $ml^{-1}$ they were infected with plaque-pure Aurora-B recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (50 mM HEPES (N-[2-hydroxyethyl]piperazine-N'-[2-ethanesulphonic acid]) pH7.5 at 4° C., 1 mM $Na_3VO_4$, 1 mM PMSF (phenylmethylsulphonyl fluoride), 1 mM dithiothreitol, 1 μg/ml aprotinin, 1 μg/ml pepstatin, 1 μg/ml leupeptin), using 1.0 ml per $2 \times 10^7$ cells. Lysis was achieved using a sonication homogeniser, following which the lysate was centrifuged at 41,000 g for 35 minutes. Aspirated supernatant was pumped onto a 5 mm diameter chromatography column containing 1.0 ml CM sepharose Fast Flow (Amersham Pharmacia Biotech) which had been equilibrated in lysis buffer. A baseline level of UV absorbance for the eluent was reached after washing the column with 12 ml of lysis buffer followed by 7 ml of wash buffer (50 mM HEPES pH7.4 at 4° C., 1 mM dithiothreitol). Bound Aurora-B B protein was eluted from the column using a gradient of elution buffer (50 mM HEPES pH7.4 at 4° C., 0.6 M NaCl, 1 mM dithiothreitol, running from 0% elution buffer to 100% elution buffer over 15 minutes at a flowrate of 0.5 ml/min). Elution fractions (1.0 ml) corresponding to the peak in UV absorbance was collected. Elution fractions were dialysed exhaustively against dialysis buffer (25 mM HEPES pH7.4 at 4° C., 45% glycerol (v/v), 100 mM KCl, 0.05% (v/v) IGEPAL CA630 (Sigma Aldrich), 1 mM dithiothreitol). Dialysed fractions were assayed for Aurora-B kinase activity.

Each new batch of Aurora-B enzyme was titrated in the assay by dilution with enzyme diluent (25 mM Tris-HCl pH7.5, 12.5 mM KCl, 0.6 mM DTT). For a typical batch, stock enzyme is diluted 1 in 40 with enzyme diluent & 20 μl of dilute enzyme is used for each assay well. Test compounds (at 10 mM in dimethylsulphoxide (DMSO)) were diluted with water & 10 μl of diluted compound was transferred to wells in the assay plates. "Total" & "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4 mM KCl, 2.5 mM NaF, 0.6 mM dithiothreitol, 6.25 mM $MnCl_2$, 37.5 mM ATP, 25 μM peptide substrate [biotin-LRRWSLGLRRWSLGLRRWSLGLRRWSLG]) containing 0.2 μCi $[\gamma^{33}P]ATP$ (Amersham Pharmacia, specific activity $\geq$2500 Ci/mmol) was then added to all test wells to start the reaction. The plates were incubated at room temperature for 60 minutes. To stop the reaction 100 μl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}P$ with a Beta plate counter. "Blank" (no enzyme) and "total" (no compound) control values were used to determine the dilution range of test compound which gave 50% inhibition of enzyme activity.

(c) In Vitro Cell Proliferation Assay

This and other assays can be used to determine the ability of a test compound to inhibit the growth of adherent mammalian cell lines, for example the human tumour cell line SW620 (ATCC CCL-227). This assay determines the ability of at test compound to inhibit the incorporation of the thymidine analogue, 5'-bromo-2'-deoxy-uridine (BrdU) into cellular DNA. SW620 or other adherent cells were typically seeded at $1 \times 10^5$ cells per well in L-15 media (GIBCO) plus 5% foetal calf serum, 1% L-glutamine (100 μl/well) in 96 well tissue culture treated 96 well plates (Costar) and allowed to adhere overnight. The following day the cells were dosed with compound (diluted from 10 mM stock in DMSO using L-15 (with 5% FCS, 1% L-glutamine). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 μl of BrdU labelling reagent (diluted 1:100 in media—L-15, 5% FCS, 1% L-glutamine) was added to each well and the plate returned to a humidified (+5% $CO_2$) 37° C. incubator for 2 hours. After 2 hours the labelling reagent was removed by decanting and tapping the plate on a paper towel. FixDenat solution (50 μl per well) was added and the plates incubated at room temperature for 45 mins with shaking. The FixDenat solution was removed by decanting and tapping the inverted plate on a paper towel. The plate was then washed once with phosphate buffered saline (PBS) and 100 μl/well of Anti-BrdU-POD antibody solution (diluted 1:100 in antibody dilution buffer) added. The plate was then incubated at room temperature with shaking for 90 min. Unbound Anti-BrdU-POD antibody was removed by decanting and washing the plate 4 times with PBS before being blotted dry. TMB substrate solution was added (100 μl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. The compounds of the invention are active at 0.001 μM to 10 μM in this test and in particular compound 8 in table 3 was active at 0.086 μM and compound 13 in table 3 was active at 0.079 μM.

(d) In Vitro Cell Cycle Analysis Assay

This assay determines the ability of a test compound to arrest cells in specific phases of the cell cycle. Many different mammalian cell lines could be used in this assay and SW620 cells are included here as an example. SW620 cells were seeded at $7 \times 10^5$ cells per T25 flask (Costar) in 5 ml L-15 (5% FCS, 1% L-glutamine). Flasks were then incubated overnight in a humidified 37° C. incubator with 5% $CO_2$. The following day, 5 μl of L-15 (5% FCS, 1% L-glutamine) carrying the appropriate concentration of test compound solubilised in DMSO was added to the flask. A no compound control treatments was also included (0.5% DMSO). The cells were then incubated for a defined time (24 hours) with compound. After this time the media was aspirated from the cells and they were washed with 5 ml of prewarmed (37° C.) sterile PBSA, then detached from the flask by brief incubation with trypsin and followed by resuspension in 5 ml of 1% Bovine Serum Albumin (BSA, Sigma-Aldrich Co.) in sterile PBSA. The samples were then centrifuged at 2200 rpm for 10 min. The supernatant was aspirated to leave 200 μl of the PBS/BSA solution. The pellet was resuspended in this 200 μl of solution by pipetting 10 times to create a single cell suspension. One ml of ice-cold 80% ethanol was slowly added to each cell suspension and the samples stored at −20° C. overnight or until required for staining. Cells were pelleted by centrifugation, ethanol aspirated off and pellets resuspended in 200 μl PBS containing 100 μg/ml RNAse (Sigma Aldrich) & 10 μg/ml propidium Iodide (Sigma Aldrich). Cell suspensions were incubated at 37° C. for 30 min, a further 200 μl PBS added and samples stored in the dark at 4° C. overnight.

Each sample was then syringed 10 times using 21-guage needle. The samples were then transferred to LPS tubes and DNA content per cell analysed by Fluorescence activated cell sorting (FACS) using a FACScan flow cytometer (Becton Dickinson). Typically 30,000 events were counted and recorded using CellQuest v1.1 software (Verity Software). Cell cycle distribution of the population was calculated using Modfit software (Verity Software) and expressed as percentage of cells with 2N (G0/G1), 2N-4N(S phase) and with 4N (G2/M) DNA content.

The following Scheme illustrates the general method for making compounds of the present invention.

Scheme 1

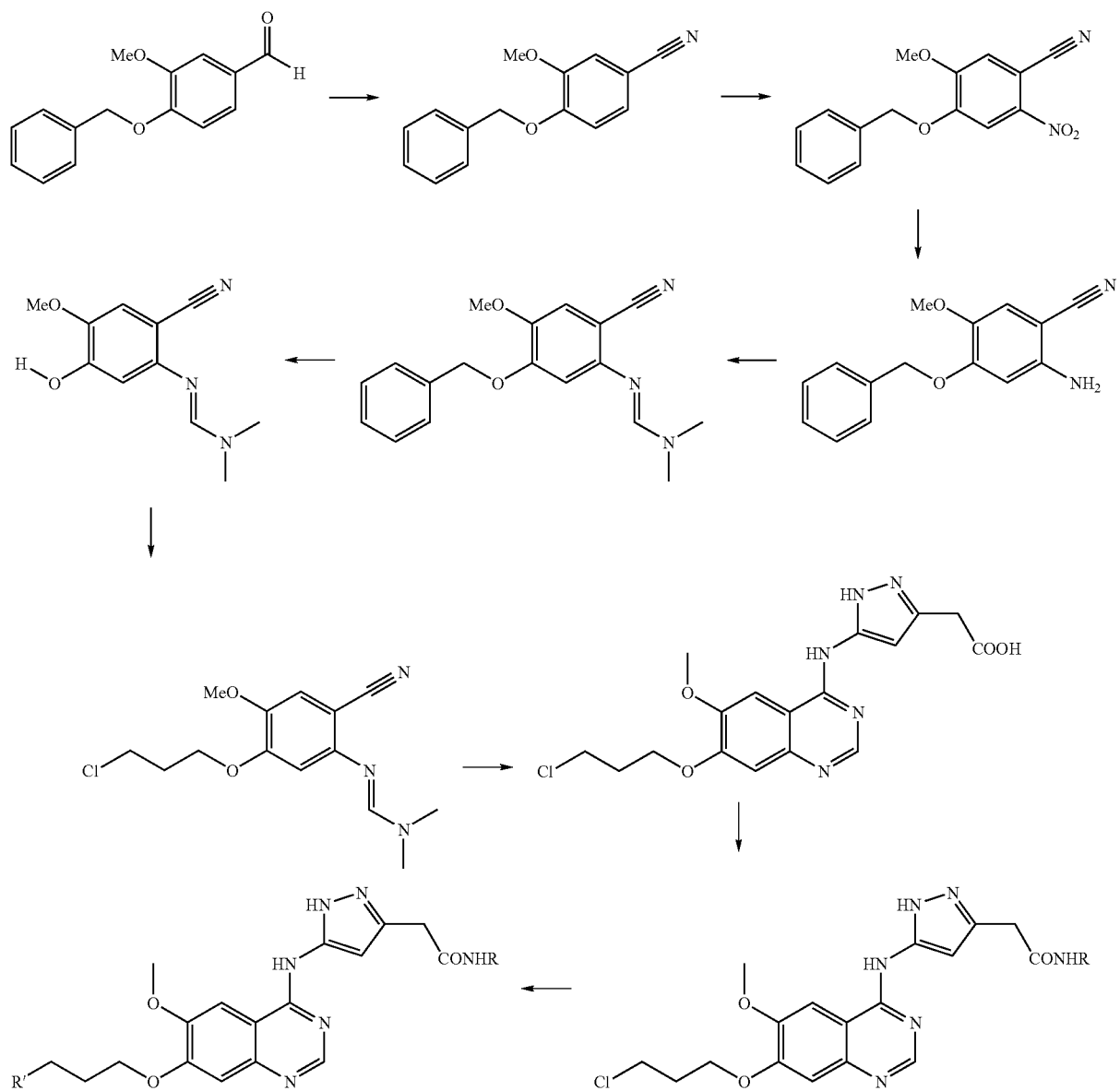

Scheme 2

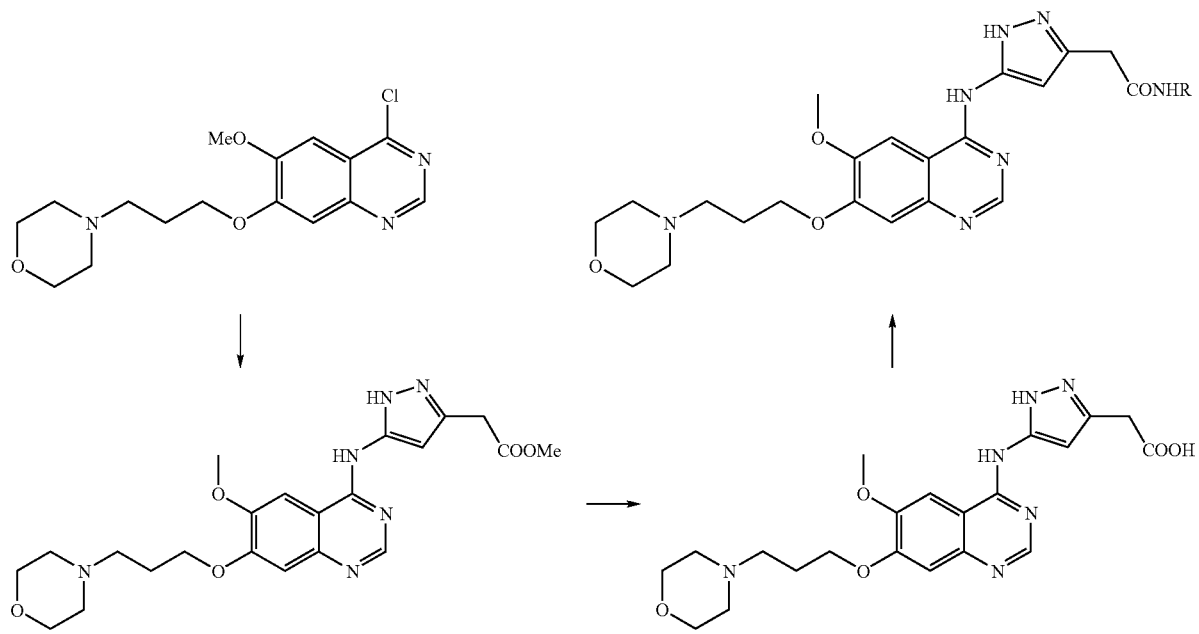

The invention will now be illustrated in the following non limiting examples, in which standard techniques known to the skilled chemist and techniques analogous to those described in these examples may be used where appropriate, and in which, unless otherwise stated:

(i) evaporations were carried out by rotary evaporation in vacuo and work up procedures were carried out after removal of residual solids such as drying agents by filtration;
(ii) operations were carried out at ambient temperature, typically in the range 18-25° C. and in air unless stated, or unless the skilled person would otherwise operate under an atmosphere of an inert gas such as argon;
(iii) column chromatography (by the flash procedure) and medium pressure liquid chromatography (MPLC) were performed on Merck Kieselgel silica (Art. 9385);
(iv) yields are given for illustration only and are not necessarily the maximum attainable;
(v) the structures of the end products of the formula (I) were generally confirmed by nuclear (generally proton) magnetic resonance (NMR) and mass spectral techniques; proton magnetic resonance chemical shift values were measured in deuterated dimethyl sulphoxide (DMSO $d_6$) (unless otherwise stated) on the delta scale (ppm downfield from tetramethylsilane) using one of the following four instruments
   Varian Gemini 2000 spectrometer operating at a field strength of 300 MHz
   Bruker DPX[300] spectrometer operating at a field strength of 300 MHz
   JEOL EX 400 spectrometer operating at a field strength of 400 MHz
   Bruker Avance 500 spectrometer operating at a field strength of 500 MHz.
   Peak multiplicities are shown as follows: s, singlet; d, doublet; dd, double doublet; t, triplet; q, quartet; qu, quintet; m, multiplet; br s, broad singlet;
(vi) robotic synthesis was carried out using a Zymate XP robot, with solution additions via a Zymate Master Laboratory Station and stirred via a Stem RS5000 Reacto-Station at 25° C.;
(vii) work up and purification of reaction mixtures from robotic synthesis was carried out as follows: evaporations were carried out in vacuo using a Genevac HT 4; column chromatography was performed using either an Anachem Sympur MPLC system on silica using 27 mm diameter columns filled with Merck silica (60 µm, 25 g); the structures of the final products were confirmed by LCMS on a Waters 2890/ZMD micromass system using the following and are quoted as retention time (RT) in minutes:
Column: waters symmetry C18 3.5 µm 4.6×50 mm
Solvent A: $H_2O$
Solvent B: $CH_3CN$
Solvent C: MeOH+5% HCOOH
Flow rate: 2.5 ml/min
Run time: 5 minutes with a 4.5 minute gradient from 0-100% C
Wavelength: 254 nm, bandwidth 10 nm
Mass detector: ZMD micromass
Injection volume 0.005 ml
(viii) Analytical LCMS for compounds which had not been prepared by robotic synthesis was performed on a Waters Alliance HT system using the following and are quoted as retention time (RT) in minutes:
Column: 2.0 mm×5 cm Phenomenex Max-RP 80A
Solvent A: Water
Solvent B: Acetonitrile Solvent C: Methanol/1% formic acid or Water/1% formic acid
Flow rate: 1.1 ml/min
Run time: 5 minutes with a 4.5 minute gradient from 0-95% B+constant 5% solvent C
Wavelength: 254 nm, bandwidth 10 nm
Injection volume 0.005 ml
Mass detector: Micromass ZMD
(ix) Preparative high performance liquid chromatography (HPLC) was performed on either
  Waters preparative LCMS instrument, with retention time (RT) measured in minutes:
Column: β-basic Hypercil (21×100 mm) 5 μm
Solvent A: Water/0.1% Ammonium carbonate
Solvent B: Acetonitrile
Flow rate: 25 ml/min
Run time: 10 minutes with a 7.5 minute gradient from 0-100% B
Wavelength: 0.254 nm, bandwidth 10 nm
Injection volume 1-1.5 ml
Mass detector: Micromass ZMD
  Gilson preparative HPLC instrument, with retention time (RT) measured in minutes:
Column: 21 mm×15 cm Phenomenex Luna2 C18
Solvent A: Water+0.1% trifluoracetic acid,
Solvent B: Acetonitrile+0.1% trifluoracetic acid
Flow rate: 21 ml min
Run time: 20 minutes with various 10 minute gradients from 5-100% B Wavelength: 254 nm, bandwidth 10 nm
Injection volume 0.1-4.0 ml (x) intermediates were not generally fully characterised and purity was assessed by thin layer chromatography (TLC), HPLC, infra-red (IR), MS or NMR analysis.

TABLE 1

(xvii)

| Compound | X |
| --- | --- |
| 1 | phenyl |
| 2 | 3-fluorophenyl |

TABLE 2

(xviii)

| Compound | X |
| --- | --- |
| 3 | 3-fluorophenyl |
| 4 | 3,5-difluorophenyl |
| 5 | 2,3-difluorophenyl |
| 6 | 3-chlorophenyl |

TABLE 3

(xix)

| Compound | X | Y |
| --- | --- | --- |
| 7 | 3-fluorophenyl | 3-[ethyl(2-hydroxyethyl)amino]propoxy |
| 8 | 3-fluorophenyl | 3-[(2S)-2-(hydroxymethyl)pyrrolidin-1-yl]propoxy |
| 9 | 3-fluorophenyl | 3-piperidin-1-ylpropoxy |
| 10 | 3-fluorophenyl | 3-pyrrolidin-1-ylpropoxy |
| 11 | 3-fluorophenyl | 3-[(2-hydroxyethyl)amino]propoxy |
| 12 | 3-fluorophenyl | 3-[(2-hydroxy-1,1-dimethylethyl)amino]propoxy |
| 13 | 3-fluorophenyl | 3-[(2-hydroxyethyl)(methyl)amino]propoxy |
| 14 | 3-fluorophenyl | 3-([1-(hydroxymethyl)-2-methylpropyl]amino)propoxy |
| 15 | 3-fluorophenyl | 3-(4-methylpiperazin-1-yl)propoxy |
| 16 | 3-fluorophenyl | 3-[(2-hydroxy-1-methylethyl)amino)propoxy |
| 17 | 3-fluorophenyl | 3-[(4-hydroxybutyl)amino]propoxy |
| 18 | 3-fluorophenyl | 3-(4-hydroxypiperidin-1-yl)propoxy |
| 19 | 3-fluorophenyl | 3-[2-(2-hydroxyethyl)piperidin-1-yl]propoxy |
| 20 | 3-fluorophenyl | 3-[4-(2-hydroxyethyl)piperazin-1-yl]propoxy |
| 21 | 3-fluorophenyl | 3-[4-(2-hydroxyethyl)piperidin-1-y]propoxy} |
| 22 | 3-fluorophenyl | 3-(3-hydroxypiperidin-1-yl)propoxy] |

TABLE 3-continued (xix)

| Compound | X | Y |
| --- | --- | --- |
| 23 | 3-fluorophenyl | 3-[(2-hydroxybutyl)amino]propoxy |
| 24 | 3-fluorophenyl | 3-[4-(hydroxymethyl)piperidin-1-yl]propoxy |
| 25 | 3-fluorophenyl | 3-[(3-hydroxy-2,2-dimethylpropyl)amino]propoxy |
| 26 | 3-fluorophenyl | 3-{[1-(hydroxymethyl)cyclopentyl]amino}propoxy |
| 27 | 3-fluorophenyl | 3-[(2R)-2-(hydroxymethyl)pyrrolidin-1-yl]propoxy |
| 28 | 3-fluorophenyl | 3-{[(2S)-2-hydroxypropyl]amino}propoxy |
| 29 | 3-fluorophenyl | 3-{[(2R)-2-hydroxypropyl]amino}propoxy |
| 30 | 3-fluorophenyl | 3-[(3S)-3-hydroxypyrrolidin-1-yl]propoxy |
| 31 | 3-fluorophenyl | 3-[(3R)-3-hydroxypyrrolidin-1-yl]propoxy |
| 32 | 3-fluorophenyl | 3-[(2-fluoroethyl)(2-hydroxyethyl)amino]propoxy |
| 33 | 3-fluorophenyl | 2-[1-(2-hydroxyethyl)piperidin-4-yl]ethoxy |
| 34 | 3-fluorophenyl | 3-[(2-hydroxyethyl)(propyl)amino]propoxy |
| 35 | 3-fluorophenyl | 3-[(2-hydroxyethyl)(isopropyl)amino]propoxy |
| 36 | 3-fluorophenyl | 3-[(2-hydroxyethyl)(isobutyl)amino]propoxy |
| 37 | 3-fluorophenyl | 3-[(2,2-dimethylpropyl)(2-hydroxyethyl)amino]propoxy |
| 38 | 3-fluorophenyl | 3-[allyl(2-hydroxyethyl)amino]propoxy |
| 39 | 3-fluorophenyl | 3-[(2-hydroxyethyl)(prop-2-yn-1-yl)amino]propoxy |
| 40 | 3-fluorophenyl | 3-[cyclopropyl(2-hydroxyethyl)amino]propoxy |
| 41 | 3-fluorophenyl | 3-[(cyclopropylmethyl)(2-hydroxyethyl)amino]propoxy |
| 42 | 3-fluorophenyl | 3-[cyclobutyl(2-hydroxyethyl)amino]propoxy |
| 43 | 3-fluorophenyl | 3-[cyclopentyl(2-hydroxyethyl)amino]propoxy |
| 44 | 3-fluorophenyl | 3-[(2,2-dimethoxyethyl)(2-hydroxyethyl)amino]propoxy |
| 45 | 3-fluorophenyl | 3-[(2,2-difluoroethyl)(2-hydroxyethyl)amino]propoxy |
| 46 | 3-fluorophenyl | 3-[(2-hydroxyethyl)(3,3,3-trifluoropropyl)amino]propoxy |
| 47 | 3-fluorophenyl | 3-[(cyclobutylmethyl)(2-hydroxyethyl)amino]propoxy |
| 48 | 3-fluorophenyl | 3-[(2-hydroxyethyl)(2-methoxyethyl)amino]propoxy |
| 49 | 3-fluorophenyl | 3-[(1,3-dioxolan-2-ylmethyl)(2-hydroxyethyl)amino]propoxy |
| 50 | 3-fluorophenyl | 4-chlorobutoxy |
| 51 | 3-fluorophenyl | 4-(2R)-2-(hydroxymethyl)pyrrolidin-1-yl]butoxy |
| 52 | 3-fluorophenyl | 4-[(2-hydroxyethyl)(isobutyl)amino]butoxy |
| 53 | 3-fluorophenyl | (2R)-1-(2-terr-butoxyethyl)pyrrolidin-2-yl]methoxy |
| 54 | 3-fluorophenyl | (2R)-1-(2-hydroxyethyl)pyrrolidin-2-yl]methoxy |
| 55 | 3,5-difluorophenyl | 3-pyrrolidin-1-ylpropoxy |
| 56 | 3,5-difluorophenyl | 3-[(2-hydroxyethyl)amino]propoxy |
| 57 | 3,5-difluorophenyl | 3-[(2-hydroxy-1,1-dimethylethyl)amino]propoxy |
| 58 | 3,5-difluorophenyl | 3-(4-methylpiperazin-1-yl)propoxy |
| 59 | 3,5-difluorophenyl | 3-[ethyl(2-hydroxyethyl)amino]propoxy |
| 60 | 3,5-difluorophenyl | 3-[2-(2-hydroxyethyl)piperidin-1-yl]propoxy |
| 61 | 3,5-difluorophenyl | 3-[4-(2-hydroxyethyl)piperazin-1-yl]propoxy |
| 62 | 3,5-difluorophenyl | 3-[4-(2-hydroxyethyl)piperidin-1-yl]propoxy |
| 63 | 3,5-difluorophenyl | 3-(3-hydroxypiperidin-1-yl)propoxy |
| 64 | 3,5-difluorophenyl | 3-[(2-hydroxybutyl)amino]propoxy |
| 65 | 3,5-difluorophenyl | 3-[4-(hydroxymethyl)piperidin-1-yl]propoxy |
| 66 | 3,5-difluorophenyl | 3-[(3-hydroxy-2,2-dimethylpropyl)amino]propoxy |
| 67 | 3,5-difluorophenyl | 3-[(2R)-2-(hydroxymethyl)pyrrolidin-1-yl]propoxy |
| 68 | 3,5-ditluorophenyl | 3-[(2S)-2-(hydroxymethyl)pyrrolidin-1-yl]propoxy |
| 69 | 3,5-difluorophenyl | 3-{[(2S)-2-hydroxypropyl]amino}propoxy |
| 70 | 3,5-difluorophenyl | 3-{[(2R)-2-hydroxypropyl]amino}propoxy |
| 71 | 3,5-difluorophenyl | 3-[(3S)-3-hydroxypyrrolidin-1-yl]propoxy |
| 72 | 3,5-difluorophenyl | 3-[(3R)-3-hydroxypyrrolidin-1-yl]propoxy |
| 73 | 3,5-difluorophenyl | 3-[(2-hydroxyethyl)(isobutyl)amino]propoxy |
| 74 | 3,5-difluorophenyl | 3-[(2-hydroxyethyl)(propyl)amino]propoxy |
| 75 | 3,5-difluorophenyl | 3-[allyl(2-hydroxyethyl)amino]propoxy |
| 76 | 3,5-difluorophenyl | 3-[(2-hydroxyethyl)(prop-2-yn-1-yl)amino]propoxy |
| 77 | 3,5-difluorophenyl | 3-[(2-hydroxyethyl)(isopropyl)amino]propoxy |
| 78 | 3,5-difluorophenyl | 3-[(2,2-dimethylpropyl)(2-hydroxyethyl)amino]propoxy |

TABLE 3-continued

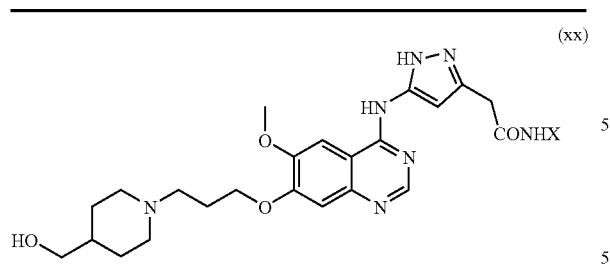

(xix)

| Compound | X | Y |
|---|---|---|
| 79 | 3,5-difluorophenyl | 3-[cyclobutyl(2-hydroxyethyl)amino]propoxy |
| 80 | 3,5-difluorophenyl | 3-[(cyclopropylmethyl)(2-hydroxyethyl)amino]propoxy |
| 81 | 2,3-difluorophenyl | 3-[(2S)-2-(hydroxymethyl)pyrrolidin-1-yl]propoxy |
| 82 | 2,3-difluorophenyl | 3-[(2,2-dimethylpropyl)(2-hydroxyethyl)amino]propoxy |
| 83 | 2,3-difluorophenyl | 3-[(2-hydroxyethyl)(propyl)amino]propoxy |
| 84 | 2,3-difluorophenyl | 3-[(2-hydroxyethyl)(isobutyl)amino]propoxy |
| 85 | 2,3-difluorophenyl | 3-[cyclobutyl(2-hydroxyethyl)amino]propoxy |
| 86 | 2,3-difluorophenyl | 3-[cyclopentyl(2-hydroxyethyl)amino]propoxy |
| 87 | 2,3-difluorophenyl | 3-[(2R)-2-(hydroxymethyl)pyrrolidin-1-yl]propoxy |
| 88 | 2,3-difluorophenyl | 3-[(2-hydroxyethyl)(prop-2-yn-1-yl)amino]propoxy |
| 89 | 2,3-difluorophenyl | 3-[(cyclopropylmethyl)(2-hydroxyethyl)amino]propoxy |
| 90 | 2,3-difluorophenyl | 3-[(cyclobutylmethyl)(2-hydroxyethyl)amino]propoxy |
| 91 | 2,3-difluorophenyl | 3-[(2,2-dimethoxyethyl)(2-hydroxyethyl)amino]propoxy |
| 92 | 2,3-difluorophenyl | 3-[4-(2-hydroxyethyl)piperidin-1-yl]propoxy |
| 93 | 2,3-difluorophenyl | 3-(4-hydroxypiperidin-1-yl)propoxy |
| 94 | 2,3-difluorophenyl | 3-[4-(2-hydroxyethyl)piperazin-1-yl]propoxy |
| 95 | 2,3-difluorophenyl | 3-[(2-hydroxyethyl)(2-methoxyethyl)amino]propoxy |
| 96 | 2,3-difluorophenyl | 3-[allyl(2-hydroxyethyl)amino]propoxy |
| 97 | 2,3-difluorophenyl | 3-[(1,3-dioxolan-2-ylmethyl)(2-hydroxyethyl)amino]propoxy |
| 98 | 2,3-difluorophenyl | 3-[ethyl(2-hydroxyethyl)amino]propoxy |
| 99 | 2,3-difluorophenyl | 3-[(2-hydroxyethyl)(isopropyl)amino]propoxy |
| 100 | 2,3-difluorophenyl | 3-[(2-hydroxy-1,1-dimethylethyl)amino]propoxy |
| 101 | 2,3-difluorophenyl | (2R)-1-(2-hydroxyethyl)pyrrolidin-2-yl]methoxy |
| 102 | 3-chlorophenyl | 3-[(2S)-2-(hydroxymethyl)pyrrolidin-1-yl]propoxy |
| 103 | 3-chlorophenyl | 3-[(2R)-2-(hydroxymethyl)pyrrolidin-1-yl]propoxy |
| 104 | 3-chlorophenyl | 3-(3-hydroxypiperidin-1-yl)propoxy |
| 105 | 3-chlorophenyl | 3-[ethyl(2-hydroxyethyl)amino]propoxy |

TABLE 4

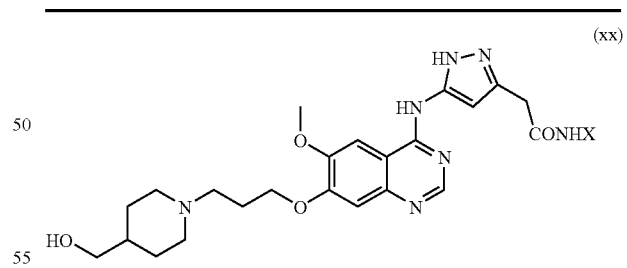

(xx)

| Compound | X |
|---|---|
| 106 | 3-methoxyphenyl |
| 107 | phenyl |
| 108 | 4-fluorophenyl |
| 109 | 3,5-dichlorophenyl |
| 110 | 2-methoxy-5-chlorophenyl |
| 111 | 3-(trifluoromethyl)phenyl |
| 112 | 3-hydroxyphenyl |
| 113 | 3-nitrophenyl |
| 114 | 5-indazolyl |
| 115 | 2-fluoro-4-bromophenyl |
| 116 | 3-chlorophenyl |
| 117 | 2-fluorophenyl |
| 118 | 3,5-dimethoxyphenyl |
| 119 | 6-(3-picolinyl) |
| 120 | 2,3-difluorophenyl |
| 121 | 2-fluoro-3-chlorophenyl |
| 122 | 2,5-difluorophenyl |
| 123 | 2-fluoro-5-(trifluoromethyl)phenyl |
| 124 | 3,4-difluorophenyl |
| 125 | 2,4-difluorophenyl |
| 126 | 3-chloro-4-fluorophenyl |

TABLE 4-continued (xx)

| Compound | X |
|---|---|
| 127 | 2-(difluoromethoxy)phenyl |
| 128 | 3-cyanophenyl |
| 129 | 3-bromophenyl |

TABLE 5

(xxi)

| Compound | R | Y |
|---|---|---|
| 130 | 2,3-difluorophenyl | 3-[ethyl(2-hydroxyethyl)amino]propoxy |
| 131 | 2,3-difluorophenyl | 3-[isopropyl(2-hydroxyethyl)amino]propoxy |
| 132 | 2,3-difluorophenyl | 3-[(2R)-2-(hydroxymethyl)pyrrolidin-1-yl]propoxy |
| 133 | 2,3-difluorophenyl | 3-[propyl(2-hydroxyethyl)amino]propoxy |
| 134 | 2,3-difluorophenyl | 3-[propargyl(2-hydroxyethyl)amino]propoxy |
| 135 | 2,3-difluorophenyl | 3-[isobutyl(2-hydroxyethyl)amino]propoxy |
| 136 | 2,3-difluorophenyl | 3-[neopentyl(2-hydroxyethyl)amino]propoxy |

TABLE 6

(xxii)

| Compound | R | Y | Z |
|---|---|---|---|
| 137 | 3-fluorophenyl | 3-(4-methylpiperazin-1-yl)propoxy | (1-(2-hydroxyethyl)-piperidin-4-yl)oxy |
| 138 | 3-fluorophenyl | methoxy | (1-methyl-piperidin-4-yl)oxy |
| 139 | 2,3-difluorophenyl | methoxy | methoxy |
| 140 | 2,3-difluorophenyl | 2-methoxyethoxy | 2-methoxyethoxy |
| 141 | 2,3-difluorophenyl | 2-methoxyethoxy | isopropoxy |
| 142 | 3-fluorophenyl | 2-methoxyethoxy | isopropoxy. |
| 143 | 3-fluorophenyl | methoxy | (1-methyl-piperidin-4-yl)oxy |
| 144 | 3-fluorophenyl | methoxy | methoxy |
| 145 | 3-fluorophenyl | 2-methoxyethoxy | 2-methoxyethoxy |

TABLE 7

(xxiii)

| Compound | X | Y |
|---|---|---|
| 146 | 3-fluorophenyl | 3-[(2-hydroxyethyl)(isobutyl)amino]propoxy |

TABLE 7-continued (xxiii)

| Compound | X | Y |
|---|---|---|
| 147 | 2,3-difluorophenyl | 3-[(2-hydroxyethyl)(isobutyl)amino]propoxy |

EXAMPLE 1

Preparation of Compound 1 in Table 1—2-(3-{[6-methoxy-7-(3-morpholin-4-ylpropoxy)quinazolin-4-yl]amino}-1H-pyrazol-5-yl)-N-phenylacetamide (5-((6-methoxy-7-(3-morpholin-4-ylpropoxy)quinazolin-4-yl)amino)-1H-pyrazol-3-yl) acetic acid (300 mg, 0.68 mmol) in dimethylformamide (5 ml) was reacted with aniline (62 μl, 0.68 mmol) in the presence of O-(7-azabenzotriazol-1-yl) N,N,N',N'-tetramethyl-uronium hexafluorophosphate (260 mg, 0.68 mmol) and diisopropylethylamine (420 μl, 2.38 mmol) at 40° C. for 36 h. The solvent was evaporated in vacuo, water was added to the residue and the mixture was acidified (with 6.0 N hydrochloric acid) to pH 3-4. The water was evaporated and the residue was dissolved in methanol, adsorbed on silica gel, and purified by chromatography on silica gel. Elution with methanol:ammonia:dichloromethane (9:1:90) to yield compound 1 in table 1 (216 mg, 62% yield):
$^1$H-NMR (DMSO d$_6$, TFA): 8.92 (s, 1H), 8.26 (s, 1H), 7.55-7.62 (m, 2H), 7.20-7.25 (m, 3H), 7.03 (m, 1H), 6.80 (s, 1H), 4.28 (m, 2H), 3.95-4.05 (m, 2H), 3.97 (m, 3H), 3.79 (s, 2H), 3.65 (m, 2H), 3.45-3.55 (m, 2H), 3.30 (m, 2H), 3.12 (m, 2H), 2.20-2.30 (m, 2H):
MS (+ve ESI): 518.6 (M+H)$^+$.

(5-((6-methoxy-7-(3-morpholin-4-ylpropoxy)quinazolin-4-yl)amino)-1H-pyrazol-3-yl) acetic acid, used as the starting material, was obtained as follows:
a) 4-chloro-6-methoxy-7-(3-morpholin-4-ylpropoxy)quinazoline (227 mg, 0.64 mmol) in pentan-2-ol (12 ml) and 6.0 N hydrochloric acid (0.25 ml, 1.5 mmol) was heated at 120° C. for 2 hours in the presence of methyl (5-amino-1H-pyrazol-3-yl)acetate (100 mg, 0.64 mmol). The reaction mixture was cooled, the solid was collected by filtration, dried and purified by chromatography on silica gel, eluting with methanol:ammonia:dichloromethane (9:1:90) to yield methyl (5-((6-methoxy-7-(3-morpholin-4-ylpropoxy)quinazolin-4-yl)amino)-1H-pyrazol-3-yl) acetate (251 mg, 85% yield):
$^1$H-NMR (DMSO d$_6$, TFA): 8.96 (s, 1H), 8.30 (s, 1H), 7.37 (s, 1H), 6.82 (s, 1H), 4.32 (m, 2H), 4.01-4.10 (m, 2H), 4.01 (s, 3H), 3.86 (s, 2H), 3.70-3.80 (m, 2H), 3.69 (s, 3H), 3.50-3.60 (m, 2H), 3.35 (m, 2H), 3.18 (m, 2H), 2.28-2.40 (m, 2H):
MS (+ve ESI): 457.6 (M+H)$^+$.
b) Methyl (5-((6-methoxy-7-(3-morpholin-4-ylpropoxy)quinazolin-4-yl)amino)-1H-pyrazol-3-yl)acetate (2.44 g, 5.35 mmol) in methanol (61 ml) and 2.0 N aqueous sodium hydroxide solution (61 ml, 122 mmol) was heated at 80° C. for 4 hours. The reaction mixture was cooled; the methanol was evaporated in vacuo and 6.0 N hydrochloric acid was added (to acidify the mixture to pH 3-4). The residual methanol was evaporated in vacuo, and the solid was purified by chromatography over an Oasis copolymer (Waters) to yield 5-((6-methoxy-7-(3-morpholin-4-ylpropoxy)quinazolin-4-yl)amino)-1H-pyrazol-3-yl)acetic acid (1.64 g, 36% yield):
$^1$H-NMR (DMSO d$_6$, TFA): 8.97 (s, 1H), 8.30 (s, 1H), 7.33 (s, 1H), 6.80 (s, 1H), 4.31 (m, 2H), 4.09 (m, 2H), 4.08 (s, 3H), 3.75 (s, 2H), 3.68 (m, 2H), 3.50-3.60 (m, 2H), 3.35 (m, 2H), 3.15 (m, 2H), 2.20-2.38 (m, 2H):
MS (+ve ESI): 443.6 (M+H)$^+$.

EXAMPLE 2

Preparation of Compound 2 in Table 1—N-(3-fluorophenyl)-2-(3-{[6-methoxy-7-(3-morpholin-4-ylpropoxy)quinazolin-4-yl]amino}-1H-pyrazol-5-yl)acetamide An analogous reaction to that described in example 1, but starting with 3-fluoroaniline (37 μl, 0.41 mmol) yielded compound 2 in table 1 (34 mg, 19% yield):
$^1$H-NMR (DMSO d$_6$, TFA): 8.96 (s, 1H), 8.30 (s, 1H), 7.60-7.70 (m, 1H), 7.32-742 (m, 2H), 7.32 (s, 1H), 6.85-6.92 (m, 1H), 6.83 (s, 1H), 4.30 (m, 2H), 4.00-4.10 (m, 2H), 4.01 (s, 3H), 3.85 (s, 2H), 3.69 (m, 2H), 3.50-3.60 (m, 2H), 3.35 (m, 2H), 3.16 (m, 2H), 2.25-2.40 (m, 2H):
MS (+ve ESI): 536.6 (M+H)$^+$.

EXAMPLE 3

Preparation of Compound 3 in Table 2—2-(3-{[7-(3-chloropropoxy)-6-methoxyquinazolin-4-yl]amino}-1H-pyrazol-5-yl)-N-(3-fluorophenyl)acetamide (5-((7-(3-chloropropoxy)-6-methoxyquinazolin-4-yl)amino)-1H-pyrazol-3-yl) acetic acid (7.83 g, 20 mmol) in dimethylformamide (78 ml) was reacted with 3-fluoroaniline (2.44 g, 22 mmol) in the presence of 1-(3-dimethylaminopropyl)-3-ethylcarbodiimide hydrochloride (4.2 g, 22 mmol), 2-hydroxypyridin-1-oxide (2.22 g, 20 mmol) and diisopropylethylamine (2.8 g, 22 mmol) at 50° C. for 1.7 hours. The solvent was removed by evaporation in vacuo, the residue was triturated with water (twice), and purified by chromatography on silica gel, eluting with dichloromethane:methanol (95:3 to 85:15) to give compound 3 in table 2 (4.5 g, 46% yield) as a beige solid:
$^1$H-NMR (DMSO d$_6$): 8.47 (s, 1H), 8.02 (s, 1H), 7.60-7.68 (m, 1H), 7.40 (m, 2H), 7.20-730 (s, 1H), 6.88 (m, 1H), 6.84 (s, 1H), 4.27 (m, 2H), 3.96 (s, 3H), 3.84 (m, 2H), 3.78 (s, 2H), 2.26 (m, 2H):
MS (+ve ESI): 485.6 (M+H)$^+$.

(5-((7-(3-chloropropoxy)-6-methoxyquinazolin-4-yl)amino)-1H-pyrazol-3-yl) acetic acid, used as the starting material, was obtained as follows:
a) A mixture of 4-benzyloxy-3-methoxybenzaldehyde (157 g, 649 mmol), sodium acetate (106 g, 1.29 mol), hydroxylamine hydrochloride (90 g, 1.29 mol) and acetic acid (500 ml) was heated at reflux for 21 hours. The solvent was evaporated and ice/water (1000 ml) was added to the residue forming a sticky solid. The mixture was neutralised with aqueous sodium hydroxide solution then extracted with dichloromethane (2×500 ml). The organic solution was washed with 1.0 N sodium hydroxide (100 ml), brine (100 ml) and then dried over magnesium sulphate. Solvent evaporation in vacuo, trituration of the residue with hexane:ethyl acetate (3:1) and collection of the solid by suction filtration yielded 4-benzyloxy-3-methoxybenzonitrile (123 g, 80% yield) as a brown solid:

$^1$H-NMR (DMSO d$_6$): 7.38 (m, 7H), 7.19 (m, 1H), 5.18 (s, 2H), 3.80 (s, 3H):

MS (−ve ESI): 238 (M−H)⁻.

b) Acetic acid (17 ml) was added slowly to nitric acid (40 ml, 440 mmol) at 5° C. Powdered 4-benzyloxy-3-methoxybenzonitrile (10 g, 42 mmol) was added and the mixture warmed to 23° C. over 10 minutes. An exotherm occurred and the temperature was controlled at <30° C. using an ice bath. The mixture was stirred at 23° C. for 20 hours then poured into ice/water (1000 ml). After stirring for two hours the yellow solid was collected by suction filtration, washed with water and dried to yield 4-benzyloxy-3-methoxy-6-nitrobenzonitrile (10.1 g, 85% yield) as a yellow solid:

$^1$H-NMR (DMSO d$_6$): 7.95 (s, 1H), 7.70 (s, 1H), 7.40 (m, 5H), 5.30 (s, 2H), 3.95 (s, 3H):

MS (−ve ESI): 283 (M−H)⁻.

c) A mixture of 4-benzyloxy-3-methoxy-6-nitrobenzonitrile (46 g, 162 mmol), sodium bicarbonate (95 g, 1.13 mol), water (750 ml), dichloromethane (550 ml) and tetrabutylammonium chloride (30 g, 108 mmol) was rapidly stirred at 20° C. and treated portionwise with sodium dithionite (66 g, 379 mmol) over 2 hours. The mixture was stirred for a further 1 hour then the phases separated. The aqueous phase was extracted with dichloromethane (2×200 ml) and the combined organic solution washed with water (300 ml) and dried over magnesium sulphate. The solution was concentrated to 250 ml and 4.0 N hydrochloric acid in 1,4-dioxane (150 ml, 0.6 mol) added. The reaction was then diluted with diethyl ether (1000 ml) and cooled on ice. The resulting solid was collected by suction filtration and washed with diethyl ether. The solid was stirred in methanol (1000 ml) and sodium bicarbonate solution (800 ml) added (pH 8) and the mixture stirred for 1 hour. The solid was collected by suction filtration, washed with water, methanol and dried in vacuo to yield 2-amino-4-(benzyloxy)-5-methoxybenzonitrile (34 g, 82% yield) as light brown solid:

$^1$H-NMR (DMSO d$_6$): 7.40 (m, 5H), 6.90 (s, 1H), 6.50 (s, 1H), 5.60 (br s, 2H), 5.02 (s, 2H), 3.65 (s, 3H):

MS (+ve ESI): 254 (M+H)⁺.

d) 2-amino-4-(benzyloxy)-5-methoxybenzonitrile (100 g, 394 mmol) in toluene (1400 ml) was treated with dimethylformamide dimethylacetal (100 ml, 940 mmol) at reflux with slow distillation of solvent to maintain the internal temperature at 105° C. After 3 hours the solution was cooled and filtered to remove a small amount of solid. The filtrate was evaporated in vacuo, the residue triturated with diethyl ether, the solid collected by suction filtration and dried in vacuo to yield N'-(5-(benzyloxy)-2-cyano-4-methoxyphenyl)-N,N-dimethylimidoformamide (110 g, 90% yield) as a brown solid:

$^1$H-NMR (DMSO d$_6$): 7.90 (s, 1H), 7.40 (m, 5H), 7.10 (s, 1H), 6.88 (s, 1H), 5.15 (s, 2H), 3.70 (s, 3H), 3.02 (s, 3H), 2.95 (s, 3H):

MS (+ve ESI): 310 (M+H)⁺.

MS (−ve ESI): 308 (M−H)⁻.

e) N'-(5-(benzyloxy)-2-cyano-4-methoxyphenyl)-N,N-dimethylimidoformamide (110 g, 356 mmol) and trifluoroacetic acid (600 ml) were heated at reflux for 15 minutes. The reaction was evaporated in vacuo and then azeotroped with toluene. The residue was triturated with diethyl ether and the solid collected by suction filtration. The solid was dried in vacuo to yield N'-(2-cyano-5-hydroxy-4-methoxyphenyl)-N,N-dimethylimidoformamide (112 g, 95% yield) as a light brown trifluoroacetate salt:

$^1$H-NMR (DMSO d$_6$): 8.39 (s, 1H), 7.38 (s, 1H), 6.90 (s, 1H), 3.80 (s, 3H), 3.25 (s, 3H), 3.17 (s, 3H):

MS (+ve ESI): 220 (M+H)⁺.

MS (−ve ESI): 218 (M−H)⁻.

f) A mixture of N'-(2-cyano-5-hydroxy-4-methoxyphenyl)-N,N-dimethylimidoformamide (21.9 g, 66 mmol), caesium carbonate (998 g, 300 mmol) and 1-bromo-3-chloropropane (11 ml, 110 mmol) in acetonitrile (300 ml) was heated at reflux for 1 hour. The reaction mixture was cooled and the solvent evaporated in vacuo. Water (200 ml) was added and this was extracted with dichloromethane (2×150 ml). The organic solution was washed with brine (50 ml) and dried over magnesium sulphate. The solvent was evaporated in vacuo and the residue triturated with diethyl ether. The solid was collected by suction filtration and dried in vacuo to yield N'-(5-(3-chloropropoxy)-2-cyano-4-methoxyphenyl)-N,N-dimethylimidoformamide (17.7 g, 91% yield) as a white solid:

$^1$H-NMR (DMSO d$_6$): 8.89 (s, 1H), 7.07 (s, 1H), 6.75 (s, 1H), 4.15 (t, 2H), 3.77 (t, 2H), 3.70 (s, 3H), 3.05 (s, 3H), 2.95 (s, 3H), 2.18 (m, 2H):

MS (+ve ESI): 296.4 (M+H)⁺.

g) N'-(5-(3-chloropropoxy)-2-cyano-4-methoxyphenyl)-N,N-dimethylimidoformamide (230 mg, 0.78 mmol) in acetic acid (0.7 ml) was heated with methyl(5-amino-1H-pyrazol-3-yl)acetate (110 mg, 0.74 mmol) at reflux for 1 hour. The mixture was cooled, the acetic acid was evaporated in vacuo, and the residue purified by chromatography on silica gel, eluting with methanol:ammonia:dichloromethane (9:1:90), to yield methyl (5-((7-(3-chloropropoxy)-6-methoxyquinazolin-4-yl)amino)-1H-pyrazol-3-yl)acetate (219 mg, 69% yield) as a cream solid:

$^1$H-NMR (DMSO d$_6$, TFA): 8.93 (s, 1H), 8.28 (s, 1H), 7.32 (s, 1H), 6.80 (s, 1H), 4.02 (m, 2H), 4.00 (s, 3H), 3.75-3.85 (m, s, 4H), 3.65 (s, 3H), 2.30 (m, 2H), 1.90 (s, 3H):

MS (+ve ESI): 406.5 (M+H)⁺.

h) Methyl (5-((7-(3-chloropropoxy)-6-methoxyquinazolin-4-yl)amino)-1H-pyrazol-3-yl)acetate (100 mg, 0.247 mmol) in tetrahydrofuran (1.2 ml)/water (0.6 ml), was stirred with lithium hydroxide (21 mg, 0.493 mmol) at ambient temperature for 18 hours. The mixture was acidified with 6.0 N hydrochloric acid to pH 4 and the solid was recovered by filtration, washed with water and dried to yield (5-((7-(3-chloropropoxy)-6-methoxyquinazolin-4-yl)amino)-1H-pyrazol-3-yl)acetic acid (72 mg, 75% yield) as a beige solid:

$^1$H-NMR (DMSO d$_6$, TFA): 8.95 (s, 1H), 8.28 (s, 1H), 7.32 (s, 1H), 6.80 (s, 1H), 4.33 (m, 2H), 4.00 (s, 3H), 3.83 (m, 2H), 3.74 (s, 2H), 2.40-2.50 (m, 2H):

MS (+ve ESI): 392.5, 394.5 (M+H)⁺.

Alternatively, N'-(5-(3-chloropropoxy)-2-cyano-4-methoxyphenyl)-N,N-dimethylimidoformamide (14.78 g, 50 mmol) in acetic acid (40 ml) was heated at reflux with (5-amino-1H-pyrazol-3-yl) acetic acid (8.1 g, 57.5 mmol) for 1.5 h. The reaction mixture was cooled to ambient temperature, water (250 ml) was added to the mixture and the solid was recovered by suction filtration. The solid was washed with 1) water, ii) ethyl acetate and iii) diethyl ether and dried in vacuo at 50° C. to yield (5-((7-(3-chloropropoxy)-6-methoxy-quinazolin-4-yl)amino)-1H-pyrazol-3-yl)acetic acid as a yellow solid (13.6 g, 69% yield):

i) (5-amino-1H-pyrazol-3-yl)acetic acid (3.02 g, 0.022 mmol) in methanol (32 ml) was added to a mixture of methanol (32 ml) and thionyl chloride (3.15 ml) at 0° C. The resulting mixture was stirred for 18 hours, evaporated and the residue purified by chromatography on silica gel, eluting with methanol:ammonia:dichloromethane (9:1:90), to yield methyl (5-amino-1H-pyrazol-3-yl)acetate (1.58 g, 48% yield):

$^1$H-NMR (CDCl$_3$): 5.52 (s, 1H), 3.70 (s, 3H), 3.61 (s, 2H).

EXAMPLE 4

Preparation of Compound 4 in Table 2—2-(3-{[7-(3-chloropropoxy)-6-methoxyquinazolin-4-yl]amino}-1H-pyrazol-5-yl)-N-(3,5-difluorophenyl)acetamide A suspension of 3-{[7-(3-chloropropoxy)-6-methoxyquinazolin-4-yl]amino}-1H-pyrazol-5-yl)acetic acid (3.91 g, 10 mmol) in dimethylformamide (20 ml) was reacted with 3,5-difluoroaniline (1.42 g, 11 mmol) in the presence of 1-(3-dimethylaminopropyl)-3-ethylcarbodimide hydrochloride (2.01 g, 10.5 mmol) and 2-hydroxypyridine-1-oxide (1.11 g, 10 mmol) at 60° C. for 1.75 hours. The solvent was evaporated in vacuo and the residue was triturated twice with water. The resulting wet paste was dissolved in a mixture of dichloromethane:methanol (80:20), adsorbed onto silica gel and purified by chromatography on silica gel, eluting with dichloromethane:methanol (95:5 to 85:15) to yield compound 4 in table 2 (2.45 g, 49% yield) as a beige solid:

$^1$H-NMR (DMSO d$_6$): 8.47 (s, 1H), 8.02 (s, 1H), 7.36 (m, 2H), 7.20 (s, 1H), 6.94 (t, 1H), 6.84 (s, 1H), 4.27 (m, 2H), 3.96 (s, 3H), 3.83 (m, 2H), 3.79 (s, 2H), 2.27 (m, 2H):

MS (+ve ESI): 503.5, 505.5 (M+H)$^+$.

EXAMPLE 5

Preparation of compound 5 in table 2—2-(3-{[7-(3-chloropropoxy)-6-methoxyquinazolin-4-yl]amino}-1H-pyrazol-5-yl)-N-(2,3-difluorophenyl)acetamide 3-{[7-(3-chloropropoxy)-6-methoxyquinazolin-4-yl]amino}-1H-pyrazol-5-yl)acetic acid (3.91 g, 10 mmol) was suspended in pyridine (20 ml) in the presence of 2,3-difluoroaniline (1.55 g, 12 mmol) under argon at 0° C. Phosphorus oxychloride (1.53 g, 10 mmol) in ethyl acetate (2 ml) was slowly added at 0° C. and the resulting mixture was allowed to warm to ambient temperature over 1.5 hours. The reaction mixture was diluted with ethyl acetate (150 ml) and diethyl ether (50 ml) resulting in the precipitation of a red solid. The solid was recovered by suction filtration, dried and re-suspended in water (100 ml). The mixture was cooled to 0° C. and the pH adjusted to 7 by addition of 1.5 N aqueous ammonium hydroxide solution. After 15 minutes stirring, the solid was recovered, dried, and purified by chromatography on silica gel. Elution with dichloromethane:methanol (95/5) and increased polarity to dichloromethane:methanolic ammonia (95:2) yielded compound 5 in table 2 as a pink solid (2.55 g, 50% yield):

$^1$H-NMR (DMSO d$_6$, TFA): 8.94 (s, 1H), 8.28 (s, 1H), 7.73 (m, 1H), 7.33 (s, 1H), 7.15-7.22 (m, 1H), 6.84 (s, 1H), 4.30 (m, 2H), 4.00 (s, 3H), 3.94 (s, 2H), 3.84 (m, 2H), 2.30 (m, 2H):

MS (+ve ESI): 503.9 (M+H)$^+$.

EXAMPLE 6

Preparation of Compound 6 in Table 2—N-(3-chlorophenyl)-2-(3-{[7-(3-chloropropoxy)-6-methoxyquinazolin-4-yl]amino}-1H-pyrazol-5-yl)acetamide 3-{[7-(3-chloropropoxy)-6-methoxyquinazolin-4-yl]amino}-1H-pyrazol-5-yl)acetic acid (1.3 g, 3 mmol) vas dissolved in dimethylformamide (13 ml) and reacted with 3-chloroaniline (536 mg, 4.2 mmol) in the presence of 1-(3-dimethylaminopropyl)-3-ethylcarbodimide hydrochloride (919 mg, 3.9 mmol) and 2-hydroxypyridine-1-oxide (433 mg, 3.9 mmol) at 50° C. for 1.5 hours. The solvent was evaporated in vacuo and the residue purified by chromatography on silica gel. Elution with dichloromethane:methanol (95:5) and increased polarity to dichloromethane:methanol (9:1) yielded compound 6 in table 2 (710 mg, 47% yield):

$^1$H-NMR (DMSO d$_6$, TFA): 8.94 (s, 1H), 8.28 (s, 1H), 7.85 (s, 1H), 7.48 (d, 1H), 7.35 (dd, 1H), 7.31 (s, 1H), 7.13 (dd, 1H), 6.83 (s, 1H), 4.32 (m, 2H), 4.00 (s, 3H), 3.84 (m, 2H), 3.83 (s, 2H), 2.30 (m, 2H):

MS (+ve ESI): 501.44 (M+H)$^+$.

EXAMPLE 7

Preparation of Compound 7 in Table 3—2-{3-[(7-{3-[ethyl(2-hydroxyethyl)amino]propoxy}-6-methoxyquinazolin-4-yl)amino]-1H-pyrazol-5-yl}-N-(3-fluorophenyl)acetamide 2-(5-((7-(3-chloropropoxy)-6-methoxyquinazolin-4-yl)amino) 1H-pyrazol-3-yl)-N-(3-fluorophenyl)acetamide (97 mg, 0.2 mmol) in dimethylacetamide (1 ml) was reacted with 2-(ethylamino)ethanol (53 mg, 0.6 mmol) at 90° C. for 8 hours. The mixture was cooled and purified by preparative LCMS to yield compound 7 in table 3 (36 mg, 33% yield):

$^1$H-NMR (DMSO d$_6$, TFA): 8.95 (s, 1H), 8.29 (s, 1H), 7.62-7.65 (m, 1H), 7.25-7.40 (m, 3H), 6.83-6.90 (m, 1H), 6.83 (s, 1H), 4.30 (m, 2H), 4.00 (s, 3H), 3.84 (s, 2H), 3.77 (m, 2H), 3.20-3.40 (m, 6H), 2.25 (m, 2H), 1.26 (t, 3H):

MS (+ve ESI): 538.6 (M+H)$^+$.

EXAMPLE 8

Preparation of Compound 8 in Table 3—N-(3-fluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide An analogous reaction to that described in example 7, but starting with L-prolinol (121 mg, 0.25 mmol) yielded compound 8 in table 3 (86 mg, 62% yield) as an off-white solid:

$^1$H-NMR (DMSO d$_6$, TFA): 8.95 (s, 1H), 8.29 (s, 1H), 7.60-7.70 (m, 1H), 7.28-7.40 (m, 3H), 6.85-6.92 (m, 1H), 6.82 (s, 1H), 4.31 (m, 2H), 4.00 (s, 3H), 3.84 (s, 2H), 3.70-3.80 (m, 1H), 3.50-3.70 (m, 4H), 3.10-3.30 (m, 2H), 2.20-2.40 (m, 2H), 2.05-2.20 (m, 1H), 1.95-2.10 (m, 1H), 1.85-1.95 (m, 1H), 1.70-1.85 (m, 1H):

MS (+ve ESI): 550.6 (M+H)$^+$.

EXAMPLE 9

Preparation of Compound 9 in Table 3—N-(3-fluorophenyl)-2-(3-{[6-methoxy-7-(3-piperidin-1-ylpropoxy)quinazolin-4-yl]amino}-1H-pyrazol-5-yl)acetamide An analogous reaction to that described in example 7, but starting with piperidine (85 mg, 1 mmol) yielded compound 9 in table 3 (31 mg, 23% yield):

$^1$H-NMR (DMSO d$_6$, TFA): 8.96 (s, 1H), 8.30 (s, 1H), 7.65 (d, 1H), 7.34 (m, 2H), 7.32 (s, 1H), 6.90 (m, 1H), 6.83 (s, 1H), 4.30 (m, 2H), 4.00 (s, 3H), 3.85 (s, 2H), 3.54 (d, 2H), 3.27 (m, 2H), 2.96 (m, 2H), 2.90 (m, 2H), 1.84 (m, 2H), 1.60-1.80 (m, 3H), 1.42 (m, 1H):

MS (+ve ESI): 534.6 (M+H)$^+$.

EXAMPLE 10

Preparation of Compound 10 in Table 3—N-(3-fluorophenyl)-2-(3-{[6-methoxy-7-(3-pyrrolidin-1-ylpropoxy)quinazolin-4-yl]amino}-1H-pyrazol-5-yl)acetamide An analogous reaction to that described in example 7, but starting with pyrrolidine (71 mg, 1 mmol) yielded compound 10 in table 3 (58 mg, 45% yield):

$^1$H-NMR (DMSO d$_6$, TFA): 8.96 (s, 1H), 8.30 (s, 1H), 7.64 (d, 1H), 7.35 (m, 2H), 7.33 (s, 1H), 6.90 (m, 1H), 6.84 (s, 1H), 4.30 (m, 2H), 4.00 (s, 3H), 3.85 (s, 2H), 3.68 (m, 2H), 3.31 (m, 2H), 3.10 (m, 2H), 2.28 (m, 2H), 1.91 (m, 2H):

MS (+ve ESI): 520.6 (M+H)$^+$.

EXAMPLE 11

Preparation of Compound 11 in Table 3—N-(3-fluorophenyl)-2-{3-[(7-{3-[(2-hydroxyethyl)amino]propoxy}-6-methoxyquinazolin-4-yl)amino]-1H-pyrazol-5-yl}acetamide An analogous reaction to that described in example 7, but starting with ethanolamine (61 mg, 1 mmol) yielded compound 11 in table 3 (80 mg, 77% yield):

$^1$H-NMR (DMSO d$_6$, TFA): 8.95 (s, 1H), 8.29 (s, 1H), 7.37 (d, 1H), 7.34 (m, 2H), 7.31 (s, 1H), 6.95 (m, 1H), 6.83 (s, 1H), 4.30 (m, 2H), 4.00 (s, 3H), 3.85 (s, 2H), 3.68 (m, 2H), 3.16 (m, 2H), 3.09 (m, 2H), 2.21 (m, 2H):

MS (+ve ESI): 509.5 (M+H)$^+$.

EXAMPLE 12

Preparation of Compound 12 in Table 3—N-(3-fluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide An analogous reaction to that described in example 7, but starting with 2-amino-2-methyl-1-propanol (89 mg, 1 mmol) yielded compound 12 in table 3 (47 mg, 35% yield):

$^1$H-NMR (DMSO d$_6$, TFA): 8.96 (s, 1H), 8.30 (s, 1H), 7.62 (m, 1H), 7.34 (m, 2H), 7.32 (s, 1H), 6.88 (m, 1H), 6.84 (s, 1H), 4.32 (m, 2H), 4.00 (s, 3H), 3.85 (s, 2H), 3.46 (s, 2H), 3.10 (m, 2H), 2.10 (m, 2H), 1.24 (s, 6H):

MS (+ve ESI): 538.6 (M+H)$^+$.

EXAMPLE 13

Preparation of Compound 13 in Table 3—N-(3-fluorophenyl)-2-{3-[(7-{3-[(2-hydroxyethyl)(methyl)amino]propoxy}-6-methoxyquinazolin-4-yl)amino]-1H-pyrazol-5-yl}acetamide An analogous reaction to that described in example 7, but starting with 2-(methylamino)ethanol (75 mg, 1 mmol) yielded compound 13 in table 3 (88 mg, 67% yield):

$^1$H-NMR (DMSO d$_6$, TFA): 8.96 (s, 1H), 8.3 (s, 1H), 7.64 (d, 1H), 7.35 (m, 2H), 7.33 (s, 1H), 6.90 (m, 1H), 6.84 (s, 1H), 4.30 (m, 2H), 4.01 (s, 3H), 3.85 (s, 2H), 3.77 (t, 2H), 3.15-3.45 (m, 4H), 2.38 (s, 3H), 2.30 (m, 2H):

MS (+ve ESI): 524.6 (M+H)$^+$.

EXAMPLE 14

Preparation of Compound 14 in Table 3—N-(3-fluorophenyl)-2-(3-{[7-(3-{[1-(hydroxymethyl)-2-methylpropyl]amino}propoxy)-6-methoxyquinazolin-4-yl]amino}-1H-pyrazol-5-yl)acetamide An analogous reaction to that described in example 7, but starting with 2-amino-3-methylbutan-1-ol (103 mg, 1 mmol) yielded compound 14 in table 3 (40 mg, 29% yield):

$^1$H-NMR (DMSO d$_6$, TFA): 8.96 (s, 1H), 8.30 (s, 1H), 7.63 (d, 1H), 7.65 (m, 2H), 7.62 (s, 1H), 6.90 (m, 1H), 6.83 (s, 1H), 4.32 (m, 2H), 4.00 (s, 3H), 3.85 (s, 2H), 3.75 (dd, 1H), 3.66 dd, 1H), 3.23 (m, 2H), 3.03 (m, 2H), 2.27 (m, 2H), 2.08 (m, 1H), 1.02 (d, 3H), 0.97 (d, 3H):

MS (+ve ESI): 552.6 (M+H)$^+$.

EXAMPLE 15

Preparation of Compound 15 in Table 3—N-(3-fluorophenyl)-2-[3-({6-methoxy-7-[3-(4-methylpiperazin-1-yl)propoxy]quinazolin-4-yl}amino)-1H-pyrazol-5-yl]acetamide An analogous reaction to that described in example 7, but starting with 1-methylpiperazine (100 mg, 1 mmol) yielded compound 15 in table 3 (51 mg, 37% yield):

$^1$H-NMR (DMSO d$_6$, TFA): 8.96 (s, 1H), 8.30 (s, 1H), 7.65 (d, 1H), 7.38 (m, 2H), 7.35 (s, 1H), 6.88 (m, 1H), 6.84 (s, 1H), 4.31 (m, 2H), 3.20-4.10 (m, 8H), 4.01 (s, 3H), 3.85 (s, 2H), 3.40 (m, 2H), 2.95 (s, 3H), 2.30 (m, 2H):

MS (+ve ESI): 549.6 (M+H)$^+$.

EXAMPLE 16

Preparation of Compound 16 in Table 3—N-(3-fluorophenyl)-2-{3-[(7-{3-[(2-hydroxy-1-methylethyl)amino]propoxy}-6-methoxyquinazolin-4-yl)amino]-1H-pyrazol-5-yl}acetamide An analogous reaction to that described in example 7, but starting with 2-amino-1-propanol (75.1 mg, 1 mmol) yielded compound 16 in table 3 (80 mg, 61% yield):

$^1$H-NMR (DMSO d$_6$, TFA): 8.96 (s, 1H), 8.30 (s, 1H), 7.64 (d, 1H), 7.36 (m, 2H), 7.34 (s, 1H), 6.88 (m, 1H), 6.84 (s, 1H), 4.32 (m, 2H), 4.01 (s, 3H), 3.85 (s, 2H), 3.69 (dd, 1H), 3.50 (dd, 1H), 3.33 (m, 1H), 3.18 (m, 2H), 2.23 (m, 2H), 1.23 (d, 3H):

MS (+ve ESI): 524.6 (M+H)$^+$.

EXAMPLE 17

Preparation of Compound 17 in Table 3—N-(3-fluorophenyl)-2-{3-[(7-{3-[(4-hydroxybutyl)amino]propoxy}-6-methoxyquinazolin-4-yl)amino]-1H-pyrazol-5-yl}acetamide An analogous reaction to that described in example 7, but starting with 4-aminobutan-1-ol (89 mg, 1 mmol) yielded compound 17 in table 3 (56 mg, 42% yield):

$^1$H-NMR (DMSO d$_6$, TFA): 8.96 (s, 1H), 8.30 (s, 1H), 7.64 (d, 1H), 7.34 (m, 2H), 7.32 (s, 1H), 6.90 (m, 1H), 6.84 (s, 1H), 4.30 (m, 2H), 4.01 (s, 3H), 3.85 (s, 2H), 3.45 (t, 2H), 3.14 (m, 2H), 2.98 (m, 2H), 2.20 (m, 2H), 1.67 (m, 2H), 1.50 (m, 2H):

MS (+ve ESI): 538.6 (M+H)$^+$.

EXAMPLE 18

Preparation of Compound 18 in Table 3—N-(3-fluorophenyl)-2-[3-({7-[3-(4-hydroxypiperidin-1-yl)propoxy]-6-methoxyquinazolin-4-yl}amino)-1H-pyrazol-5-yl]acetamide An analogous reaction to that described in example 7, but starting with piperidin-4-ol (101 mg, 1 mmol) yielded compound 18 in table 3 (75 mg, 57% yield):
$^1$H-NMR (DMSO d$_6$, TFA): 8.96 (s, 1H), 8.29 (s, 1H), 7.64 (m, 1H), 7.36 (m, 2H), 7.34 (s, 1H), 6.90 (m, 1H), 6.83 (s, 1H), 4.29 (t, 2H), 4.00 (s, 3H), 3.85 (s, 2H), 3.66 (m, 1H), 3.55 (d, 1H), 3.40 (m, 1H), 3.12-3.35 (m, 3H), 3.00 (t, 1H), 2.80 (m, 2H), 2.00 (m, 1H), 1.75-1.95 (m, 2H), 1.60 (m, 1H):
MS (+ve ESI): 550.6 (M+H)$^+$.

EXAMPLE 19

Preparation of Compound 19 in Table 3—N-(3-fluorophenyl)-2-{3-[(7-{3-[2-(2-hydroxyethyl)piperidin-1-yl]propoxy}-6-methoxyquinazolin-4-yl)amino]-1H-pyrazol-5-yl}acetamide An analogous reaction to that described in example 7, but starting with 2-(2-hydroxy-ethyl)piperidine (129 mg, 1 mmol) yielded compound 19 in table 3 (63 mg, 44% yield):
$^1$H-NMR (DMSO d$_6$, TFA): 8.96 (s, 1H), 8.30 (s, 1H), 7.63 (d, 1H), 7.34 (m, 2H), 7.32 (s, 1H), 6.90 (m, 1H), 6.83 (s, 1H), 4.30 (m, 2H), 4.00 (s, 3H), 3.85 (s, 2H), 3.10-3.70 (m, 7H), 2.20-2.30 (m, 2H), 2.00-2.20 (m, 1H), 1.60-1.90 (m, 6H), 1.50 (m, 1H):
MS (+ve ESI): 578.7 (M+H)$^+$.

EXAMPLE 20

Preparation of Compound 20 in Table 3—N-(3-fluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide An analogous reaction to that described in example 7, but starting with 2-piperazin-1-ylethanol (130 mg, 1 mmol) yielded compound 20 in table 3 (69 mg, 48% yield):
$^1$H-NMR (DMSO d$_6$, TFA): 8.96 (s, 1H), 8.30 (s, 1H), 7.63 (d, 1H), 7.36 (s, 1H), 7.34 (m, 2H), 6.90 (m, 1H), 6.84 (s, 1H), 4.31 (m, 2H), 2.70-4.10 (m, 8H), 4.01 (s, 3H), 3.85 (s, 2H), 3.79 (m, 2H), 3.40 (m, 2H), 3.35 (m, 2H), 2.29 (m, 2H):
MS (+ve ESI): 579.6 (M+H)$^+$.

EXAMPLE 21

Preparation of Compound 21 in Table 3—N-(3-fluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide Analogous reaction to that described in example 7, but starting with 4-(2-hydroxyethyl)piperidine (129 mg, 1 mmol) yielded compound 21 in table 3 (91 mg, 63% yield):
$^1$H-NMR (DMSO d$_6$, TFA): 8.96 (s, 1H), 8.30 (s, 1H), 7.64 (d, 1H), 7.35 (m, 2H), 7.33 (s, 1H), 6.88 (m, 1H), 6.84 (s, 1H), 4.30 (m, 2H), 4.00 (s, 3H), 3.85 (s, 2H), 3.55 (m, 2H), 3.48 (m, 2H), 3.25 (m, 2H), 2.98 (m, 2H), 2.28 (m, 2H), 1.90 (m, 2H), 1.70 (m, 1H), 1.40 (m, 4H):
MS (+ve ESI): 578.7 (M+H)$^+$.

EXAMPLE 22

Preparation of Compound 22 in Table 3—N-(3-fluorophenyl)-2-[3-({7-[3-(3-hydroxypiperidin-1-yl)propoxy]-6-methoxyquinazolin-4-yl}amino)-1H-pyrazol-5-yl]acetamide An analogous reaction to that described in example 7, but starting with piperidin-3-ol (101 mg, 1 mmol) yielded compound 22 in table 3 (65 mg, 47% yield):
$^1$H-NMR (DMSO d$_6$, TFA): 8.96 (s, 1H), 8.29 (s, 1H), 7.62 (d, 1H), 7.38 (m, 2H), 7.34 (m, 2H), 7.34 (s, 1H), 6.90 (m, 1H), 6.84 (s, 1H), 4.28 (m, 2H), 4.10 (m, 1H), 4.00 (s, 3H), 3.85 (s, 2H), 2.80-3.50 (m, 6H), 1.30-2.40 (m, 6H):
MS (+ve ESI): 550.6 (M+H)$^+$.

EXAMPLE 23

Preparation of Compound 23 in Table 3—N-(3-fluorophenyl)-2-{3-[(7-{3-[(2-hydroxybutyl)amino]propoxy}-6-methoxyquinazolin-4-yl)amino]-1H-pyrazol-5-yl}acetamide An analogous reaction to that described in example 7, but starting with 1-aminobutan-2-ol (89 mg, 1 mmol) yielded compound 23 in table 3 (79 mg, 59% yield):
$^1$H-NMR (DMSO d$_6$, TFA): 8.96 (s, 1H), 8.29 (s, 1H), 7.64 (d, 1H), 7.32-7.41 (m, 2H), 7.32 (s, 1H), 6.90 (t, 1H), 6.83 (s, 1H), 4.30 (t, 2H), 4.01 (s, 3H), 3.85 (s, 2H), 3.68 (m, 1H), 3.16 (t, 2H), 3.09 (d, 1H), 2.83 (t, 1H), 2.25 (m, 2H), 1.45 (m, 2H), 0.92 (t, 3H):
MS (+ve ESI): 538.6 (M+H)$^+$.

EXAMPLE 24

Preparation of Compound 24 in Table 3—N-(3-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 7, but starting with 4-(hydroxymethyl)piperidine (115 mg, 1 mmol) yielded compound 24 in table 3 (80 mg, 57% yield):
$^1$H-NMR (DMSO d$_6$, TFA): 8.96 (s, 1H), 8.30 (s, 1H), 7.63 (m, 1H), 7.36 (m, 3H), 6.90 (m, 1H), 6.84 (s, 1H), 4.30 (t, 2H), 4.01 (s, 3H), 3.85 (s, 2H), 3.62 (d, 2H), 3.32 (d, 2H), 3.27 (m, 2H), 2.98 (t, 2H), 2.29 (m, 2H), 1.90 (d, 2H), 1.67 (m, 1H), 1.42 (m, 2H):
MS (+ve ESI): 564.6 (M+H)$^+$.

EXAMPLE 25

Preparation of Compound 25 in Table 3—N-(3-fluorophenyl)-2-{3-[(7-{3-[(3-hydroxy-2,2-dimethylpropyl)amino]propoxy}-6-methoxyquinazolin-4-yl)amino]-1H-pyrazol-5-yl}acetamide An analogous reaction to that described in example 7, but starting with 3-amino-2,2-dimethylpropan-1-ol (103 mg, 1 mmol) yielded compound 25 in table 3 (63 mg, 46% yield):
$^1$H-NMR (DMSO d$_6$, TFA): 8.96 (s, 1H), 8.29 (s, 1H), 7.64 (d, 1H), 7.31-7.41 (m, 2H), 7.35 (s, 1H), 6.90 (t, 1H), 6.83 (s, 1H), 4.30 (t, 2H), 4.01 (s, 3H), 3.85 (s, 2H), 3.29 (s, 2H), 3.16 (t, 2H), 2.92 (t, 2H), 2.28 (m, 2H), 0.95 (s, 6H):
MS (+ve ESI): 552.7 (M+H)$^+$.

EXAMPLE 26

Preparation of Compound 26 in Table 3—N-(3-fluorophenyl)-2-(3-{[7-(3-{[1-(hydroxymethyl)cyclopentyl]amino}propoxy)-6-methoxyquinazolin-4-yl]amino}-1H-pyrazol-5-yl)acetamide An analogous reaction to that described in example 7, but starting with (1-amino-cyclopentyl)methanol (115 mg, 1 mmol) yielded compound 26 in table 3 (69 mg, 49% yield):
$^1$H-NMR (DMSO $d_6$, TFA): 8.96 (s, 1H), 8.30 (s, 1H), 7.64 (d, 1H), 7.32-7.41 (m, 3H), 6.90 (t, 1H), 6.83 (s, 1H), 4.32 (t, 2H), 4.01 (s, 3H), 3.85 (s, 2H), 3.48 (s, 2H), 3.12 (m, 2H), 2.23 (m, 2H), 1.68-1.83 (m, 6H), 1.59 (m, 2H):
MS (+ve ESI): 564.6 $(M+H)^+$.

EXAMPLE 27

Preparation of Compound 27 in Table 3—N-(3-fluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide An analogous reaction to that described in example 7, but starting with D-prolinol (101 mg, 1 mmol) yielded compound 27 in table 3 (61 mg, 44% yield):
$^1$H-NMR (DMSO $d_6$, TFA): 8.96 (s, 1H), 8.30 (s, 1H), 7.65 (d, 1H), 7.31-7.41 (m, 2H), 7.34 (s, 1H), 6.90 (t, 1H), 6.84 (s, 1H), 4.31 (t, 2H), 4.01 (s, 3H), 3.85 (s, 2H), 3.77 (m, 1H), 3.53-3.68 (m, 4H), 3.15-3.30 (m, 2H), 2.30 (m, 2H), 2.13 (m, 1H), 2.02 (m, 1H), 1.90 (m, 1H), 1.78 (m, 1H):
MS (+ve ESI): 550.6 $(M+H)^+$.

EXAMPLE 28

Preparation of Compound 28 in Table 3—N-(3-fluorophenyl)-2-(3-{[7-(3-{[(2S)-2-hydroxypropyl]amino}propoxy)-6-methoxyquinazolin-4-yl]amino}-1H-pyrazol-5-yl)acetamide An analogous reaction to that described in example 7, but starting with (S)-(+)-1-aminopropan-2-ol (75 mg, 1 mmol) yielded compound 28 in table 3 (70 mg, 53% yield):
$^1$H-NMR (DMSO $d_6$, TFA): 8.95 (s, 1H), 8.29 (s, 1H), 7.64 (d, 1H), 7.31-7.40 (m, 2H), 7.32 (s, 1H), 6.90 (t, 1H), 6.83 (s, 1H), 4.30 (t, 2H), 4.01 (s, 3H), 3.95 (m, 1H), 3.85 (s, 2H), 3.15 (t, 2H), 3.05 (dd, 1H), 2.83 (dd, 1H), 2.23 (m, 2H), 1.15 (d, 3H):
MS (+ve ESI): 524.6 $(M+H)^+$.

EXAMPLE 29

Preparation of Compound 29 in Table 3—N-(3-fluorophenyl)-2-(3-{[7-(3-{[(2R)-2-hydroxypropyl]amino}propoxy)-6-methoxyquinazolin-4-yl]amino}-1H-pyrazol-5-yl)acetamide An analogous reaction to that described in example 7, but starting with (R)-(−)-1-aminopropan-2-ol (75 mg, 1 mmol) yielded compound 29 in table 3 (80 mg, 61% yield):
$^1$H-NMR (DMSO $d_6$, TFA): 8.95 (s, 1H), 8.29 (s, 1H), 7.64 (d, 1H), 7.31-7.40 (m, 2H), 7.31 (s, 1H), 6.90 (t, 1H), 6.83 (s, 1H), 4.30 (t, 2H), 4.01 (s, 3H), 3.95 (m, 1H), 3.85 (s, 2H), 3.15 (m, 2H), 3.06 (d, 1H), 2.83 (dd, 1H), 2.24 (m, 2H), 1.14 (d, 3H):
MS (+ve ESI): 524.6 $(M+H)^+$.

EXAMPLE 30

Preparation of Compound 30 in Table 3—N-(3-fluorophenyl)-2-{3-[(7-{3-[(3S)-3-hydroxypyrrolidin-1-yl]propoxy}-6-methoxyquinazolin-4-yl)amino]-1H-pyrazol-5-yl}acetamide An analogous reaction to that described in example 7, but starting with (S)-(−)-3-hydroxypyrrolidine (87 mg, 1 mmol) yielded compound 30 in table 3 (84 mg, 63% yield):
$^1$H-NMR (DMSO $d_6$, TFA): 8.96 (s, 1H), 8.30 (s, 1H), 7.65 (d, 1H), 7.30-7.40 (m, 3H), 6.88 (t, 1H), 6.84 (s, 1H), 4.43-4.51 (m, 1H), 4.29 (m, 2H), 4.02 (s, 3H), 3.86 (s, 2H), 3.73 (m, 2H), 3.02-3.53 (m, 4H), 2.27 (m, 3H), 1.85-2.04 (m, 1H):
MS (+ve ESI): 536.6 $(M+H)^+$.

EXAMPLE 31

Preparation of Compound 31 in Table 3—N-(3-fluorophenyl)-2-{3-[(7-{3-[(3R)-3-hydroxypyrrolidin-1-yl]propoxy}-6-methoxyquinazolin-4-yl)amino]-1H-pyrazol-5-yl}acetamide An analogous reaction to that described in example 7, but starting with (R)-(+)-3-hydroxypyrrolidine (87 mg, 1 mmol) yielded compound 31 in table 3 (70 mg, 52% yield):
$^1$H-NMR (DMSO $d_6$, TFA): 10.45 (s, 1H), 10.18 (s, 1H), 8.46 (s, 1H), 7.98 (br s, 1H), 7.63 (d, 1H), 7.32-7.41 (m, 2H), 7.34 (s, 1H), 7.15 (s, 1H), 6.91 (t, 1H), 6.83 (br s, 1H), 4.69 (s, 1H), 4.15-4.24 (m, 3H), 3.94 (s, 3H), 3.76 (s, 2H), 2.72 (dd, 1H), 2.41-2.64 (m, 4H), 2.34 (dd, 1H), 1.91-2.04 (m, 3H), 1.55 (m, 1H):
MS (+ve ESI): 536.6 $(M+H)^+$.

EXAMPLE 32

Preparation of Compound 32 in Table 3—2-{3-[(7-{3-[(2-fluoroethyl)(2-hydroxyethyl)amino]propoxy}-6-methoxyquinazolin-4-yl)amino]-1H-pyrazol-5-yl}-N-(3-fluorophenyl)acetamide An analogous reaction to that described in example 7, but starting with 2-((2-fluoroethyl)amino)ethanol (180 mg, 1.68 mmol) and carrying out the reaction in N-methyl pyrrolidinone at 100° C. for 8 hours yielded compound 32 in table 3 (12 mg, 5% yield):
$^1$H-NMR (DMSO $d_6$): 10.45 (s, 1H), 10.18 (s, 1H), 8.47 (s, 1H), 8.00 (s, 1H), 7.63 (d, 1H), 7.37 (m, 1H), 7.35 (s, 1H), 7.15 (s, 1H), 6.91 (t, 1H), 6.83 (s, 1H), 4.54 (t, 1H), 4.43 (t, 1H), 4.37 (t, 1H), 4.18 (t, 2H), 3.95 (s, 3H), 3.77 (s, 2H), 3.46 (dd, 2H), 2.78 (t, 1H), 2.70 (t, 1H), 2.60 (t, 2H), 2.52 (t, 2H), 1.92 (m, 2H):
MS (+ve ESI): 556.4 $(M+H)^+$.

2-((2-fluoroethyl)amino)ethanol used as starting material was obtained as follows:

Potassium carbonate (22 g, 159 mmol) was added to a solution of ethanolamine (4.75 ml, 78.7 mmol) and 1-bromo-2-fluoroethane (10.0 g, 78.7 mmol) in dioxane (100 ml) and the reaction mixture was heated at 80° C. for 10 hours. The reaction was concentrated and purified by chromatography on silica gel. Elution with dichloromethane:methanol (95:5) and increased polarity to dichloromethane:methanol:ammonia (90:5:5) yielded 2-((2-fluoroethyl)amino)ethanol (7.94 g, 74% yield). This compound was further purified by distillation under reduced pressure to give 2-((2-fluoroethyl)amino) ethanol (3.44 g, 32% yield):

¹H-NMR (DMSO d₆, TFA): 9.94 (br s, 1H), 4.79 (t, 1H), 4.68 (t, 1H), 3.67 (t, 2H), 3.37 (d, 1H), 3.30 (d, 1H), 3.07 (d, 2H).

EXAMPLE 33

Preparation of Compound 33 in Table 3—N-(3-fluorophenyl)-2-{3-[(7-{2-[1-(2-hydroxyethyl)piperidin-4-yl]ethoxy}-6-methoxyquinazolin-4-yl)amino]-1H-pyrazol-5-yl}acetamide 2-{3-[(7-{2-[1-(2-ter-butoxyethyl)piperidin-4-yl]ethoxy}-6-methoxyquinazolin-4-yl)amino]-1H-pyrazol-5-yl}-N-(3-fluorophenyl)acetamide (160 mg, 0.25 mmol) was reacted with trifluoroacetic acid (3 ml) in dichloromethane (3 ml) at 40° C. for 1 hour. The solvent was evaporated, the residue dissolved in a mixture of dichloromethane:methanol. Hydrogen chloride (2.0 N in ether, 0.4 ml) was added resulting in the precipitation of a beige solid which was isolated and purified by preparative LCMS to yield compound 33 in table 3 as a beige solid (95 mg, 58% yield):
¹H-NMR (DMSO d₆, TFA): 8.94 (s, 1H), 8.29 (s, 1H), 7.63 (m, 1H), 7.35 (m, 3H), 6.89 (m, 1H), 6.83 (s, 1H), 4.24 (m, 2H), 3.99 (s, 3H), 3.85 (s, 2H), 3.76 (m, 2H), 3.52 (d, 2H), 3.26 (m, 1H), 3.14 (m, 2H), 2.98 (t, 2H), 1.94 (d, 2H), 1.81 (m, 2H), 1.57 (m, 2H):
MS (+ve ESI): 564.2 (M+H)⁺.

2-{3-[(7-{2-[1-(2-tert-butoxyethyl)piperidin-4-yl]ethoxy}-6-methoxyquinazolin-4-yl)amino]-1H-pyrazol-5-yl}-N-(3-fluorophenyl)acetamide used as starting material was obtained as follows.

a) 4-(2-hydroxyethyl)piperidine (1.94 g, 15 mmol) in dimethylformamide (20 ml) was reacted with 2-(2-bromoethoxy)-2-methylpropane (3.13 g, 17.3 mmol) at 50° C. for 15 hours. The mixture was cooled and the solid removed by filtration. The solid was washed with ethyl acetate and the organics were washed with water, dried (magnesium sulphate) and concentrated to give 2-(1-(2-tert-butoxy ethyl)piperidin-4-yl)ethanol as a yellow oil (2.35 g, 100% yield):
¹H-NMR (DMSO d₆, TFA): 3.63 (m, 2H), 3.40-3.50 (m, 4H), 3.20 (m, 2H), 2.93 (t, 2H), 1.84 (d, 2H), 1.50-1.70 (m, 1H), 1.30-1.45 (4H), 1.18 (s, 9H).

b) N'-(2-cyano-5-hydroxy-4-methoxyphenyl)-N,N-dimethylimidoformamide (876 mg, 4 mmol) in dichloromethane (2 ml) was reacted with 2-(1-(2-tert-butoxyethyl)piperidin-4-yl)ethanol (916 mg, 4.4 mmol) in the presence of triphenylphosphine (1.2 g, 4.6 mmol) by slow addition of a solution of di-tert-butyl azodicarboxylate (1.058 g, 4.6 mmol) in dichloromethane (5 ml). The mixture was stirred for 2 hours at ambient temperature and purified by chromatography. Elution with dichloromethane:ethyl acetate:methanol (5:4:1) yielded N'-(5-{2-[1-(2-tert-butoxyethyl)piperidin-4-yl]ethoxy}-2-cyano-4-methoxyphenyl)-N,N-dimethylimidoformamide (720 mg, 42% yield):
¹H-NMR (DMSO d₆, TFA): 8.54 (s, 1H), 7.50 (s, 1H), 7.29 (s, 1H), 4.14 (m, 2H), 3.85 (s, 3H), 3.64 (m, 2H), 3.53 (d, 2H), 3.37 (s, 3H), 3.33 (m, 1H), 3.27 (s, 3H), 3.21 (m, 2H), 2.98 (t, 2H), 1.80-2.00 (m, 2H), 1.60-1.80 (m, 2H), 1.30-1.60 (m, 2H), 1.18 (s, 9H):
MS (+ve ESI): 431.28 (M+H)⁺.

c) N'-(5-{2-[1-(2-tert-butoxyethyl)piperidin-4-yl]ethoxy}-2-cyano-4-methoxyphenyl)-N,N-dimethylimidoformamide (654 mg, 1.5 mmol) in acetic acid (1.35 ml) was heated with (3-amino-1H-pyrazol-5-yl)acetic acid (214 mg, 1.52 mmol) at reflux for 45 minutes. Acetic acid was evaporated and the residue taken up in a mixture of dichloromethane:methanol. Excess diisopropylethylamine was added, and the solvent evaporated in vacuo. Dichloromethane was added to the solid, which was filtered and dried to yield {3-[(7-{2-[1-(2-tert-butoxyethyl)piperidin-4-yl]ethoxy}-6-methoxyquinazolin-4-yl)amino]-1H-pyrazol-5-yl}acetic acid as a white powder (530 mg, 66% yield):
¹H-NMR (DMSO d₆): 8.94 (s, 1H), 8.27 (s, 1H), 7.33 (s, 1H), 6.80 (s, 1H), 4.27 (m, 2H), 3.99 (s, 3H), 3.74 (s, 2H), 3.65 (m, 2H), 3.52 (d, 2H), 3.20-3.30 (m, 3H), 2.99 (t, 2H), 1.98 (d, 2H), 1.9-1.7 (m, 2H), 1.5 (m, 2H), 1.82 (s, 9H):
MS (+ve ESI): 527.2 (M+H)⁺.

d) {3-[(7-{2-[1-(2-tert-butoxyethyl)piperidin-4-yl]ethoxy}-6-methoxyquinazolin-4-yl)amino]-1H-pyrazol-5-yl}acetic acid (210 mg, 0.4 mmol) in dimethylformamide (2.1 ml) was reacted with 3-fluoroaniline (58 mg, 0.52 mmol) in the presence of 1-(3-dimethylaminopropyl)-3-ethylcarbodiimide hydrochloride (107 mg, 0.56 mmol) and 2-hydroxypyridine-1-oxide (53 mg, 0.48 mmol) at 55° C. for 1.5 hours. The reaction mixture was cooled, diluted with dichloromethane (7 ml) and purified by chromatography on silica gel. Elution with dichloromethane:methanol (9:1) and increased polarity to dichloromethane:methanol:ammonia (9:1:0.1) yielded 2-{3-[(7-{2-[1-(2-tert-butoxyethyl)piperidin-4-yl]ethoxy}-6-methoxyquinazolin-4-yl)amino]-1H-pyrazol-5-yl}-N-(3-fluorophenyl)acetamide (162 mg, 65% yield) as a light pink solid:
¹H-NMR (DMSO d₆, TFA): 8.94 (s, 1H), 8.27 (s, 1H), 7.63 (m, 1H), 7.32-7.40 (m, 3H), 6.89 (m, 1H), 6.82 (s, 1H), 4.25 (m, 2H), 3.99 (s, 3H), 3.84 (s, 2H), 3.64 (m, 2H), 3.51 (d, 2H), 3.10-3.30 (m, 3H), 2.99 (t, 2H), 1.97 (d, 2H), 1.60-1.95 (m, 2H), 1.78 (s, 9H), 1.51 (m, 2H):
MS (+ve ESI): 620.3 (M+H)⁺.

EXAMPLE 34

Preparation of Compound 34 in Table 3—N-(3-fluorophenyl)-2-{3-[(7-{3-[(2-hydroxyethyl)(propyl)amino]propoxy}-6-methoxyquinazolin-4-yl)amino]-1H-pyrazol-5-yl}acetamide An analogous reaction to that described in example 7, but starting with 2-(propylamino)ethanol (160 mg, 1.55 mmol) and carrying out the reaction in N-methyl pyrrolidinone (2.5 ml) in the presence of potassium iodide (103 mg, 0.62 mmol) at 60° C. for 8 hours yielded compound 34 in table 3 (21 mg, 12% yield):
¹H-NMR (DMSO d₆, TFA): 8.98 (s, 1H), 8.32 (s, 1H), 7.66 (d, 1H), 7.35-7.41 (m, 2H), 7.36 (s, 1H), 6.91 (t, 1H), 6.85 (s, 1H), 4.32 (t, 2H), 4.02 (s, 3H), 3.86 (s, 2H), 3.78 (t, 2H), 3.35 (m, 2H), 3.28 (m, 2H), 3.17 (m, 2H), 2.29 (m, 2H), 1.73 (m, 2H):
MS (+ve ESI): 552.2 (M+H)⁺.

EXAMPLE 35

Preparation of Compound 35 in Table 3—N-(3-fluorophenyl)-2-{3-[(7-{3-[(2-hydroxyethyl)(isopropyl)amino]propoxy}-6-methoxyquinazolin-4-yl)amino]-1H-pyrazol-5-yl}acetamide An analogous reaction to that described in example 34, but starting with 2-(isopropyl amino)ethanol (160 mg, 1.55 mmol) yielded compound 35 in table 3 (98 mg, 57% yield):
¹H-NMR (DMSO d₆, TFA): 8.98 (s, 1H), 8.31 (s, 1H), 7.66 (d, 1H), 7.32-7.41 (m, 2H), 7.37 (s, 1H), 6.92 (t, 1H), 6.85 (s, 1H), 4.33 (t, 2H), 4.02 (s, 3H), 3.86 (s, 2H), 3.79 (m, 2H), 3.33 (m, 4H), 3.17 (m, 1H), 2.33 (m, 2H), 1.31 (t, 6H):
MS (+ve ESI): 552.2 (M+H)⁺.

EXAMPLE 36

Preparation of Compound 36 in Table 3—N-(3-fluorophenyl)-2-{3-[(7-{3-[(2-hydroxyethyl)(isobutyl)amino]propoxy}-6-methoxyquinazolin-4-yl)amino]-1H-pyrazol-5-yl}acetamide An analogous reaction to that described in example 34, but starting with 2-(isobutyl amino)ethanol (181 mg, 1.55 mmol) yielded compound 36 in table 3 (101 mg, 57% yield):

$^1$H-NMR (DMSO d$_6$, TFA): 8.96 (s, 1H), 8.30 (s, 1H), 7.63 (d, 1H), 7.32-7.41 (m, 2H), 7.34 (s, 1H), 6.90 (t, 1H), 6.83 (s, 1H), 4.30 (t, 2H), 4.00 (s, 3H), 3.84 (s, 2H), 3.80 (t, 2H), 3.37 (t, 2H), 3.28 (t, 2H), 3.00-3.15 (m, 2H), 2.29 (m, 2H), 2.12 (m, 2H), 1.00 (d, 6H):

MS (+ve ESI): 566.3 (M+H)$^+$.

2-(isobutylamino)ethanol used as starting material was obtained as follows:

Ethylene oxide (5.28 g, 120 mmol) in methanol (14 ml), cooled to −60° C., was slowly added to a solution of isobutylamine (30.7 g, 420 mmol) in methanol (100 ml) at −65° C. under argon. The mixture was allowed to stir at ambient temperature for 14 hours, concentrated and the residual oil was purified by distillation (130° C. @ 0.5 mm Hg) to yield 2-(isobutylamino)ethanol (11 g, 78% yield):

$^1$H-NMR (DMSO d$_6$): 4.40 (m, 1H), 3.42 (m, 2H), 2.50 (m, 2H), 2.30 (d, 2H), 1.63 (m, 1H), 0.85 (d, 6H).

EXAMPLE 37

Preparation of Compound 37 in Table 3—2-{3-[(7-{3-[(2,2-dimethylpropyl)(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-(2,2-dimethylpropyl)amino)ethanol (203 mg, 1.55 mmol) yielded compound 37 in table 3 (111 mg, 61% yield):

$^1$H-NMR (DMSO d$_6$, TFA): 8.96 (s, 1H), 8.30 (s, 1H), 7.64 (d, 1H), 7.32-7.41 (m, 2H), 7.34 (s, 1H), 6.90 (t, 1H), 6.83 (s, 1H), 4.31 (t, 2H), 3.99 (s, 3H), 3.84 (s, 2H), 3.83 (t, 2H), 3.42 (t, 2H), 3.32 (t, 2H), 3.20 (dd, 2H), 2.35 (m, 2H), 1.07 (s, 9H):

MS (+ve ESI): 580.3 (M+H)$^+$.

2-((2,2-dimethylpropyl)amino)ethanol used as starting material was obtained as follows:

Ethylene oxide (2.5 ml, 5.0 mmol) cooled to −20° C. was slowly added to a solution of (2,2-dimethylpropyl)amine (13 g, 150 mmol) in methanol (15 ml) at −30° C. under argon. The mixture was stirred at ambient temperature for 16 hours. The solvent was evaporated, and the residue purified by distillation (b.p. 132° C. @ 9 mmHg) to yield 2-((2,2-dimethylpropyl)amino)ethanol (6.4 g, 97% yield):

$^1$H-NMR (DMSO d$_6$, TFA): 3.70 (m, 2H), 3.02 (m, 2H), 2.81 (m, 2H), 0.98 (s, 9H).

EXAMPLE 38

Preparation of Compound 38 in Table 3—2-{3-[(7-{3-[allyl(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-(allylamino)ethanol (156 mg, 1.55 mmol) yielded compound 38 in table 3 (33 mg, 19% yield):

$^1$H-NMR (DMSO d$_6$, TEA): 8.98 (s, 1H), 8.31 (s, 1H), 7.65 (d, 1H), 7.34-7.43 (m, 2H), 7.34 (s, 1H), 6.92 (t, 1H), 6.85 (s, 1H), 6.01 (m, 1H), 5.64 (d, 1H), 5.58 (d, 1H), 4.31 (t, 2H), 4.02 (s, 3H), 3.92 (t, 2H), 3.86 (s, 2H), 3.81 (t, 2H), 3.20-3.40 (m, 4H), 2.31 (m, 2H):

MS (+ve ESI): 550.2 (M+H)$^+$.

2-(allylamino)ethanol used as starting material was obtained as follows:

Ethylene oxide (2.5 ml, 50 mmol) cooled to −20° C. was added to a solution of allylamine (14 g, 250 mmol) in methanol (20 ml) at −20° C. The mixture was stirred at ambient temperature for 14 hours, the solvent was evaporated, and the residual oil purified by distillation (b.p.140° C. @ 14 mmHg) to yield 2-(allylamino)ethanol (4.2 g, 84% yield):

$^1$H-NMR (DMSO d$_6$): 5.80-5.86 (m, 1H), 5.14 (m, 1H), 5.02 (m, 1H), 3.43 (m, 2H), 3.14 (m, 2H), 2.50 (m, 2H).

EXAMPLE 39

Preparation of Compound 39 in Table 3—N-(3-fluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide An analogous reaction to that described in example 34, but starting with 2-(prop-2-yn-1-ylamino)ethanol (153 mg, 1.55 mmol) yielded compound 39 in table 3 (48 mg, 28% yield):

$^1$H-NMR (DMSO d$_6$, TFA): 8.96 (s, 1H), 8.29 (s, 1H), 7.64 (d, 1H), 7.32-7.41 (m, 2H), 7.32 (s, 1H), 6.90 (t, 1H), 6.90 (s, 1H), 4.31 (t, 2H), 4.29 (s, 2H), 4.00 (s, 3H), 3.90 (s, 1H), 3.84 (s, 2H), 3.79 (t, 2H), 3.43 (m, 2H), 3.34 (m, 2H), 2.30 (m, 2H):

MS (+ve ESI): 548.2 (M+H)$^+$.

2-(prop-2-yn-1-ylamino)ethanol used as starting material was obtained as follows:

Ethylene oxide (3.3 g, 75 mmol) in methanol (10 ml) cooled to −40° C. was slowly added to a solution of propargylamine (16.5 g, 300 mmol) in methanol (60 ml) cooled to −65° C. under argon. The mixture was stirred at ambient temperature for 16 hours, the solvent was evaporated, and the residue purified by distillation to yield 2-(prop-2-yn-1-ylamino)ethanol (5 g, 67% yield):

$^1$H-NMR (DMSO d$_6$, TFA): 3.91 (m, 2H), 3.65 (m, 3H), 3.06 (m, 2H).

EXAMPLE 40

Preparation of Compound 40 in Table 3—2-{3-[(7-{3-[cyclopropyl(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-(cyclopropylamino)ethanol (156 mg, 1.55 mmol, obtained as described by Morrow, D, F et al in *J. Med. Chem.* 1973, 16, 736-9) yielded compound 40 in table 3 (22 mg, 13% yield):

$^1$H-NMR (DMSO d$_6$, TFA): 8.97 (s, 1H), 8.31 (s, 1H), 7.65 (d, 1H), 7.33-7.42 (m, 2H), 7.37 (s, 1H), 6.92 (t, 1H), 6.85 (s, 1H), 4.33 (m, 2H), 4.02 (s, 3H), 3.86 (s, 2H), 3.79 (t, 2H), 3.48 (m, 2H), 3.42 (t, 2H), 2.97 (m, 1H), 2.36 (m, 2H), 1.04 (m, 2H), 0.94 (m, 2H):

MS (+ve ESI): 550.2 (M+H)$^+$.

EXAMPLE 41

Preparation of Compound 41 in Table 3—2-{3-[(7-{3-[(cyclopropylmethyl)(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-((cyclopropylmethyl)amino)ethanol (178 mg, 1.55 mmol) yielded compound 41 in table 3 (19 mg, 11% yield):

$^1$H-NMR (DMSO $d_6$, TFA): 8.97 (s, 1H), 8.31 (s, 1H), 7.66 (d, 1H), 7.33-7.42 (m, 2H), 7.34 (s, 1H), 6.91 (t, 1H), 6.85 (s, 1H), 4.32 (t, 2H), 4.01 (s, 3H), 3.86 (s, 2H), 3.81 (t, 2H), 3.44 (m, 2H), 3.35 (m, 2H), 3.18 (t, 2H), 2.30 (m, 2H), 1.16 (m, 1H), 0.61 (m, 2H), 0.46 (m, 2H):

MS (+ve ESI): 564.2 (M+H)$^+$.

2-((cyclopropylmethyl)amino)ethanol used as starting material was obtained as follows:

a) A solution of ethyl oxalyl chloride (4.2 ml, 37.6 mmol) in dichloromethane (35 ml) was added over 30 minutes to a solution of cyclopropylmethylamine (3 ml, 34.6 mmol) and triethylamine (7 ml) in dichloromethane (35 ml) at 0° C. The mixture was stirred at ambient temperature for 2 hours. Water (20 ml) was added and the pH adjusted to 3 using 2.0 N hydrochloric acid. The organic phase was separated, dried (magnesium sulphate) and concentrated to yield ethyl [(cyclopropylmethyl)amino](oxo)acetate (5.9 g, 100% yield):

$^1$H-NMR (CDCl$_3$): 7.24 (br s, 1H), 3.24 (m, 2H), 1.43 (t, 3H), 1.04 (m, 1H), 0.29 (m, 2H):

MS (+ve ESI): 172 (M+H)*.

b) A solution of ethyl [(cyclopropylmethyl)amino](oxo)acetate (5.9 g, 34.6 mmol) in tetrahydrofuran (30 ml) was added at ambient temperature to a mixture of borane-tetrahydrofuran complex (130 ml of a 1.0 N solution in THF, 130 mmol) and chlorotrimethylsilane (34 ml, 268 mmol). The reaction mixture was stirred at ambient temperature for 48 hours. Methanol (20 ml) was added and the reaction stirred for a further 30 minutes before dilution with dichloromethane followed by addition of a concentrated solution of hydrochloric acid (4 ml). The mixture was stirred for 30 minutes, basified with methanolic ammonia (7 N) and the resultant solid filtered and washed with dichloromethane. The organic phases were recovered, concentrated and purified by chromatography on silica gel. Elution with dichloromethane followed by increased polarity to dichloromethane:methanol (95:5), dichloromethane:methanolic ammonia (9:1) yielded 2-((cyclopropylmethyl)amino)ethanol as a pale yellow liquid (2.99 g, 75% yield):

$^1$H-NMR (DMSO $d_6$, TFA): 3.66 (t, 2H), 3.02 (t, 2H), 2.84 (d, 2H), 1.06 (m, 1H), 0.58 (m, 2H), 0.35 (m, 2H).

EXAMPLE 42

Preparation of Compound 42 in Table 3—2-{3-[(7-{3-[cyclobutyl(2-hydroxyethyl)amino]propoxy}-6-methoxyquinazolino-4-yl)amino]-1H-pyrazol-5-yl}-N-(3-fluorophenyl)acetamide An analogous reaction to that described in example 34, but starting with 2-(cyclobutylamino)ethanol (178 mg, 1.55 mmol—obtained as described by D. F. Morrow et al, J. Med. Chem. 1973, 16, 736-9) yielded compound 42 in table 3 (42 mg, 24% yield):

$^1$H-NMR (DMSO $d_6$, TFA): 8.96 (s, 1H), 8.29 (s, 1H), 7.64 (d, 1H), 7.36 (m, 2H), 7.34 (s, 1H), 6.90 (t, 1H), 6.83 (s, 1H), 4.29 (t, 2H), 4.00 (s, 3H), 3.94 (m, 1H), 3.85 (s, 2H), 3.75 (m, 2H), 3.25 (m, 2H), 3.17 (m, 2H), 2.08-2.39 (m, 6H), 1.76 (m, 1H), 1.69 (m, 1H):

MS (+ve ESI): 564.2 (M+H)$^+$.

EXAMPLE 43

Preparation of Compound 43 in Table 3—2-{3-[(7-{3-[cyclopentyl(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-(cyclopentylamino)ethanol (200 mg, 1.55 mmol—obtained as described by D. F. Morrow et al J. Med. Chem. 1973, 16, 736-9) yielded compound 43 in table 3 (30 mg, 17% yield):

$^1$H-NMR (DMSO $d_6$, TFA): 8.96 (s, 1H), 8.30 (s, 1H), 7.64 (d, 1H), 7.34-7.42 (m, 2H), 7.33 (s, 1H), 6.90 (t, 1H), 6.84 (s, 1H), 4.31 (t, 2H), 4.00 (s, 3H), 3.85 (s, 2H), 3.65 (t, 2H), 3.48 (m, 1H), 3.37 (m, 2H), 3.28 (m, 2H), 2.30 (m, 2H), 2.08 (m, 2H), 1.72 (m, 3H), 1.58 (m, 3H):

MS (+ve ESI): 578.3 (M+H)$^+$.

EXAMPLE 44

Preparation of Compound 44 in Table 3—2-{3-[(7-{3-[(2,2-dimethoxyethyl)(2-hydroxyethyl)amino]propoxy}-6-methoxyquinazolin 4-yl)amino]-1H-pyrazol-5-yl}-N-(3-fluorophenyl)acetamide An analogous reaction to that described in example 34, but starting with 2-((2,2-dimethoxyethyl)amino)ethanol (231 mg, 1.55 mmol) yielded compound 44 in table 3 (89 mg, 48% yield):

$^1$H-NMR (DMSO $d_6$, TFA): 8.95 (s, 1H), 8.29 (s, 1H), 7.63 (d, 1H), 7.31-7.40 (m, 2H), 7.33 (s, 1H), 6.89 (t, 1H), 6.83 (s, 1H), 4.85 (t, 1H), 4.28 (t, 2H), 4.00 (s, 3H), 3.84 (s, 2H), 3.80 (t, 2H), 3.41 (s, 6H), 3.37 (m, 6H), 2.29 (m, 2H):

MS (+ve ESI): 598.2 (M+H)$^+$.

2-((2,2-dimethoxyethyl)amino)ethanol used as starting material was obtained as follows.

Ethanolamine (4 ml, 66.3 mmol) in dioxane (50 ml) in the presence of potassium carbonate (6.9 g, 50 mmol) was reacted with 2-bromo-1,1-dimethoxyethane (5 ml, 42.3 mmol) at 75° C. for 6 hours. The solid was filtered and washed with dioxane. The recovered organic phase was concentrated and purified by chromatography on silica gel. Elution with dichloromethane followed by increased polarity to dichloromethane:methanol (97:3), dichloromethane:methanolic ammonia (94:6) yielded 2-((2,2-dimethoxyethyl)amino)ethanol (2.4 g, 38% yield) as a pale yellow liquid:

$^1$H-NMR (DMSO $d_6$, AcOD): 4.64 (t, 1H), 3.61 (t, 2H), 3.34 (s, 6H), 2.99 (m, 2H), 2.93 (m, 2H).

EXAMPLE 45

Preparation of Compound 45 in Table 3—2-{3-[(7-{3-[(2,2-difluoroethyl)(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-((2,2-difluoroethyl)amino)ethanol (194 mg, 1.55 mmol) yielded compound 45 in table 3 (27 mg, 15% yield):

¹H-NMR (DMSO d₆, TFA): 8.96 (s, 1H), 8.30 (s, 1H), 7.64 (d, 1H), 7.33-7.40 (m, 2H), 7.33 (s, 1H), 6.89 (t, 1H), 6.84 (s, 1H), 6.61 (t, 1H), 4.30 (t, 2H), 4.01 (s, 3H), 3.90 (t, 2H), 3.85 (m, 4H), 3.48 (m, 2H), 3.42 (m, 2H), 2.34 (m, 2H):

MS (+ve ESI): 574.3 (M+H)⁺.

2-((2,2-difluoroethyl)amino)ethanol used as starting material was obtained as follows:

a) Methyl difluoroacetate (5 g, 45 mmol) in acetonitrile (50 ml) was reacted with ethanolamine (2.66 ml, 45.4 mmol) at ambient temperature for 24 hours. The solvent was evaporated and the residual oil was purified by chromatography on silica gel, eluting with dichloromethane:methanol (96:4) then dichloromethane:methanolic ammonia (94:6) to yield 2,2-difluoro-N-(2-hydroxyethyl)acetamide (6.18 g, 98% yield):

¹H-NMR (DMSO d₆): 8.76 (br s, 1H), 6.21 (t, 1H), 4.78 (t, 1H), 3.46 (t, 2H), 3.22 (t, 2H):

MS (+ve ESI): 140 (M+H)⁺.

b) Borane-tetrahydrofuran complex (40 ml of a 1.0 N solution in THF, 40 mmol) was added dropwise at 0° C. to a solution of 2,2-difluoro-N-(2-hydroxyethyl)acetamide (2.78 g, 20 mmol) in tetrahydrofuran (30 ml). The mixture was warmed to ambient temperature and then heated at reflux for 18 hours. The reaction mixture was cooled to ambient temperature and concentrated hydrochloric acid (6 ml) was added dropwise. The solvent was evaporated and the crude product was purified by chromatography on silica gel. Elution with dichloromethane:methanolic ammonia (96:4) then dichloromethane:methanolic ammonia (94:6) yielded 2-((2,2-difluoroethyl)amino)ethanol (0.97 g, 39% yield):

¹H-NMR (DMSO d₆, TFA): 6.40 (m, 1H), 3.69 (t, 2H), 3.56 (m, 2H), 3.11 (t, 2H).

EXAMPLE 46

Preparation of compound 46 in table 3—N-(3-fluorophenyl)-2-{3-[(7-{3-[(2-hydroxyethyl)(3,3,3-trifluoropropyl)amino]propoxy}-6-methoxyquinazolin-4-yl)amino]-1H-pyrazol-5-yl}acetamide An analogous reaction to that described in example 34, but starting with 2-((3,3,3-trifluoropropyl)amino)ethanol (221 mg, 1.55 mmol) yielded compound 46 in table 3 (77 mg, 41% yield):

¹H-NMR (DMSO d₆, TFA): 8.96 (s, 1H), 8.29 (s, 1H), 7.63 (d, 1H), 7.31-7.40 (m, 2H), 7.33 (s, 1H), 6.89 (t, 1H), 6.83 (s, 1H), 4.29 (t, 2H), 3.99 (s, 3H), 3.84 (s, 2H), 3.79 (t, 2H), 3.51 (m, 2H), 3.38 (m, 2H), 2.91 (m, 2H), 2.29 (m, 2H):

MS (+ve ESI): 606.2 (M+H)⁺.

2-((3,3,3-trifluoropropyl)amino)ethanol used as starting material was obtained as follows:

3-bromo-1,1,1-trifluoropropane (5.5 ml, 51.65 mmol) in dioxane (50 ml) in the presence of potassium carbonate (14.15 g, 102.5 mmol) was reacted with ethanolamine (3.0 ml, 51 mmol) at 60° C. for 36 hours. The solvent was evaporated and the residue purified by chromatography on silica gel. Elution with dichloromethane:methanol (95:5) then increased polarity to dichloromethane:methanolic ammonia (95:5) yielded 2-((3,3,3-trifluoropropyl)amino)ethanol (4.47 g, 55% yield):

¹H-NMR (DMSO d₆, TFA): 3.56 (t, 2H), 2.97 (t, 2H), 2.82 (t, 2H), 2.57 (m, 2H).

EXAMPLE 47

Preparation of Compound 47 in Table 3—2-{3-[(7-{3-[(cyclobutylmethyl)(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-((cyclobutylmethyl)amino)ethanol (200 mg, 1.55 mmol) yielded compound 47 in table 3 (87 mg, 49% yield):

¹H-NMR (DMSO d₆, TFA): 8.96 (s, 1H), 8.30 (s, 1H), 7.64 (d, 1H), 7.32-7.43 (m, 2H), 7.32 (s, 1H), 6.89 (t, 1H), 6.83 (s, 1H), 4.29 (t, 2H), 4.00 (s, 3H), 3.85 (s, 2H), 3.77 (t, 2H), 3.19-3.34 (m, 6H), 2.75-3.03 (m, 1H), 2.27 (m, 2H), 2.11 (m, 2H), 1.85 (m, 6H):

MS (+ve ESI): 578.3 (M+H)⁺.

2-((cyclobutylmethyl)amino)ethanol used as starting material was obtained as follows:

a) Cyclobutane carbonyl chloride (5 ml, 43.8 mmol) was slowly added to a solution of ethyl glycinate (5.86 g, 42 mmol) in dichloromethane (100 ml) and triethylamine (14.6 ml, 105 mmol) at 0° C. The mixture was then stirred at ambient temperature for 14 hours. The reaction mixture was washed with 1.0 N hydrochloric acid and the organic phase separated, dried (magnesium sulphate) and evaporated in vacuo to yield a yellow solid. Recrystallisation from dichloromethane:petroleum ether, yielded ethyl N-(cyclobutylcarbonyl)glycinate as a white solid (7.78 g, 100% yield):

¹H-NMR (DMSO d₆): 8.08 (t, 1H), 4.09 (q, 2H), 3.79 (s, 2H), 3.07 (m, 1H), 2.00-2.18 (m, 4H), 1.89 (m, 1H), 1.78 (m, 1H), 1.20 (t, 3H).

b) Ethyl N-(cyclobutylcarbonyl)glycinate (7.6 g, 41 mmol) in tetrahydrofuran (40 ml) was added to borane-tetrahydrofuran complex (100 ml of a 1.0 N solution in tetrahydrofuran, 100 mol) and heated at 60° C. for 24 hours. Additional borane-tetrahydrofuran complex (20 ml) was added to the mixture and heating continued for a further 8 hours. The reaction mixture was then diluted slowly with methanol (20 ml) and stirred at ambient temperature for 0.5 hour. A concentrated solution of hydrochloric acid (6 ml) was slowly added following dilution with dichloromethane. The solid which precipitated was removed by filtration and washed with dichloromethane. The organic phase was dried (magnesium sulphate), concentrated and purified by chromatography on silica gel. Elution with dichloromethane:methanol (96:4) then dichloromethane:methanolic ammonia (94:6) yielded 2-((cyclobutylmethyl)amino)ethanol (4.16 g, 78% yield):

¹H-NMR (DMSO d₆, TFA): 8.38 (br s, 1H), 3.65 (t, 2H), 2.98 (m, 4H), 2.62 (m, 2H), 206 (m, 2H), 1.72-1.94 (m, 4H).

EXAMPLE 48

Preparation of Compound 48 in Table 3—N-(3-fluorophenyl)-2-{3-[(7-{3-[(2-hydroxyethyl)(2-methoxyethyl)amino]propoxy}-6-methoxyquinazolin-4-yl) amino]-1H-pyrazol-5-yl}acetamide An analogous reaction to that described in example 34, but starting with 2-((2-methoxy ethyl)amino)ethanol (184 mg, 1.55 mmol—obtained according to A. A. Santilli at al, *J. Heterocycl. Chem.* 1972, 9, 309-13) yielded compound 48 in table 3 (37 mg, 21% yield):

¹H-NMR (DMSO d₆, TFA): 8.95 (s, 1H), 8.29 (s, 1H), 7.64 (d, 1H), 7.31-7.42 (m, 2H), 7.32 (s, 1H), 6.89 (t, 1H), 6.83 (s, 1H), 4.29 (t, 2H), 4.00 (s, 3H), 3.84 (s, 2H), 3.78 (t, 1H), 3.71

(t, 1H), 3.65 (t, 1H), 3.59 (t, 1H), 3.35-3.53 (m, 4H), 3.14 (t, 1H), 3.02 (t, 1H), 2.29 (m, 2H):
MS (+ve ESI): 568.2 (M+H)$^+$.

EXAMPLE 49

Preparation of Compound 49 in Table 3—2-{3-[(7-{3-[(1,3-dioxolan-2-ylmethyl)(2-hydroxyethyl)amino]propoxy}-6-methoxyquinazolin-4-yl)amino]-1H-pyrazol-5-yl}-N-(3-fluorophenyl)acetamide An analogous reaction to that described in example 34, but starting with 2-((1,3-dioxolan-2-ylmethyl)amino)ethanol (227 mg, 1.55 mmol) yielded compound 49 in table 3 (105 mg, 57% yield):
$^1$H-NMR (DMSO d$_6$, TA): 8.95 (s, 1H), 8.29 (s, 1H), 7.64 (d, 1H), 7.31-7.41 (m, 2H), 6.88 (t, 1H), 6.83 (s, 1H), 5.31 (t, 1H), 4.29 (t, 2H), 4.00 (s, 3H), 4.00 (t, 2H), 3.89 (t, 2H), 3.84 (s, 2H), 3.81 (t, 2H), 3.34-3.55 (m, 6H), 2.31 (m, 2H):
MS (+ve ESI): 596.3 (M+H)$^+$.

2-((1,3-dioxolan-2-ylmethyl)amino)ethanol used as starting material was obtained as follows:

2-(bromomethyl)-1,3-dioxolane (4.4 ml, 42.5 mmol) in dioxane (60 ml) was reacted with ethanolamine (4 ml, 66.3 mmol) in the presence of potassium carbonate (6.9 g, 50 mmol) at 75° C. for 7 hours. The mixture was concentrated and purified by chromatography on silica gel, eluting with dichloromethane:methanol (97:3) then dichloromethane:methanolic ammonia (94:6), to yield 2-((1,3-dioxolan-2-ylmethyl)amino)ethanol (1.90 g, 24% yield):
$^1$H-NMR (DMSO d$_6$, TFA): 5.17 (t, 1H), 3.86-4.04 (m, 4H), 3.67 (t, 2H), 3.20 (m, 2H), 3.06 (m, 2H).

EXAMPLE 50

Preparation of Compound 50 in Table 3—2-(3-{[7-(4-chlorobutoxy)-6-methoxyquinazolin-4-yl]amino}-1H-pyrazol-5-yl)-N-(3-fluorophenyl)acetamide An analogous reaction to that described in example 3, but starting with (3-{[7-(4-chlorobutoxy)-6-methoxyquinazolin-4-yl]amino}-1H-pyrazol-5-yl)acetic acid (2.05 g, 5 mmol) yielded compound 50 in table 3 as an off-white solid (1.45 g, 58% yield):
$^1$H-NMR (DMSO d$_6$, TFA): 8.94 (s, 1H), 8.27 (s, 1H), 7.64 (m, 1H), 7.33-7.40 (m, 2H), 7.29 (s, 1H), 6.72-6.88 (m, 1H), 6.83 (s, 1H), 4.27 (m, 2H), 4.01 (s, 3H), 3.85 (s, 2H), 3.76 (m, 2H), 1.92-1.99 (m, 4H):
MS (+ve ESI): 499.1 (M+H)$^+$.

(3-{[7-(4-chlorobutoxy)-6-methoxyquinazolin-4-yl]amino}-1H-pyrazol-5-yl)acetic acid used as starting material was obtained as follows:

a) A solution of N'-(2-cyano-5-hydroxy-4-methoxyphenyl)-N,N-dimethylimidoformamide (3.29 g, 1.5 mmol) in dimethylformamide (33 ml) and potassium carbonate (4.14 g, 30 mmol) was reacted with 1-bromo 4-chorobutane (3.86 g, 2.5 mmol) at 60° C. for 2 hours. Water was added to the reaction mixture which was then extracted with ethyl acetate. The organic phase was dried (magnesium sulphate), concentrated and the residue was purified by chromatography on silica gel. Elution with dichloromethane:ethyl acetate (8:2) then increased polarity to (6:4) yielded N'-[5-(4-chlorobutoxy)-2-cyano-4-methoxyphenyl]-N,N-dimethylimidoformamide as a white solid (3.7 g, 80% yield):
$^1$H-NMR (DMSO d$_6$): 7.97 (s, 1H), 7.09 (s, 1H), 6.74 (s, 1H), 4.07 (m, 2H), 3.73 (m, 5H), 3.06 (s, 3H), 2.96 (s, 3H), 1.87 (m, 4H).

b) N'-[5-(4-chlorobutoxy)-2-cyano-4-methoxyphenyl]-N,N-dimethylimidoformamide (464 g, 15 mmol) in acetic acid (13.5 ml, 225 mmol) was reacted with (3-amino-1H-pyrazol-5-yl)acetic acid (2.22 g, 15.8 mmol) at reflux for 1 hour. The mixture was cooled, diluted with ethanol (25 ml) and the resultant precipitate recovered by suction filtration. The solid was stirred in water for 1 hour, collected by suction filtration and dried to yield (3-([7-(4-chlorobutoxy)-6-methoxyquinazolin-4-yl]amino)-1H-pyrazol-5-yl)acetic acid (4.5 g, 74% yield):
$^1$H-NMR (DMSO d$_6$, TFA): 8.47 (s, 1H), 7.97 (s, 1H), 7.15 (s, 1H), 6.69 (s, 1H), 4.18 (m, 2H), 3.94 (s, 3H), 3.76 (m, 2H), 3.65 (s, 2H), 1.93 (m, 4H):
MS (+ve ESI): 406.14 (M+H)$^+$.

EXAMPLE 51

Preparation of Compound 51 in Table 3—N-(3-fluorophenyl)-2-{3-[(7-{4-[(2R)-2-(hydroxymethyl)pyrrolidin-1-yl]butoxy}-6-methoxyquinazolin-4-yl)amino]-1H-pyrazol-5-yl}acetamide An analogous reaction to that described in example 7, but starting with 2-(3-{[7-(4-chlorobutoxy)-6-methoxyquinazolin-4-yl]amino}-1H-pyrazol-5-yl)-N-(3-fluorophenyl)acetamide (125 mg, 0.25 mmol) and D-prolinol (76 mg, 0.75 mmol) in the presence of potassium iodide (83 mg, 0.5 mmol) and heating for 3 hours, yielded compound 51 in table 3 as a pale yellow solid (68 mg, 48% yield):
$^1$H-NMR (DMSO d$_6$, TFA): 8.96 (s, 1H), 8.29 (s, 1H), 7.64 (m, 1H), 7.34-7;40 (m, 2H), 7.33 (s, 1H), 6.90 (m, 1H), 6.84 (s, 1H), 4.25 (m, 2H), 4.01 (s, 3H), 3.79 (s, 2H), 3.77 (m, 1H), 3.58-3.65 (m, 3H), 3.40-3.50 (m, 1H), 3.14 (m, 2H), 2.10 (m, 1H), 2.00 (m, 1H), 1.80-1.95 (m, 5H), 1.75 (m, 1H):
MS (+ve ESI): 564.3 (M+H)$^+$.

EXAMPLE 52

Preparation of Compound 52 in Table 3—N-(3-fluorophenyl)-2-{3-[(7-{4-[(2-hydroxyethyl)(isobutyl)amino]butoxy}-6-methoxyquinazolin-4-yl)amino]-1H-pyrazol-5-yl}acetamide An analogous reaction to that described in example 51, but starting with 2-(isobutyl amino)ethanol (117 mg, 0.75 mmol) yielded compound 52 in table 3 as a yellow solid (88 mg, 60% yield):
$^1$H-NMR (DMSO d$_6$, TEA): 8.96 (s, 1H), 8.30 (s, 1H), 7.65 (m, 1H), 7.33-7.38 (m, 3H), 6.89 (m, 1H), 6.85 (s, 1H), 4.26 (m, 2H), 4.01 (s, 3H), 3.86 (s, 2H), 3.79 (m, 2H), 3.23-3.29 (m, 2H), 3.09 (m, 1H), 2.98 (m, 1H), 2.10 (m, 1H), 1.91 (m, 4H), 0.99 (d, 6H):
MS (+ve ESI): 580.2 (M+H)$^+$.

EXAMPLE 53

Preparation of Compound 53 in Table 3—2-{3-[(7-{[(2R)-1-(2-tert-butoxyethyl)pyrrolid-2-yl]methoxy}-6-methoxyquinazolin-4-yl)amino]-1H-pyrazol-5-yl}-N-(3-fluorophenyl)acetamide An analogous reaction to that described in example 3, but starting with 3-[(7-{[(2R)-1-(2-tert-butoxyethyl)pyrrolidin-2-yl]methoxy}-6-methoxyquinazolin-4-yl)amino]-1H-pyrazol-5-yl}acetic acid (450 mg, 0.9 mmol) yielded compound 53 in table 3 (130 mg, 24% yield):

¹H-NMR (DMSO d₆): 10.45 (s, 1H), 10.18 (s, 1H), 8.45 (s, 1H), 7.95 (s, 1H), 7.62 (d, 1H), 7.36 (m, 2H), 7.14 (s, 1H), 6.90 (m, 1H), 6.73 (s, 1H), 4.06 (m, 1H), 3.93 (m, 4H), 3.73 (s, 2H), 3.40 (m, 2H), 3.00 (m, 4H), 2.36 (m, 2H), 1.75 (m, 3H), 1.11 (s, 9H):

MS (+ve ESI): 592.2 (M+H)⁺.

3-[(7-{[(2R)-1-(2-tert-butoxyethyl)pyrrolidin-2-yl]methoxy}-6-methoxyquinazolin-4-yl)amino]-1H-pyrazol-5-yl) acetic acid used as starting material was obtained as follows:

a) A solution of N'-(2-cyano-5-hydroxy-4-methoxyphenyl)-N,N-dimethyl-imidoformamide (3.00 g, 13.7 mmol) in dichloromethane (30 ml) was reacted with tert-butyl (2R)-2-(hydroxymethyl)pyrrolidine-1-carboxylate (3.03 g, 15 mmol) in the presence of triphenylphosphine (5.38 g, 20.5 mmol) and diethyl azodicarboxylate (3.23 ml, 20.5 mmol).

The mixture was stirred at ambient temperature for 2 hours, the solvent was evaporated, and the residue purified by chromatography on silica gel. Elution with ethyl acetate:petroleum ether (2:8) then (1:1) yielded tert-butyl(2R)-2-[(4-cyano-5-{[(1E)-(dimethylamino)methylene]amino}-2-methoxyphenoxy)methyl]pyrrolidine-1-carboxylate (5.4 g, 99% yield):

¹H-NMR (DMSO d₆): 7.88-8.00 (m, 1H), 6.92-7.10 (m, 1H), 6.73 (s, 1H), 4.08 (m, 2H), 3.98 (m, 1H), 3.73 (s, 3H), 3.26 (m, 2H), 3.05 (s, 3H), 2.95 (s, 3H), 1.99 (m, 2H), 1.96 (m, 2H), 1.41 (s, 9H):

MS (+ve ESI): 403.3 (M+H)⁺.

b) tert-butyl (2R)-2-[(4-cyano-5-{[(1E)-(dimethylamino)methylene]amino}-2-methoxyphenoxy)methyl]pyrrolidine-1-carboxylate (5.4 g, 13 mmol) was reacted with a mixture of dichloromethane/trifluoroacetic acid (5:1) at ambient temperature for 14 hours.

The solvent was evaporated, and the residue purified by chromatography on silica gel, eluting with dichloromethane:methanol (9:1) then dichloromethane:methanolic ammonia (9:1), to yield N'-{2-cyano-4-methoxy-5-[(2R)-pyrrolidin-2-ylmethoxy]phenyl}-N,N-dimethylimidoformamide (1.5 g, 35% yield):

¹H-NMR (DMSO d₆, TFA): 8.56 (s, 1H), 7.57 (s, 1H, 7.36 (s, 1H), 4.40 (m, 1H), 4.21 (m, 1H), 4.05 (m, 1H), 3.90 (s, 3H), 3.27 (m, 2H), 3.39 (s, 3H), 3.29 (s, 3H), 2.20 (m, 1H), 2.02 (m, 1H), 1.95 (m, 1H), 1.75 (m, 1H):

MS (+ve ESI): 330.2 (M+H)⁺.

c) N'-(2-cyano-4-methoxy-5-[(2R)-pyrrolidin-2-ylmethoxy]phenyl)-N,N-dimethylimidoformamide (1.23 g, 4.06 mmol) in dimethylformamide (13 ml) was reacted with 2-(2-bromoethoxy)-2-methylpropane (809 mg, 4.47 mmol) in the presence of potassium carbonate (842 mg, 6.1 mmol) at 50° C. for 5 hours. The solvent was then evaporated, and the residue purified by chromatography on silica gel, eluting with dichloromethane:methanol (98:2) then (95:5), to yield N'-(5-{[(2R)-1-(2-tert-butoxyethyl)pyrrolidin-2-yl]methoxy}-2-cyano-4-methoxyphenyl)-N,N-dimethylimidoformamide (908 mg, 56% yield):

¹H-NMR (DMSO d₆): 7.91 (s, 1H), 7.07 (s, 1H), 6.74 (s, 1H), 3.97 (m, 1H), 3.84 (m, 1H), 3.72 (s, 3H), 3.39 (m, 2H), 2.92 (m, 2H), 2.50 (m, 1H), 2.31 (m, 1H), 1.91 (m, 1H), 1.68 (m, 2H), 1.57 (m, 1H), 1.11 (s, 9H):

MS (+ve ESI): 403.25 (M+H)⁺.

d) N'-(5-{[(2R)-1-(2-tert-butoxyethyl)pyrrolidin-2-yl]methoxy}-2-cyano-4-methoxyphenyl)-N,N-dimethylimidoformamide (300 mg, 0.74 mmol) in acetic acid (0.64 ml) was reacted with (3-amino-1H-pyrazol-5-yl)acetic acid (110 mg, 0.78 mmol) at 120° C. for 20 minutes. The solvent was evaporated, and the residue triturated with dichloromethane to yield {3-[(7-{[(2R)-1-(2-tert-butoxyethyl)pyrrolidin-2-yl]methoxy}-6-methoxyquinazolin-4-yl)amino]-1H-pyrazol-5-yl}acetic acid (183 mg, 47% yield):

¹H-NMR (DMSO d₆): 10.25 (s, 1H), 8.44 (s, 1H), 7.97 (s, 1H), 7.13 (s, 1H), 6.65 (s, 1H), 4.06 (m, 1H), 3.93 (m, 4H), 3.64 (s, 2H), 3.40 (m, 2H), 3.05 (m, 4H), 2.36 (m, 2H), 1.75 (m, 3H), 1.11 (s, 9H):

MS (+ve ESI): 499.17 (M+H)⁺.

EXAMPLE 54

Preparation of Compound 54 in Table 3—N-(3-fluorophenyl)-2-{3-[(7-{[(2R)-1-(2-hydroxyethyl)pyrrolidin-2-yl]methoxy}-6-methoxyquinazolin-4-yl)amino]-1H-pyrazol-5-yl}acetamide 2-{3-[(7-{[(2R)-1-(2-tert-butoxyethyl)pyrrolidin-2-yl]methoxy}-6-methoxyquinazolin-4-yl)amino]-1H-pyrazol-5-yl}-N-(3-fluorophenyl)acetamide (120 mg, 0.2 mmol) was reacted with a mixture of dichloromethane/trifluoroacetic acid (5:2) at ambient temperature for 18 hours. The solvent was evaporated in vacuo and the residue purified by chromatography on silica gel, eluting with dichloromethane:methanol (9:1) then dichloromethane:methanolic ammonia (95:5), to yield compound 54 in table 3 (40 mg, 37% yield):

¹H-NMR (DMSO d₆): 11.00 (s, 1H), 10.33 (s, 1H), 8.45 (s, 1H), 7.99 (s, 1H), 7.62 (d, 1H), 7.34 (m, 2H), 7.15 (s, 1H), 6.89 (t, 1H), 6.83 (s, 1H), 4.40 (s, 1H), 4.07 (s, 1H), 3.93 (m, 4H), 3.76 (s, 2H), 3.50 (s, 2H), 3.09 (m, 1H), 2.97 (m, 2H), 2.31 (m, 1H), 1.94 (m, 1H), 1.73 (m, 2H), 1.65 (m, 1H):

MS (+ve ESI): 536.2 (M+H)⁺.

EXAMPLE 55

Preparation of Compound 55 in Table 3—N-(3,5-difluorophenyl)-2-(3-{[6-methoxy-7-(3-pyrrolidin-1-ylpropoxy)quinazolin-4-yl]amino}-1H-pyrazol-5-yl) acetamide An analogous reaction to that described in example 7, but starting with 2-(5-((7-(3-chloropropoxy)-6-methoxyquinazolin-4-yl)amino)-1H-pyrazol-3-yl)-N-(3,5-difluorophenyl)acetamide (130 mg, 0.26 mmol) and pyrrolidine (71 mg, 1 mmol) yielded compound 55 in table 3 (24 mg, 17% yield):

¹H-NMR (DMSO d₆, TFA): 8.96 (s, 1H), 8.30 (s, 1H), 7.25-7.45 (m, 3H), 6.91 (m, 1H), 6.84 (s, 1H), 4.30 (m, 2H), 4.01 (s, 3H), 3.86 (s, 2H), 3.60-3.75 (m, 2H), 3.30-3.45 (m, 2H), 3.00-3.15 (m, 2H), 2.20-2.32 (m, 2H), 2.00-2.15 (m, 2H), 1.80-2.00 (m, 2H):

MS (+ve ESI): 538.5 (M+H)⁺.

EXAMPLE 56

Preparation of Compound 56 in Table 3—N-(3,5-difluorophenyl)-2-{3-[(7-{3-[(2-hydroxyethyl)amino]propoxy}-6-methoxyquinazolin-4-yl)amino]-1H-pyrazol-5-yl}acetamide An analogous reaction to that described in example 55 but starting with ethanolamine (61 mg, 1 mmol) yielded compound 56 in table 3 (50 mg, 36% yield):

¹H-NMR (DMSO d₆, TFA): 8.95 (s, 1H), 8.29 (s, 1H), 7.36 (d, 1H), 7.35 (d, 1H), 7.31 (s, 1H), 6.92 (t, 1H), 6.83 (s, 1H), 4.30 (t, 2H), 4.01 (s, 3H), 3.86 (s, 2H), 3.69 (t, 2H), 3.16 (m, 2H), 3.09 (m, 2H), 2.23 (m, 2H):

MS (+ve ESI): 528.5 (M+H)⁺.

EXAMPLE 57

Preparation of Compound 57 in Table 3—N-(3,5-difluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide An analogous reaction to that described in example 55, but starting with 2-amino-2-methyl-1-propanol (89 mg, 1 mmol) yielded compound 57 in table 3 (50 mg, 35% yield):

$^1$H-NMR (DMSO $d_6$, TFA): 8.96 (s, 1H), 8.30 (s, 1H), 7.37 (d, 1H), 7.35 (d, 1H), 7.33 (s, 1H), 6.91 (t, 1H), 6.84 (s, 1H), 4.32 (t, 2H), 4.01 (s, 3H), 3.86 (s, 2H), 3.46 (s, 2H), 3.10 (m, 2H), 2.22 (m, 2H), 1.25 (s, 6H):

MS (+ve ESI): 556.5 (M+H)$^+$.

EXAMPLE 58

Preparation of Compound 58 in Table 3—N-(3,5-difluorophenyl)-2-[3-({6-methoxy-7-[3-(4-methylpiperazin-1-yl)propoxy]quinazolin-4-yl}amino)-1H-pyrazol-5-yl]acetamide An analogous reaction to that described in example 55, but starting with 1-methylpiperazine (100 mg, 1 mmol) yielded compound 58 in table 3 (60 mg, 41% yield):

$^1$H-NMR (DMSO $d_6$, TFA): 8.96 (s, 1H), 8.30 (s, 1H), 7.37 (d, 1H), 7.35 (s, 1H), 7.34 (d, 1H), 6.91 (t, 1H), 6.84 (s, 1H), 4.31 (t, 1H), 4.01 (s, 3H), 3.86 (s, 2H), 3.20-3.95 (m, 8H), 3.44 (t, 2H), 2.95 (s, 3H), 2.30 (m, 2H):

MS (+ve ESI): 567.5 (M+H)$^+$.

EXAMPLE 59

Preparation of Compound 59 in Table 3—N-(3,5-difluorophenyl)-2-{3-[(7-{3-[ethyl(2-hydroxyethyl)amino]propoxy}-6-methoxyquinazolin-4-yl)amino]-1H-pyrazol-5-yl}acetamide An analogous reaction to that described in example 55, but starting with 2-(ethylamino)ethanol (89 mg, 1 mmol) yielded compound 59 in table 3 (124 mg, 86% yield):

$^1$H-NMR (DMSO $d_6$, TFA): 8.96 (s, 1H), 8.30 (s, 1H), 7.35 (m, 2H), 7.33 (s, 1H), 6.90 (m, 1H), 6.84 (s, 1H), 4.30 (m, 2H), 4.01 (s, 3H), 3.86 (s, 2H), 3.78 (t, 2H), 3.30 (m, 6H), 2.29 (m, 2H), 1.27 (t, 3H):

MS (+ve ESI): 556.5 (M+H)$^+$.

EXAMPLE 60

Preparation of Compound 60 in Table 3—N-(3,5-difluorophenyl)-2-{3-[(7-{3-[2-(2-hydroxyethyl)piperidin-1-yl]propoxy}-6-methoxyquinazolin-4-yl)amino]-1H-pyrazol-5-yl}acetamide An analogous reaction to that described in example 55, but starting with 2-(2-hydroxyethyl)piperidine (129 mg, 1 mmol) yielded compound 60 in table 3 (58 mg, 37% yield):

$^1$H-NMR (DMSO $d_6$, TFA): 8.95 (s, 1H), 8.29 (s, 1H), 7.36 (m, 3H), 6.95 (t, 1H), 6.90 (s, 1H), 4.30 (m, 2H), 4.00 (s, 3H), 3.85 (s, 2H), 3.10-3.70 (m, 7H), 2.25 (m, 2H), 1.80 (m, 6H), 1.50 (m, 2H):

MS (+ve ESI): 596.6 (M+H)$^+$.

EXAMPLE 61

Preparation of Compound 61 in Table 3—N-(3,5-difluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide An analogous reaction to that described in example 55, but starting with 2-piperazin-1-ylethanol (130 mg, 1 mmol) yielded compound 61 in table 3 (80 mg, 52% yield):

$^1$H-NMR (DMSO $d_6$, TFA): 8.96 (s, 1H), 8.30 (s, 1H), 7.36 (m, 3H), 6.95 (t, 1H), 6.83 (s, 1H), 4.31 (m, 2H), 4.00 (s, 3H), 3.86 (s, 2H), 3.30-3.90 (m, 14H), 2.30 (m, 2H):

MS (+ve ESI): 597.5 (M+H)$^+$.

EXAMPLE 62

Preparation of Compound 62 in Table 3—N-(3,5-difluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide An analogous reaction to that described in example 55, but starting with 4-(2-hydroxyethyl)piperidine (129 mg, 1 mmol) yielded compound 62 in table 3 (67 mg, 43% yield):

$^1$H-NMR (DMSO $d_6$, TFA): 8.45 (s, 1H), 8.00 (s, 1H), 7.37 (m, 2H), 7.14 (s, 1H), 6.95 (m, 1H), 6.84 (s, 1H), 4.34 (t, 1H), 4.17 (m, 2H), 3.94 (s, 3H), 3.79 (s, 2H), 3.45 (m, 2H), 2.88 (m, 2H), 2.40 (t, 2H), 1.90 (m, 4H), 1.62 (d, 2H), 1.36 (m, 3H), 1.15 (m, 2H):

MS (+ve ESI): 596.6 (M+H)$^+$.

EXAMPLE 63

Preparation of Compound 63 in Table 3—N-(3,5-difluorophenyl)-2-[3-({7-[3-(3-hydroxypiperidin-1-yl)propoxy]-6-methoxyquinazolin-4-yl}amino)-1H-pyrazol-5-yl]acetamide An analogous reaction to that described in example 55, but starting with piperidin-3-ol (101 mg, 1 mmol) yielded compound 63 in table 3 (105 mg, 71% yield):

$^1$H-NMR (DMSO $d_6$, TFA): 8.96 (s, 1H), 8.29 (s, 1H), 7.97 (m, 3H), 6.92 (t, 1H), 6.86 (s, 1H), 4.30 (m, 2H), 4.00 (s, 3H), 3.86 (s, 2H), 2.80-3.60 (m, 6H), 1.70-2.30 (m, 2H):

MS (+ve ESI): 568.5 (M+H)$^+$.

EXAMPLE 64

Preparation of Compound 64 in Table 3—N-(3,5-difluorophenyl)-2-{3-[(7-{3-[(2-hydroxybutyl)amino]propoxy}-6-methoxyquinazolin-4-yl)amino]-1H-pyrazol-5-yl}acetamide An analogous reaction to that described in example 55, but starting with 1-aminobutan-2-ol (89 mg, 1 mmol) yielded compound 64 in table 3 (80 mg, 55% yield):

$^1$H-NMR (DMSO $d_6$, TFA): 8.96 (s, 1H), 8.29 (s, 1H), 7.37 (m, 3H), 6.90 (t, 1H), 6.83 (s, 1H), 4.30 (m, 2H), 4.00 (s, 3H), 3.85 (s, 2H), 3.70 (m, 1H), 2.80-3.20 (m, 4H), 2.25 (m, 2H), 1.45 (m, 2H), 0.90 (t, 3H):

MS (+ve EST): 556.5 (M+H)$^+$.

EXAMPLE 65

Preparation of Compound 65 in Table 3—N-(3,5-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 55, but starting with 4-(hydroxymethyl)piperidine (115 mg, 1 mmol) yielded compound 65 in table 3 (54 mg, 35% yield):
$^1$H-NMR (DMSO d$_6$, TFA): 8.96 (s, 1H), 8.29 (s, 1H), 7.37 (m, 3H), 6.92 (t, 1H), 6.83 (s, 1H), 4.30 (t, 2H), 4.00 (s, 3H), 3.86 (s, 2H), 3.61 (d, 2H), 3.30 (m, 4H), 3.00 (t, 2H), 2.30 (m, 2H), 1.90 (d, 2H), 1.65 (m, 1H), 1.40 (m, 2H):
MS (+ve ESI): 582.6 (M+H)$^+$.

EXAMPLE 66

Preparation of Compound 66 in Table 3—N-(3,5-difluorophenyl)-2-{3-[(7-{3-[(3-hydroxy-2,2-dimethylpropyl)amino]propoxy}-6-methoxyquinazolin-4-yl)amino]-1H-pyrazol-5-yl}acetamide An analogous reaction to that described in example 55, but starting with 3-amino-2,2-dimethylpropan-1-ol (103 mg, 1 mmol) yielded compound 66 in table 3 (53 mg, 36% yield):
$^1$H-NMR (DMSO d$_6$, TFA): 8.96 (s, 1H), 8.29 (s, 1H), 7.36 (m, 3H), 6.92 (t, 1H), 6.83 (s, 1H), 4.30 (t, 2H), 4.00 (s, 3H), 3.85 (s, 2H), 3.28 (s, 2H), 3.16 (m, 2H), 2.91 (s, 2H), 2.26 (m, 2H), 0.94 (s, 6H):
MS (+ve ESI): 570.6 (M+H)$^+$.

EXAMPLE 67

Preparation of Compound 67 in Table 3—N-(3,5-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide An analogous reaction to that described in example 55, but starting with D-prolinol (101 mg, 1 mmol) yielded compound 67 in table 3 (83 mg, 56% yield):
$^1$H-NMR (DMSO d$_6$, TFA): 8.96 (s, 1H), 8.30 (s, 1H), 7.30-7.40 (m, 3H), 6.85-6.95 (m, 1H), 6.84 (s, 1H), 4.30 (m, 2H), 4.01 (s, 3H), 3.86 (s, 2H), 3.72-3.82 (m, 1H), 3.50-3.70 (m, 4H), 3.15-3.30 (m, 2H), 2.25-2.40 (m, 2H), 1.95-2.20 (m, 2H), 1.85-1.95 (m, 1H), 1.70-1.85 (m, 1H):
MS (+ve ESI): 568.5 (M+H)$^+$.

EXAMPLE 68

Preparation of Compound 68 in Table 3—N-(3,5-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide An analogous reaction to that described in example 55, but starting with L-prolinol (101 mg, 1 mmol) yielded compound 68 in table 3 (85 mg, 57% yield):
$^1$H-NMR (DMSO d$_6$, TFA): 8.96 (s, 1H), 8.30 (s, 1H), 7.30-7.40 (m, 3H), 6.85-6.95 (m, 1H), 6.84 (s, 1H), 4.30 (m, 2H), 4.01 (s, 3H), 3.86 (s, 2H), 3.72-3.82 (m, 1H), 3.50-3.70 (m, 4H), 3.15-3.30 (m, 2H), 2.25-2.40 (m, 2H), 1.95-2.20 (m, 2H), 1.85-1.95 (m, 1H), 1.70-1.85 (m, 1H):
MS (+ve ESI): 568.5 (M+H)$^+$.

EXAMPLE 69

Preparation of Compound 69 in Table 3—N-(3,5-difluorophenyl)-2-(3-{[7-(3-{[(2S)-2-hydroxypropyl]amino}propoxy)-6-methoxyquinazolin-4-yl]amino}-1H-pyrazol-5-yl)acetamide An analogous reaction to that described in example 55, but starting with (S)-(+)-1-aminopropan-2-ol (75 mg, 1 mmol) yielded compound 69 in table 3 (67 mg, 48% yield):
$^1$H-NMR (DMSO d$_6$, TFA): 8.96 (s, 1H), 8.29 (s, 1H), 7.36 (m, 3H), 6.90 (t, 1H), 6.84 (s, 1H), 4.31 (t, 2H), 4.01 (s, 3H), 3.95 (m, 1H), 3.86 (s, 2H), 3.16 (m, 2H), 3.07 (m, 1H), 2.85 (m, 1H), 2.25 (m, 2H), 1.15 (d, 3H):
MS (+ve ESI): 542.5 (M+H)$^+$.

EXAMPLE 70

Preparation of Compound 70 in Table 3—N-(3,5-difluorophenyl)-2-(3-{[7-(3-{[(2R)-2-hydroxypropyl]amino}propoxy)-6-methoxyquinazolin-4-yl]amino}-1H-pyrazol-5-yl)acetamide An analogous reaction to that described in example 55, but starting with (R)-(−)-1-aminopropan-2-ol (75 mg, 1 mmol) yielded compound 70 in table 3 (52 mg, 37% yield):
$^1$H-NMR (DMSO d$_6$, TFA): 8.96 (s, 1H), 8.29 (s, 1H), 7.36 (m, 3H), 6.91 (t, 1H), 6.83 (s, 1H), 4.29 (t, 2H), 4.00 (s, 3H), 3.95 (m, 1H), 3.85 (s, 2H), 3.15 (m, 2H), 3.07 (m, 1H), 2.85 (m, 1H), 2.25 (m, 2H), 1.15 (d, 3H):
MS (+ve ESI): 542.5 (M+H)$^+$.

EXAMPLE 71

Preparation of Compound 71 in Table 3—N-(3,5-difluorophenyl)-2-{3-[(7-{3-[(3S)-3-hydroxypyrrolidin-1-yl]propoxy}-6-methoxyquinazolin-4-yl)amino]-1H-pyrazol-5-yl}acetamide An analogous reaction to that described in example 55, but starting with (S)-(−)-3-hydroxypyrrolidine (87 mg, 1 mmol) yielded compound 71 in table 3 (76 mg, 53% yield):
$^1$H-NMR (DMSO d$_6$, TFA): 8.96 (s, 1H), 8.29 (s, E$^1$H), 7.34 (m, 3H), 6.91 (t, 1H), 6.83 (s, 1H), 4.45 (m, 1H), 4.30 (m, 2H), 4.00 (s, 3H), 3.86 (s, 2H), 3.00-3.80 (m, 6H), 2.25 (m, 2H), 1.95 (m, 2H):
MS (+ve ESI): 554.5 (M+H)$^+$.

EXAMPLE 72

Preparation of Compound 72 in Table 3—N-(3,5-difluorophenyl)-2-{3-[(7-{3-[(3R)-3-hydroxypyrrolidin-1-yl]propoxy}-6-methoxyquinazolin-4-yl)amino]-1H-pyrazol-5-yl}acetamide An analogous reaction to that described in example 55, but starting with (R)-(+)-3-hydroxypyrrolidine (87 mg, 1 mmol) yielded compound 72 in table 3 (76 mg, 53% yield):
$^1$H-NMR (DMSO d$_6$, TFA): 8.96 (s, 1H), 8.29 (s, 1H), 7.35 (m, 3H), 6.90 (t, 1H), 6.84 (s, 1H), 4.45 (m, 1H), 4.30 (m, 2H), 4.01 (s, 3H), 3.86 (s, 2H), 3.00-3.80 (m, 6H), 2.25 (m, 2H), 1.95 (m, 2H):
MS (+ve ESI): 554.5 (M+H)$^+$.

EXAMPLE 73

Preparation of Compound 73 in Table 3—N-(3,5-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide 2-(3-{[7-(3-chloropropoxy)-6-methoxyquinazolin-4-yl]amino}-1H-pyrazol-5-yl)-N-(3,5-difluorophenyl)acetamide (2 g, 4 mmol) in 1-methyl-2-pyrrolidinone (20 ml) was reacted with potassium iodide (1.33 g, 8 mmol) and 2-(isobutylamino)ethanol (1.88 g, 16 mmol) under argon, at 60° C. for 8 hours. The solvent was evaporated, and the residue purified by chromatography on silica gel, eluting with dichloromethane:methanol (95:5) then dichloromethane:methanolic ammonia (95:5), to yield compound 73 in table 3 (1.05 g, 45% yield):

$^1$H-NMR (DMSO d$_6$, TFA): 8.95 (s, 1H), 8.29 (s, 1H), 7.35 (d, 2H), 7.34 (s, 1H), 6.92 (t, 1H), 6.83 (s, 1H), 4.30 (m, 2H), 4.00 (s, 3H), 3.86 (s, 2H), 3.82 (t, 2H), 3.89 (m, 2H), 3.29 (m, 2H), 2.17-2.98 (m, 2H), 2.30 (m, 2H), 2.13 (m, 1H), 1.01 (d, 6H):

MS (+ve ESI): 584.3 (M+H)$^+$.

EXAMPLE 74

Preparation of Compound 74 in Table 3—N-(3,5-difluorophenyl)-2-{3-[(7-{3-[(2-hydroxyethyl)(propyl)amino]propoxy}-6-methoxyquinazolin-4-yl)amino]1H-pyrazol-5-yl}acetamide An analogous reaction to that described in example 73, but starting with 2-(propylamino)ethanol (1.83 ml, 16 mmol) yielded compound 74 in table 3 (900 mg, 39% yield):

$^1$H-NMR (DMSO d$_6$): 10.63 (s, 1H), 10.17 (s, 1H), 8.46 (s, 1H), 8.00 (s, 1H), 7.36 (d, 2H), 7.14 (s, 1H), 6.94 (t, 1H), 6.85 (s, 1H), 4.35 (br s, 1H), 4.20 (t, 2H), 3.95 (s, 3H), 3.79 (s, 2H), 3.46 (m, 2H), 2.63 (m, 2H), 2.52 (m, 2H), 2.42 (m, 2H), 1.92 (m, 2H), 1.42 (m, 2H), 0.83 (t, 3H):

MS (+ve ESI): 570.3 (M+H)$^+$.

EXAMPLE 75

Preparation of Compound 75 in Table 3—2-{3-[(7-{3-[allyl(2-hydroxyethyl)amino]propoxy}-6-methoxyquinazolin-4-yl)amino]-1H-pyrazol-5-yl}-N-(3,5-difluorophenyl)acetamide An analogous reaction to that described in example 73, but starting with 2-(allylamino)ethanol (101 mg, 1 mmol) in dimethylacetamide (1.4 ml) at 110° C. for 2.5 hours yielded compound 75 in table 3 (52 mg, 33% yield):

$^1$H-NMR (DMSO d$_6$, TFA): 8.96 (s, 1H), 8.30 (s, 1H), 7.35 (m, 2H), 7.32 (s, 1H), 6.91 (m, 1H), 6.84 (s, 1H), 5.90-6.10 (m, 1H), 5.50-5.75 (m, 2H), 4.30 (m, 2H), 4.00 (s, 3H), 3.86-4.00 (m, 2H), 3.86 (s, 2H), 3.79 (m, 2H), 3.20-3.40 (m, 4H), 2.20-2.40 (m, 2H):

MS (+ve ESI): 568.2 (M+H)$^+$.

EXAMPLE 76

Preparation of Compound 76 in Table 3—N-(3,5-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide An analogous reaction to that described in example 73, but starting with 2-(prop-2-yn-1-ylamino)ethanol (99 mg, 1 mmol) and heating at 105° C. for 12 hours yielded compound 76 in table 3 (50 mg, 31% yield):

$^1$H-NMR (DMSO d$_6$, TFA): 8.95 (s, 1H), 8.29 (s, 1H), 7.34 (m, 2H), 7.31 (s, 1H), 6.91 (m, 1H), 6.83 (s, 1H), 4.29 (m, 4H), 4.00 (s, 3H), 3.89 (m, 1H), 3.86 (s, 2H), 3.80 (m, 2H), 3.43 (m, 2H), 3.36 (m, 2H), 2.30 (m, 2H):

MS (+ve ESI): 566.2 (M+H)$^+$.

EXAMPLE 77

Preparation of Compound 77 in Table 3—N-(3,5-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide An analogous reaction to that described in example 73, but starting with 2-(isopropylamino)ethanol (130 mg, 1 mmol) and heating at 105° C. for 12 hours and 125° C. for 8 hours, yielded compound 77 in table 3 (40 mg, 25% yield):

$^1$H-NMR (DMSO d$_6$, TFA): 8.96 (s, 1H), 8.30 (s, 1H), 7.30-7.40 (m, 3H), 6.89 (m, 1H), 6.84 (s, 1H), 4.30 (m, 2H), 4.00 (s, 3H), 3.86 (s, 2H), 3.76 (m, 2H), 3.35 (m, 4H), 3.18 (m, 1H), 2.30 (m, 2H), 1.30 (m, 6H):

MS (+ve ESI): 570.3 (M+H)$^+$.

EXAMPLE 78

Preparation of Compound 78 in Table 3—N-(3,5-difluorophenyl)-2-{3-[(7-{3-[(2,2-dimethylpropyl)(2-hydroxyethyl)amino]propoxy}-6-methoxyquinazolin-4-yl)amino]-1H-pyrazol-5-yl}acetamide An analogous reaction to that described in example 73, but starting with 2-((2,2-dimethylpropyl)amino)ethanol (131 mg, 1 mmol) and heating at 130° C. for 2 hours, yielded compound 78 in table 3 (42 mg, 25% yield):

$^1$H-NMR (DMSO d$_6$, TFA): 8.95 (s, 1H), 8.29 (s, 1H), 7.30-7.40 (m, 3H), 6.88 (m, 1H), 6.83 (s, 1H), 4.30 (m, 2H), 3.99 (s, 3H), 3.85 (s, 2H), 3.78-3.85 (m, 2H), 3.40 (m, 2H), 3.30 (m, 2H), 3.22 (m, 1H), 3.12 (m, 1H), 2.30 (m, 2H):

MS (+ve ESI): 598.2 (M+H)$^+$.

EXAMPLE 79

Preparation of Compound 79 in Table 3—2-{3-[(7-{3-[cyclobutyl(2-hydroxyethyl)amino]propoxy}-6-methoxyquinazolin-4-yl)amino]-1H-pyrazol-5-yl}-N-(3,5-difluorophenyl)acetamide An analogous reaction to that described in example 73, but starting with 2-(cyclobutylamino)ethanol (115 mg, 1 mmol) and heating at 80° C. for 6 hours in the presence of potassium iodide (93 mg, 0.56 mmol), yielded compound 79 in table 3 (33 mg, 20% yield):

$^1$H-NMR (DMSO d$_6$, TFA): 8.95 (s, 1H), 8.29 (s, 1H), 7.35 (m, 2H), 7.32 (s, 1H), 6.88 (m, 1H), 6.83 (s, 1H), 4.29 (m, 2H), 4.00 (s, 3H), 3.87-3.99 (m, 1H), 3.86 (s, 2H), 3.72 (m, 2H), 3.35 (m, 2H), 3.15 (m, 2H), 2.30 (m, 2H), 2.20 (m, 4H), 1.85 (m, 2H):

MS (+ve ESI): 582.3 (M+H)$^+$.

EXAMPLE 80

Preparation of Compound 80 in Table 3—2-{3-[(7-{3-[(cyclopropylmethyl)(2-hydroxyethyl)amino] propoxy}-6-methoxyquinazolin-4-yl)amino]-1H-pyrazol-5-yl}-N-(3,5-difluorophenyl)acetamide An analogous reaction to that described in example 79, but starting with 2-((cyclopropylmethyl)amino)ethanol (115 mg, 1 mmol) yielded compound 80 in table 3 (33 mg, 20% yield):

$^1$H-NMR (DMSO d$_6$, TFA): 8.95 (s, 1H), 8.30 (s, 1H), 7.35 (m, 2H), 7.33 (s, 1H), 6.88 (m, 1H), 6.84 (s, 1H), 4.30 (m, 2H), 4.00 (s, 3H), 3.86 (s, 2H), 3.80 (s, 2H), 3.20-3.45 (m, 4H), 3.15 (m, 2H), 2.30 (m, 2H), 1.12 (m, 1H), 0.68 (m, 2H), 0.42 (m, 2H):

MS (+ve ESI): 582.3 (M+H)$^+$.

EXAMPLE 81

Preparation of Compound 81 in Table 3—N-(2,3-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide An analogous reaction to that described in example 73, but starting with L-prolinol (1.3 ml, 13.17 mmol) and 2-(3-{[7-(3-chloropropoxy)-6-methoxyquinazolin-4-yl]amino}-1H-pyrazol-5-yl)-N-(2,3-difluorophenyl)acetamide (1.63 g, 3.24 mmol) yielded compound 81 in table 3 (1.64 g, 89% yield):

$^1$H-NMR (DMSO d$_6$, TFA): 8.96 (s, 1H), 8.30 (s, 1H), 7.74 (m, 1H), 7.33 (s, 1H), 7.19 (t, 2H), 6.84 (s, 1H), 4.31 (t, 2H), 4.01 (s, 3H), 3.94 (s, 2H), 3.77 (q, 1H), 3.64 (m, 4H), 3.22 (m, 2H), 2.30 (m, 2H), 2.14 (m, 1H), 2.03 (m, 1H), 1.90 (m, 1H), 1.78 (m, 1H):

MS (+ve ESI): 568.3 (M+H)$^+$.

EXAMPLE 82

Preparation of Compound 82 in Table 3—N-(2,3-difluorophenyl)-2-{3-[(7-{3-[(2,2-dimethylpropyl)(2-hydroxyethyl)amino]propoxy}-6-methoxyquinazolin-4-yl)amino]-1H-pyrazol-5-yl}acetamide An analogous reaction to that described in example 81, but starting with 2-((2,2-dimethylpropyl)amino)ethanol (131 mg, 1 mmol) in dimethylacetamide at 70° C. for 10 hours yielded compound 82 in table 3 (64 mg, 33% yield):

$^1$H-NMR (DMSO d$_6$, TFA): 8.96 (s, 1H), 8.30 (s, 1H), 7.74 (m, 1H), 7.35 (s, 1H), 7.19 (m, 2H), 6.84 (s, 1H), 4.31 (m, 2H), 3.99 (s, 3H), 3.94 (s, 2H), 3.84 (m, 2H), 3.42 (m, 2H), 3.3 (m, 2H), 3.22 (d, 1H), 3.15 (d, 1H), 3.13 (m, 2H), 2.35 (m, 2H), 1.09 (s, 9H):

MS (+ve ESI): 598.3 (M+H)$^+$.

EXAMPLE 83

Preparation of Compound 83 in Table 3—N-(2,3-difluorophenyl)-2-{3-[(7-{3-[(2-hydroxyethyl)(propyl)amino]propoxy}-6-methoxyquinazolin-4-yl)amino]-1H-pyrazol-5-yl}acetamide An analogous reaction to that described in example 81, but starting with 2-(propylamino)ethanol (700 mg, 68 mmol) and heating at 85° C. for 5 hours, yielded compound 83 in table 3 as an off-white solid (650 mg, 67% yield):

$^1$H-NMR (DMSO d$_6$, TFA): 8.96 (s, 1H), 8.30 (s, 1H), 7.75 (m, 1H), 7.33 (s, 1H), 7.18-7.22 (m, 2H), 6.84 (s, 1H), 4.30 (m, 2H), 4.00 (s, 3H), 3.94 (s, 2H), 3.78 (m, 2H), 3.30-3.45 (m, 2H), 3.28 (m, 2H), 3.15-3.20 (m, 2H), 2.28 (m, 2H), 1.73 (m, 2H), 0.95 (t, 3H):

MS (+ve ESI): 570.3 (M+H)$^+$.

EXAMPLE 84

Preparation of Compound 84 in Table 3—N-(2,3-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide An analogous reaction to that described in example 81, but starting with 2-(isobutylamino)ethanol (936 mg, 80 mmol) and heating at 90° C. for 3.5 hours, yielded compound 84 in table 3 as an off-white solid (810 mg, 69% yield):

$^1$H-NMR (DMSO d$_6$, TFA): 8.96 (s, 1H), 8.30 (s, 1H), 7.45 (m, 1H), 7.34 (s, 1H), 7.21 (m, 2H), 6.84 (s, 1H), 4.31 (m, 2H), 4.00 (s, 3H), 3.95 (s, 2H), 3.81 (m, 2H), 3.36 (m, 2H), 3.30 (m, 2H), 3.12 (m, 1H), 3.06 (m, 1H), 2.31 (m, 2H), 2.13 (m, 1H), 1.01 (d, 6H):

MS (+ve ESI): 584.3 (M+H)$^+$.

EXAMPLE 85

Preparation of Compound 85 in Table 3—2-{3-[(7-{3-[cyclobutyl(2-hydroxyethyl)amino]propoxy}-6-methoxyquinazolin-4-yl)amino]-1H-pyrazol-5-yl}-N-(2,3-difluorophenyl)acetamide An analogous reaction to that described in example 81, but starting with 2-(cyclobutylamino)ethanol (117 mg, 1 mmol) and potassium iodide (103 mg, 0.62 mmol) in dimethylacetamide (2 ml) at 95° C. for 4 hours under argon yielded compound 85 in table 3 (97 mg, 56% yield):

$^1$H-NMR (DMSO d$_6$, TFA): 8.92 (s, 1H), 8.27 (s, 1H), 7.74 (m, 1H), 7.29 (s, 1H), 7.15-7.20 (m, 2H), 6.83 (s, 1H), 4.30 (m, 2H), 3.98 (s, 3H), 3.98 (m, 3H), 3.68-3.80 (m, 2H), 3.20-3.30 (m, 2H), 3.15 (m, 2H), 2.30 (m, 2H), 2.22 (m, 4H), 1.65-1.82 (m, 2H):

MS (+ve ESI): 582.2 (M+H)$^+$.

EXAMPLE 86

Preparation of Compound 86 in Table 3—2-{3-[(7-{3-[cyclopentyl(2-hydroxyethyl)amino]propoxy}-6-methoxyquinazolin-4-yl)amino]-1H-pyrazol-5-yl}-N-(2,3-difluorophenyl)acetamide An analogous reaction to that described in example 85, but starting with 2-(cyclopentylamino)ethanol (129 mg, 1 mmol) yielded compound 86 in table 3 (86 mg, 48% yield):

$^1$H-NMR (DMSO d$_6$, TFA): 8.93 (s, 1H), 8.28 (s, 1H), 7.73 (m, 1H), 7.30 (s, 1H), 7.14 (m, 2H), 6.83 (s, 1H), 4.29 (m, 2H), 3.98 (s, 3H), 3.93 (s, 2H), 3.78 (m, 3H), 3.37 (m, 2H), 3.26 (m, 2H), 2.30 (m, 2H), 2.09 (m, 2H), 1.74 (m, 4H), 1.72 (m, 2H):

MS (+ve ESI): 596.2 (M+H)$^+$.

EXAMPLE 87

Preparation of Compound 87 in Table 3—N-(2,3-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide An analogous reaction to that described in example 81, but starting with (2R)-pyrrolidin-2-ylmethanol (101 mg, 1 mmol) yielded compound 87 in table 3 (134 mg, 79% yield):
$^1$H-NMR (DMSO d$_6$, TFA): 8.95 (s, 1H), 8.29 (s, 1H), 7.75 (m, 1H), 7.32 (s, 1H), 7.16 (m, 2H), 6.84 (s, 1H), 4.30 (m, 2H), 4.00 (s, 3H), 3.94 (s, 2H), 3.70-3.85 (m, 1H), 3.52-3.70 (m, 4H), 3.15-3.30 (m, 2H), 2.25 (m, 2H), 1.75-2.20 (m, 4H):
MS (+ve ESI): 568.2 (M+H)$^+$.

EXAMPLE 88

Preparation of Compound 88 in Table 3—N-(2,3-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide An analogous reaction to that described in example 81, but starting with 2-(prop-2-yn-1-ylamino)ethanol (99 mg, 1 mmol) yielded compound 88 in table 3 (128 mg, 75% yield):
$^1$H-NMR (DMSO d$_6$, TFA): 8.95 (s, 1H), 8.29 (s, 1H), 7.74 (m, 1H), 7.31 (s, 1H), 7.18 (m, 2H), 6.83 (s, 1H), 4.30 (m, 4H), 4.00 (s, 3H), 3.94 (s, 2H), 3.87 (m, 1H), 3.80 (m, 2H), 3.44 (m, 2H), 3.35 (m, 2H), 2.30 (m, 2H):
MS (+ve ESI): 566.2 (M+H)$^+$.

EXAMPLE 89

Preparation of Compound 89 in Table 3—2-{3-[(7-{3-[(cyclopropylmethyl)(2-hydroxyethyl)amino]propoxy}-6-methoxyquinazolin-4-yl)amino]-1H-pyrazol-5-yl}-N-(2,3-difluorophenyl)acetamide An analogous reaction to that described in example 81, but starting with 2-(cyclopropylmethyl)amino)ethanol (115 mg, 1 mmol) yielded compound 89 in table 3 (6 mg, 3% yield):
$^1$H-NMR (DMSO d$_6$): 10.23 (s, 1H), 10.16 (s, 1H), 8.44 (s, 1H), 7.98 (s, 1H), 7.72 (m, 1H), 7.18 (m, 2H), 7.14 (s, 1H), 6.84 (s, 1H), 4.32 (s, 1H), 4.18 (t, 2H), 3.93 (s, 3H), 3.85 (s, 2H), 3.45 (m, 2H), 2.69 (t, 2H), 2.58 (t, 2H), 2.35 (d, 2H), 1.90 (m, 2H), 0.83 (m, 1H), 0.41 (m, 2H), 0.08 (m, 2H):
MS (+ve ESI): 582.2 (M+H)$^+$.

EXAMPLE 90

Preparation of Compound 90 in Table 3—2-{3-[(7-{3-[(cyclobutylmethyl)(2-hydroxyethyl)amino]propoxy}-6-methoxyquinazolin-4-yl)amino]-1H-pyrazol-5-yl}-N-(2,3-difluorophenyl)acetamide An analogous reaction to that described in example 81, but starting with 2-((cyclobutylmethyl)amino)ethanol (129 mg, 1 mmol) yielded compound 90 in table 3 (134 mg, 75% yield):
$^1$H-NMR (DMSO d$_6$): 8.49 (s, 1H), 8.00 (s, 1H), 7.70-7.78 (m, 1H), 7.15-7.30 (m, 3H), 6.75 (m, 1H), 4.25 (m, 2H), 3.96 (s, 3H), 3.86 (s, 2H), 3.60-3.80 (m, 2H), 3.00-3.40 (m, 4H), 2.50-2.80 (m, 4H), 1.61-2.40 (m, 7H):
MS (+ve ESI): 596.2 (M+H)$^+$.

EXAMPLE 91

Preparation of Compound 91 in Table 3—N-(2,3-difluorophenyl)-2-{3-[(7-{3-[(2,2-dimethoxyethyl)(2-hydroxyethyl)amino]propoxy}-6-methoxyquinazolin-4-yl)amino]-1H-pyrazol-5-yl}acetamide An analogous reaction to that described in example 81, but starting with 2-((2,2-dimethoxyethyl)amino)ethanol (149 mg, 1 mmol) yielded compound 91 in table 3 (94 mg, 51% yield):
$^1$H-NMR (DMSO d$_6$, TFA): 8.95 (s, 1H), 8.29 (s, 1H), 7.70-7.80 (m, 1H), 7.32 (s, 1H), 7.17 (m, 2H), 6.84 (s, 1H), 4.85 (t, 1H), 4.30 (m, 2H), 4.00 (s, 3H), 3.94 (s, 2H), 3.81 (m, 2H), 3.30-3.55 (m, 10H), 2.30 (m, 2H):
MS (+ve ESI): 616.2 (M+H)$^+$.

EXAMPLE 92

Preparation of Compound 92 in Table 3—N-(2,3-difluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide An analogous reaction to that described in example 81, but starting with 4-(2-hydroxyethyl)piperidine (129 mg, 1 mmol) yielded compound 92 in table 3 (113 mg, 63.% yield):
$^1$H-NMR (DMSO d$_6$, TFA): 8.94 (s, 1H), 8.28 (s, 1H), 7.73 (m, 1H), 7.31 (s, 1H), 7.10-7.20 (m, 2H), 6.83 (s, 1H), 4.30 (m, 2H), 3.99 (s, 3H), 3.93 (s, 2H), 3.56 (d, 2H), 3.47 (m, 2H), 3.26 (m, 2H), 2.96 (m, 2H), 2.30 (m, 2H), 1.75-1.95 (m, 2H), 1.60-1.75 (m, 1H), 1.30-1.45 (m, 4H):
MS (+ve ESI): 596.2 (M+H)$^+$.

EXAMPLE 93

Preparation of Compound 93 in Table 3—N-(2,3-difluorophenyl)-2-[3-({7-[3-(4-hydroxypiperidin-1-yl)propoxy]-6-methoxyquinazolin-4-yl}amino)-1H-pyrazol-5-yl]acetamide An analogous reaction to that described in example 81, but starting with piperidin-4-ol (101 mg, 1 mmol) yielded compound 93 in table 3 (146 mg, 86% yield):
$^1$H-NMR (DMSO d$_6$, TFA): 8.95 (s, 1H), 8.29 (s, 1H), 7.73 (m, 1H), 7.32 (s, 1H), 7.19 (m, 2H), 6.84 (s, 1H), 4.30 (m, 2H), 4.00 (s, 3H), 3.94 (s, 2H), 3.70-3.80 (m, 1H), 3.55-3.70 (m, 2H), 3.35-3.45 (m, 1H), 3.25-3.35 (m, 2H), 2.95-3.10 (m, 1H), 2.30 (m, 2H), 1.95-2.05 (m, 1H), 1.75-1.95 (m, 2H), 1.55-1.70 (m, 1H):
MS (+ve ESI): 568.2 (M+H)$^+$.

EXAMPLE 94

Preparation of Compound 94 in Table 3—N-(2,3-difluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide An analogous reaction to that described in example 81, but starting with 2-piperazin-1-ylethanol (130 mg, 1 mmol) yielded compound 94 in table 3 (52 mg, 29% yield):
$^1$H-NMR (DMSO d$_6$, TFA): 8.95 (s, 1H), 8.30 (s, 1H), 7.72 (m, 2H), 7.32 (s, 1H), 7.17 (m, 2H), 6.84 (s, 1H), 4.33 (m, 2H), 4.00 (s, 3H), 3.94 (s, 2H), 3.78 (m, 2H), 3.45-3.78 (m, 8H), 3.44 (m, 2H), 3.37 (m, 2H), 2.30 (m, 2H):
MS (+ve ESI): 597.2 (M+H)$^+$.

EXAMPLE 95

Preparation of Compound 95 in Table 3—N-(2,3-difluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide An analogous reaction to that described in example 81, but starting with 2-((2-methoxyethyl)amino)ethanol (119 mg, 1 mmol) yielded compound 95 in table 3 (124 mg, 71% yield):
$^1$H-NMR (DMSO d$_6$, TFA): 8.97 (s, 1H), 8.31 (s, 1H), 7.76 (m, 1H), 7.33 (s, 1H), 7.19 (m, 2H), 6.85 (s, 1H), 4.31 (t, 2H), 4.02 (s, 3H), 3.95 (s, 2H), 3.80 (t, 2H), 3.73 (t, 2H), 3.45 (m, 4H), 3.36 (m, 5H), 2.31 (m, 2H):
MS (+ve ESI): 586.2 (M+H)$^+$.

EXAMPLE 96

Preparation of Compound 96 in Table 3—2-{3-[(7-{3-[allyl(2-hydroxyethyl)amino]propoxy}-6-methoxyquinazolin-4-yl)amino]-1H-pyrazol-5-yl}-N-(2,3-difluorophenyl)acetamide An analogous reaction to that described in example 81, but starting with 2-(allylamino)ethanol (101 mg, 1 mmol) yielded compound 96 in table 3 (99 mg, 58% yield):
$^1$H-NMR (DMSO d$_6$, TFA): 8.97 (s, 1H), 8.32 (s, 1H), 7.77 (m, 1H), 7.33 (s, 1H), 7.18 (m, 2H), 6.87 (s, 1H), 6.01 (m, 1H), 5.60 (m, 2H), 4.31 (t, 2H), 4.02 (s, 3H), 3.94 (m, 4H), 3.82 (t, 2H), 3.35 (m, 4H), 2.34 (m, 2H):
MS (+ve ESI): 568.2 (M+H)$^+$.

EXAMPLE 97

Preparation of Compound 97 in Table 3—N-(2,3-difluorophenyl)-2-{3-[(7-{3-[(1,3-dioxolan-2-ylmethyl)(2-hydroxyethyl)amino]propoxy}-6-methoxyquinazolin-4-yl)amino]-1H-pyrazol-5-yl}acetamide An analogous reaction to that described in example 81, but starting with 2-((1,3-dioxolan-2-ylmethyl)amino)ethanol (147 mg, 1 mmol) yielded compound 97 in table 3 (126 mg, 68% yield):
$^1$H-NMR (DMSO d$_6$, TFA): 8.94 (s, 1H), 8.29 (s, 1H), 7.75 (m, 1H), 7.31 (s, 1H), 7.16 (m, 2H), 6.83 (s, 1H), 5.30 (m, 1H), 4.30 (m, 2H), 4.01 (m, 5H), 3.99 (s, 2H), 3.93 (m, 2H), 3.89 (m, 2H), 3.45 (m, 6H), 2.30 (m, 2H):
MS (+ve ESI): 614.2 (M+H)$^+$.

EXAMPLE 98

Preparation of Compound 98 in Table 3—N-(2,3-difluorophenyl)-2-{3-[(7-{3-[ethyl(2-hydroxyethyl)amino]propoxy}-6-methoxyquinazolin-4-yl)amino]-1H-pyrazol-5-yl}acetamide An analogous reaction to that described in example 81, but starting with 2-(ethylamino)ethanol (89 mg, 1 mmol) yielded compound 98 in table 3 (94 mg, 56% yield):
$^1$H-NMR (DMSO d$_6$, TFA): 8.94 (s, 1H), 8.29 (s, 1H), 7.75 (m, 1H), 7.31 (s, 1H), 7.15 (m, 2H), 6.83 (s, 1H), 4.31 (m, 2H), 3.99 (s, 3H), 3.93 (s, 2H), 3.76 (m, 2H), 3.30 (m, 6H), 2.26 (m, 2H), 1.25 (t, 3H):
MS (+ve ESI): 556.2 (M+H)$^+$.

EXAMPLE 99

Preparation of Compound 99 in Table 3—N-(2,3-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide An analogous reaction to that described in example 81, but starting with 2-(isopropylamino)ethanol (103 mg, 1 mmol) yielded compound 99 in table 3 (84 mg, 49% yield):
$^1$H-NMR (DMSO d$_6$, TFA): 8.97 (s, 1H), 8.33 (s, 1H), 7.79 (m, 1H), 7.35 (s, 1H), 7.18 (m, 2H), 6.88 (s, 1H), 4.34 (t, 2H), 4.03 (s, 3H), 3.98 (s, 2H), 3.81 (m, 3H), 3.40 (m, 3H), 3.20 (m, 1H), 2.35 (m, 2H), 1.33 (m, 6H):
MS (+ve ESI): 570.2 (M+H)$^+$.

EXAMPLE 100

Preparation of Compound 100 in Table 3—N-(2,3-difluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide An analogous reaction to that described in example 81, but starting with 2-amino-2-methylpropan-1-ol (101 mg, 1 mmol) yielded compound 100 in table 3 (165 mg, 99% yield):
$^1$H-NMR (DMSO d$_6$): 8.48 (s, 1H), 7.99 (s, 1H), 7.72 (m, 1H), 7.22 (m, 4H), 4.25 (t, 2H), 3.95 (s, 3H), 3.85 (s, 2H), 3.35 (m, 2H), 2.95 (m, 2H), 2.10 (m, 2H), 1.16 (s, 6H):
MS (+ve ESI): 556.2 (M+H)$^+$.

EXAMPLE 101

Preparation of Compound 101 in Table 3—N-(2,3-difluorophenyl)-2-{3-[(7-{[(2R)-1-(2-hydroxyethyl)pyrrolidin-2-yl]methoxy}-6-methoxyquinazolin-4-yl)amino]-1H-pyrazol-5-yl}acetamide An analogous reaction to that described in example 54, but starting with 2-{3-[(7-{[(2R)-1-(2-tert-butoxyethyl)pyrrolidin-2-yl]methoxy}-6-methoxyquinazolin-4-yl)amino]-1H-pyrazol-5-yl}-N-(2,3-difluorophenyl)acetamide (67 mg, 0.11 mmol) yielded compound 101 in table 3 (36 mg, 59% yield):
$^1$H-NMR (DMSO d$_6$, TFA): 8.98 (s, 1H), 8.35 (s, 1H), 7.76 (m, 1H), 7.36 (s, 1H), 7.19 (m, 2H), 6.87 (s, 1H), 4.62 (m, 1H), 4.50 (m, 1H), 4.20 (m, 1H), 4.04 (s, 3H), 3.96 (s, 2H), 3.81 (m, 2H), 3.73 (m, 2H), 3.33 (m, 2H), 2.34 (m, 1H), 2.11 (m, 2H), 1.91 (m, 1H):
MS (+ve ESI): 554.1 (M+H)$^+$.

2-{3-[(7-{[(2R)-1-(2-tert-butoxyethyl)pyrrolidin-2-yl]methoxy}-6-methoxyquinazolin-4-yl)amino]-1H-pyrazol-5-yl}-N-(2,3-difluorophenyl)acetamide use as starting material was obtained as follows:

An analogous reaction to that described in example 5, but starting with {3-[(7-{[(2R)-1-(2-tert-butoxyethyl)pyrrolidin-2-yl]methoxy}-6-methoxyquinazolin-4-yl)amino]-1H-pyrazol-5-yl}acetic acid (240 mg, 0.48 mmol) yielded 2-{3-[(7-{[(2R)-1-(2-tert-butoxyethyl)pyrrolidin-2-yl]methoxy}-6-methoxyquinazolin-4-yl)amino]-1H-pyrazol-5-yl}N-(2,3-difluorophenyl)acetamide (72 mg, 25% yield):
$^1$H-NMR (DMSO d$_6$, TFA): 8.98 (s, 1H), 8.34 (s, 1H), 7.75 (m, 1H), 7.35 (s, 1H), 7.19 (m, 2H), 6.85 (s, 1H), 4.62 (m, 1H), 4.50 (m, 1H), 4.20 (m, 1H), 4.03 (s, 3H), 3.95 (s, 2H), 3.72 (m, 4H), 3.40 (m, 2H), 2.34 (m, 1H), 2.11 (m, 2H), 1.91 (m, 1H), 1.20 (s, 9H):
MS (+ve ESI): 610.2 (M+H)$^+$.

EXAMPLE 102

Preparation of Compound 102 in Table 3—N-(3-chlorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide An analogous reaction to that described in example 7, but starting with 2-(5-((7-(3-chloropropoxy)-6-methoxyquinazolin-4-yl)amino)-1H-pyrazol-3-yl)-N-(3-chlorophenyl)acetamide (100 mg, 0.2 mmol) and L-prolinol (71 mg, 0.7 mmol) yielded compound 102 in table 3 (73 mg, 64% yield):

$^1$H-NMR (DMSO d$_6$, TFA): 8.95 (s, 1H), 8.29 (s, 1H), 7.86 (m, 1H), 7.40-7.50 (m, 1H), 7.30-7.40 (m, 2H), 7.10-7.15 (m, 1H), 6.83 (s, 1H), 4.30 (m, 2H), 4.00 (s, 3H), 3.84 (s, 2H), 3.70-3.80 (m, 1H), 3.47-3.70 (m, 4H), 3.12-3.35 (m, 2H), 2.20-2.40 (m, 2H), 1.97-2.20 (m, 2H), 1.85-1.97 (m, 1H), 1.70-1.85 (m, 1H):

MS (+ve ESI): 566.5 (M+H)$^+$.

EXAMPLE 103

Preparation of Compound 103 in Table 3—N-(3-chlorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide An analogous reaction to that described in example 102, but starting with D-prolinol (71 mg, 0.7 mmol) yielded compound 103 in table 3 (75 mg, 66% yield):

$^1$H-NMR (DMSO d$_6$, TFA): 8.94 (s, 1H), 8.29 (s, 1H), 7.86 (s, 1H), 7.48 (m, 1H), 7.34 (m, 2H), 7.12 (m, 1H), 6.82 (s, 1H), 4.30 (m, 2H), 3.99 (s, 3H), 3.83 (s, 2H), 3.76 (m, 1H), 3.60 (m, 4H), 3.20 (m, 2H), 2.30 (m, 2H), 1.95 (m, 4H):

MS (+ve ESI): 566.5 (M+H)$^+$.

EXAMPLE 104

Preparation of Compound 104 in Table 3—N-(3-chlorophenyl)-2-[3-({7-[3-(3-hydroxypiperidin-1-yl)propoxy]-6-methoxyquinazolin-4-yl}amino)-1H-pyrazol-5-yl]acetamide An analogous reaction to that described in example 102, but starting with piperidin-3-ol (71 mg, 0.7 mmol) yielded compound 104 in table 3 (82 mg, 72% yield):

$^1$H-NMR (DMSO d$_6$, TFA): 8.94 (s, 1H), 8.29 (s, 1H), 7.86 (s, 1H), 7.47 (m, 1H), 7.34 (m, 2H), 7.12 (m, 1H), 6.82 (s, 1H), 4.28 (m, 2H), 4.09 (m, 0.5H), 3.99 (s, 3H), 3.83 (s, 2H), 3.70 (m, 0.5H), 2.60-3.55 (m, 6H), 1.15-3.40 (m, 6H):

MS (+ve ESI): 566.5 (M+H)$^+$.

EXAMPLE 105

Preparation of Compound 105 in Table 3—N-(3-chlorophenyl)-2-{3-[(7-{3-[ethyl(2-hydroxyethyl)amino]propoxy}-6-methoxyquinazolin-4-yl)amino]-1H-pyrazol-5-yl}acetamide An analogous reaction to that described in example 102, but starting with 2-(ethyl-amino)ethanol (78 mg, 0.87 mmol) yielded compound 105 in table 3 (72 mg, 52% yield):

$^1$H-NMR (DMSO d$_6$, TFA): 8.95 (s, 1H), 8.29 (s, 1H), 7.86 (m, 1H), 7.45-7.52 (m, 1H), 7.25-7.30 (m, 2H), 7.08-7.15 (m, 1H), 6.83 (s, 1H), 4.29 (m, 2H), 4.00 (s, 3H), 3.84 (s, 2H), 3.70-3.82 (m, 2H), 3.20-3.45 (m, 6H), 2.20-2.35 (m, 2H), 1.26 (t, 3H):

MS (+ve ESI): 554.5 (M+H)$^+$.

EXAMPLE 106

Preparation of Compound 106 in Table 4—2-{3-[(7-{3-[4-(hydroxymethyl)piperidin-1-yl]propoxy}-6-methoxyquinazolin-4-yl)amino]-1H-pyrazol-5-yl}-N-(3-methoxyphenyl)acetamide {3-[(7-{3-[4-(hydroxymethyl)piperidin-1-yl]propoxy}-6-methoxyquinazolin-4-yl)amino]-1H-pyrazol-5-yl}acetic acid (118 mg, 0.25 mmol) in dimethylformamide (1.2 ml) was reacted with 3-methoxyaniline (46 mg, 0.37 mmol) in the presence of 1-(3-dimethylamino-propyl)-3-ethyl-carbodiimide hydrochloride (81 mg, 0.42 mmol), 2-hydroxypyridin-1-oxide (42 mg, 0.37 mmol) at 55° C. for 2 hours. The solvent was evaporated, and the residue purified by preparative LCMS to yield compound 106 in table 4 (50 mg, 35% yield):

$^1$H-NMR (DMSO d$_6$, TFA): 8.96 (s, 1H), 8.30 (s, 1H), 7.35 (m, 2H), 7.23 (t, 1H), 7.16 (d, 1H), 6.83 (s, 1H), 6.66 (m, 1H), 4.30 (t, 2H), 4.01 (s, 3H), 3.82 (s, 2H), 3.74 (s, 3H), 3.60 (d, 2H), 3.30 (m, 4H), 2.98 (t, 2H), 2.28 (m, 2H), 1.87 (d, 2H), 1.65 (m, 1H), 1.44 (m, 2H):

MS (+ve ESI): 576.6 (M+H)$^+$.

{3-[(7-{3-[4-(hydroxymethyl)piperidin-1-yl]propoxy}-6-methoxyquinazolin-4-yl)amino]-1H-pyrazol-5-yl}acetic acid used as starting material was obtained as follows:

(3-{[7-(3-chloropropoxy)-6-methoxyquinazolin-4-yl]amino}-1H-pyrazol-5-yl)acetic acid (7.83 g, 20 mmol) in dimethylacetamide (30 ml) was reacted with 4-(hydroxymethyl)piperidine (8.05 g, 70 mmol) at 100° C. for 2 hours. The solvent was evaporated, and the residue triturated with a mixture of dichloromethane:ethyl acetate (1:1). The paste was recovered, and dissolved in a mixture of dichloromethane:methanol. Ethanolic HCl (7.0 N) (10 ml, 70 mmol) was added to the mixture and the solvents were evaporated. Methanol (200 ml) was added to the solid and the mixture was stirred for 0.5 hour. The reaction mixture was reduced in volume and dichloromethane added. The resultant solid was recovered by filtration and dried to yield {3-[(7-{3-[4-(hydroxymethyl)piperidin-1-yl]propoxy}-6-methoxyquinazolin-4-yl)amino]-1H-pyrazol-5-yl}acetic acid (6.5 g, 60% yield) as a yellow solid:

$^1$H-NMR (DMSO d$_6$, TFA): 8.96 (s, 1H), 8.31 (s, 1H), 7.37 (s, 1H), 6.80 (s, 1H), 4.31 (m, 2H), 4.00 (s, 3H), 3.75 (s, 2H), 3.59 (d, 2H), 3.24-3.30 (m, 4H), 2.97 (t, 2H), 2.35 (m, 2H), 1.86-1.91 (m, 2H), 1.68 (m, 1H), 1.47 (m, 2H).

EXAMPLE 107

Preparation of Compound 107 in Table 4—2-{3-[(7-{3-[4-(hydroxymethyl)piperidin-1-yl]propoxy}-6-methoxyquinazolin-4-yl)amino]-1H-pyrazol-5-yl}-N-phenylacetamide An analogous reaction to that described in example 106, but starting with aniline (35 mg, 0.37 mmol) yielded compound 107 in table 4 (106 mg, 75% yield):

$^1$H-NMR (DMSO d$_6$, TFA): 8.94 (s, 1H), 8.29 (s, 1H), 7.63 (d, 2H), 7.31 (t, 3H), 7.05 (t, 1H), 6.83 (s, 1H), 4.27 (t, 2H), 3.99 (s, 3H), 3.82 (s, 2H), 3.60 (d, 2H), 3.30 (m, 4H), 2.97 (t, 2H), 2.27 (m, 2H), 1.89 (d, 2H), 1.65 (m, 1H), 1.44 (m, 2H):

MS (+ve ESI): 546.5 (M+H)$^+$.

EXAMPLE 108

Preparation of Compound 108 in Table 4—N-(4-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 4-fluoroaniline (42 mg, 0.37 mmol) yielded compound 108 in table 4 (127 mg, 88% yield):
$^1$H-NMR (DMSO d$_6$, TFA): 8.94 (s, 1H), 8.29 (s, 1H), 7.65 (m, 2H), 7.31 (s, 1H), 7.14 (t, 2H), 6.82 (s, 1H), 4.27 (t, 2H), 3.99 (s, 3H), 3.82 (s, 2H), 3.60 (d, 2H), 3.30 (m, 4H), 2.97 (t, 2H), 2.27 (m, 2H), 1.89 (d, 2H), 1.65 (m, 1H), 1.44 (m, 2H):
MS (+ve ESI): 564.5 (M+H)$^+$.

EXAMPLE 109

Preparation of Compound 109 in Table 4—N-(3,5-dichlorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 3,5-dichloroaniline (62 mg, 0.37 mmol) yielded compound 109 in table 4 (46 mg, 28% yield):
$^1$H-NMR (DMSO d$_6$, TFA): 8.95 (s, 1H), 8.30 (s, 1H), 7.70 (m, 2H), 7.33 (s, 1H), 7.27 (s, 1H), 6.84 (s, 1H), 4.27 (t, 2H), 3.99 (s, 3H), 3.82 (s, 2H), 3.60 (d, 2H), 3.30 (m, 4H), 2.97 (t, 2H), 2.27 (m, 2H), 1.89 (d, 2H), 1.65 (m, 1H), 1.44 (m, 2H):
MS (+ve ESI): 614.4 (M+H)$^+$.

EXAMPLE 110

Preparation of Compound 110 in Table 4—N-(5-chloro-2-methoxyphenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 5-chloro-2-methoxyaniline (60 mg, 0.37 mmol) yielded compound 110 in table 4 (65 mg, 41% yield):
$^1$H-NMR (DMSO d$_6$, TFA): 8.95 (s, 1H), 8.29 (s, 1H), 8.15 (s, 1H), 7.32 (s, 1H), 7.08 (m, 2H), 6.81 (s, 1H), 4.27 (t, 2H), 3.99 (s, 3H), 3.82 (s, 2H), 3.60 (d, 2H), 3.30 (m, 4H), 2.97 (t, 2H), 2.27 (m, 2H), 1.69 (d, 2H), 1.65 (m, 1H), 1.44 (m, 2H):
MS (+ve ESI): 610.5 (M+H)$^+$.

EXAMPLE 111

Preparation of Compound 111 in Table 4—2-{3-[(7-{3-[4-(hydroxymethyl)piperidin-1-yl]propoxy}-6-methoxyquinazolin-4-yl)amino]-1H-pyrazol-5-yl}-N-[3-(trifluoromethyl)phenyl]acetamide An analogous reaction to that described in example 106, but starting with 3-trifluoro-methylaniline (61 mg, 0.37 mmol) yielded compound 111 in table 4 (75 mg, 47% yield):
$^1$H-NMR (DMSO d$_6$, TFA): 8.95 (s, 1H), 8.29 (s, 1H), 8.14 (s, 1H), 7.80 (d, 1H), 7.52 (t, 1H), 7.40 (d, 1H), 7.31 (s, 1H), 6.85 (s, 1H), 4.29 (t, 2H), 4.00 (s, 3H), 3.87 (s, 2H), 3.60 (d, 2H), 3.30 (m, 4H), 2.97 (t, 2H), 2.27 (m, 2H), 1.89 (d, 2H), 1.65 (m, 1H), 1.44 (m, 2H):
MS (+ve ESI): 614.5 (M+H)$^+$.

EXAMPLE 112

Preparation or Compound 112 in Table 4—2-{3-[(7-{3-[4-(hydroxymethyl)piperidin-1-yl]propoxy}-6-methoxyquinazolin-4-yl)amino]-1H-pyrazol-5-yl}-N-(3-hydroxyphenyl)acetamide An analogous reaction to that described in example 106, but starting with 3-hydroxyaniline (41 mg, 0.37 mmol) yielded compound 112 in table 4 (118 mg, 82% yield):
$^1$H-NMR (DMSO d$_6$, TFA): 8.95 (s, 1H), 8.29 (s, 1H), 7.31 (s, 1H), 7.21 (s, 1H), 7.07 (t, 1H), 7.01 (d, 1H), 6.81 (s, 1H), 6.45 (d, 1H), 4.28 (t, 2H), 3.99 (s, 3H), 3.79 (s, 2H), 3.58 (d, 2H), 3.30 (m, 4H), 2.97 (t, 2H), 2.27 (m, 2H), 1.89 (d, 2H), 1.65 (m, 1H), 1.44 (m, 2H):
MS (+ve ESI): 562.5 (M+H)$^+$.

EXAMPLE 113

Preparation of Compound 113 in Table 4—2-{3-[(7-{3-[4-(hydroxymethyl)piperidin-1-yl]propoxy}-6-methoxyquinazolin-4-yl)amino]-1H-pyrazol-5-yl}-N-(3-nitrophenyl)acetamide An analogous reaction to that described in example 106, but starting with 3-nitroaniline (52 mg, 0.37 mmol) yielded compound 113 in table 4 (62 mg, 40% yield):
$^1$H-NMR (DMSO d$_6$, TFA): 8.95 (s, 1H), 8.70 (s, 1H), 8.30 (s, 1H), 7.94 (d, 2H), 7.62 (t, 1H), 7.32 (s, 1H), 6.86 (s, 1H), 4.29 (t, 2H), 4.00 (s, 3H), 3.79 (s, 2H), 3.58 (d, 2H), 3.30 (d, 2H), 2.97 (t, 2H), 2.27 (m, 2H), 1.89 (d, 2H), 1.65 (m, 1H), 1.44 (m, 2H):
MS (+ve ESI): 591.5 (M+H)$^+$.

EXAMPLE 114

Preparation of Compound 114 in Table 4—2-{3-[(7-{3-[4-(hydroxymethyl)piperidin-1-yl]propoxy}-6-methoxyquinazolin-4-yl)amino]-1H-pyrazol-5-yl}-N-1H-indazol-5-ylacetamide An analogous reaction to that described in example 106, but starting with 1H-indazol-5-amine (51 mg, 0.37 mmol) yielded compound 114 in table 4 (95 mg, 63% yield):
$^1$H-NMR (DMSO d$_6$, TFA): 8.94 (s, 1H), 8.29 (s, 1H), 8.18 (s, 1H), 8.03 (s, 1H), 7.50 (m, 2H), 7.35 (s, 1H), 6.84 (s, 1H), 4.28 (t, 2H), 3.99 (s, 3H), 3.83 (s, 2H), 3.60 (d, 2H), 3.30 (m, 4H), 2.97 (t, 2H), 2.27 (m, 2H), 1.89 (d, 2H), 1.65 (m, 1H), 1.44 (m, 2H):
MS (+ve ESI): 586.5 (M+H)$^+$.

EXAMPLE 115

Preparation of Compound 115 in Table 4—N-(4-bromo-2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 4-bromo-2-fluoroaniline (72 mg, 0.37 mmol) yielded compound 115 in table 4 (28 mg, 16% yield):
$^1$H-NMR (DMSO d$_6$, TFA): 8.94 (s, 1H), 8.28 (s, 1H), 7.95 (t, 1H), 7.53 (m, 1H), 7.35 (d, 1H), 7.31 (s, 1H), 6.82 (s, 1H), 4.28 (t, 2H), 3.99 (s, 3H), 3.92 (s, 2H), 3.60 (d, 2H), 3.30 (m, 4H), 2.97 (t, 2H), 2.27 (m, 2H), 1.89 (d, 2H), 1.65 (m, 1H), 1.44 (m, 2H):
MS (+ve ESI): 644.4 (M+H)$^+$.

EXAMPLE 116

Preparation of Compound 116 in Table 4—N-(3-chlorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 3-chloroaniline (48 mg, 0.37 mmol) yielded compound 116 in table 4 (96 mg, 64% yield):
$^1$H-NMR (DMSO d$_6$, TFA): 8.95 (s, 1H), 8.30 (s, 1H), 7.86 (s, 1H), 7.48 (d, 1H), 7.34 (m, 2H), 7.13 (d, 1H), 6.84 (s, 1H), 4.28 (t, 2H), 4.00 (s, 3H), 3.84 (s, 2H), 3.60 (d, 2H), 3.30 (m, 4H), 2.97 (t, 2H), 2.27 (in, 2H), 1.89 (d, 2H), 1.65 (m, 1H), 1.44 (m, 2H):
MS (+ve ESI): 580.5 (M+H)$^+$.

EXAMPLE 117

Preparation of Compound 117 in Table 4—N-(2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 2-fluoroaniline (42 mg, 0.37 mmol) yielded compound 117 in table 4 (74 mg, 50% yield):
$^1$H-NMR (DMSO d$_6$, TFA): 8.95 (s, 1H), 8.29 (s, 1H), 7.94 (m, 1H), 7.33 (s, 1H), 7.26 (m, 1H), 7.16 (m, 2H), 6.83 (s, 1H), 4.28 (t, 2H), 4.00 (s, 3H), 3.92 (s, 2H), 3.60 (d, 2H), 3.30 (m, 4H), 2.97 (t, 2H), 2.27 (m, 2H), 1.89 (d, 2H), 1.65 (m, 1H), 1.44 (m, 2H):
MS (+ve ESI): 564.5 (M+H)$^+$.

EXAMPLE 118

Preparation of Compound 118 in Table 4—N-(3,5-dimethoxyphenyl)-2-{3-[(7-{3-[4-(hydroxymethyl)piperidin-1-yl]propoxy}-6-methoxyquinazolin 4-yl)amino]-1H-pyrazol-5-yl}acetamide An analogous reaction to that described in example 106, but starting with 3,5-dimethoxyaniline (58 mg, 0.37 mmol) yielded compound 118 in table 4 (89 mg, 57% yield):
$^1$H-NMR (DMSO d$_6$, TFA): 8.95 (s, 1H), 8.29 (s, 1H), 7.31 (s, 1H), 6.89 (m, 2H), 6.82 (s, 1H), 6.24 (m, 1H), 4.29 (t, 2H), 4.00 (s, 3H), 3.80 (s, 2H), 3.71 (s, 6H), 3.60 (m, 2H), 3.30 (m, 4H), 3.00 (t, 2H), 2.30 (m, 2H), 1.90 (m, 2H), 1.65 (m, 1H), 1.40 (m, 2H):
MS (+ve ESI): 606.5 (M+H)$^+$.

EXAMPLE 119

Preparation of Compound 119 in Table 4—2-{3-[(7-{3-[4-(hydroxymethyl)Piperidin-1-yl]propoxy}-6-methoxyquinazolin-4-yl)amino]-1H-pyrazol-5-yl}-N-(5-methylpyridin-2-yl)acetamide An analogous reaction to that described in example 106, but starting with 2-amino-5-picoline (41 mg, 0.37 mmol) yielded compound 119 in table 4 (89 mg, 62% yield):
$^1$H-NMR (DMSO d$_6$, TFA): 8.94 (s, 1H), 8.29 (s, 1H), 8.26 (s, 1H), 8.05 (m, 1H), 7.75 (m, 1H), 7.35 (s, 1H), 6.87 (s, 1H), 4.29 (t, 2H), 4.00 (m, 5H), 3.60 (d, 2H), 3.30 (m, 4H), 3.00 (t, 2H), 2.34 (s, 3H), 2.30 (m, 2H), 1.90 (m, 2H), 1.65 (m, 1H), 1.40 (m, 2H):
MS (+ve ESI): 561.6 (M+H)$^+$.

EXAMPLE 120

Preparation of Compound 120 in Table 4—N-(2,3-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 81, but starting with 4-(hydroxymethyl)piperidine (115 mg, 1 mmol) yielded compound 120 in table 4 (138 mg, 79% yield):
$^1$H-NMR (DMSO d$_6$, TFA): 8.95 (s, 1H), 8.29 (s, 1H), 7.75 (m, 1H), 7.32 (s, 1H), 7.17 (m, 2H), 6.83 (s, 1H), 4.29 (m, 2H), 4.00 (s, 3H), 3.93 (s, 2H), 3.60 (d, 2H), 3.30 (m, 4H), 3.00 (t, 2H), 2.30 (m, 2H), 1.90 (m, 2H), 1.70 (m, 1H), 1.40 (m, 2H):
MS (+ve ESI): 582.2 (M+H)$^+$.

EXAMPLE 121

Preparation of Compound 121 in Table 4—N-(3-chloro-2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 3-chloro-2-fluoroaniline (55 mg, 0.37 mmol) yielded compound 121 in table 4 (16 mg, 9% yield):
$^1$H-NMR (DMSO d$_6$, TFA): 8.95 (s, 1H), 8.29 (s, 1H), 7.89 (m, 1H), 7.32 (m, 2H), 7.21 (m, 1H), 6.83 (s, 1H), 4.29 (m, 2H), 4.00 (s, 3H), 3.93 (s, 2H), 3.59 (d, 2H), 3.30 (m, 4H), 2.97 (m, 2H), 2.30 (m, 2H), 1.86 (m, 2H), 1.68 (m, 1H), 1.40 (m, 2H):
MS (+ve ESI): 598.5 (M+H)$^+$.

EXAMPLE 122

Preparation of Compound 122 in Table 4—N-(2,5-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 2,5-difluoroaniline (49 mg, 0.37 mmol) yielded compound 122 in table 4 (15 mg, 8% yield):
$^1$H-NMR (DMSO ds, TFA): 8.94 (s, 1H), 8.29 (s, 1H), 7.95 (m, 1H), 7.25-7.40 (m, 1H), 7.32 (s, 1H), 6.95 (m, 1H), 4.31 (m, 2H), 4.00 (s, 3H), 3.93 (s, 2H), 3.59 (d, 2H), 3.30 (m, 4H), 2.97 (t, 2H), 2.30 (m, 2H), 1.86 (m, 2H), 1.65 (m, 1H), 1.43 (m, 2H):
MS (+ve ESI): 582.5 (M+H)$^+$.

EXAMPLE 123

Preparation of Compound 123 in Table 4—N-[2-fluoro-5-(trifluoromethyl)phenyl]-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 2-fluoro-5-trifluoromethylaniline (68 mg, 0.37 mmol) yielded compound 123 in table 4 (6 mg, 1% yield):
$^1$H-NMR (DMSO d$_6$, TFA): 8.94 (s, 1H), 8.48 (d, 1H), 8.30 (s, 1H), 7.52 (s, 1H), 7.50 (m, 1H), 7.31 (s, 1H), 6.84 (s, 1H), 4.30 (m, 2H), 3.99 (s, 3H), 3.98 (s, 2H), 3.60 (m, 2H), 3.20-3.35 (m, 4H), 2.98 (m, 2H), 2.30 (m, 2H), 1.88 (m, 2H), 1.67 (m, 1H), 1.42 (m, 2H):
MS (+ve ESI): 632.5 (M+H)$^+$.

EXAMPLE 124

Preparation of Compound 124 in Table 4—N-(3,4-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 3,4-difluoroaniline (49 mg, 0.37 mmol) yielded compound 124 in table 4 (85 mg, 56% yield):
$^1$H-NMR (DMSO $d_6$, TFA): 8.95 (s, 1H), 8.30 (s, 1H), 7.83 (m, 1H), 7.35 (m, 2H), 7.33 (s, 1H), 6.84 (s, 1H), 4.30 (m, 2H), 4.00 (s, 3H), 3.84 (s, 2H), 3.60 (d, 2H), 3.30 (m, 4H), 2.98 (t, 2H), 2.31 (m, 2H), 1.87 (m, 2H), 1.68 (m, 1H), 1.44 (m, 2H):
MS (+ve ESI): 582.5 (M+H)$^+$.

EXAMPLE 125

Preparation of Compound 125 in Table 4—N-(2,4-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 2,4-difluoroaniline (49 mg, 0.37 mmol) yielded compound 125 in table 4 (62 mg, 41% yield):
$^1$H-NMR (DMSO $d_6$, TFA): 8.96 (s, 1H), 8.30 (s, 1H), 7.88 (m, 1H), 7.33 (s, 1H), 7.29 (m, 1H), 7.06 (m, 1H), 6.84 (s, 1H), 4.30 (m, 2H), 4.00 (s, 3H), 3.90 (s, 2H), 3.61 (d, 2H), 3.31 (m, 2H), 3.28 (m, 2H), 3.00 (t, 2H), 2.31 (m, 2H), 1.87 (m, 2H), 1.65 (m, 1H), 1.42 (m, 2H):
MS (+ve ESI): 582.5 (M+H)$^+$.

EXAMPLE 126

Preparation of Compound 126 in Table 4—N-(3-chloro-4-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 3-chloro-4-fluoroaniline (55 mg, 0.37 mmol) yielded compound 126 in table 4 (84 mg, 54% yield):
$^1$H-NMR (DMSO $d_6$, TFA): 8.95 (s, 1H), 8.30 (s, 1H), 7.97 (m, 1H), 7.49 (m, 1H), 7.35 (t, 1H), 7.32 (s, 1H), 6.84 (s, 1H), 4.30 (m, 2H), 4.00 (s, 3H), 3.84 (s, 2H), 3.61 (d, 2H), 3.30 (m, 2H), 3.27 (m, 2H), 2.98 (t, 2H), 2.30 (m, 2H), 1.87 (m, 2H), 1.68 (m, 1H), 1.45 (m, 2H):
MS (+ve ESI): 598.5 (M+H)$^+$.

EXAMPLE 127

Preparation of Compound 127 in Table 4—N-[2-(difluoromethoxy)phenyl]-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 2-difluoro-methoxyaniline (60 mg, 0.37 mmol) yielded compound 127 in table 4 (49 mg, 30% yield):
$^1$H-NMR (DMSO $d_6$, TFA): 8.93 (s, 1H), 8.29 (s, 1H), 7.95 (m, 1H), 7.31 (s, 1H), 7.10-7.30 (m, 3H), 6.84 (s, 1H), 4.3 (m, 2H), 3.99 (s, 3H), 3.92 (s, 2H), 3.59 (d, 2H), 3.20-3.30 (m, 4H), 2.97 (t, 2H), 2.26 (m, 2H), 1.86 (m, 2H), 1.65 (m, 1H), 1.42 (m, 2H):
MS (+ve ESI): 612.5 (M+H)$^+$.

EXAMPLE 128

Preparation of Compound 128 in Table 4—N-(3-cyanophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 3-cyanoaniline (45 mg, 0.37 mmol) yielded compound 128 in table 4 (65 mg, 43% yield):
$^1$H-NMR (DMSO $d_6$, TFA): 8.93 (s, 1H), 8.28 (s, 1H), 8.14 (s, 1H), 7.81 (d, 1H), 7.51 (m, 2H), 7.30 (s, 1H), 6.84 (s, 1H), 4.28 (m, 2H), 3.99 (s, 3H), 3.86 (s, 2H), 3.59 (d, 2H), 3.20-3.35 (m, 4H), 2.96 (t, 2H), 2.30 (m, 2H), 1.88 (m, 2H), 1.68 (m, 1H), 1.44 (m, 2H):
MS (+ve ESI): 571.6 (M+H)$^+$.

EXAMPLE 129

Preparation of Compound 129 in Table 4—N-(3-bromophenyl)-2-{3-[(7-{3-[4-(hydroxymethyl)piperidin-1-yl]propoxy}-6-methoxyquinazolin-4-yl)amino]-1H-pyrazol-5-yl}acetamide An analogous reaction to that described in example 106, but starting with 3-bromoaniline (65 mg, 0.37 mmol) yielded compound 129 in table 4 (62 mg, 32% yield):
$^1$H-NMR (DMSO $d_6$, TFA): 8.95 (s, 1H), 8.30 (s, 1H), 8.00 (s, 1H), 7.52 (d, 1H), 7.32 (s, 1H), 7.26-7.31 (m, 2H), 6.84 (s, 1H), 4.29 (m, 2H), 4.00 (s, 3H), 3.84 (s, 2H), 3.60 (m, 2H), 3.20-3.35 (m, 4H), 2.98 (t, 2H), 2.30 (m, 2H), 1.87 (m, 2H), 1.65 (m, 1H), 1.44 (m, 2H):
MS (+ve ESI): 626.4 (M+H)$^+$.

EXAMPLE 130

Preparation of Compound 130 in Table 5—N-(2,3-difluorophenyl)-2-{3-[(7-{3-[ethyl(2-hydroxyethyl)amino]propoxy}quinazolin-4-yl)amino]-1H-pyrazol-5-yl}acetamide 2-(3-{[7-(3-chloropropoxy)quinazolin-4-yl]amino}-1H-pyrazol-5-yl)-N-(2,3-difluorophenyl)acetamide (300 mg, 0.634 mmol), potassium iodide (210 mg, 1.27 mmol), dimethylamine (2 ml) and 2-(ethylamino)ethanol (226 mg, 2.54 mmol) were combined and heated to 50° C. for 72 hours. The reaction was diluted with dichloromethane (20 ml) and loaded onto a 40S silica biotage column. Elution with dichloromethane followed by increased polarity to dichloromethane:methanol (9:1), then dichloromethane:methanol:ammonia (9:1:0.8) yielded compound 130 in table 5 as a pale pink solid (181 mg, 54% yield):
$^1$H-NMR (DMSO $d_6$): 12.35 (s, 1H), 10.25 (s, 2H), 8.52 (s, 2H), 7.71 (m, 1H), 7.16 (m, 4H), 6.78 (s, 1H), 4.33 (t, 1H), 4.17 (t, 2H), 3.84 (s, 2H), 3.43 (m, 2H), 2.60 (t, 2H), 2.49 (m, 4H), 1.88 (m, 2H), 0.96 (t, 3H):
MS (−ve ESI): 524 (M−H)$^−$,
MS (+ve ESI): 526 (M+H)$^+$.

2-{3-[7-(3-chloropropoxy)quinazolin-4-yl]amino}-1H-pyrazol-5-yl)-N-(2,3-difluorophenyl)acetamide, used as the starting material was obtained as follows:

a) 2-Amino-4-fluorobenzoic acid (15 g, 96 mmol) was dissolved in 2-methoxyethanol (97 ml). Formamidine acetate (20.13 g, 193.4 mmol) was added and the mixture heated to reflux for 18 hours. The reaction was cooled, concentrated and the residue stirred in aqueous ammonium hydroxide (0.01 N, 250 ml) for 1 hour. The suspension was filtered, washed with water and dried over phosphorus pentoxide to yield 7-fluoroquinazolin-4(3H)-one as an off-white solid (10.35 g, 65% yield):

$^1$H-NMR (DMSO d$_6$): 12.32 (br s, 1H), 8.19 (dd, 1H), 8.14 (s, 1H), 7.45 (dd, 1H), 7.39 (m, 1H):

MS (−ve ESI): 163 (M−H)$^-$,
MS (+ve EST): 165 (M+H)$^+$.

b) Sodium hydride (14.6 g, 365 mmol) was added at 0° C. to a solution of 1,3-propanediol (27.8 g, 365 mmol) in dimethylformamide (70 ml). 7-Fluoroquinazolin-4(3H)-one (10 g, 60.9 mmol) was added portionwise and the reaction mixture heated at 60° C., then at 110° C. for 3 hours. The reaction was cooled to 0° C., quenched with water (280 ml) and adjusted to pH 5.9. The resulting suspension was filtered, washed with water then ether and dried over phosphorus pentoxide to afford 7-(3-hydroxypropoxy)quinazolin-4(3H)-one as a white powder (12.41 g, 92% yield):

$^1$H-NMR (DMSO d$_6$): 11.90 (br s, 1H), 8.04 (s, 1H), 8.00 (d, 1H), 7.10 (m, 2H), 4.17 (t, 2H), 3.58 (t, 2H), 1.92 (m, 2H):

MS (+ve ESI): 221 (M+H)$^+$.

c) 7-(3-hydroxypropoxy)quinazolin-4(3H)-one (10.5 g, 47.7 mmol) and thionyl chloride (100 ml, 137 mmol) were combined. Dimethylformamide (1 ml) was added and the reaction mixture heated to 85° C. for 1 hour. The mixture was cooled to room temperature, diluted with toluene and evaporated to dryness. This was repeated until all thionyl chloride was removed. The residue was dissolved in dichloromethane and washed with a saturated sodium bicarbonate solution. The aqueous layer was extracted with dichloromethane. The organics were combined, dried (magnesium sulphate) and concentrated to leave a yellow solid. Trituration with ether removed a less soluble impurity and the ether filtrate was concentrated to leave 4-chloro-7-(3-chloropropoxy)quinazoline as an off-white solid (8.5 g, 70% yield):

$^1$H-NMR (DMSO d$_6$): 13.25 (br s, 1H), 8.34 (s, 1H), 8.06 (d, 1H), 7.17 (m, 2H), 4.21 (t, 2H), 3.83 (t, 2H), 2.23 (m, 2H):

MS (+ve ESI): 257, 259 (M+H)$^+$.

d) 4-chloro-7-(3-chloropropoxy)quinazoline (2.5 g, 9.72 mmol) and (3-amino-1H-pyrazol-5-yl)acetic acid (1.37 g, 9.72 mmol) were combined in dimethylformamide (25 ml). A solution of 4M HCl in dioxane (1.25 ml, 4.8 mmol) was added and the reaction heated to 90° C. for 40 minutes. The solution was cooled to room temperature, diluted with water (250 ml) and filtered through celite. The acidic solution was basified to pH 4.9 and the yellow powder filtered. (At pH 3, a red solid precipitated which was isolated, suspended in water and basified to pH 12. Careful adjustment back to pH 4.8 resulted in the precipitation of a yellow powder, which was combined with the first crop). The solid was washed with diethyl ether and dried over phosphorus pentoxide to yield (3-{[7-(3-chloropropoxy)quinazolin-4-yl]amino}-1H-pyrazol-5-yl)acetic acid as a pale orange solid (2.88 g, 82% yield):

$^1$H-NMR (DMSO d$_6$): 12.60 (br s, 2H), 10.78 (br s, 1H), 8.65 (s, 1H), 8.60 (d, 1H), 7.26 (d, 1H), 7.22 (s, 1H), 6.67 (s, 1H), 4.28 (t, 2H), 3.83 (t, 2H), 3.67 (s, 2H), 2.24 (m, 2H):

MS (−ve ESI): 360, 362 (M−H)$^-$,
MS (+ve ESI): 362, 364 (M+H)$^+$.

e) 2,3-difluoroaniline (1.15 g, 8.95 mmol) was added to a suspension of (3-{[7-(3-chloropropoxy)quinazolin-4-yl]amino}-1H-pyrazol-5-yl)acetic acid (2.70 g, 7.46 mmol) in pyridine (30 ml) and the reaction cooled to 0° C. Phosphorous oxychloride (1.14 g, 7.46 mmol) was added dropwise and the reaction stirred at 0° C. for 1 hour. The reaction was warmed to ambient temperature and more phosphorous oxychloride (0.5 ml) added. The reaction was stirred for 4.5 hours. The reaction mixture was diluted with ethyl acetate:ether (100 ml: 37 ml) and stirred for 18 hours. The precipitate was filtered, suspended in water and neutralised with ammonium hydroxide (7%, 15 ml). The resultant yellow suspension was filtered, washed with water and dried (phosphorous pentoxide) to yield 2-(3-{[7-(3-chloropropoxy)quinazolin-4-yl]amino}-1H-pyrazol-5-yl)-N-(2,3-difluorophenyl)acetamide as an orange powder (3.15 g, 89% yield):

$^1$H-NMR (DMSO d$_6$): 10.64 (br s, 1H), 10.27 (s, 1H), 8.60 (s, 1H), 8.55 (d, 1H), 7.70 (m, 1H), 7.20 (m, 6H), 6.68 (s, 1H), 4.27 (t, 2H), 3.83 (m, 4H), 2.25 (m, 2H):

MS (−ve ESI): 471, 473 (M−H)$^-$,
MS (+ve ESI): 473, 475 (M+H)$^+$.

EXAMPLE 131

Preparation of Compound 131 in Table 5—N-(2,3-difluorophenyl)-2-{3-[(7-{3-[(2-hydroxyethyl)(isopropyl)amino]propoxy}quinazolin-4-yl)amino]-1H-pyrazol-5-yl}acetamide An analogous reaction to that described in example 130, but starting with 2-(isopropylamino)ethanol (262 mg, 2.54 mmol) yielded compound 131 in table 5 as a pink solid (182 mg, 53% yield):

$^1$H-NMR (DMSO d$_6$): 12.35 (s, 1H), 10.20 (s, 1H), 8.50 (s, 2H), 7.71 (m, 1H), 7.20 (m, 4H), 6.78 (s, 1H), 4.29 (br s, 1H), 4.19 (t, 2H), 3.85 (s, 2H), 3.38 (dt, 2H), 2.88 (m, 1H), 2.55 (t, 2H), 2.45 (t, 2H), 1.82 (m, 2H), 0.93 (d, 6H):

MS (−ve ESI): 538 (M−H)$^-$,
MS (+ve ESI): 540 (M+H)$^+$.

EXAMPLE 132

Preparation of Compound 132 in Table 5—N-(2,3-difluorophenyl)-2-{3-[(7-{3-[(2R)-2-(hydroxymethyl)pyrrolidin-1-yl]propoxy}quinazolin-4-yl)amino]-1H-pyrazol-5-yl}acetamide An analogous reaction to that described in example 130, but starting with D-prolinol (257 mg, 2.54 mmol) yielded compound 132 in table 5 as a pink solid (206 mg, 60% yield):

$^1$H-NMR (DMSO d$_6$, AcOD): 11.60 (br s, 7H), 10.25 (s, 1H), 8.52 (m, 2H), 7.75 (m, 1H), 7.16 (m, 4H), 6.67 (s, 1H), 4.22 (t, 2H), 3.84 (s, 2H), 3.50 (d, 2H), 3.35 (m, 1H), 3.28 (m, 1H), 3.07 (m, 1H), 2.86 (m, 1H), 2.72 (m, 1H), 2.05 (m, 2H), 1.95 (m, 1H), 1.60-1.90 (m, 4H):

MS (−ve ESI): 536 (M−H)$^-$,
MS (+ve ESI): 538 (M+H)$^+$.

EXAMPLE 133

Preparation of Compound 133 in Table 5—N-(2,3-difluorophenyl)-2-{3-[(7-{3-[(2-hydroxyethyl)(propyl)amino]propoxy}quinazolin-4-yl)amino]-1H-pyrazol-5-yl}acetamide An analogous reaction to that described in example 130, but starting with 2-(n-propylamino)ethanol (262 mg, 2.54 mmol) yielded compound 133 in table 5 as a pink solid (168 mg, 49% yield):

$^1$H-NMR (DMSO d$_6$): 12.35 (s, 1H), 10.22 (s, 2H), 8.51 (s, 2H), 7.71 (m, 1H), 7.20 (m, 4H), 6.78 (s, 1H), 4.30 (t, 1H), 4.17 (t, 2H), 3.85 (s, 2H), 3.43 (m, 2H), 2.59 (t, 2H), 2.49 (m, 2H), 2.39 (t, 2H), 1.87 (m, 2H), 1.39 (m, 2H), 0.82 (t, 3H):

MS (−ve ESI): 538 (M−H)$^-$,
MS (+ve ESI): 540 (M+H)$^+$.

EXAMPLE 134

Preparation of Compound 134 in Table 5—N-(2,3-difluorophenyl)-2-{3-[(7-{3-[(2-hydroxyethyl)(prop-2-yn-1-yl)amino]propoxy}quinazolin-4-yl)amino]-1H-pyrazol-5-yl}acetamide An analogous reaction to that described in example 130, but starting with 2-(prop-2-yn-1-ylamino)ethanol (220 mg, 2.22 mmol) yielded compound 134 in table 5 as a beige solid (162 mg, 48% yield):
$^1$H-NMR (DMSO d$_6$): 12.40 (s, 1H), 10.22 (br s, 1H), 8.50 (s, 2H), 7.73 (m, 1H), 7.17 (m, 4H), 6.78 (br s, 1H), 4.52 (br s, 1H), 4.17 (t, 2H), 3.84 (s, 2H), 3.49 (s, 4H), 3.17 (s, 1H), 2.70 (s, 2H), 2.60 (s, 2H), 1.93 (m, 2H):
MS (−ve ESI): 534 (M−H)$^-$,
MS (+ve ESI): 536 (M+H)$^+$.

EXAMPLE 135

Preparation of Compound 135 in Table 5—N-(2,3-difluorophenyl)-2-{3-[(7-{3-[(2-hydroxyethyl)(isobutyl)amino]propoxy}quinazolin-4-yl)amino]-1H-pyrazol-5-yl}acetamide An analogous reaction to that described in example 130, but starting with 2-(isobutylamino)ethanol (260 mg, 2.22 mmol) yielded compound 135 in table 5 as a beige solid (168 mg, 48% yield):
$^1$H-NMR (DMSO d$_6$): 12.35 (s, 1H), 10.28 (br s, 2H), 8.50 (s, 2H), 7.72 (m, 1H), 7.16 (m, 4H), 6.78 (s, 1H), 4.32 (s, 1H), 4.20 (t, 2H), 3.85 (s, 2H), 3.45 (m, 2H), 2.57 (br s, 2H), 2.48 (m, 2H), 2.16 (d, 2H), 1.89 (m, 2H), 1.66 (m, 1H), 0.83 (d, 6H):
MS (−ve ESI): 552 (M−H)$^-$,
MS (+ve ESI): 554 (M+H)$^+$.

EXAMPLE 136

Preparation of Compound 136 in Table 5—N-(2,3-difluorophenyl)-2-{3-[(7-{3-[(2,2-dimethylpropyl)(2-hydroxyethyl)amino]propoxy}quinazolin-4-yl)amino]-1H-pyrazol-5-yl}acetamide An analogous reaction to that described in example 130, but starting with 2-[(2,2-dimethylpropyl)amino]ethanol (291 mg, 2.22 mmol) yielded compound 136 in table 5 as a beige solid (93 mg, 26% yield):
$^1$H-NMR (DMSO d$_6$): 12.36 (s, 1H), 10.22 (s, 1H), 8.52 (s, 2H), 7.72 (m, 1H), 7.19 (m, 4H), 6.77 (s, 1H), 4.34 (s, 1H), 4.19 (m, 2H), 3.83 (s, 2H), 3.45 (m, 2H), 2.64 (m, 2H), 2.54 (m, 2H), 2.21 (s, 2H), 1.89 (m, 2H), 0.83 (s, 9H):
MS (−ve ESI): 566 (M−H)$^-$,
MS (+ve ESI): 568 (M+H)$^+$.

EXAMPLE 137

Preparation of Compound 137 in Table 6—N-(3-fluorophenyl)-2-[3-({5-{[1-(2-hydroxyethyl)piperidin-4-yl]oxy}-7-[3-(4-methylpiperazin-1-yl)propoxy]quinazolin-4-yl}amino)-1H-pyrazol-5-yl]acetamide 2-[3-({5-{[1-(2-tert-butoxyethyl)piperidin-4-yl]oxy}-7-[3-(4-methylpiperazin-1-yl)propoxy]quinazolin-4-yl}amino)-1H-pyrazol-5-yl]-N-(3-fluorophenyl)acetamide (102 mg, 0.117 mmol) was treated with a mixture of dichloromethane:trifluoroacetic acid (5:1) at ambient temperature for 16 hours. The solvent was evaporated, and the residue purified by preparative LCMS to yield compound 137 in table 6 (55 mg, 71% yield):
$^1$H-NMR (DMSO d$_6$): 10.44 (s, 1H), 10.28 (s, 1H), 8.44 (s, 1H), 7.61 (d, 1H), 7.31-7.39 (m, 1H), 7.33 (s, 1H), 6.91 (t, 1H), 6.87 (s, 1H), 6.77 (s, 1H), 6.75 (s, 1H), 4.87 (br s, 1H), 4.40 (t, 1H), 4.13 (t, 2H), 3.76 (s, 2H), 3.50 (s, 2H), 2.78 (m, 2H), 2.19-2.47 (m, 14H), 2.14 (s, 3H), 2.09 (m, 2H), 1.91 (m, 2H), 1.84 (m, 2H):
MS (+ve ESI): 662.3 (M+H)$^+$.

2-[3-({5-{[1-(2-tert-butoxyethyl)piperidin-4-yl]oxy}-7-[3-(4-methylpiperazin-1-yl)propoxy]quinazolin-4-yl}amino)-1H-pyrazol-5-yl]-N-(3-fluorophenyl)acetamide used as starting material was obtained as follows:

a) A solution of 5,7-difluoroquinazolin-4(3H)-one (1.82 g, 10 mmol) and 1-(2-tert-butoxyethyl)piperidin-4-ol (1.91 g, 9.5 mmol) in tetrahydrofuran (40 ml) was treated with potassium tert-butoxide (3.36 g, 30 mmol). The mixture was heated at 70° C. for 5 hours. The solvent was evaporated and the residue purified by chromatography on silica gel. Elution with dichloromethane:methanolic ammonia (95:5) yielded 5-{[1-(2-ten-butoxyethyl)piperidin-4-yl]oxy}-7-fluoroquinazolin-4(3H)-one (2.88 g, 83% yield):
$^1$H-NMR (DMSO d$_6$): 7.98 (s, 1H), 7.01 (d, 1H), 6.90 (d, 1H), 4.58 (br s, 1H), 3.43 (t, 2H), 2.74 (m, 2H), 2.43 (t, 2H), 2.34 (m, 2H), 1.90 (m, 2H), 1.71 (m, 2H), 1.13 (s, 9H):
MS (+ve ESI): 364.3 (M+H)$^+$.

b) 5-{[1-(2-tert-butoxyethyl)piperidin-4-yl]oxy}-7-fluoroquinazolin-4(3H)-one (5.45 mg, 1.5 mmol) in anhydrous diglyme (15 ml) was reacted with 3-(4-methylpiperazin-1-yl)propan-1-ol (474 mg, 3 mmol) in the presence of potassium tert-butoxide (11.77 g, 10 mmol) at 100° C. for 4 hours. The reaction mixture was diluted with dichloromethane (10 ml) and water (10 ml) and the pH adjusted to 7.7. The mixture was extracted several times with dichloromethane and the organic phase dried (magnesium sulphate), evaporated and the residue purified by chromatography on silica gel. Elution with dichloromethane:methanolic ammonia (9:1) yielded 5-{[1-(2-tert-butoxyethyl)piperidin-4-yl]oxy}-7-[3-(4-methylpiperazin-1-yl)propoxy]quinazolin-4(3H)-one (411 mg, 55% yield):
$^1$H-NMR (DMSO d$_6$): 7.89 (s, 1H), 6.63 (s, 1H), 6.55 (s, 1H), 4.49 (br s, 1H), 4.09 (t, 2H), 3.40 (t, 2H), 2.75 (m, 2H), 2.52 (m, 2H), 2.22-2.43 (m, 12H), 2.14 (s, 3H), 1.88 (m, 4H), 1.69 (m, 2H), 1.12 (s, 9H):
MS (+ve ESI): 502.4 (M+H)$^+$.

c) 5-{[1-(2-ten-butoxyethyl)piperidin-4-yl]oxy}-7-[3-(4-methylpiperazin-1-yl)propoxy]quinazolin-4(3H)-one (400 mg, 0.8 mmol) in dichloroethane (8 ml) was reacted with triphenylphosphine (420 mg, 1.6 mmol) and carbon tetrachloride (0.78 ml, 8 mmol) at 70° C. for 1.5 hours. The solvent was evaporated, the residue dissolved in isopropanol (8 ml) and reacted with (3-amino-1H-pyrazol-5-yl)acetic acid (124 mg, 0.88 mmol) at 80° C. under argon for 2 hours. The solvent was evaporated, and the residue purified by preparative LCMS to yield [3-({5-{[1-(2-tert-butoxyethyl)piperidin-4-yl]oxy}-7-[3-(4-methylpiperazin-1-yl)propoxy]quinazolin-4-yl}amino)-1H-pyrazol-5-yl]acetic acid (270 mg, 54% yield):
$^1$H-NMR (DMSO d$_6$): 8.99 (s, 1H), 7.09-7.15 (m, 1H), 6.96 (m, 1H), 6.88 (m, 1H), 5.08-5.38 (m, 1H), 4.30 (t, 2H), 3.29-3.95 (m, 21H), 3.22 (t, 1H), 2.74 (s, 3H), 2.08-2.39 (m, 6H), 1.20 (m, 9H):
MS (+ve ESI): 625.3 (M+H)$^+$.

d) [3-({5-{[1-(2-tert-butoxyethyl)piperidin-4-yl]oxy}-7-[3-(4-methylpiperazin-1-yl)propoxy]quinazolin-4-yl}amino)-1H-pyrazol-5-yl]acetic acid (140 mg, 0.22 mmol)

in dimethylformamide (1 ml) was reacted with 3-fluoroaniline (24 μl, 0.25 mmol) in the presence of 1-(3-dimethylamino-propyl)-3-ethylcarbodiimide hydrochloride (48 mg, 0.25 mmol) and 2-hydroxypyridin-1-oxide (27 mg, 0.24 mmol) at 50° C. for 45 minutes. The solvent was evaporated and the residue purified by chromatography on silica gel. Elution with dichloromethane:methanol (97:3) then dichloromethane:methanolic ammonia (95:5) yielded 2-[3-({5-{[1-(2-tert-butoxyethyl)piperidin-4-yl]oxy}-7-[3-(4-methylpiperazin-1-yl)propoxy]quinazolin-4-yl}amino)-1H-pyrazol-5-yl]-N-(3-fluorophenyl)acetamide (109 mg, 58% yield):

$^1$H-NMR (DMSO $d_6$): 10.44 (s, 1H), 10.27 (s, 1H), 8.44 (s, 1H), 7.61 (d, 1H), 7.30-7.38 (m, 1H), 7.33 (s, 1H), 6.88 (t, 1H), 6.87 (s, 1H), 6.76 (s, 1H), 6.75 (s, 1H), 4.86 (br s, 1H), 4.13 (t, 2H), 3.75 (s, 2H), 3.41 (t, 2H), 2.78 (m, 2H), 2.20-2.48 (m, 12H), 2.17 (t, 2H), 2.14 (s, 3H), 2.07 (m, 2H), 1.90 (t, 2H), 1.82 (m, 2H), 1.11 (s, 9H):

MS (+ve ESI): 718.1 (M+H)$^+$.

EXAMPLE 138

Preparation of Compound 138 in Table 6—N-(3-fluorophenyl)-2-[5-({7-methoxy-5-[(1-methylpiperidin-4-yl)oxy]quinazolin-4-yl}amino)-1H-pyrazol-3-yl]acetamide

[5-({7-methoxy-5-[(1-methylpiperidin-4-yl)oxy]quinazolin-4-yl}amino)-1H-pyrazol-3-yl]acetic acid (95 mg, 0.2 mmol) in dimethylformamide (1 ml) was reacted with 3-fluoroaniline (21 μl, 0.22 mmol) in the presence of 1-(3-dimethylamino-propyl)-3-ethylcarbodiimide hydrochloride (46 mg, 0.24 mmol) and 2-hydroxypyridin-1-oxide (24 mg, 0.22 mmol) at 60° C. for 2.5 hours. The solvent was evaporated, and the residue purified by chromatography on silica gel. Elution with dichloromethane then increased polarity to dichloromethane:methanolic ammonia (9:1) yielded compound 138 in table 6 (30 mg, 30% yield):

$^1$H-NMR (DMSO $d_6$): 8.47 (s, 1H), 7.63 (d, 1H), 7.35 (m, 2H), 6.90 (m, 2H), 6.80 (m, 2H), 4.88 (m, 1H), 3.90 (s, 3H), 3.77 (s, 2H), 2.68 (m, 2H), 2.39 (m, 2H), 2.23 (s, 3H), 2.12 (m, 2H), 1.90 (m, 2H):

MS (+ve ESI): 506.2 (M+H)$^+$.

[5-({7-methoxy-5-[(1-methylpiperidin-4-yl)oxy]quinazolin-4-yl}amino)-1H-pyrazol-3-yl]acetic acid used as starting material was obtained as follows:

a) 3,5-Dimethoxyaniline hydrochloride (80.21 g, 0.424 mol) was added cautiously to oxalyl chloride (136 ml, 1.56 mol) and the solution heated at reflux for 3 hours. The solution was cooled and concentrated in vacuo. Methanol (300 ml) was added to the residue and the mixture heated at reflux for 1 hour. The reaction was allowed to cool, and the resulting precipitate filtered and washed with methanol to yield 4,6-dimethoxyisatin (40.4 g, 46%) as a yellow solid.

$^1$H-NMR (DMSO $d_6$): 10.86 (br s, 1H), 6.17 (d, 1H), 6.00 (d, 1H), 3.86 (s, 3H), 3.83 (s, 3H).

b) 4,6-Dimethoxyisatin (5.00 g, 24.0 mmol) was dissolved in 33% (w/v) aqueous sodium hydroxide solution (42 ml) at 75° C. To this solution was added hydrogen peroxide (30%, 8 ml) dropwise over 30 minutes. The reaction was stirred for an hour at 75° C. and then cooled to room temperature. Ice was added, and the reaction mixture acidified to pH 1 with concentrated hydrochloric acid. The resulting precipitate was filtered, washed with water and dried in vacuo to yield 2-amino-4,6-dimethoxybenzoic acid hydrochloride salt (3.3 g, 59% yield) acid as a pale yellow solid:

$^1$H-NMR (DMSO $d_6$): 5.92 (d, 1H), 5.77 (d, 1H), 3.75 (s, 3H), 3.69 (s, 3H):

MS (+ve ESI): 198 (M+H)$^+$.

c) Dimethyl sulfate (1.04 ml, 11.0 mmol) was added dropwise to a mixture of potassium carbonate (3.34 g, 24.2 mmol) and 2-amino-4,6-dimethoxybenzoic acid (2.56 g, 11.0 mmol) in dimethylformamide (70 ml) at 0° C. The reaction was stirred for 1 hour, then poured into water. The resulting precipitate was filtered, washed with water and dried in vacuo. The filtrate was extracted with ethyl acetate, and the combined organic extracts were dried (magnesium sulphate) and concentrated in vacuo. The combined solids were dried in vacuo to yield methyl 2-amino-4,6-dimethoxybenzoate (1.8 g, 77% yield) as a yellow crystalline solid:

$^1$H-NMR (DMSO $d_6$): 6.13 (s, 2H), 5.90 (d, 1H), 5.75 (d, 1H), 3.68 (s, 3H), 3.67 (s, 3H), 3.66 (s, 3H).

d) A solution of methyl 2-amino-4,6-dimethoxybenzoate (600 mg, 2.8 mmol) and formamidine acetate (650 mg, 6.3 mmol) in 2-methoxyethanol (7 ml) was heated at 120° C. for 16 hours. The reaction was cooled, concentrated in vacuo, and the residue triturated with methanol to give 5,7-dimethoxy-3,4-dihydroquinazolin-4(3H)-one as a beige solid (290 mg, 58% yield):

$^1$H-NMR (DMSO $d_6$): 11.62 (br s, 1H), 7.88 (s, 1H), 6.63 (d, 1H), 6.51 (d, 1H), 3.84 (s, 3H), 3.80 (s, 3H):

MS (+ve ESI): 207 (M+H)$^+$.

e) Magnesium bromide (3.83 g, 20.8 mmol) was added cautiously to 5,7-dimethoxy-3,4-dihydroquinazolin-4(3H)-one (4.29 g, 20.8 mmol) in pyridine (60 ml) and the solution heated at reflux for 1 hour. The reaction mixture was cooled, concentrated in vacuo and the residue triturated with water and filtered to yield 7-methoxyquinazoline-4,5-diol (3.72 g, 93% yield): as an off-white solid:

MS (+ve ESI): 193 (M+H)$^+$.

f) Sodium hydride (60 mg, 1.49 mmol) was added portionwise over 5 minutes to 7-methoxyquinazoline-4,5-diol (260 mg, 1.35 mmol) in dimethylformamide (2 ml) at 0° C. Chloromethyl pivalate (200 μl, 1.36 mmol) was added dropwise over 15 minutes to give a clear orange solution. The reaction mixture was allowed to warm to ambient temperature and stirred for a further 18 hours. Incomplete reaction was seen by tlc, therefore the reaction was cooled to 0° C. and sodium hydride (10 mg, 0.25 mmol) was added followed by chloromethyl pivalate (26 μl, 6.18 mmol). The reaction was complete after stirring for 1 hour at ambient temperature. The reaction mixture was concentrated in vacuo and purified by chromatography on silica gel, eluting with 2-10% methanol in dichloromethane, to yield (5-hydroxy-7-methoxy-4-oxoquinazolin-3(4H)-yl)methyl pivalate (170 mg, 41% yield) as a cream solid:

$^1$H-NMR (DMSO $d_6$): 11.42 (s, 1H), 8.37 (s, 1H), 6.66 (d, 1H), 6.51 (d, 1H), 5.86 (s, 2H), 3.85 (s, 3H), 1.11 (s, 9H):

MS (+ve ESI): 305 (M+H)$^+$.

g) (5-hydroxy-7-methoxy-4-oxoquinazolin-3(4H)-yl)methyl pivalate (500 mg, 1.63 mmol), 4-hydroxy-N-methylpiperidine (280 mg, 2.45 mmol) and triphenylphosphine (640 mg, 2.45 mmol) were dissolved in anhydrous dichloromethane (8 ml), under a nitrogen atmosphere at 0° C. A solution of di-tert-butyl azodicarboxylate (560 mg, 2.45 mmol) in dichloromethane (1 ml) was added dropwise over 5 minutes and the resulting yellow solution was allowed to warm to ambient temperature and stirred for 18 hours. A further 1 equivalent of all reagents was added in the same sequence as above under the same reaction conditions and was left to stir for a further 12 hours at ambient temperature. The reaction mixture was concentrated in vacuo and the residue purified by chromatography on silica gel, eluting with 2-8% methanol in dichloromethane, to yield (7-methoxy-5-((1-methylpiperidin 4-yl)oxy)-4-oxoquinazolin-3(4H)-yl) methyl pivalate (370 mg, 56% yield) as a cream solid:

$^1$H-NMR (DMSO d$_6$): 8.16 (s, 1H), 6.67 (d, 1H), 6.61 (d, 1H), 5.79 (s, 2H), 4.52 (m, 1H), 3.84 (s, 3H), 2.57 (m, 2H), 2.18 (m, 2H), 2.13 (s, 3H), 1.87 (m, 2H), 1.71 (m, 2H), 1.11 (s, 9H):

MS (+ve ESI): 405 (M+H)$^+$.

h) 7.0 N ammonia in methanol (25 ml) was added to (7-methoxy-5-((1-methylpiperidin-4-yl)oxy)-4-oxoquinazolin-3(4H)-yl)methyl pivalate (370 mg, 0.92 mmol) and the solution stirred at ambient temperature for 18 hours. The reaction mixture was concentrated in vacuo to give an oil which was triturated with diethyl ether to give an orange solid which was collected by suction filtration and dried in vacuo to yield 7-methoxy-5-((1-methylpiperidin-4-yl)oxy)quinazolin-4(3H)-one (200 mg, 75% yield):

$^1$H-NMR (DMSO d$_6$): 11.60 (br s, 1H), 7.86 (s, 1H), 6.64 (d, 2H), 6.53 (d, 2H), 4.45 (m, 1H), 3.82 (s, 3H), 2.61 (m, 2H), 2.18 (m, 2H), 2.11 (s, 3H), 1.84 (m, 2H), 1.68 (m, 2H):

MS (+ve ESI): 290 (M+H)$^+$.

i) A solution of 7-methoxy-5-((1-methylpiperidin-4-yl)oxy)quinazolin-4(3H)-one (3.00 g, 10.4 mmol) and diisopropyl ethylamine (5 ml) in dichloromethane (300 ml) was stirred at ambient temperature under an atmosphere of nitrogen. Phosphoryl chloride (10 ml) was added, and the resultant orange solution was heated at reflux for 20 hours. The reaction mixture was then cooled to ambient temperature and concentrated in vacuo. Residual phosphoryl chloride was then removed by azeotrope with toluene to give the crude product as an orange oil. Purification by chromatography on silica gel, eluting with 5% triethylamine in dichloromethane, gave an orange solid, which was further purified by trituration under acetonitrile, and then dried in vacuo to yield 4-chloro-5-(N-methylpiperidin-4-yloxy)-7-methoxyquinazoline (2.4 g, 75% yield) as a pale yellow amorphous solid:

$^1$H-NMR (CDCl$_3$) 8.80 (s, 1H), 6.94 (d, 1H), 6.60 (d, 1H), 4.58 (s, 1H), 3.95 (s, 3H), 2.74 (m, 2H), 2.44 (m, 2H), 2.35 (s, 3H), 2.10 (m, 4H):

MS (+ve ESI): 308, 310 (M+H)$^+$.

j) 4-chloro-7-methoxy-5-[(1-methylpiperidin-4-yl)oxy]quinazoline (307 mg, 0.85 mmol) was condensed with (3-amino-1H-pyrazol-5-yl)acetic acid (132 mg, 0.93 mmol) in dimethylacetamide (3 ml) and hydrochloric acid in dioxane (4.0 N solution, 467 μl) at 90° C. for 1 hour. The solvent was evaporated, and the residual oil was triturated with ethanol: diethyl ether to yield [5-({7-methoxy-5-[(1-methylpiperidin-4-yl)oxy]quinazolin-4-yl}amino)-1H-pyrazol-3-yl]acetic acid as a beige solid (320 mg, 78% yield):

$^1$H-NMR (DMSO d$_6$): 8.88 (m, 1H), 7.12 (m, 1H), 6.88 (m, 1H), 6.82 (m, 1H), 5.05-5.45 (m, 1H), 3.96 (m, 3H), 3.73 (s, 2H), 3.10-3.60 (m, 4H), 2.80 (m, 3H), 2.00-2.50 (m, 4):

MS (+ve ESI): 413.2 (M+H)$^+$.

EXAMPLE 139

Preparation of Compound 139 in Table 6—N-(2,3-difluorophenyl)-2-{3-[(5,7-dimethoxyquinazolin-4-yl)amino]-1H-pyrazol-5-yl}acetamide An analogous reaction to that described in example 137d but starting with {3-[(5,7-dimethoxyquinazolin-4-yl)amino]-1H-pyrazol-5-yl}acetic acid (165 mg, 0.5 mmol) and 2,3-difluoroaniline (70 μl, 0.6 mmol) at 50° C. for 10 hours yielded compound 139 in table 6 (30 mg, 14% yield):

$^1$H-NMR (DMSO d$_6$, TFA): 8.82 (s, 1H), 7.65 (m, 1H), 7.09-7.16 (m, 1H), 7.12 (s, 1H), 6.92 (s, 1H), 6.79 (d, 1H), 6.66 (d, 1H), 4.10 (s, 3H), 3.92 (s, 3H), 3.85 (s, 2H):

MS (+ve ESI): 441.0 (M+H)$^+$.

{3-[(5,7-dimethoxyquinazolin-4-yl)amino]-1H-pyrazol-5-yl}acetic acid used as starting material was obtained as follows:

a) An analogous reaction to that described in example 137c, but starting with 5,7-dimethoxyquinazolin-4(3H)-one (618 mg, 3 mmol—see patent WO 0194341) yielded {3-[(5,7-dimethoxyquinazolin-4-yl)amino]-1H-pyrazol-5-yl}acetic acid (913 mg, 92% yield):

$^1$H-NMR (DMSO d$_6$): 10.72 (s, 1H), 8.85 (s, 1H), 7.00 (s, 1H), 6.96 (s, 1H), 6.67 (s, 1H), 4.16 (s, 3H), 3.97 (s, 3H), 3.72 (s, 2H):

MS (+ve ESI): 330.1 (M+H)$^+$.

EXAMPLE 140

Preparation of Compound 140 in Table 6—2-(3-{[5,7-bis(2-methoxyethoxy)quinazolin-4-yl]amino}-1H-pyrazol-5-yl)-N-(2,3-difluorophenyl)acetamide A solution of phosphoryl chloride (51 μl, 0.55 mmol) in dichloromethane (0.5 ml) was added slowly at 0° C. to a solution of (3-{[5,7-bis(2-methoxyethoxy)quinazolin-4-yl]amino}-1H-pyrazol-5-yl)acetic acid (209 mg, 0.5 mmol) and 2,3-difluoroaniline (61 μl, 0.6 mmol) in pyridine (2 ml. The mixture was stirred at ambient temperature for 6 hours. Ice was then added to the reaction mixture at 0° C., and the solvent was evaporated. The crude product was purified by preparative LCMS to yield compound 140 in table 6 (26 mg, 10% yield):

$^1$H-NMR (DMSO d$_6$): 10.22 (s, 1H), 10.15 (s, 1H), 8.45 (s, 1H), 7.71 (t, 1H), 7.14-7.23 (m, 1H), 7.18 (s, 1H), 6.86 (s, 1H), 6.79 (s, 1H), 6.74 (s, 1H), 4.40 (s, 2H), 4.24 (t, 2H), 3.84 (s, 4H), 3.71 (t, 2H), 3.42 (s, 3H), 3.33 (s, 3H):

MS (+ve ESI): 529.1 (M+H)$^+$.

(3-{[5,7-bis(2-methoxyethoxy)quinazolin-4-yl]amino}-1H-pyrazol-5-yl)acetic acid used as starting material was obtained as follows a) 5,7-difluoroquinazolin-4(3H)one (728 mg, 4 mmol) in diglyme (15 ml) and potassium tert-butoxide (4.48 g, 32 mmol) were reacted with 2-methoxyethanol (2.52 ml, 32 mmol) at 110° C. for 1 hour. The mixture was cooled and purified by chromatography on silica gel. Elution with dichloromethane:methanol (96:4) then increased polarity to dichloromethane:methanolic ammonia (95:5) yielded 5,7-bis(2-methoxyethoxy)quinazolin-4(3H)-one (982 mg, 99% yield):

$^1$H-NMR (DMSO d$_6$): 11.71 (br s, 1H), 7.90 (s, 1H), 6.66 (d, 1H), 6.56 (d, 1H), 4.20 (t, 2H), 4.15 (t, 2H), 3.69 (m, 4H), 3.36 (s, 3H), 3.32 (s, 3H):

MS (+ve ESI): 295.1 (M+H)$^+$.

b) An analogous reaction to that described in example 137c, but starting with 5,7-bis(2-methoxyethoxy)quinazolin-4(3H)-one (648 mg, 2.2 mmol) yielded (3-{[5,7-bis(2-methoxyethoxy)quinazolin-4-yl]amino}-1H-pyrazol-5-yl)acetic acid (632 mg, 68% yield) as a beige solid:

$^1$H-NMR (DMSO d$_6$): 10.90 (s, 1H), 8.86 (s, 1H), 7.02 (s, 1H), 6.96 (s, 1H), 6.78 (s, 1H), 4.52 (t, 2H), 4.31 (t, 2H), 3.85 (t, 2H), 3.74 (t, 2H), 3.71 (s, 2H), 3.42 (s, 3H), 3.33 (s, 3H):

MS (+ve ESI): 418.1 (M+H)$^+$.

EXAMPLE 141

Preparation of Compound 141 in Table 6—N-(2,3-difluorophenyl)-2-(3-{[5-isopropoxy-7-(2-methoxyethoxy)quinazolin-4-yl]amino}-1H-pyrazol-5-yl)acetamide An analogous reaction to that described in example 140, but starting with (3-{[5-isopropoxy-7-(2-methoxyethoxy)quinazolin-4-yl]amino}-1H-pyrazol-5-yl)acetic acid (230 mg, 0.5 mmol) yielded compound 141 in table 6 (68 mg, 31% yield) as a beige solid:

$^1$H-NMR (DMSO d$_6$, TFA): 8.92 (s, 1H), 7.73 (m, 1H), 7.17-7.23 (m, 2H), 7.07 (s, 1H), 6.88 (s, 1H), 6.85 (s, 1H), 5.19 (m, 1H), 4.33 (t, 2H), 3.93 (s, 2H), 3.75 (t, 2H), 3.54 (s, 3H), 1.52 (s, 3H), 1.51 (s, 3H):

MS (+ve ESI): 513.16 (M+H)$^+$.

(3-{[5-isopropoxy-7-(2-methoxyethoxy)quinazolin-4-yl]amino}-1H-pyrazol-5-yl)acetic acid used as starting material was obtained as follows.

a) 5,7-Difluoroquinazolin-4(3H)one (2.73 g, 15 mmol) in dimethylformamide (20 ml) was reacted with isopropanol (1.26 ml, 16.4 mmol) and sodium hydride (1.8 g, 45 mmol) at 0° C. under argon. The mixture was stirred at ambient temperature for 14 hours, acidified with acetic acid and concentrated. The residue was washed with water and dried to yield 7-fluoro-5-isopropoxyquinazolin-4(3H)-one (3.17 g, 95% yield) as a beige solid:

$^1$H-NMR (DMSO d$_6$): 11.92 (br s, 1H), 7.97 (s, 1H), 6.95 (dd, 1H), 6.89 (dd, 1H), 4.73 (m, 1H), 1.32 (s, 3H), 1.31 (s, 3H):

MS (+ve ESI): 223.1 (M+H)$^+$.

b) An analogous reaction to that described in example 137b, but starting with 7-fluoro-5-isopropoxyquinazolin-4(3H)-one (444 mg, 2 mmol) and 2-methoxyethanol (0.32 ml, 4.06 mmol) and heating at 120° C. for 1.5 hours yielded 5-isopropoxy-7-(2-methoxyethoxy)quinazolin-4(3H)-one (155 mg, 28% yield) as a beige solid:

$^1$H-NMR (DMSO d$_6$): 11.62 (m, 1H), 7.88 (s, 1H), 6.64 (d, 1H), 6.54 (d, 1H), 4.66 (m, 1H), 4.66 (m, 2H), 4.20 (m, 2H), 1.30 (s, 3H), 1.29 (s, 3H):

MS (+ve ESI): 279.2 (M+H)$^+$.

c) An analogous reaction to that described in example 137c, but starting with 5-isopropoxy-7-(2-methoxyethoxy)quinazolin-4(3H)-one (935 mg, 3.36 mmol) yielded (3-{[5-isopropoxy-7-(2-methoxyethoxy)quinazolin-4-yl]amino}-1H-pyrazol-5-yl)acetic acid as a beige solid (1.0 g, 74% yield):

$^1$H-NMR (DMSO ds): 11.06 (s, 1H), 8.87 (s, 1H), 7.03 (s, 1H), 6.94 (s, 1H), 6.82 (s, 1H), 5.17 (m, 1H), 4.31 (t, 2H), 3.74 (t, 2H), 3.72 (s, 2H), 3.34 (s, 3H), 1.51 (s, 3H), 1.49 (s, 3H):

MS (+ve ESI): 402.1 (M+H)$^+$.

EXAMPLE 142

Preparation of Compound 142 in Table 6—N-(3-fluorophenyl)-2-(3-{[5-isopropoxy-7-(2-methoxyethoxy)quinazolin-4-yl]amino}-1H-pyrazol-5-yl)acetamide An analogous reaction to that described in example 140, but starting with (3-{[5-isopropoxy-7-(2-methoxyethoxy)quinazolin-4-yl]amino}-1H-pyrazol-5-yl)acetic acid (308 mg, 0.7 mmol) and 3-fluoroaniline (81 μl, 0.84 mmol) yielded compound 142 in table 6 as a white solid (62 mg, 18% yield):

$^1$H-NMR (DMSO ds): 10.44 (s, 1H), 10.33 (s, 1H), 8.44 (s, 1H), 7.61 (d, 1H), 7.30-7.39 (m, 1H), 7.32 (s, 1H), 6.89 (t, 1H), 6.85 (s, 1H), 6.77 (s, 1H), 6.76 (s, 1H), 5.01 (m, 1H), 4.24 (t, 2H), 3.75 (s, 2H), 3.71 (t, 2H), 3.33 (s, 3H), 1.47 (s, 3H), 1.46 (s, 3H):

MS (+ve ESI): 495.1 (M+H)$^+$.

EXAMPLE 143

Preparation of Compound 143 in Table 6—N-(3-fluorophenyl)-2-{3-[(5-{[1-(2-hydroxyethyl)piperidin-4-yl]oxy}-7-methoxyquinazolin-4-yl)amino]-1H-pyrazol-5-yl}acetamide An analogous reaction to that described in example 137, but starting with 2-{3-[(5-{[1-(2-tert-butoxyethyl)piperidin-4-yl]oxy}-7-methoxyquinazolin-4-yl)amino]-1H-pyrazol-5-yl}-N-(3-fluorophenyl)acetamide (39 mg, 0.066 mmol) yielded compound 143 in table 6 as a beige solid (26 mg, 74% yield):

$^1$H-NMR (DMSO d$_6$, TFA): 8.94 (s, 1H), 7.61 (d, 1H), 7.29-7.37 (m, 2H), 7.12-7.18 (m, 1H), 6.91-6.85 (m, 3H), 5.10-5.35 (s, 0.5H), 3.97 (s, 3H), 3.83 (s, 2H), 3.79 (t, 1H), 3.76 (t, 1H), 3.71 (d, 1H), 3.60 (d, 1H), 3.41 (t, 1H), 3.32 (s, 1H), 3.23 (m, 1H), 3.19 (t, 1H), 2.52 (m, 1H), 2.30 (m, 2H), 2.14 (m, 1H):

MS (+ve ESI): 536.1 (M+H)$^+$.

2-{3-[(5-{[1-(2-tert-butoxyethyl)piperidin-4-yl]oxy}-7-methoxyquinazolin-4-yl)amino]-1H-pyrazol-5-yl}-N-(3-fluorophenyl)acetamide used as starting material was obtained as follows.

a) An analogous reaction to that described in example 137b, but starting with 5-{[1-(2-tert-butoxyethyl)piperidin-4-yl]oxy}-7-fluoroquinazolin-4(3H)-one (363 mg, 1 mmol) and methanol (162 μl, 4 mmol) at 110° C. for 2 hours yielded 5-{[1-(2-tert-butoxyethyl)piperidin-4-yl]oxy}-7-methoxyquinazolin-4(3H)-one (237 mg, 63% yield):

$^1$H-NMR (DMSO d$_6$): 11.64 (br s, 1H), 7.91 (s, 1H), 6.65 (d, 1H), 6.56 (d, 1H), 4.48 (m, 1H), 3.84 (s, 3H), 3.40 (t, 2H), 2.74 (m, 2H), 2.41 (t, 2H), 2.29 (m, 2H), 1.87 (m, 2H), 1.69 (m, 2H), 1.12 (s, 9H):

MS (+ve ESI): 376.2 (M+H)$^+$.

b) An analogous reaction to that described in example 137c, but starting with 5-{[1-(2-tert-butoxyethyl)piperidin-4-yl]oxy}-7-methoxyquinazolin-4(3H)-one (458 mg, 1.22 mmol) and heating for 4 hours yielded {3-[(5-{[1-(2-tert-butoxyethyl)piperidin-4-yl]oxy}-7-methoxyquinazolin-4-yl)amino]-1H-pyrazol-5-yl}acetic acid as a beige solid (386 mg, 63% yield):

$^1$H-NMR (DMSO d$_6$): 8.97 (s, 1H), 7.14-7.20 (m, 1H), 6.98 (s, 1H), 6.86 (m, 1H), 5.10-5.35 (m, 1H), 3.99 (s, 3H), 3.67-3.80 (m, 3H), 3.75 (s, 2H), 3.60 (m, 1H), 3.27-3.46 (m, 3H), 3.22 (t, 1H), 2.52 (m, 1H), 2.34 (br s, 2H), 2.15 (m, 1H), 1.21 (s, 3H), 1.16 (s, 3H):

MS (+ve ESI): 499.1 (M+H)$^+$.

c) An analogous reaction to that described in example 137d, but starting with {3-[(5-{[1-(2-tert-butoxyethyl)piperidin-4-yl]oxy}-7-methoxyquinazolin-4-yl)amino]-1H-pyrazol-5-yl}acetic acid (250 mg, 0.5 mmol) and heating for 4 hours yielded 2-{3-[(5-{[1-(2-tert-butoxyethyl)piperidin-4-yl]oxy}-7-methoxyquinazolin-4-yl)amino]-1H-pyrazol-5-yl}-N-(3-fluorophenyl)acetamide as a yellow solid (44 mg, 15% yield):

$^1$H-NMR (DMSO d$_6$): 12.36 (s, 1H), 10.44 (s, 1H), 10.28 (s, 1H), 8.45 (s, 1H), 7.61 (d, 1H), 7.31-7.37 (m, 2H), 6.89 (t, 1H), 6.87 (s, 1H), 6.79 (s, 1H), 6.78 (s, 1H), 4.85 (br s, 1H), 3.89 (s, 3H), 3.75 (s, 2H), 3.41 (t, 2H), 2.79 (m, 2H), 2.46 (m, 4H), 2.07 (m, 2H), 1.83 (m, 2H), 1.11 (s, 9H):

MS (+ve ESI): 592.2 (M+H)$^+$.

EXAMPLE 144

Preparation of Compound 144 in Table 6—2-{3-[(5, 7-dimethoxyquinazolin-4-yl)amino]-1H-pyrazol-5-yl}-N-(3-fluorophenyl)acetamide An analogous reaction to that described in example 140, but starting with {3-[(5,7-dimethoxyquinazolin-4-yl)amino]-1H-pyrazol-5-yl}acetic acid (230 mg, 0.70 mmol) and 3-fluoroaniline (81 μl, 0.84 mmol) yielded compound 144 in table 6 as a pale orange solid (43 mg, 15% yield):

$^1$H-NMR (DMSO d$_6$): 12.39 (s, 1H), 10.44 (s, 1H), 9.88 (s, 1H), 8.45 (s, 1H), 7.61 (d, 1H), 7.30-7.39 (m, 1H), 7.33 (s, 1H), 6.89 (t, 1H), 6.82 (s, 1H), 6.80 (s, 1H), 6.72 (s, 1H), 4.08 (s, 3H), 3.90 (s, 3H), 3.76 (s, 2H):

MS (+ve ESI): 423 (M+H)$^+$.

EXAMPLE 145

Preparation or Compound 145 in Table 6—2-(3-{[5, 7-bis(2-methoxyethoxy)quinazolin-4-yl]amino}-1H-pyrazol-5-yl)-N-(3-fluorophenyl)acetamide An analogous reaction to that described in example 140, but starting with (3-{[5,7-bis(2-methoxyethoxy)quinazolin-4-yl]amino}-1H-pyrazol-5-yl)acetic acid (222 mg, 0.70 mmol) and 3-fluoroaniline (81 μl, 0.84 mmol) yielded compound 145 in table 6 as a beige solid (108 mg, 30% yield):

$^1$H-NMR (DMSO d$_6$): 8.90 (s, 1H), 7.61 (d, 1H), 7.30-7.38 (m, 2H), 7.32 (s, 1H), 7.05 (s, 1H), 6.88 (t, 1H), 6.85 (s, 1H), 6.82 (s, 1H), 4.53 (t, 2H), 4.32 (t, 2H), 3.85 (t, 2H), 3.81 (s, 2H), 3.73 (t, 2H), 3.42 (s, 3H), 3.33 (s, 3H):

MS (+ve ESI): 511.1 (M+H)$^+$.

EXAMPLE 146

Preparation of Compound 146 in Table 7—N-(3-fluorophenyl)-3-[(7-{3-[(2-hydroxyethyl)(isobutyl)amino]propoxy}-6-methoxyquinazolin-4-yl)amino]-1H-pyrazole-5-carboxamide An analogous reaction to that described in example 7, but starting with 2-(isobutylamino)ethanol (110 mg, 0.94 mmol) and 3-{[7-(3-chloropropoxy)-6-methoxyquinazolin-4-yl]amino}-N-(3-fluorophenyl)-1H-pyrazole-5-carboxamide (120 mg, 0.23 mmol) in the presence of potassium iodide (78 mg, 0.47 mmol) and heating for 3 hours yielded compound 146 in table 7 (96 mg, 73% yield):

$^1$H-NMR (DMSO d$_6$, TFA): 9.04 (s, 1H), 8.34 (s, 1H), 7.81 (m, 1H), 7.74 (s, 1H), 7.62 (m, 1H), 7.43 (m, 2H), 6.96 (m, 1H), 4.34 (s, 2H), 4.04 (s, 3H), 3.84 (t, 2H), 3.38 (m, 2H), 3.32 (m, 2H), 3.11 (m, 2H), 2.36 (m, 2H), 2.16 (m, 1H), 1.04 (d, 6H):

MS (+ve ESI): 552.2 (M+H)$^+$.

3-{[7-(3-chloropropoxy)-6-methoxyquinazolin-4-yl]amino}-N-(3-fluorophenyl)-1H-pyrazole-5-carboxamide used as starting material was obtained as follows:

a) 3-nitro-1H-pyrazole-5-carboxylic acid (1 g, 6.36 mmol) in dimethylformamide (10 ml) was reacted with 3-fluoroaniline (673 μl, 7 mmol) in the presence of 1-(3-dimethylamino-propyl)-3-ethylcarbodiimide hydrochloride (1.34 g, 7 mmol) and 2-hydroxy-pyridin-1-oxide (778 mg, 7 mmol) at 40° C. for 1.5 hour. The solvent was evaporated, and the residue purified by chromatography on silica gel. Elution with dichloromethane:methanol (99:1) then (97:3) yielded N-(3-fluorophenyl)-3-nitro-1H-pyrazole-5-carboxamide (668 mg, 42% yield):

$^1$H-NMR (DMSO d$_6$): 7.86 (s, 1H), 7.71 (m, 1H), 7.51 (m, 1H), 7.44 (m, 1H), 7.01 (m, 1H).

b) N-(3-fluorophenyl)-3-nitro-1H-pyrazole-5-carboxamide (100 mg, 0.4 mmol) in ethyl acetate:ethanol (10:4) was stirred with platinum dioxide (10 mg) under an atmosphere of hydrogen (70 psi) for 3 hours. The catalyst was filtered off and the solvent was evaporated in vacuo to yield 3-amino-N-(3-fluorophenyl)-1H-pyrazole-5-carboxamide (65 mg, 73% yield):

$^1$H-NMR (DMSO d$_6$): 7.76 (m, 1H), 7.60 (s, 1H), 7.33 (m, 1H), 6.86 (s, 1H), 5.71 (s, 1H), 5.22 (s, 2H):

MS (+ve ESI): 221.2 (M+H)$^+$.

c) 3-Amino-N-(3-fluorophenyl)-1H-pyrazole-5-carboxamide (153 mg, 0.69 mmol) in dimethylacetamide (1.8 ml) and HCl in dioxane (4 M solution in dioxane, 174 μl, 0.69 mmol) was reacted with 4-chloro-7-(3-chloropropoxy)-6-methoxyquinazoline (200 mg, 0.69 mmol) at 90° C. for 1.5 hour. Dichloromethane (35 ml) was added to the cooled reaction mixture, and the solid recovered by filtration, washed with dichloromethane and dried to yield 3-{[7-(3-chloropropoxy)-6-methoxyquinazolin-4-yl]amino}-N-(3-fluorophenyl)-1H-pyrazole-5-carboxamide (286 mg, 81% yield):

$^1$H-NMR (DMSO d$_6$, TFA): 9.03 (s, 1H), 8.33 (s, 1H), 7.80 (m, 1H), 7.73 (s, 1H), 7.62 (m, 1H), 7.44 (m, 2H), 6.96 (m, 1H), 4.36 (t, 2H), 4.04 (s, 3H), 3.85 (t, 2H), 2.33 (t, 2H):

MS (+ve ESI): 471.0 (M+H)$^+$.

4-chloro-7-(3-chloropropoxy)-6-methoxyquinazoline was itself made as follows:

d) A mixture of 2-amino-4-benzyloxy-5-methoxybenzamide (10 g, 0.04 mol), (prepared according to *J. Med. Chem.* 1977, 20, 146-149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried.

Recrystallisation from acetic acid yielded 7-benzyloxy-6-methoxy-3,4-dihydroquinazolin-4-one (8.7 g, 84% yield) as a white solid.

e) Chloromethyl pivalate (225 ml, 1.56 mol) was added dropwise to a stirred mixture of 6-methoxy-7-benzyloxyquinazol-4-one (400 g, 1.42 mol) and potassium carbonate (783 g, 5.67 mol) in dimethylacetamide (5500 ml). The reaction was heated to 90° C. for 4 hours. The reaction was cooled and filtered to remove inorganic salts. The filtrate was concentrated in vacuo to yield, crude tert-butyl 2-[7-(benzyloxy)-6-methoxy-4-oxo-3(4H)-quinazolinyl]acetate (562 g, 100% yield):

$^1$H-NMR (DMSO d$_6$): 8.33 (s, 1H), 7.30-7.50 (m, 6H), 7.25 (s, 1H), 5.90 (s, 2H), 5.25 (s, 2H), 3.88 (s, 3H), 1.10 (s, 9H):

MS (+ve ESI): 397 (M+H)$^+$.

f) 10% palladium on carbon (56 g, 53 mmol) was added to a solution of tert-butyl 2-[7-(benzyloxy)-6-methoxy-4-oxo-3(4H)-quinazolinyl]acetate (562 g, 1.42 mmol) in dimethylacetamide (3500 ml) at ambient temperature and stirred for 3 hours under an atmosphere of hydrogen (1 bar). The reaction was filtered through a pad of celite and the solvent evaporated in vacuo. The residual solid was dissolved in 20% methanol in dichloromethane and passed through a pad of silica gel. Evaporation of the solvent in vacuo followed by trituration with methanol yielded, tert-butyl 2-[7-hydroxy-6-methoxy-4-oxo-3(4H)-quinazolinyl]acetate (188 g, 43% yield):

$^1$H-NMR (DMSO d$_6$): 8.25 (s, 1H), 7.45 (s, 1H), 6.97 (s, 1H), 5.85 (s, 2H), 4.04 (s, 1H), 3.87 (s, 3H), 1.10 (s, 9H):

MS (+ve ESI): 307 (M+H)$^+$.

g) A mixture of tert-butyl 2-[7-hydroxy-6-methoxy-4-oxo-3(4H)-quinazolinyl]-acetate (100 g, 0.327 mol), 3-bromopropanol (49.3 g, 0.355 mol) and potassium carbonate (133 g, 0.967 mol) in dimethylformamide (500 ml) was stirred at 80° C. for 20 hours. The reaction was cooled and concentrated to quarter volume in vacuo. The residue was poured into ice/water (1500 ml) and the resulting solid collected by suction filtration. Purification by crystallisation from ethanol, yielded crude tert-butyl 2-[7-(3-hydroxypropoxy)-6-methoxy-4-oxo-3(4H)-quinazolinyl]acetate (33.8 g, 41% yield) as a beige solid:

$^1$H-NMR (DMSO d$_6$): 7.95 (s, 1H), 7.43 (s, 1H), 7.10 (s, 1H), 4.16 (t, 2H), 3.86 (m, 5H), 2.08 (t, 2H), 1.12 (s, 9H):

MS (+ve ESI): 365 (M+H)$^+$.

h) Aqueous sodium hydroxide solution (100 ml, 0.2 mol) was added to a solution of tert-butyl 2-[7-(3-hydroxypropoxy)-6-methoxy-4-oxo-3(4H)-quinazolinyl]acetate (33.8 g, 93 mmol) in methanol (300 ml) and the solution heated to reflux for 1 hour. The methanol was evaporated in vacuo, the residue was acidified with aqueous hydrochloric acid, sodium bicarbonate was added and the solid was collected by suction filtration. Washing with water and drying yielded 7-(3-hydroxypropoxy)-6-methoxy-4-quinazolone (26 g, 95% yield):

$^1$H-NMR (DMSO d$_6$): 7.96 (s, 1H), 7.41 (s, 1H), 7.07 (s, 1H), 4.14 (t, 2H), 3.84 (s, 3H), 3.55 (t, 2H), 1.90 (t, 2H):

MS (+ve ESI): 251 (M+H)$^+$.

i) 7-(3-hydroxypropoxy)-6-methoxy-4-quinazolone (25 g, 100 mmol) was added slowly to a solution of dimethylformamide (1 ml) in thionyl chloride (250 ml). The mixture was heated to reflux for 4 hours then cooled and the solvents evaporated in vacuo. The residue was dissolved in dichloromethane and washed with aqueous sodium bicarbonate, brine, dried over magnesium sulphate and evaporated. Trituration and collection of the solid by suction filtration yielded, 4-chloro-6-methoxy-7-(3-chloroxypropoxy)quinazoline (19.5 g, 68% yield): as a yellow solid:

$^1$H-NMR (CDCl$_3$): 8.85 (s, 1H), 7.40 (s, 1H), 7.38 (s, 1H), 4.38 (t, 2H), 4.03 (s, 3H), 3.80 (t, 2H), 2.40 (m, 2H):

MS (+ve ESI): 287 (M+H)$^+$.

EXAMPLE 147

Preparation of Compound 147 in Table 7—N-(2,3-difluorophenyl)-3-[(7-{3-[(2-hydroxyethyl)(isobutyl)amino]propoxy}-6-methoxyquinazolin-4-yl)amino]-1H-pyrazole-5-carboxamide An analogous reaction to that described in example 146, but starting with 3-{[7-(3-chloropropoxy)-6-methoxyquinazolin-4-yl]amino}-N-(2,3-difluorophenyl)-1H-pyrazole-5-carboxamide (120 mg, 0.23 mmol) yielded compound 147 in table 7 (59 mg, 45% yield):

$^1$H-NMR (DMSO d$_6$, TFA): 9.03 (s, 1H), 8.32 (s, 1H), 7.69 (s, 1H), 7.50 (m, 1H), 7.41 (s, 1H), 7.30 (m, 3H), 4.33 (m, 2H), 4.03 (s, 3H), 3.82 (m, 2H), 3.40 (m, 2H), 3.31 (m, 2H), 3.13 (m, 2H), 2.33 (m, 2H), 2.15 (m, 1H), 1.03 (d, 6H):

MS (+ve ESI): 570.2 (M+H)$^+$.

3-{[7-(3-chloropropoxy)-6-methoxyquinazolin-4-yl]amino}-N-(2,3-difluorophenyl)-1H-pyrazol-5-carboxamide used as starting material was obtained as follows:

a) An analogous reaction to that described in 146a, but starting with 2,3-difluoroaniline (212 μl, 2.1 mmol) yielded N-(2,3-difluorophenyl)-3-nitro-1H-pyrazole-5-carboxamide (200 mg, 0.74 mmol) (230 mg, 45% yield):

$^1$H-NMR (DMSO d$_6$): 7.86 (s, 1H), 7.43 (m, 1H), 7.37 (m, 1H), 7.29 (m, 1H).

b) An analogous reaction to that described in 146b, but starting with N-(2,3-difluorophenyl)-3-nitro-1H-pyrazole-5-carboxamide (200 mg, 0.74 mmol) yielded 3-amino-N-(2,3-difluorophenyl)-1H-pyrazole-5-carboxamide (161 mg, 91% yield):

$^1$H-NMR (DMSO d$_6$): 9.50 (s, 1H), 7.72 (s, 1H), 7.20 (m, 2H), 5.72 (s, 1H), 5.28 (s, 2H).

c) An analogous reaction to that described in 146c, but starting with 3-amino-N-(2,3-difluorophenyl)-1H-pyrazole-5-carboxamide (124 mg, 0.52 mmol) yielded 3-{[7-(3-chloropropoxy)-6-methoxyquinazolin-4-yl]amino}-N-(2,3-difluorophenyl)-1H-pyrazole-5-carboxamide (246 mg, 89% yield):

$^1$H-NMR (DMSO d$_6$, TFA): 9.02 (s, 1H), 8.32 (s, 1H), 7.69 (s, 1H), 7.52 (m, 1H), 7.43 (s, 1H), 7.27 (m, 2H), 4.36 (t, 2H), 4.04 (s, 3H), 3.85 (t, 2H), 2.33 (m, 2H):

MS (+ve ESI): 489.0 (M+H)$^+$.

What is claimed is:

1. A compound of formula (IA):

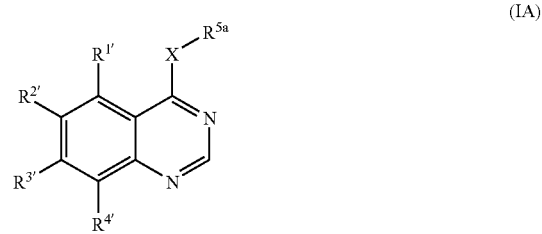

(IA)

or a salt, ester or amide thereof;

X is O or S, S(O) or S(O)$_2$, or NR$^6$ where R$^6$ is hydrogen or C$_{1-6}$alkyl;

R$^{5a}$ is a group of formula (a) or (b):

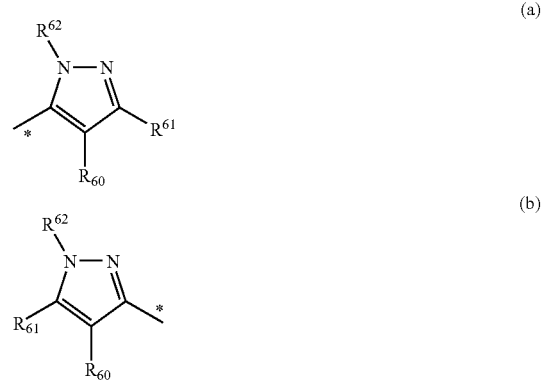

where * indicates the point of attachment to the group X in formula (I);

R$^{1'}$, R$^{2'}$, R$^{3'}$, R$^{4'}$ are independently selected from hydrogen, halo, cyano, nitro, trifluoromethyl, C$_{1-3}$alkyl, —NR$^7$R$^8$ or —X$^1$R$^9$; wherein at least one of R$^{1'}$, R$^{2'}$, R$^{3'}$ and R$^{4'}$ is —X$^1$R$^9$;

R$^7$ and R$^8$ are independently hydrogen or C$_{1-3}$alkyl;

X$^1$ is —O—, —CH$_2$—, —OCO—, carbonyl, —S—, —SO—, —SO$_2$—, —NR$^{10}$CO—, —CONR$^{11}$—, —SO$_2$NR$^{12}$—, —NR$^{13}$SO$_2$— or —NR$^{14}$—;

R$^{10}$, R$^{11}$, R$^{12}$, R$^{13}$ and R$^{14}$ are independently hydrogen, C$_{1-3}$alkyl or C$_{1-3}$alkoxyC$_{2-3}$alkyl;

R$^9$ is selected from one of the following groups:

1) hydrogen or $C_{1-5}$alkyl which may be unsubstituted or which may be substituted with one or more groups selected from hydroxy, fluoro or amino;
2) $C_{1-5}$alkyl$X^2COR^{15}$ wherein $X^2$ represents —O— or —NR$^{16}$— in which $R^{15}$ represents hydrogen, $C_{1-3}$alkyl or $C_{1-3}$alkoxy$C_{2-3}$alkyl and $R^{16}$ represents $C_{1-3}$alkyl, —NR$^{17}R^{18}$ or —OR$^{19}$ wherein $R^{17}$, $R^{18}$ and $R^{19}$ which may be the same or different each represents hydrogen, $C_{1-3}$alkyl or $C_{1-3}$alkoxy$C_{2-3}$alkyl;
3) $C_{1-5}$alkyl$X^3R^{20}$ wherein $X^3$ represents —O—, —S—, —SO—, —SO$_2$—, —OCO—, —NR$^{21}$CO—, —CONR$^{22}$—, —SO$_2$NR$^{23}$—, —NR$^{24}$SO$_2$— or —NR$^{25}$— wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl and $R^{20}$ represents hydrogen, $C_{1-3}$alkyl, cyclopentyl, cyclohexyl or a 5- or 6-membered saturated heterocyclic group with 1 or 2 heteroatoms, selected independently from O, S and N, which $C_{1-3}$alkyl group may bear 1 or 2 substituents selected from oxo, hydroxy, halo and $C_{1-4}$alkoxy and which cyclic group may bear 1 or 2 substituents selected from oxo, hydroxy, halo, $C_{1-4}$alkyl, $C_{1-4}$hydroxyalkyl and $C_{1-4}$alkoxy;
4) $C_{1-5}$alkyl$X^4C_{1-5}$alkyl$X^5R^{26}$ wherein $X^4$ and $X^5$ which may be the same or different are each —O—, —S—, —SO—, —SO$_2$—, —NR$^{27}$CO—, —CONR$^{28}$—, —SO$_2$NR$^{29}$—, —NR$^{30}$SO$_2$— or —NR$^{31}$— wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl and $R^{26}$ represents hydrogen or $C_{1-3}$alkyl;
5) $R^{32}$ wherein $R^{32}$ is a 5- or 6-membered saturated heterocyclic group linked via carbon or nitrogen with 1 or 2 heteroatoms, selected independently from O, S and N, which heterocyclic group may bear 1 or 2 substituents selected from oxo, hydroxy, halo, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl;
6) $C_{1-5}$alkyl$R^{32}$ wherein $R^{32}$ is as defined hereinbefore;
7) $C_{2-5}$alkenyl$R^{32}$ wherein $R^{32}$ is as defined hereinbefore;
8) $C_{2-5}$alkynyl$R^{32}$ wherein $R^{32}$ is as defined hereinbefore;
9) $R^{33}$ wherein $R^{33}$ represents a pyridone group, a phenyl group or a 5- or 6-membered aromatic heterocyclic group linked via carbon or nitrogen with 1, 2 or 3 heteroatoms selected from O, N and S, which pyridone, phenyl or aromatic heterocyclic group may carry up to 5 substituents on available carbon atoms selected from hydroxy, halo, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —CONR$^{34}R^{35}$ and —NR$^{36}$COR$^{37}$ wherein $R^{34}$, $R^{35}$, $R^{36}$ and $R^{37}$, which may be the same or different, each represents hydrogen, $C_{1-4}$alkyl or $C_{1-3}$alkoxy$C_{2-3}$alkyl;
10) $C_{1-5}$alkyl$R^{33}$ wherein $R^{33}$ is as defined hereinbefore;
11) $C_{2-5}$alkenyl$R^{33}$ wherein $R^{33}$ is as defined hereinbefore;
12) $C_{2-5}$alkynyl$R^{33}$ wherein $R^{33}$ is as defined hereinbefore;
13) $C_{1-5}$alkyl$X^6R^{33}$ wherein $X^6$ represents —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl and $R^{33}$ is as defined hereinbefore;
14) $C_{2-5}$alkenyl$X^7R^{33}$ wherein $X^7$ represents —O—, —S—, —SO—, —SO$_2$—, —NR$^{43}$CO—, —CONR$^{44}$—, —SO$_2$NR$^{45}$—, —NR$^{46}$SO$_2$— or —NR$^{47}$— wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl and $R^{33}$ is as defined hereinbefore;
15) $C_{2-5}$alkynyl$X^8R^{33}$ wherein $X^8$ represents —O—, —S—, —SO—, —SO$_2$—, —NR$^{48}$CO—, —CONR$^{49}$—, —SO$_2$NR$^{50}$—, —NR$^{51}$SO$_2$— or —NR$^{52}$— wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl and $R^{33}$ is as defined hereinbefore;
16) $C_{1-3}$alkyl$X^9C_{1-3}$alkyl$R^{33}$ wherein $X^9$ represents —O—, —S—, —SO—, —SO$_2$—, —NR$^{53}$CO—, —CONR$^{54}$—, —SO$_2$NR$^{55}$—, —NR$^{56}$SO$_2$— or —NR$^{57}$— wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl and $R^{33}$ is as defined hereinbefore;
17) $C_{1-3}$alkyl$X^9C_{1-3}$alkyl$R^{32}$ wherein $X^9$ and $R^{32}$ are as defined hereinbefore;
18) $C_{1-5}$alkyl optionally substituted by 1, 2 or 3 halo;
19) $C_{1-5}$alkyl$X^{10}C_{1-5}$alkyl$X^{11}R^{90}$ wherein $X^{10}$ and $X^{11}$, which may be the same or different, are each —O—, —S—, —SO—, —SO$_2$—, —NR$^{91}$CO—, —CONR$^{92}$—, —SO$_2$NR$^{93}$—, —NR$^{94}$SO$_2$— or —NR$^{95}$— where $R^{91}$, $R^{92}$, $R^{93}$, $R^{94}$ and $R^{95}$ each independently represents $C_{1-5}$alkyl, $C_{1-3}$alkyl substituted by 1, 2 or 3 halo, $C_{1-4}$alkyl or $C_{1-4}$alkoxy groups and where there are 2 $C_{1-4}$alkoxy groups the $C_{1-4}$alkyl groups of alkoxy may together form a 5- or 6-membered saturated heterocyclic group having 2 oxygen atoms, $C_{2-5}$alkenyl, $C_{2-5}$alkynyl, $C_{3-6}$cycloalkyl optionally substituted by halo, hydroxy, $C_{1-3}$alkyl or $C_{1-4}$hydroxyalkyl, $C_{3-6}$cycloalkyl$C_{1-3}$alkyl optionally substituted by halo, hydroxy, $C_{1-3}$alkyl or $C_{1-4}$hydroxyalkyl or $C_{1-3}$alkoxy$C_{2-3}$alkyl and $R^{90}$ represents hydrogen or $C_{1-3}$alkyl;
20) $C_{3-6}$cycloalkyl;
21) $R^{96}$ wherein $R^{96}$ is a 5- or 6-membered heterocyclic group which may be saturated or unsaturated linked via carbon or nitrogen with 1 or 2 heteroatoms, selected independently from O, S and N which heterocyclic group may bear 1 or 2 substituents selected from $C_{1-4}$hydroxyalkyl, $C_{1-4}$alkyl, hydroxy and $C_{1-4}$alkoxy$C_{1-4}$alkyl;
22) $C_{1-5}$alkyl$R^{96}$ wherein $R^{96}$ is defined hereinbefore; and where:
$R^{60}$ is hydrogen, nitro, halo, cyano, or $C_{1-3}$alkyl;
$R^{61}$ is a group of sub-formula (k):

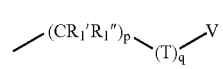

(k)

where:
p is 0 or 1;
q is 1;
$R_1'$ and $R_1''$ are independently hydrogen, hydroxy, halo, cyano, $C_{1-10}$alkyl, $C_{3-10}$cycloalkyl, $C_{2-10}$alkenyl or $C_{2-10}$alkynyl; wherein $C_{1-10}$alkyl, $C_{3-10}$cycloalkyl, $C_{2-10}$alkenyl and $C_{2-10}$alkynyl are optionally substituted by halo, nitro, cyano, hydroxy, trifluoromethyl, amino, carboxy, carbamoyl, mercapto, sulphamoyl, $C_{1-4}$alkyl, $C_{2-4}$alkenyl, $C_{2-4}$alkynyl, $C_{3-6}$cycloalkyl, $C_{3-6}$cycloalkenyl, $C_{1-4}$alkoxy, $C_{1-4}$alkanoyl, $C_{1-4}$alkanoyloxy, $C_{1-4}$alkanoylamino, N,N-di($C_{1-4}$alkanoyl)amino, N-($C_{1-4}$alkyl)carbamoyl, N,N-di($C_{1-4}$alkyl)carbamoyl, $C_{1-4}$alkylS, $C_{1-4}$alkylS(O), $C_{1-4}$alkylS(O)$_2$, $C_{1-4}$alkoxycarbonyl, N-($C_{1-4}$ alkyl)sulphamoyl, N,N-di($C_{1-4}$alkyl) sulphamoyl, $C_{1-4}$alkylsulphonylamino or heterocyclyl;
or $R_1'$ and $R_1''$ can together form a 3- to 6-membered ring which may be saturated or unsaturated;

T is C=O or SO$_n$ wherein n is 0, 1 or 2;

V is independently selected from R$^{63}$ or N(R$^{63}$)R$^{64}$;

R$^{63}$ is —(CH$_2$)$_q$R$^{70}$ or aryl or heteroaryl where the latter two groups are optionally substituted by 1 or 2 substituents independently selected from halo, C$_{1-4}$alkyl, C$_{1-4}$alkoxy, trifluoromethyl, trifluoromethoxy, hydroxy, nitro, difluoromethyl, difluoromethoxy and cyano;

R$^{64}$ is hydrogen or C$_{1-3}$alkyl;

q' is 0 or 1

R$^{70}$ is of formula (III):

K is a bond;

J is aryl or heteroaryl which are both optionally substituted by 1, 2 or 3 substituents selected from halo, C$_{1-3}$alkyl, C$_{3-4}$cycloalkyl, C$_{3-4}$cycloalkylC$_{1-3}$alkyl, cyano and C$_{1-3}$alkoxy; and R$^{62}$ is hydrogen, halo or C$_{1-3}$alkyl.

2. A compound according to claim 1, or a salt, ester or amide thereof, wherein R$_1$' and R$_1$" are independently hydrogen or C$_{1-3}$alkyl; T is C=O; and V is N(R$^{63}$)R$^{64}$.

3. A compound according to claim 2, or a salt, ester or amide thereof, wherein R$^{63}$ is aryl optionally substituted by 1 or 2 substituents independently selected from halo, C$_{1-4}$alkyl, C$_{1-4}$alkoxy, trifluoromethyl, trifluoromethoxy, hydroxy, nitro, difluoromethyl, difluoromethoxy and cyano.

4. A compound according to claim 1, or a salt, ester or amide thereof, wherein R$^{60}$ and R$^{62}$ are both hydrogen, R$^{61}$ is —CH$_2$—CONR$^{64}$-J and wherein J is phenyl optionally substituted by 1 or 2 halo.

5. A compound according to claim 1, or a salt, ester or amide thereof, wherein R$^9$ is hydrogen, C$_{3-6}$cycloalkyl, —C$_{1-5}$ alkyl-O—C$_{1-3}$alkyl or a 5- to 6-membered saturated heterocyclic group linked via carbon or nitrogen with 1 or 2 heteroatoms selected independently from O, S or N which heterocyclic group is optionally substituted by C$_{1-4}$alkyl or R$^9$ is a 5- or 6-membered aromatic heterocyclic group linked via carbon or nitrogen with 1, 2 or 3 heteroatoms or R$^9$ is —C$_{1-5}$alkylR$^{32}$, —C$_{1-5}$alkylR$^{96}$, C$_{1-5}$alkyl optionally substituted by halo, —C$_{1-5}$alkyl-OR$^{20}$, —C$_{1-5}$alkyl-NHR$^{20}$, —C$_{1-5}$ alkyl-N(C$_{1-3}$alkyl)-R$^{20}$, —C$_{1-5}$alkyl-NH—C$_{1-5}$alkyl-OH, —C$_{1-5}$alkyl-N(C$_{1-3}$alkyl)-C$_{1-5}$alkyl-OH and —C$_{1-5}$alkyl-NR$^{95}$—C$_{1-5}$alkyl-OH and wherein R$^{32}$, R$^{96}$, R$^{20}$ and R$^{95}$ are as defined in claim 1.

6. A compound according to claim 2, or a salt, ester or amide thereof, wherein R$^{1'}$ is hydrogen, methoxy, N—(C$_{1-4}$alkyl)piperid in-4-yloxy, prop-2-yloxy or methoxyethoxy;

R$^{2'}$ is hydrogen or methoxy; and R$^{4'}$ is hydrogen.

7. A method for treating colorectal or breast cancer in a warm blooded animal, such as man, in need of such treatment, which comprises administering to said animal an effective amount of a compound of formula (IA), or a pharmaceutically acceptable salt, or an in vivo hydrolysable ester thereof as defined in claim 1.

8. A pharmaceutical composition comprising a compound according to claim 1, or a pharmaceutically acceptable salt thereof in combination with a pharmaceutically acceptable carrier.

9. A process for the preparation of a compound according to claim 1 comprising the step of:

a) when X is NH, reacting a compound of formula (VII)

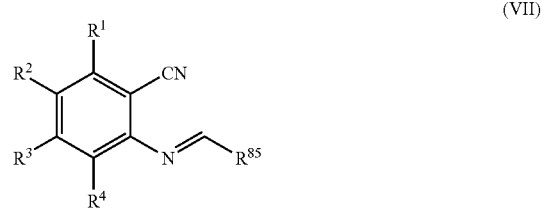

where R$^1$, R$^2$, R$^3$, and R$^4$ are R$^{1'}$, R$^{2'}$, R$^{3'}$, and R$^{4'}$ as defined in claim 7 and R$^{85}$ is a group NR$^{86}$R$^{87}$ where R$^{86}$ and R$^{87}$ are independently selected from C$_{1-4}$alkyl, with a compound of formula (VIII)

where R$^{5'}$ is a group R$^{5a}$ as defined in claim 7; or b) when X is as defined in claim 1, reacting a compound of formula (X)

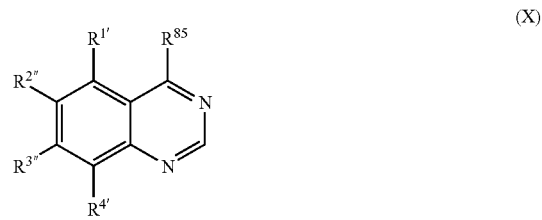

where R$^{1'}$, R$^{2''}$, R$^{3''}$, and R$^{4'}$ are equivalent to a group R$^{1'}$, R$^{2'}$, R$^{3'}$ and R$^{4'}$ as defined in claim 7, and R$^{85}$ is a leaving group, with a compound of formula (XI)

and R$^5$ is R$^{5a}$ as defined in claim 1.

10. A compound according to claim 2, or a salt, ester or amide thereof, wherein R$^{60}$ and R$^{62}$ are both hydrogen.

11. A compound according to claim 2, or a salt, ester or amide thereof, wherein R$^{63}$ is —(CH$_2$)$_q$R$^{70}$ and J is phenyl optionally substituted by 1 or 2 halo.

12. A compound according to claim 3, or a salt, ester or amide thereof, wherein p is 1.

13. A compound according to claim 11, or a salt, ester or amide thereof, wherein p is 1.

14. A compound according to claim 2, or a salt, ester or amide thereof, wherein X$^1$ is —O— or —N(C$_{1-3}$alkyl)—.

15. A compound according to claim 5, or a salt, ester or amide thereof, wherein X$^1$ is —O— or —N(C$_{1-3}$alkyl)—.

16. A compound according to claim 1, or a salt, ester or amide thereof, wherein R$^{1'}$ is —X$^1$R$^9$ where X$^1$ is —O—, —NH— or —NMe— and R$^9$ is selected from a group 1), 3), 5), 9) or 20) as defined in claim 1.

17. A compound according to claim 2, or a salt, ester or amide thereof, wherein R$^{1'}$ is —X$^1$R$^9$ where X$^1$ is —O— or —NH— and R$^9$ is hydrogen, C$_{1-5}$alkyl, C$_{3-6}$cycloalkyl, —C$_{1-5}$ alkyl-O—C$_{1-3}$alkyl or a 5- to 6-membered saturated heterocyclic group linked via carbon or nitrogen with 1 or 2 heteroatoms selected independently from O, S or N which heterocyclic groups is optionally substituted by C$_{1-4}$alkyl or a 5- or 6-membered aromatic heterocyclic group linked via carbon or nitrogen with 1, 2 or 3 heteroatoms.

18. A compound according to claim 2, or a salt, ester or amide thereof, wherein $R^{1'}$ is hydrogen, methoxy, N—($C_{1-4}$ alkyl)piperidin-4-yloxy, prop-2-yloxy or methoxyethoxy.

19. A compound according to claim 2, or a salt, ester or amide thereof, wherein $R^{1'}$ is hydrogen.

20. A compound according to claim 1, or a salt, ester or amide thereof, wherein $R^{2'}$ is hydrogen, halo, —$X^1R^9$ where $X^1$ is —O— and $R^9$ is a group 1) as defined in claim 1.

21. A compound according to claim 2, or a salt, ester or amide thereof, wherein $R^{2'}$ is hydrogen or methoxy.

22. A compound according to claim 1, or a salt, ester or amide thereof, wherein $R^{3'}$ is —$X^1R^9$ where $X^1$ is —O— and $R^9$ is selected from a group 3), 4), 6), 18), 19) or 22) as defined in claim 1.

23. A compound according to claim 2, or a salt, ester or amide thereof, wherein $R^{3'}$ is —$X^1R^9$ where $X^1$ is —O— and $R^9$ is —$C_{1-5}$alkyl$R^{32}$, —$C_{1-5}$alkyl$R^{96}$, $C_{1-5}$alkyl optionally substituted by halo, —$C_{1-5}$alkyl-$OR^{20}$, —$C_{1-5}$alkyl-$NHR^{20}$, —$C_{1-5}$alkyl-N($C_{1-3}$alkyl)-$R^{20}$, —$C_{1-5}$alkyl-NH—$C_{1-5}$alkyl-OH, —$C_{1-5}$alkyl-N($C_{1-3}$alkyl)-$C_{1-5}$alkyl-OH and —$C_{1-5}$alkyl-$NR^{95}$—$C^{1-5}$alkyl-OH.

24. A compound according to claim 2, or a salt, ester or amide thereof, wherein $R^{3'}$ is —$X^1R^9$ where $X^1$ is —O— and $R^9$ is —$C_{1-5}$alkyl$R^{32}$ where $R^{32}$ is pyrrolidinyl, piperidinyl or piperazinyl each being optionally substituted by hydroxy, hydroxymethyl, 2-hydroxyethyl, methyl or 2-(tert-butoxy) ethyl; —$C_{1-5}$alkyl-$NHR^{20}$; —$C_{1-5}$alkyl-NH—$C_{1-5}$alkyl-OH; —$C_{1-5}$alkyl-N($C_{1-3}$alkyl)-$C_{1-5}$alkyl-OH and —$C_{1-5}$alkyl-$NR^{95}$—$C_{1-5}$alkyl-OH.

25. A compound according to claim 2, or a salt, ester or amide thereof, wherein $R^{3'}$ is 3-morpholinopropoxy, 3-chloropropoxy,
   3-[N-ethyl-N-(2-hydroxyethyl)amino]propoxy, 3-(2-hydroxymethylpyrrolidin-1-yl)propoxy,
   3-(piperidin-1-yl)propoxy, 3-(pyrrolidin-1-yl)propoxy, 3-(N-(2-hydroxyethyl)amino]propoxy,
   3-[N-(2-hydroxy-1,1-dimethylethyl)amino}propoxy,
   3-[N-methyl-N-(2-hydroxyethyl)amino]propoxy,
   3-[N-(1-hydroxymethyl-2-methylpropyl)amino]propoxy, 3-(4-methylpiperazin-1-yl)propoxy,
   3-[N-(2-hydroxy-1-methylethyl)amino]propoxy, 3-[N-(4-hydroxybutyl)amino]propoxy,
   3-(4-hydroxypiperidin-1-yl)propoxy, 3-[2-(2-hydroxyethyl)piperidin-1-yl]propoxy,
   3-[4-(2-hydroxyethyl)piperazin-1-yl]propoxy, 3-[4-(2-hydroxyethyl)piperidin-1-yl]propoxy,
   3-(3-hydroxypiperidin-1-yl)propoxy, 3-[N-2-(hydroxybutyl)amino]propoxy,
   3-(4-hydroxymethylpiperidin-1-yl)propoxy, 3-[N-(3-hydroxy-2,2-dimethylpropyl)amino]propoxy,
   3-[N-(1-hydroxymethylcyclopent-1-yl)amino]propoxy, 3-[N-(2-hydroxypropyl)amino]propoxy,
   3-(3-hydroxypyrrolidin-1-yl)propoxy, 3-[N-(2-fluoroethyl)-N-(2-hydroxyethyl)amino]propoxy,
   2-[1-(2-hydroxyethyl)piperidin-4-yl]ethoxy, 3-[N-(2-hydroxyethyl)-N-propylamino]propoxy,
   3-[N-(2-hydroxyethyl)-N-(prop-2-yl)amino]propoxy,
   3-[N-(2-hydroxyethyl)-N-isobutylamino]propoxy,
   3-[N-(2-hydroxyethyl)-N-neopentylamino]propoxy,
   3-[N-allyl-N-(2-hydroxyethyl)amino]propoxy,
   3-[N-(2-hydroxyethyl)-N-(prop-2-yn-1-yl)amino]propoxy,
   3-[N-cyclopropyl-N-(2-hydroxyethyl)amino]propoxy,
   3-[N-cyclopropylmethyl-N-(2-hydroxyethyl)amino]propoxy,
   3-[N-cyclobutyl-N-(2-hydroxyethyl)amino]propoxy,
   3-[N-cyclopentyl-N-(2-hydroxyethyl)amino]propoxy,
   3-[N-(2,2-dimethoxyethyl)-N-(2-hydroxyethyl)amino] propoxy,
   3-[N-(2,2-difluoroethyl)-N-(2-hydroxyethyl)amino]propoxy,
   3-[N-(2-hydroxyethyl)-N-(3,3,3-trifluoropropyl)amino] propoxy,
   3-[N-cyclobutylmethyl-N-(2-hydroxyethyl)amino]propoxy,
   3-[N-(2-hydroxyethyl)-N-(2-methoxyethyl)amino]propoxy,
   3-[N-(1,3-dioxolan-2-ylmethyl)-N-(2-hydroxyethyl) amino]propoxy, 4-chlorobutoxy,
   4-[(2-hydroxymethyl)pyrrolidin-1-yl]butoxy, 4-[N-(2-hydroxyethyl)-N-isobutylamino]butoxy,
   1-(2-tert-butoxyethyl)pyrrolidin-2-ylmethoxy, 1-(2-hydroxyethyl)pyrrolidin-2-ylmethoxy,
   3-[N-2-(hydroxyethyl)-N-(iso-butyl)amino]propoxy,
   3-[N-2-(hydroxyethyl)-N-(neopentyl)amino]propoxy,
   3-[N-2-(hydroxyethyl)-N-(tert-butyl)amino]propoxy,
   methoxy and methoxyethoxy.

26. A compound according to claim 2, or a salt, ester or amide thereof, wherein $R^{4'}$ is hydrogen.

27. A compound according to claim 23, or a salt, ester or amide thereof, wherein $R^{1'}$ is hydrogen, $R^{2'}$ is hydrogen or methoxy and $R^{4'}$ is hydrogen.

28. A compound according to claim 25, or a salt, ester or amide thereof, wherein $R^{1'}$ is hydrogen, $R^{2'}$ is hydrogen or methoxy and $R^{4'}$ is hydrogen.

29. A compound according to claim 2, or a salt, ester or amide thereof, wherein X is $NR^6$ or O.

30. A compound according to claim 2, or a salt, ester or amide thereof, wherein X is NH.

31. A compound according to claim 27, or a salt, ester or amide thereof, wherein X is NH.

32. A compound according to claim 28, or a salt, ester or amide thereof, wherein X is NH.

33. A compound according to claim 1 selected from:
   2-(3-{[6-methoxy-7-(3-morpholin-4-ylpropoxy)quinazolin-4-yl]amino}-1H-pyrazol-5-yl)-N-phenylacetamide;
   N-(3-fluorophenyl)-2-(3-{[6-methoxy-7-(3-morpholin-4-ylpropoxy)quinazolin-4-yl]amino}-1H-pyrazol-5-yl) acetamide;
   2-(3-{[7-(3-chloropropoxy)-6-methoxyquinazolin-4-yl] amino}-1H-pyrazol-5-yl)-N-(3-fluorophenyl)acetamide;
   2-(3-{[7-(3-chloropropoxy)-6-methoxyquinazolin-4-yl] amino}-1H-pyrazol-5-yl)-N-(3,5-difluorophenyl)acetamide;
   2-(3-{[7-(3-chloropropoxy)-6-methoxyquinazolin-4-yl] amino}-1H-pyrazol-5-yl)-N-(2,3-difluorophenyl)acetamide;
   N-(3-chlorophenyl)-2-(3-{[7-(3-chloropropoxy)-6-methoxyquinazolin-4-yl]amino}-1H-pyrazol-5-yl)acetamide;
   2-{3-[(7-{3-[ethyl(2-hydroxyethyl)amino]propoxy}-6-methoxyquinazolin-4-yl)amino]-1H-pyrazol-5-yl}-N-(3-fluorophenyl)acetamide;
   N-(3-fluorophenyl)-2-{3-[(7-{3-[(2S)-2-(hydroxymethyl) pyrrolidin-1-yl]propoxy}-6-methoxyquinazolin-4-yl) amino]-1H-pyrazol-5-yl}acetamide;
   N-(3-fluorophenyl)-2-(3-{[6-methoxy-7-(3-piperidin-1-ylpropoxy)quinazolin-4-yl]amino}-1H-pyrazol-5-yl) acetamide;
   N-(3-fluorophenyl)-2-(3-{[6-methoxy-7-(3-pyrrolidin-1-ylpropoxy)quinazolin-4-yl]amino}-1H-pyrazol-5-yl) acetamide;

N-(3-fluorophenyl)-2-{3-[(7-{3-[(2-hydroxyethyl)amino]propoxy}-6-methoxyquinazolin-4-yl)amino]-1H-pyrazol-5-yl}acetamide;

N-(3-fluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide;

N-(3-fluorophenyl)-2-{3-[(7-{3-[(2-hydroxyethyl)(methyl)amino]propoxy}-6-methoxyquinazolin-4-yl)amino]-1H-pyrazol-5-yl}acetamide;

N-(3-fluorophenyl)-2-(3-{[7-(3-{[1-(hydroxymethyl)-2-methylpropyl]amino}propoxy)-6-methoxyquinazolin-4-yl]amino}-1H-pyrazol-5-yl)acetamide;

N-(3-fluorophenyl)-2-[3-({6-methoxy-7-[3-(4-methylpiperazin-1-yl)propoxy]quinazolin-4-yl}amino)-1H-pyrazol-5-yl]acetamide;

N-(3-fluorophenyl)-2-{3-[(7-{3-[(2-hydroxy-1-methylethyl)amino]propoxy}-6-methoxyquinazolin-4-yl)amino]-1H-pyrazol-5-yl}acetamide;

N-(3-fluorophenyl)-2-{3-[(7-{3-[(4-hydroxybutyl)amino]propoxy}-6-methoxyquinazolin-4-yl)amino]-1H-pyrazol-5-yl}acetamide;

N-(3-fluorophenyl)-2-[3-({7-[3-(4-hydroxypiperidin-1-yl)propoxy]-6-methoxyquinazolin-4-yl}amino)-1H-pyrazol-5-yl]acetamide;

N-(3-fluorophenyl)-2-{3-[(7-{3-[2-(2-hydroxyethyl)piperidin-1-yl]propoxy}-6-methoxyquinazolin-4-yl)amino]-1H-pyrazol-5-yl}acetamide;

N-(3-fluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide;

N-(3-fluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide;

N-(3-fluorophenyl)-2-[3-({7-[3-(3-hydroxypiperidin-1-yl)propoxy]-6-methoxyquinazolin-4-yl}amino)-1H-pyrazol-5-yl]acetamide;

N-(3-fluorophenyl)-2-{3-[(7-{3-[(2-hydroxybutyl)amino]propoxy}-6-methoxyquinazolin-4-yl)amino]-1H-pyrazol-5-yl}acetamide;

N-(3-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-fluorophenyl)-2-{3-[(7-{3-[(3-hydroxy-2,2-dimethylpropyl)amino]propoxy}-6-methoxyquinazolin-4-yl)amino]-1H-pyrazol-5-yl}acetamide;

N-(3-fluorophenyl)-2-(3-{[7-(3-{[1-(hydroxymethyl)cyclopentyl]amino}propoxy)-6-methoxyquinazolin-4-yl]amino}-1H-pyrazol-5-yl)acetamide;

N-(3-fluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(3-fluorophenyl)-2-(3-{[7-(3-{[(2S)-2-hydroxypropyl]amino}propoxy)-6-methoxyquinazolin-4-yl]amino}-1H-pyrazol-5-yl)acetamide;

N-(3-fluorophenyl)-2-(3-{[7-(3-{[(2R)-2-hydroxypropyl]amino}propoxy)-6-methoxyquinazolin-4-yl]amino}-1H-pyrazol-5-yl)acetamide;

N-(3-fluorophenyl)-2-{3-[(7-{3-[(3S)-3-hydroxypyrrolidin-1-yl]propoxy}-6-methoxyquinazolin-4-yl)amino]-1H-pyrazol-5-yl}acetamide;

N-(3-fluorophenyl)-2-{3-[(7-{3-[(3R)-3-hydroxypyrrolidin-1-yl]propoxy}-6-methoxyquinazolin-4-yl)amino]-1H-pyrazol-5-yl}acetamide;

2-{3-[(7-{3-[(2-fluoroethyl)(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{2-[1-(2-hydroxyethyl)piperidin-4-yl]ethoxy}-6-methoxyquinazolin-4-yl)amino]-1H-pyrazol-5-yl}acetamide;

N-(3-fluorophenyl)-2-{3-[(7-{3-[(2-hydroxyethyl)(propyl)amino]propoxy}-6-methoxyquinazolin-4-yl)amino]-1H-pyrazol-5-yl}acetamide;

N-(3-fluorophenyl)-2-{3-[(7-{3-[(2-hydroxyethyl)(isopropyl)amino]propoxy}-6-methoxyquinazolin-4-yl)amino]-1H-pyrazol-5-yl}acetamide;

N-(3-fluorophenyl)-2-{3-[(7-{3-[(2-hydroxyethyl)(isobutyl)amino]propoxy}-6-methoxyquinazolin-4-yl)amino]-1H-pyrazol-5-yl}acetamide;

2-{3-[(7-{3-[(2,2-dimethylpropyl)(2-hydroxyethyl)amino]propoxy}-6-methoxyquinzolin-4-yl)amino]-1H-pyrazol-5-yl}-N-(3-fluorophenyl)acetamide;

2-{3-[(7-{3-[allyl(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide;

2-{3-[(7-{3-[cyclopropyl(2-hydroxyethyl)amino]propoxy}-6-methoxyquinazolin-4-yl)amino]-1H-pyrazol-5-yl}-N-(3-fluorophenyl)acetamide;

2-{3-[(7-{3-[(cyclopropylmethyl)(2-hydroxyethyl)amino]propoxy}-6-methoxyquinazolin-4-yl)amino]-1H-pyrazol-5-yl}-N-(3-fluorophenyl)acetamide;

2-{3-[(7-{3-[cyclobutyl(2-hydroxyethyl)amino]propoxy}-6-methoxyquinazolin-4-yl)amino]-1H-pyrazol-5-yl}-N-(3-fluorophenyl)acetamide;

2-{3-[(7-{3-[cyclopentyl(2-hydroxyethyl)amino]propoxy}-6-methoxyquinazolin-4-yl)amino]-1H-pyrazol-5-yl}-N-(3-fluorophenyl)acetamide;

2-{3-[(7-{3-[(2,2-dimethoxyethyl)(2-hydroxyethyl)amino]propoxy}-6-methoxyquinazolin-4-yl)amino]-1H-pyrazol-5-yl}-N-(3-fluorophenyl)acetamide;

2-{3-[(7-{3-[(2,2-difluoroethyl)(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{3-[(2-hydroxyethyl)(3,3,3-trifluoropropyl)amino]propoxy}-6-methoxyquinazolin-4-yl)amino]-1H-pyrazol-5-yl}acetamide;

2-{3-[(7-{3-[(cyclobutylmethyl)(2-hydroxyethyl)amino]propoxy}-6-methoxyquinazolin-4-yl)amino]-1H-pyrazol-5-yl}-N-(3-fluorophenyl)acetamide;

N-(3-fluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide;

2-{3-[(7-{3-[(1,3-dioxolan-2-ylmethyl)(2-hydroxyethyl)amino]propoxy}-6-methoxyquinazolin-4-yl)amino]-1H-pyrazol-5-yl}-N-(3-fluorophenyl)acetamide;

2-(3-{[7-(4-chlorobutoxy)-6-methoxyquinazolin-4-yl]amino}-1H-pyrazol-5-yl)-N-(3-fluorophenyl)acetamide;

N-(3-fluorophenyl)-2-{3-[(7-{4-[(2R)-2-(hydroxymethyl)pyrrolidin-1-yl]butoxy}-6-methoxyquinazolin-4-yl)amino]-1H-pyrazol-5-yl}acetamide;

N-(3-fluorophenyl)-2-{3-[(7-{4-[(2-hydroxyethyl)(isobutyl)amino]butoxy}-6-methoxyquinazolin-4-yl)amino]-1H-pyrazol-5-yl}acetamide;

2-{3-[(7-{[(2R)-1-(2-tert-butoxyethyl)pyrrolidin-2-yl]methoxy}-6-methoxyquinazolin-4-yl)amino]-1H-pyrazol-5-yl}-N-(3-fluorophenyl)acetamide;

N-(3-fluorophenyl)-2-{3-[(7-{[(2R)-1-(2-hydroxyethyl)pyrrolidin-2-yl]methoxy}-6-methoxyquinazolin-4-yl)amino]-1H-pyrazol-5-yl}acetamide;

N-(3,5-difluorophenyl)-2-(3-{[6-methoxy-7-(3-pyrrolidin-1-ylpropoxy)quinazolin-4-yl]amino}-1H-pyrazol-5-yl)acetamide;

N-(3,5-difluorophenyl)-2-{3-[(7-{3-[(2-hydroxyethyl)amino]propoxy}-6-methoxyquinazolin-4-yl)amino]-1H-pyrazol-5-yl}acetamide;

N-(3,5-difluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide;

N-(3,5-difluorophenyl)-2-[3-({6-methoxy-7-[3-(4-methylpiperazin-1-yl)propoxy]quinazolin-4-yl}amino)-1H-pyrazol-5-yl]acetamide;

N-(3,5-difluorophenyl)-2-{3-[(7-{3-[ethyl(2-hydroxyethyl)amino]propoxy}-6-methoxyquinazolin-4-yl)amino]-1H-pyrazol-5-yl}acetamide;

N-(3,5-difluorophenyl)-2-{3-[(7-{3-[2-(2-hydroxyethyl)piperidin-1-yl]propoxy}-6-methoxyquinazolin-4-yl)amino]-1H-pyrazol-5-yl}acetamide;

N-(3,5-difluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide;

N-(3,5-difluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide;

N-(3,5-difluorophenyl)-2-[3-({7-[3-(3-hydroxypiperidin-1-yl)propoxy]-6-methoxyquinazolin-4-yl}amino)-1H-pyrazol-5-yl]acetamide;

N-(3,5-difluorophenyl)-2-{3-[(7-{3-[(2-hydroxybutyl)amino]propoxy}-6-methoxyquinazolin-4-yl)amino]-1H-pyrazol-5-yl}acetamide;

N-(3,5-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3,5-difluorophenyl)-2-{3-[(7-{3-[(3-hydroxy-2,2-dimethylpropyl)amino]propoxy}-6-methoxyquinazolin-4-yl)amino]-1H-pyrazol-5-yl}acetamide;

N-(3,5-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(3,5-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(3,5-difluorophenyl)-2-(3-{[7-(3-{[(2S)-2-hydroxypropyl]amino}propoxy)-6-methoxyquinazolin-4-yl]amino}-1H-pyrazol-5-yl)acetamide;

N-(3,5-difluorophenyl)-2-(3-{[7-(3-{[(2R)-2-hydroxypropyl]amino}propoxy)-6-methoxyquinazolin-4-yl]amino}-1H-pyrazol-5-yl)acetamide;

N-(3,5-difluorophenyl)-2-{3-[(7-{3-[(3S)-3-hydroxypyrrolidin-1-yl]propoxy}-6-methoxyquinazolin-4-yl)amino]-1H-pyrazol-5-yl}acetamide;

N-(3,5-difluorophenyl)-2-{3-[(7-{3-[(3R)-3-hydroxypyrrolidin-1-yl]propoxy}-6-methoxyquinazolin-4-yl)amino]-1H-pyrazol-5-yl}acetamide;

N-(3,5-difluorophenyl)-2-{3-[(7-{3-[(2-hydroxyethyl)(isobutyl)amino]propoxy}6-methoxyquinazolin-4-yl)amino]-1H-pyrazol-5-yl}acetamide;

N-(3,5-difluorophenyl)-2-{3-[(7-{3-[(2-hydroxyethyl)(propyl)amino]propoxy}-6-methoxyquinazolin-4-yl)amino]-1H-pyrazol-5-yl}acetamide;

2-{3-[(7-{3-[allyl(2-hydroxyethyl)amino]propoxy}-6-methoxyquinazolin-4-yl)amino]-1H-pyrazol-5-yl}-N-(3,5-difluorophenyl)acetamide;

N-(3,5-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide;

N-(3,5-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide;

N-(3,5-difluorophenyl)-2-{3-[(7-{3-[(2,2-dimethylpropyl)(2-hydroxyethyl)amino]propoxy}-6-methoxyquinazolin-4-yl)amino]-1H-pyrazol-5-yl}acetamide;

2-{3-[(7-{3-[cyclobutyl(2-hydroxyethyl)amino]propoxy}-6-methoxyquinazolin-4-yl)amino]-1H-pyrazol-5-yl}-N-(3,5-difluorophenyl)acetamide;

2-{3-[(7-{3-[(cyclopropylmethyl)(2-hydroxyethyl)amino]propoxy}-6-methoxyquinazolin-4-yl)amino]-1H-pyrazol-5-yl}-N-(3,5-difluorophenyl)acetamide;

N-(2,3-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(2,3-difluorophenyl)-2-{3-[(7-{3-[(2,2-dimethylpropyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(propyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide;

2-{3-[(7-{3-[cyclobutyl(2-hydroxyethyl)amino]propoxy}-6-methoxyquinazolin-4-yl)amino]-1H-pyrazol-5-yl}-N-(2,3-difluorophenyl)acetamide;

2-{3-[(7-{3-[cyclopentyl(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide;

2-{3-[(7-{3-[(cyclopropylmethyl)(2-hydroxyethyl)amino]propoxy}-6-methoxyquinazolin-4-yl)amino]-1H-pyrazol-5-yl}-N-(2,3-difluorophenyl)acetamide;

2-{3-[(7-{3-[(cyclobutylmethyl)(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(2,2-dimethoxyethyl)(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[4-(2-hydroxyethyl)piperidin-1-yl]propoxy}-6-methoxyquinazolin-4-yl)amino]-1H-pyrazol-5-yl}acetamide;

N-(2,3-difluorophenyl)-2-[3-({7-[3-(4-hydroxypiperidin-1-yl)propoxy]-6-methoxyquinazolin-4-yl}amino)-1H-pyrazol-5-yl]acetamide;

N-(2,3-difluorophenyl)-2-{3-[(7-{3-[4-(2-hydroxyethyl)piperazin-1-yl]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide;

2-{3-[(7-{3-[allyl(2-hydroxyethyl)amino]propoxy}-6-methoxyquinazolin-4-yl)amino]-1H-pyrazol-5-yl}-N-(2,3-difluorophenyl)acetamide;

N-(2,3-difluorophenyl)-2-{3-[(7-{3-[(1,3-dioxolan-2-ylmethyl )(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[ethyl(2-hydroxyethyl)amino]propoxy}-6-methoxyquinazolin-4-yl)amino]-1H-pyrazol-5-yl}acetamide;

N-(2,3-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide;

N-(2,3-difluorophenyl)-2-{3-[(7-{3-[(2-hydroxy-1,1-dimethylethyl)amino]propoxy}-6-methoxyquinazolin-4-yl)amino]-1H-pyrazol-5-yl}acetamide;

N-(2,3-difluorophenyl)-2-{3-[(7-{[(2R)-1-(2-hydroxyethyl)pyrrolidin-2-yl]methoxy}-6-methoxyquinazolin-4-yl)amino]-1H-pyrazol-5-yl}acetamide;

N-(3-chlorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide;

N-(3-chlorophenyl)-2-{3-[(7-{3-[(2R)-2-(hydroxymethyl)pyrroldin-1-yl]propoxy}-6-methoxyquinazolin-4-yl)amino]-1H-pyrazol-5-yl}acetamide;

N-(3-chlorophenyl)-2-[3-({7-[3-(3-hydroxypiperidin-1-yl)propoxy]-6-methoxyquinazolin-4-yl}amino)-1H-pyrazol-5-yl]acetamide;

N-(3-chlorophenyl)-2-{3-[(7-{3-[ethyl(2-hydroxyethyl)amino]propoxy}-6-methoxyquinazolin-4-yl)amino]-1H-pyrazol-5-yl}acetamide;

2-{3-[(7-{3-[4-(hydroxymethyl)piperidin-1-yl]propoxy}-6-methoxyquinazolin-4-yl)amino]-1H-pyrazol-5-yl}-N-(3-methoxyphenyl)acetamide;

2-{3-[(7-{3-[4-(hydroxymethyl)piperidin-1-yl]propoxy}-6-methoxyquinazolin-4-yl)amino]-1H-pyrazol-5-yl}-N-phenylacetamide;

N-(4-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3,5-dichlorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(5-chloro-2-methoxyphenyl)-2-{3-[(7-{3-[4-(hydroxymethyl)piperidin-1-yl]propoxy}-6-methoxyquinazolin-4-yl)amino]-1H-pyrazol-5-yl}acetamide;

2-{3-[(7-{3-[4-(hydroxymethyl)piperidin-1-yl]propoxy}-6-methoxyquinazolin-4-yl)amino]-1H-pyrazol-5-yl}-N-[3-(trifluoromethyl)phenyl]acetamide;

2-{3-[(7-{3-[4-(hydroxymethyl)piperidin-1-yl]propoxy}-6-methoxyquinazolin-4-yl)amino]-1H-pyrazol-5-yl}-N-(3-hydroxyphenyl)acetamide;

2-{3-[(7-{3-[4-(hydroxymethyl)piperidin-1-yl]propoxy}-6-methoxyquinazolin-4-yl)amino]-1H-pyrazol-5-yl}-N-(3-nitrophenyl)acetamide;

2-{3-[(7-{3-[4-(hydroxymethyl)piperidin-1-yl]propoxy}-6-methoxyquinazolin-4-yl)amino]-1H-pyrazol-5-yl}-N-1H-indazol-5-ylacetamide;

N-(4-bromo-2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-chlorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3,5-dimethoxyphenyl)-2-{3-[(7-{3-[4-(hydroxymethyl)piperidin-1-yl]propoxy}-6-methoxyquinazolin-4-yl)amino]-1H-pyrazol-5-yl}acetamide;

2-{3-[(7-{3-[4-(hydroxymethyl)piperidin-1-yl]propoxy}-6-methoxyquinazolin-4-yl)amino]-1H-pyrazol-5-yl}-N-(5-methylpyridin-2-yl)acetamide;

N-(2,3-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-chloro-2-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2,5-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-[2-fluoro-5-(trifluoromethyl)phenyl]-2-{3-[(7-{3-[4-(hydroxymethyl)piperidin-1-yl]propoxy}-6-methoxyquinazolin-4-yl)amino]-1H-pyrazol-5-yl}acetamide;

N-(3,4-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2,4-difluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-chloro-4-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-[2-(difluoromethoxy)phenyl]-2-{3-[(7-{3-[4-(hydroxymethyl)piperidin-1-yl]propoxy}-6-methoxyquinazolin-4-yl)amino]-1H-pyrazol-5-yl}acetamide;

N-(3-cyanophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(3-bromophenyl)-2-{3-[(7-{3-[4-(hydroxymethyl)piperidin-1-yl]propoxy}-6-methoxyquinazolin-4-yl)amino]-1H-pyrazol-5-yl}acetamide;

N-(2,3-difluorophenyl)-2-{3-[(7-{3-[ethyl(2-hydroxyethyl)amino]propoxy}quinazolin-4-yl)amino]-1H-pyrazol-5-yl}acetamide;

N-(2,3-difluorophenyl)-2-{3-[(7-{3-[(2-hydroxyethyl)(isopropyl)amino]propoxy}quinazolin-4-yl)amino]-1H-pyrazol-5-yl}acetamide;

N-(2,3-difluorophenyl)-2-{3-[(7-{3-[(2R)-2-(hydroxymethyl)pyrrolidin-1-yl]propoxy}quinazolin-4-yl)amino]-1H-pyrazol-5-yl}acetamide;

N-(2,3-difluorophenyl)-2-{3-[(7-{3-[(2-hydroxyethyl)(propyl)amino]propoxy}quinazolin-4-yl)amino]-1H-pyrazol-5-yl}acetamide;

N-(2,3-difluorophenyl)-2-{3-[(7-{3-[(2-hydroxyethyl)(prop-2-yn-1-yl)amino]propoxy}quinzolin-4-yl)amino]-1H-pyrazol-5-yl}acetamide;

N-(2,3-difluorophenyl)-2-{3-[(7-{3-[(2-hydroxyethyl)(isobutyl)amino]propoxy}quinazolin-4-yl)amino]-1H-pyrazol-5-yl}acetamide;

N-(2,3-difluorophenyl)-2-{3-[(7-{3-[(2,2-dimethylpropyl)(2-hydroxyethyl)amino]propoxy}quinazolin-4-yl)amino]-1H-pyrazol-5-yl}acetamide;

N-(3-fluorophenyl)-2-[3-({5-{[1-(2-hydroxyethyl)piperidin-4-yl]oxy}-7-[3-(4-methylpiperazin-1-yl)propoxy]quinazolin-4-yl}amino)-1H-pyrazol-5-yl]acetamide;

N-(3-fluorophenyl)-2-[5-({7-methoxy-5-[(1-methylpiperidin-4-yl)oxy]quinazolin-4-yl}amino)-1H-pyrazol-3-yl]acetamide;

N-(2,3-difluorophenyl)-2-{3-[(5,7-dimethoxyquinazolin-4-yl)amino]-1H-pyrazol-5-yl}acetamide;

2-(3-{[5,7-bis(2-methoxyethoxy)quinazolin-4-yl]amino}-1H-pyrazol-5-yl)-N-(2,3-difluorophenyl)acetamide;

N-(2,3-difluorophenyl)-2-(3-{[5-isopropoxy-7-(2-methoxyethoxy)quinazolin-4-yl]amino}-1H-pyrazol-5-yl)acetamide;

N-(3-fluorophenyl )-2-(3-{[5-isopropoxy-7-(2-methoxyethoxy)quinazolin-4-yl]amino}-1H-pyrazol-5-yl)acetamide;

N-(3-fluorophenyl)-2-{3-[(5-{[1-(2-hydroxyethyl)piperidin-4-yl]oxy}-7-methoxyquinazolin-4-yl)amino]-1H-pyrazol-5-yl}acetamide;

2-{3-[(5,7-dimethoxyquinazolin-4-yl)amino]-1H-pyrazol-5-yl}-N-(3-fluorophenyl)acetamide;

2-(3-{[5,7-bis(2-methoxyethoxy)quinazolin-4-yl]amino}-1H-pyrazol-5-yl)-N-(3-fluorophenyl)acetamide;

N-(3-fluorophenyl)-3-[(7-{3-[(2-hydroxyethyl)(isobutyl)amino]propoxy}-6-methoxyquinazolin-4-yl)amino]-1H-pyrazole-5-carboxamide; and N-(2,3-difluorophenyl)-3-[(7-{3-[(2-hydroxyethyl)(isobutyl)amino]propoxy}-6-methoxyquinazolin-4-yl)amino]-1H-pyrazole-5-carboxamide;

or a pharmaceutically acceptable salt thereof.

* * * * *